US012708332B2

(12) United States Patent
Jagadeesan et al.

(10) Patent No.: US 12,708,332 B2
(45) Date of Patent: Aug. 18, 2026

(54) SYSTEM AND METHOD FOR PERCUTANEOUS DEPLOYMENT OF SENSORS

(71) Applicants: The Brigham and Women's Hospital, Inc., Boston, MA (US); Navigation Sciences, Inc., Brookline, MA (US)

(72) Inventors: Jayender Jagadeesan, Bedford, MA (US); Raphael Bueno, Brookline, MA (US); Alan D. Lucas, Brookline, MA (US); Timothy W. Robinson, Sandown, NH (US); Laurence A. Roth, Windham, NH (US)

(73) Assignees: The Brigham and Women's Hospital, Inc., Boston, MA (US); Navigation Sciences, Inc., Brookline, MA (US)

( * ) Notice: Subject to any disclaimer, the term of this patent is extended or adjusted under 35 U.S.C. 154(b) by 0 days.

(21) Appl. No.: 19/161,145

(22) PCT Filed: Aug. 23, 2024

(86) PCT No.: PCT/US2024/043588
§ 371 (c)(1),
(2) Date: Aug. 29, 2025

(87) PCT Pub. No.: WO2025/049290
PCT Pub. Date: Mar. 6, 2025

(65) Prior Publication Data

US 2026/0108221 A1 Apr. 23, 2026

Related U.S. Application Data

(60) Provisional application No. 63/534,915, filed on Aug. 28, 2023.

(51) Int. Cl.
*A61B 6/12* (2006.01)
*A61B 1/267* (2006.01)
(Continued)

(52) U.S. Cl.
CPC .............. *A61B 6/12* (2013.01); *A61B 1/2676* (2013.01); *A61B 5/055* (2013.01); *A61B 5/064* (2013.01);
(Continued)

(58) Field of Classification Search
CPC ........ A61B 5/055; A61B 5/6852; A61B 5/742
See application file for complete search history.

(56) References Cited

U.S. PATENT DOCUMENTS

2004/0124105 A1 7/2004 Seiler et al.
2010/0036241 A1 2/2010 Mayse et al.
(Continued)

OTHER PUBLICATIONS

International Search Report in International Application No. PCT/US2024/043588; received on Nov. 25, 2024.

*Primary Examiner* — Serkan Akar
*Assistant Examiner* — Kaitlyn Eunji Kim
(74) *Attorney, Agent, or Firm* — QUARLES & BRADY LLP

(57) ABSTRACT

A method for tracking the location of a tissue mass comprising disposing a J-bar and electrical lead assembly within a needle cannula lumen; disposing the needle cannula within an outer cannula lumen; inserting the outer cannula into the anatomy of the patient; moving the needle cannula distally relative to the outer cannula; applying a force so that the J-bar and electrical lead assembly moves distally such that the fiducial sensor is anchored proximate to the tissue mass; moving the outer cannula and needle cannula proximally in concert, until the distal end of the outer cannula and the distal end of the needle cannula are disposed at the surface of the skin; applying a force so that the expandable basket moves distally, such that the expandable basket is disposed at the surface of the patient's skin with the electrical lead extending between the fiducial sensor and the expandable basket.

20 Claims, 69 Drawing Sheets

(51) Int. Cl.

| | |
|---|---|
| ***A61B 5/00*** | (2006.01) |
| ***A61B 5/055*** | (2006.01) |
| ***A61B 5/06*** | (2006.01) |
| ***A61B 6/00*** | (2006.01) |
| ***A61B 6/03*** | (2006.01) |
| ***A61B 8/08*** | (2006.01) |

(52) U.S. Cl.
CPC ............ *A61B 5/6852* (2013.01); *A61B 5/742* (2013.01); *A61B 6/032* (2013.01); *A61B 6/4441* (2013.01); *A61B 8/085* (2013.01)

(56) References Cited

U.S. PATENT DOCUMENTS

| | | | | |
|---|---|---|---|---|
| 2011/0021888 | A1 | 1/2011 | Sing et al. | |
| 2013/0345561 | A1 | 12/2013 | Quigley | |
| 2022/0273340 | A1 | 9/2022 | Bueno et al. | |
| 2022/0361941 | A1* | 11/2022 | Townley ............ | A61B 18/1485 |

* cited by examiner 100A
110A
140A
135A
105A
20
150A
160A
145A 135A
105A
130A
120A
121A
125A
20
20
115A 155A
165A
150A
110A
139A
139
140A
160A
145A
170A

SYSTEM AND METHOD FOR PERCUTANEOUS DEPLOYMENT OF SENSORS

CROSS REFERENCE TO RELATED APPLICATIONS

This patent application claims benefit of U.S. Provisional Patent Application Ser. No. 63/534,915, filed Aug. 28, 2023, by The Brigham and Women's Hospital, Inc. et al. for SYSTEM AND METHOD FOR A TISSUE RESECTION MARGIN MEASUREMENT DEVICE. The above-identified patent application is hereby incorporated herein by reference.

FIELD

This invention relates to methods and apparatus for performing surgery in general, and more particularly to methods and apparatus for performing minimally-invasive computer-assisted surgery.

BACKGROUND

Minimally invasive surgical resection of lesions involves the precise excision of the lesion while sparing surrounding healthy and critical tissue. Some examples include, but are not limited to, breast conserving surgery and Video-Assisted Thoracic Surgery (VATS). Surgical resection of the lesion generally requires the removal of a margin of tissue around the lesion to ensure complete removal of the lesion cells and improved long-term survival. The default resection margin (sometimes simply referred to as "the margin") is dependent on the type of lesion and micro-invasion of the lesion into the surrounding tissue. While this is particularly true in cancer, where the size of the original lesion and the margin of normal tissue resected with the lesion is associated with survival, this is also true for non-cancerous lesions. Significant deformation of the tissue due to high viscoelasticity, physiological motion (such as collapsing of the lung, breathing or beating motion, etc.), or tissue manipulation can lead to difficulty in localizing the lesion and precisely removing the lesion while maintaining an adequate margin around the lesion. As a result, this can lead to insufficient resection, lesion recurrence locally or by metastasis (in the case of cancer), and poorer long-term benefits compared with cases where a sufficient margin is obtained. Two surgical applications are listed below as an example of where a target tissue mass (sometimes referred to as "a lesion") must be removed from a host tissue mass, where the host tissue mass is deformable, and where the resection line must be along or exterior to a resection margin. However, the disclosed system and method may be applied for the resection or biopsy of other lesions through a minimally invasive or image-guided approach or open-surgery, or a combination of approaches.

Lung Lesion Surgery

Current clinical practice to remove lung tissue segments involves opening the chest by cutting the sternum and spreading the ribs. Many times ribs are broken in the process and often segments of ribs are surgically removed during these procedures. The orthopedic trauma alone presents considerable pain and it can complicate the recovery process with patients. Thoracic pain of this magnitude also complicates the task of recovering a patient from general anesthesia since the body acclimates to forced ventilation, and the pain associated with sternum cutting and rib spreading can interrupt natural chest rhythm. Patients benefit dramatically from minimally invasive procedures that are performed through small incisions or ports in the chest without causing this orthopedic trauma.

Even though minimally invasive or VATS techniques are well known to provide benefit to the patient by minimizing trauma and speeding recovery times compared to open chest procedures, a substantial number of open chest procedures are currently still performed. This is due, at least in part, to the fact that there are only a limited number of instruments designed specifically to facilitate thoracic procedures in this way.

Surgery for lung cancer, however, is moving to a minimally invasive approach using VATS and smaller anatomic or non-anatomic lung resection (e.g., a wedge resection or segmentectomy), particularly for small lesions. In the conventional method of performing VATS, however, the lesion is imaged prior to surgery while the lung is inflated, and then the lung is collapsed during surgery, leading to difficulty in precisely locating the lesion and determining the resection margins. Additionally, palpation of lung tissue is not always possible (particularly in the case of smaller or early stage cancers) when utilizing a minimally invasive approach to surgery. Imprecise surgical resection could lead to incomplete resection and subsequent lesion recurrence.

Breast Lesion Surgery

Breast conserving surgery (BCS) involves the removal of a lesion while sparing the healthy breast parenchyma around the lesion. Studies have shown that BCS combined with chemotherapy has similar long-term benefits as mastectomy with the additional cosmetic advantage. However, identifying and resecting the entire lesion with an appropriate resection margin is a challenging task due to the highly deformable nature of the breast. Achieving the negative surgical margin with minimal damage to the healthy parenchyma is non-trivial due to the soft-tissue nature of the breast. In fact, studies show that up to 25% of breast resections leave positive margins and require re-treatment.

Therefore, a tissue resection margin measuring device is needed that overcomes the above limitations by providing an improved approach for precisely locating a lesion and determining the resection margins.

SUMMARY OF THE INVENTION

The present invention relates to a system and method for resecting a tissue mass while compensating for tissue deformation due to its elastic nature and physiologically induced motion. In a non-limiting example, the invention enables minimally invasive surgical procedures for resecting a tissue mass so as to remove a lesion by providing a device and method to perform tissue resection that discriminates against traumatizing critical tissue and precisely determines the resection margin. Additionally, auditory, visual and haptic cues may be provided to the surgeon to identify and more precisely measure the lesion margins and critical structures surrounding the lesions to ensure complete and safe resection of the lesion.

Some embodiments of the invention provide a system for resecting a tissue mass, e.g., so as to remove a lesion. The system includes a surgical instrument and a first sensor (sometimes also referred to as "a first fiducial sensor", or "a tissue sensor", or "a sensor", etc.) for measuring a first signal. The first sensor is dimensioned to fit inside of or next to (e.g., in close proximity to) the target lesion, usually at a location between the target lesion and the ultimate cut area-margin (i.e., the resection line). The system also includes a second sensor (sometimes also referred to as "a second fiducial sensor", or "an instrument sensor", or "a sensor", etc.) for measuring a second signal, and the second sensor is coupled to the surgical instrument. A controller is in communication with the first sensor and the second sensor, and the controller executes a stored program to calculate a distance between the first sensor and the second sensor based on the first signal and the second signal. The controller is preferably also configured to calculate a distance between the second sensor and a pre-determined resection margin disposed about the target tissue mass (i.e., the target lesion) based on the measurements of the first sensor. More particularly, the present invention permits the surgeon to insert a virtual object representing a pre-determined resection margin into a virtual model of the anatomy (see discussion above), and the controller uses the data from the first and second sensors to place the virtual model into registration, i.e., the controller (i) uses information from the first sensor to track the location of the target tissue mass, (ii) uses information from the second sensor to track the location of the surgical instrument, and (iii) uses information from the first sensor to keep the three-dimensional tissue mass model in registration with the target tissue mass (and hence keep the three-dimensional virtual margin model in registration with the target tissue mass), such that the controller can calculate a distance between the second sensor and the pre-determined resection margin (i.e., the virtual object inserted into the virtual model).

In some embodiments the system may further include a sleeve dimensioned to engage at least one of a housing of the surgical device (also sometimes referred to as "a surgical instrument") and the second sensor. The second sensor may be coupled to the housing of the surgical instrument by an adhesive, for example. The surgical device may be, for example, a stapler, a Bovi pencil or a cutting device configured to cut along (or preferably just outside of) a resection margin surrounding the target tissue mass, which may be a lesion (e.g., a tumor, a nodule, etc.). The resection margin may be included within the distance calculated between the first sensor and the second sensor. Other factors may be included in calculating the margins, such as the distance between the target tissue mass and the first sensor, the configuration of the target tissue mass, and the deformability of tissue located external to the target tissue mass and within the resection margin.

In one embodiment, the first signal received by the first sensor can indicate a position and an orientation of the target tissue mass relative to the surgical instrument in real time. Similarly, the second signal received by the second sensor can indicate a position and an orientation of the surgical instrument relative to the target tissue mass. In one embodiment, the second sensor indicates a position and an orientation of the surgical instrument in the same frame of reference as the first sensor. The first sensor may be a fiducial marker (sometimes referred to as a fiducial sensor or a fiducial tracker) embedded within an anchor made from superelastic material, and the second sensor may be an instrument sensor (sometimes referred to as an instrument tracker) mounted to the instrument (e.g., near the distal end of the instrument). In one embodiment, the first sensor may be configured to measure a position and an orientation of the target tissue mass, and the second sensor may be configured to measure a position and an orientation of the surgical instrument. In one embodiment, a controller calculates a distance between the first sensor and the second sensor based on the first signal and the second signal. In one embodiment, the controller is configured to calculate a distance between the second sensor and a pre-determined resection margin disposed about a target tissue mass (i.e., a target lesion) based on the measurements of the first sensor, i.e., the controller (i) uses information from the first sensor to track the location of the target tissue mass, (ii) uses information from the second sensor to track the location of the surgical instrument, and (iii) uses information from the first sensor to keep the three-dimensional tissue mass model (including the virtual object that is representative of the pre-determined resection margin) in registration with the target tissue mass (and hence keep the three-dimensional virtual margin model in registration with the target tissue mass), such that the controller can calculate a distance between the second sensor and the pre-determined resection margin.

In one embodiment, the system may further include a third sensor for measuring a third signal. The third sensor may be dimensioned to fit next to the target tissue mass at a position opposite the first sensor, such that the third signal received by the third sensor indicates a position and an orientation of the target tissue mass relative to the first sensor.

In one embodiment, the first sensor may be embedded within a hook structure made of a superelastic material, e.g., Nitinol. The hook structure may be in the form of a T-bar or J-bar and dimensioned to fit inside a delivery needle and/or a sheath. The delivery needle and/or the sheath may be configured to guide the first sensor, and the hook structure may be configured to anchor the first sensor within, or next to, the target tissue mass. In one embodiment, the first sensor that is embedded within the hook structure may be inserted into, or next to, the target tissue mass under real-time image guidance.

In one embodiment, the first sensor is embedded within a hook structure that includes a plurality of prongs, and the first sensor may be dimensioned to fit inside a delivery needle and/or a sheath. The delivery needle and/or the sheath may be configured to guide the first sensor, and the plurality of prongs may be configured to anchor the first sensor within, or next to, the target tissue mass. The hook structure may further comprise a plurality of extensions extending from a tube portion of the hook structure, such that the plurality of extensions may be dimensioned to receive the first sensor.

The system may further include a display in communication with the controller. The display may be coupled to the surgical instrument and configured to display the distance between the first sensor and the second sensor as calculated by a stored program executed by the controller, which may also be configured to include additional calculations. Preferably the controller is also configured to calculate a distance between the surgical instrument and a pre-determined resection margin disposed about the target tissue mass. Distances from the base, mid and tip of the surgical instrument (e.g., a cutting instrument such as a stapler) from the first sensor and/or the pre-determined resection margin can also be displayed. The display may be, but is not limited to, an OLED display or an LCD display. In one embodiment, the system may include an audible source for emitting an audible signal. The audible source may be in communication with the controller, which is configured to execute a stored program to alter the audible signal based on the distance between the first sensor and the second sensor and/or the distance between the second sensor and the resection margin. In one embodiment, the stored program is a navigation system.

The system may further include a piezoelectric actuator coupled to a handle of the surgical instrument. The piezoelectric actuator may be configured to emit a haptic signal. The piezoelectric actuator may be in communication with the controller, which is configured to execute a stored program to alter the haptic signal based on the distance between the first sensor and the second sensor and/or the distance between the second sensor and the pre-determined resection margin.

The system may further include a monitor for emitting a visual signal in some embodiments. The monitor may be in communication with the controller, which is configured to execute a stored program to alter the visual signal based on the distance between the first sensor and the second sensor and/or the distance between the second sensor and the pre-determined resection margin. Additionally or alternatively, the system may include a monitor for displaying a video overlay. The monitor may be in communication with the controller, which is configured to execute a stored program to fuse a laparoscopy, thoracoscopy or endoscopy image (i.e., a "scope image") with a virtual model image (i.e., an image computer-generated from a virtual model of the anatomy), so as to create the video overlay of the scope image with the virtual model image. The video overlay may be configured to identify a position of the tissue mass and the first sensor.

In one embodiment, the invention provides a method for resection of a target tissue mass inside a patient. The method includes inserting a first sensor inside of or next to the target tissue mass (e.g., in close proximity to the target tissue mass) and capturing at least one image of the first sensor embedded within or next to (e.g., in close proximity to) the target tissue mass. An appropriate resection margin is calculated so as to extend around the target tissue mass using the at least one image. A surgical instrument is inserted into the patient, and the surgical instrument is coupled to a second sensor. The second sensor is tracked relative to the resection margin, and the surgical instrument is used to cut on (or preferably just outside of) the resection margin. The surgeon will determine, based on the diagnosis and size of the mass, what is the best resection margin to accomplish complete removal of the lesion while minimizing the risk of recurrence. This information may also be used to determine the exact operation required.

In some embodiments the method may further include dimensioning a sleeve to engage at least one of a housing of the surgical instrument and the second sensor. Or the second sensor may be coupled to the housing of the surgical instrument by an adhesive, for example. In another embodiment, the second sensor may be embedded within the surgical instrument, or the second sensor may be built into the surgical instrument. The surgical instrument may be, for example, a stapler, a Bovi pencil, a lung crushing clamp (LCC), ring forceps, Kitner probe, etc. or a cutting device configured to cut along (or preferably just outside of) a resection margin surrounding the target tissue mass, which may be a lesion (e.g., a tumor, a nodule, etc.).

In some embodiments, the first signal received by the first sensor can indicate a position and an orientation of the first sensor (and hence the target tissue mass) relative to the surgical instrument in real time. Similarly, the second signal received by the second sensor can indicate a position and an orientation of the surgical instrument relative to the target tissue mass in real time. In one embodiment, the second sensor indicates a position and an orientation of the surgical instrument in the same frame of reference as the first sensor. The first sensor may be a fiducial marker constructed from a superelastic material, and the second sensor may be an instrument sensor. In one embodiment, the first sensor may be configured to measure a position and an orientation of the target tissue mass, and the second sensor may be configured to measure a position and an orientation of the surgical instrument. In one embodiment, a controller calculates a distance between the first sensor and the second sensor based on the first signal and the second signal. In one embodiment the controller is configured to calculate a distance between the second sensor and a pre-determined resection margin disposed about a target tissue mass (i.e., the target lesion) and based on the measurements of the first sensor, i.e., the controller (i) uses information from the first sensor to track the location of the target tissue mass, (ii) uses information from the second sensor to track the location of the surgical instrument, and (iii) uses information from the first sensor to keep the three-dimensional tissue mass model in registration with the target tissue mass (and hence keep the three-dimensional virtual margin model in registration with the target tissue mass), such that the controller can calculate a distance between the second sensor and the pre-determined resection margin.

In one embodiment, the method may further include providing a third sensor for measuring a third signal. The third sensor may be dimensioned to fit next to the target tissue mass at a position opposite the first sensor, such that the third signal received by the third sensor indicates a position and an orientation of the target tissue mass relative to the first sensor.

In some embodiments, the first sensor may be embedded within a hook structure. The hook structure may be in the form of a T-bar or J-bar and dimensioned to fit inside a delivery needle and/or a sheath. The delivery needle and/or the sheath may be configured to guide the first sensor, and the hook structure may be configured to anchor the first sensor within, or next to, the target tissue mass. In one embodiment, the first sensor that is embedded within the hook structure may be inserted into, or next to, the target tissue mass under real-time image guidance or under direct visual guidance.

In one embodiment, the first sensor is embedded within a hook structure that includes a plurality of prongs, and the first sensor may be dimensioned to fit inside a delivery needle and/or a sheath. The delivery needle and/or the sheath may be configured to guide the first sensor, and the plurality of prongs may be configured to anchor the first sensor within, or next to, the target tissue mass. The hook structure may further comprise a plurality of extensions extending from a tube portion of the hook structure, such that the plurality of extensions may be dimensioned to receive the first sensor.

The method may further include providing a display in communication with a controller. The display may be coupled to the surgical instrument and configured to display the distance calculated by the stored program executed by the controller. The display may be, but is not limited to, an OLED display or an LCD display. The display may also include information as to the distances between various sensors, and/or the distances between the surgical instrument and the pre-determined resection margin, as well as to the quality of the measurements. In some embodiments, the method may include emitting an audible signal from an audible source. The audible source may be in communication with the controller, which is configured to execute a stored program to alter the audible signal based on the distance between the first sensor and the second sensor and/or the distance between the second sensor and the pre-determined resection margin. In one embodiment, the stored program is a navigation method.

The method may further include emitting a haptic signal from a piezoelectric actuator coupled to a handle of the surgical instrument. The piezoelectric actuator may be in communication with the controller, which is configured to execute a stored program to alter the haptic signal based on the distance between the first sensor and the second sensor and/or the distance between the second sensor and the pre-determined resection margin.

In some embodiments, the method may further include emitting a visual signal on a monitor. The monitor may be in communication with the controller, which is configured to execute a stored program to alter the visual signal based on the distance between the first sensor and the second sensor and/or the distance between the second sensor and the pre-determined resection margin. Additionally or alternatively, the method may include displaying a video overlay on the monitor. The monitor may be in communication with the controller, which is configured to execute a stored program to fuse a laparoscopy/thoracoscopy/endoscopy scope image(s) to a virtual model image so as to create the video overlay. The video overlay may be configured to identify a position of the tissue mass and the first sensor.

In one form of the invention, the system is configured to show the position of a surgical instrument relative to the pre-determined resection margin, so that a surgeon using the system can ensure that the resection line effected by the surgical instrument is beyond the pre-determined resection margin, whereby to achieve the goal of excising the pre-determined resection margin along with the lesion itself.

And in one form of the invention, the system is particularly well suited for resecting a target tissue mass from a host tissue mass, wherein the host tissue mass is deformable.

To this end, the system is provided with a three-dimensional tissue mass model (sometimes also referred to as "a model", or "a virtual model", or a "virtual object", etc.) generated from previously-acquired scan data. Note that this three-dimensional tissue mass model is in the context of a model frame of reference. The system provides the surgeon with means for inserting a three-dimensional virtual margin model (sometimes also referred to as "a model", or "a virtual model", or a "virtual object", etc.) into the three-dimensional tissue mass model. Note that the three-dimensional virtual margin model (i.e., the virtual object representing the pre-determined resection margin) is also in the context of the model frame of reference.

The system is also provided with a fiducial sensor and an instrument sensor which provide information on the location of those sensors in a real-world frame of reference. The fiducial sensor is configured to be disposed within, or next to, a target tissue mass, and the instrument sensor is configured to be disposed on a surgical instrument which is to be guided during surgery.

The system is also provided with a controller which (i) receives the three-dimensional tissue mass model and the three-dimensional virtual margin model, which are provided in the context of the model frame of reference, (ii) receives information from the fiducial sensor and the instrument sensor in a real-world frame of reference, (iii) places the model frame of reference and the real-world frame of reference in registration with one another, and (iv) outputs information showing the position of the instrument sensor relative to the three-dimensional virtual margin model. In this way, the surgeon will know the position of the surgical instrument relative to the three-dimensional virtual margin model, so that the surgeon can ensure that the resection line does not intrude into the resection margin.

Thus, in one form of the invention, there is provided a system for resecting a target tissue mass from a host tissue mass, wherein the host tissue mass is deformable, the system comprising:

a surgical instrument;

a first fiducial sensor dimensioned to fit at least one of inside of and next to the target tissue mass, the first fiducial sensor including a hook to anchor the first fiducial sensor at least one of inside of and next to the target tissue mass so that the first fiducial sensor remains in known spatial relation to the target tissue mass, the first fiducial sensor adapted to measure position (and preferably also orientation) of the first fiducial sensor within a first frame of reference;

a second fiducial sensor coupled to the surgical instrument, the second fiducial sensor adapted to measure position (and preferably also orientation) of the second fiducial sensor within the first frame of reference; and a controller in communication with the first fiducial sensor and the second fiducial sensor, the controller being configured to:

receive a three-dimensional tissue mass model and a three-dimensional virtual margin model;

register the position (and preferably also orientation) of the first fiducial sensor, the second fiducial sensor, the three-dimensional tissue mass model, and the three-dimensional virtual margin model in a common frame of reference;

update, in real-time, the position (and preferably also orientation) of the implantable fiducial sensor, the tissue mass surface model, and the virtual margin surface model in the common frame of reference based on the measured position (and preferably also orientation) of the first implantable sensor within the first frame of reference; and update, in real-time, the position (and preferably also orientation) of the second fiducial sensor in the common frame of reference based on the measured position (and preferably also orientation) of the second fiducial sensor within the first frame of reference;

such that the positions (and preferably also orientations) of the three-dimensional tissue mass model, the three-dimensional virtual margin model, and the instrument fiducial sensor are determined relative to one another regardless of deformation of the host tissue mass.

And in one form of the invention, there is provided a method for resection of a target tissue mass from a host tissue mass inside a patient, wherein the host tissue mass is deformable, the method comprising:

(a) anchoring a first fiducial sensor at least one of inside and next to the target tissue mass so that the first fiducial sensor remains in known spatial relation to the target tissue mass, the first fiducial sensor adapted to measure position (and preferably also orientation) of the first fiducial sensor within a first frame of reference;

(b) inserting a surgical instrument into the patient, the surgical instrument coupled to a second fiducial sensor, the second fiducial sensor adapted to measure position (and preferably also orientation) of the second fiducial sensor within the first frame of reference;

(c) receive a three-dimensional tissue mass model and a three-dimensional virtual margin model;

(d) register the position (and preferably also orientation) of the first fiducial sensor, the second fiducial sensor, the three-dimensional tissue mass model, and the three-dimensional virtual margin model in a common frame of reference;

(e) update, in real-time, the position (and preferably also orientation) of the implantable fiducial sensor, the tissue mass surface model, and the virtual margin surface model in the common frame of reference based on the measured position (and preferably also orientation) of the first implantable sensor within the first frame of reference; and (f) update, in real-time, the position (and preferably also orientation) of the second fiducial sensor in the common frame of reference based on the measured position (and preferably also orientation) of the second fiducial sensor within the first frame of reference;

such that the positions (and preferably also orientations) of the three-dimensional tissue mass model, the three-dimensional virtual margin model, and the instrument fiducial sensor are determined relative to one another regardless of deformation of the host tissue mass.

In one form of the invention, the system may be used to identify the location of a particular airway. In this form of the invention, the system comprises means for bronchoscopic positioning of a sensor into an airway of the lung. This bronchoscopic positioning of the sensor in an airway of the lung (e.g., by positioning the sensor on a bronchoscope or on a catheter within the brochoscope and advancing the bronchoscope into the airway of interest) can be used to define the lobar, segmental or subsegmental bronchus for surgery such as segmentectomy, lobectomy or wedge resection during the actual operation. This function can be independent of the resection margin measurement, and the position of the sensor identifying the bronchus can be correlated with the position of another device (e.g., a surgical instrument) carrying another sensor so that the surgeon can define the correct bronchus for surgery from the chest side of the operation. Thus, in this form of the invention, one sensor is positioned on a bronchoscope or on a catheter placed within the bronchoscope which is inserted into a specific airway so as to define the location of that specific airway, and another sensor is positioned on a surgical instrument which is advanced for surgery from the chest side of the operation, with the system continuously tracking the position of the sensor on the surgical instrument vis-á-vis the position of the sensor on the bronchoscope, so that the surgeon can continuously track the location of the surgical instrument relative to the airway of interest (identified by the sensor on the bronchoscope), e.g., to target the airway identified by the sensor on the bronchoscope, to avoid the airway identified by the sensor on the bronchoscope, etc.

In one form of the invention, the system comprises means for mapping and tracking airways surrounding a lesion.

In one form of the invention, the system comprises means for bronchoscopic deployment of the fiducial sensor or another sensor into tissue (e.g., bronchoscopic deployment of the fiducial sensor into the mass or adjacent to the mass).

In one form of the invention, the system comprises means for measuring the articulation of a surgical stapler.

In one form of the invention, the system comprises means for marking the boundary of a resection margin of a lesion and positioning a surgical stapler adjacent to the boundary of a resection margin of a lesion.

In one form of the invention, there is provided a method for determining the position of an instrument relative to a selected lumen in an anatomical structure, the method comprising:

positioning a tracked catheter in the selected lumen of the anatomical structure, wherein the tracked catheter is tracked relative to a given frame of reference; and determining the position of a tracked instrument relative to the tracked catheter, wherein the tracked instrument is tracked relative to the given frame of reference, whereby to determine the position of the tracked instrument relative to the selected lumen of the anatomical structure.

In another form of the invention, there is provided a system for determining the position of an instrument relative to a selected lumen in an anatomical structure, the system comprising:

a catheter sized to be disposable in the selected lumen of the anatomical structure;

a catheter tracker for providing a catheter signal representative of the position of the catheter tracker relative to a given frame of reference, the catheter tracker being carried by the catheter;

an instrument;

an instrument tracker for providing an instrument signal representative of the position of the instrument tracker relative to the given frame of reference, the instrument tracker being carried by the instrument; and a controller for determining the position of the tracked instrument relative to the tracked catheter, whereby, when the tracked catheter is disposed in the selected lumen of the anatomical structure, the controller determines the position of the tracked instrument relative to the selected lumen in the anatomical structure.

In another form of the invention, there is provided a method for mapping and tracking a plurality of lumens in an anatomical structure, wherein the anatomical structure is deformable, the method comprising:

providing a virtual model of the anatomical structure while the anatomical structure is in a first configuration;

while the anatomical structure is in the first configuration, positioning a tracked catheter in one of the lumens in the anatomical structure which is to be mapped and tracked, and determining the position of the tracked catheter in that lumen so as to map the position of that lumen;

repeating the foregoing step for each of the lumens in the anatomical structure which is to be mapped and tracked so that those lumens are mapped;

supplementing the virtual model with the mapped lumens, whereby to provide a supplemented virtual model of the anatomical structure and the mapped lumens while the anatomical structure is in its first configuration;

maintaining the tracked catheter in one of the mapped lumens of the anatomical structure as the anatomical structure is deformed from its first configuration to a second configuration;

determining the position of the tracked catheter in the anatomical structure while the anatomical structure is in the second configuration; and modifying the supplemented virtual model so as to represent the anatomical structure and the mapped lumens while the anatomical structure is in its second configuration, whereby to provide a modified supplemented virtual model, wherein modification is effected by:

determining the spatial transformation of the tracked catheter as the anatomical structure deforms from its first configuration to its second configuration; and applying the spatial transformation of the tracked catheter to the mapped lumens of the supplemented virtual model so as to provide the modified supplemented virtual model of the anatomical structure and the mapped lumens while the anatomical structure is in its second configuration.

In another form of the invention, there is provided a method for mapping and tracking a selected lumen in an anatomical structure, wherein the anatomical structure is deformable, the method comprising:

positioning a tracked catheter in the selected lumen of the anatomical structure while the anatomical structure is in a first configuration;

determining the position of the tracked catheter while the anatomical structure is in the first configuration;

scanning the anatomical structure and the tracked catheter positioned in the selected lumen of the anatomical structure while the anatomical structure is in the first configuration;

creating a virtual model of the scanned anatomical structure and the tracked catheter positioned in the selected lumen of the anatomical structure while the anatomical structure is in its first configuration;

maintaining the tracked catheter in position within the selected lumen of the anatomical structure while the anatomical structure deforms to a second configuration;

determining the position and orientation of the tracked catheter while the anatomical structures is in its second configuration, whereby to determine the position of the selected lumen of the anatomical structure while the anatomical structure is in the second configuration; and adjusting the virtual model so as to represent the anatomical structure and the selected lumen while the anatomical structure is in its second configuration, whereby to provide an adjusted virtual model, wherein modification is effected by:

determining the spatial transformation of the tracked catheter as the anatomical structure deforms from its first configuration to its second configuration; and applying the spatial transformation of the tracked catheter to the selected lumen of the virtual model so as to provide the adjusted virtual model of the anatomical structure and the selected lumen while the anatomical structure is in its second configuration.

In another form of the invention, there is provided a system for mapping and tracking a plurality of lumens in an anatomical structure, wherein the anatomical structure is deformable, the system comprising:

a catheter sized to be disposed in the plurality of lumens of the anatomical structure which are to be mapped and tracked, and configured to remain in a selected lumen of the anatomical structure during deformation of the anatomical structure;

a catheter tracker for providing a catheter signal representative of the position of the catheter tracker, the catheter tracker being carried by the catheter, a virtual model of the anatomical structure representing the anatomical structure while it is in a first configuration; and a controller for:

(i) determining the position of the tracked catheter as the tracked catheter is disposed within each of the plurality of lumens so as to map the plurality of lumens while the anatomical structure is in its first configuration; and (ii) supplementing the virtual model with the mapped lumens, whereby to provide a supplemented virtual model of the anatomical structure and the mapped lumens representing the anatomical structure while it is in its first configuration.

In another form of the invention, there is provided a system for mapping and tracking a selected lumen in an anatomical structure, wherein the anatomical structure is deformable, the system comprising:

a catheter sized to be disposed in the selected lumen of the anatomical structure and configured to remain in the selected lumen of the anatomical structure during deformation of the anatomical structure;

a catheter tracker for providing a catheter signal representative of the position of the catheter tracker, the catheter tracker being carried by the catheter;

a virtual model of the anatomical structure and the tracked catheter positioned in the selected lumen of the anatomical structure, wherein the virtual model is created while the anatomical structure is in a first configuration; and a controller for:

(i) determining the position of the tracked catheter after the anatomical structure has assumed a second configuration; and (ii) adjusting the virtual model of the anatomical structure and the tracked catheter so that the virtual model conforms to the position of the tracked catheter when the anatomical structure is in its second configuration.

In another form of the invention, there is provided a method for tracking a tissue mass disposed in or on an anatomical structure, wherein the anatomical structure comprises at least one lumen, the method comprising:

advancing a scope along the at least one lumen until the distal end of the scope is disposed in the vicinity of the selected tissue mass;

advancing a fiducial sensor through the scope, into the anatomical structure, and securing the fiducial sensor to the anatomical structure in the vicinity of the tissue mass; and detecting the position of the fiducial sensor within the anatomical structure.

In another form of the invention, there is provided a method for tracking a tissue mass disposed in or on an anatomical structure, wherein the anatomical structure comprises at least one lumen, the method comprising:

providing a sensor assembly comprising a fiducial sensor and an electrical lead extending distally from the fiducial sensor, and providing a deployment assembly comprising a needle cannula and a pusher, wherein the sensor assembly is slidably disposed in the needle cannula distal to the pusher;

advancing a scope along the at least one lumen until the distal end of the scope is disposed in the vicinity of the selected tissue mass;

advancing the needle cannula through the scope, into the anatomical structure, and through an outer surface of the anatomical structure;

retracting the needle cannula so as to expose a portion of the electrical lead extending through the outer surface of the anatomical structure;

supplying electrical power to the fiducial sensor via the electrical lead extending through the outer surface of the anatomical structure;

securing the fiducial sensor to the anatomical structure in the vicinity of the tissue mass by advancing the pusher relative to the needle cannula or by retracting the needle cannula relative to the pusher; and detecting the position of the fiducial sensor within the anatomical structure.

In another form of the invention, there is provided a system for determining the position of an instrument relative to a tissue mass carried by an anatomical structure, the system comprising:

a wireless fiducial tracker for providing a fiducial signal representative of the position of the wireless fiducial tracker, the wireless fiducial tracker adapted to be secured in the anatomical structure in the vicinity of the tissue mass;

an instrument;

an instrument tracker for providing an instrument signal representative of the position of the instrument tracker, the instrument tracker being carried by the instrument; and a controller for determining the position of the tracked instrument relative to the wireless fiducial tracker.

In another form of the invention, there is provided a system for determining the position of an instrument relative to a tissue mass carried by an anatomical structure, the system comprising:

a fiducial tracker for providing a fiducial signal representative of the position and orientation of the fiducial tracker, the fiducial tracker adapted to be secured in the anatomical structure in the vicinity of the tissue mass;

an electrical lead for providing electrical power to the fiducial tracker, the electrical lead being releasably connected to the fiducial tracker;

an instrument;

an instrument tracker for providing an instrument signal representative of the position of the instrument tracker, the instrument tracker being carried by the instrument; and a controller for determining the position of the tracked instrument relative to the fiducial tracker.

In another form of the invention, there is provided a system for determining the position and orientation of an instrument relative to a tissue mass disposed in or on an anatomical structure, the system comprising:

a sensor assembly comprising:

a fiducial tracker for providing a fiducial signal representative of the position of the fiducial tracker, the fiducial tracker adapted to be secured in the anatomical structure in the vicinity of the tissue mass; and an electrical lead for providing electrical power to the fiducial tracker, the electrical lead extending distally from the fiducial tracker;

an instrument;

an instrument tracker for providing an instrument signal representative of the position and orientation of the instrument tracker, the instrument tracker being carried by the instrument; and a controller for determining the position and orientation of the tracked instrument relative to the fiducial tracker.

In another form of the invention, there is provided a system for determining the position and orientation of an instrument relative to a tissue mass disposed in or on an anatomical structure, the system comprising:

a sensor assembly comprising:

a fiducial tracker for providing a fiducial signal representative of the position of the fiducial tracker, the fiducial tracker adapted to be secured in the anatomical structure in the vicinity of the tissue mass; and an electrical lead for providing electrical power to the fiducial tracker, the electrical lead extending distally from the fiducial tracker;

a deployment assembly comprising a needle cannula and a pusher, wherein the sensor assembly is slidably disposed within the needle cannula distal to the pusher;

an instrument;

an instrument tracker for providing an instrument signal representative of the position and orientation of the instrument tracker, the instrument tracker being carried by the instrument; and a controller for determining the position and orientation of the tracked instrument relative to the fiducial tracker.

In another form of the invention, there is provided a method for determining the position of an end effector of an instrument relative to a tissue mass carried by an anatomical structure, wherein the instrument comprises a shaft and the end effector, and wherein the disposition of the end effector relative to the shaft is adjustable, the method comprising:

tracking the position of the tissue mass;

tracking the shaft of the instrument;

determining the disposition of the end effector relative to the shaft; and determining the disposition of the end effector relative to the tissue mass.

In another form of the invention, there is provided a system for determining the position of an end effector of instrument relative to a tissue mass carried by an anatomical structure, the system comprising:

a wireless fiducial tracker for providing a fiducial signal representative of the position of the wireless fiducial tracker, the wireless fiducial tracker adapted to be secured in the anatomical structure in the vicinity of the tissue mass;

an instrument comprising a shaft and an end effector, wherein the disposition of the end effector relative to the shaft is adjustable, an instrument tracker for providing an instrument signal representative of the position of the instrument tracker, the instrument tracker being carried by the shaft of the instrument;

a sensor for detecting the disposition of the end effector relative to the shaft; and a controller for determining the position of the tracked instrument relative to the wireless fiducial tracker.

In another form of the invention, there is provided a method for directing the position of an instrument relative to a tissue mass carried by an anatomical structure, the method comprising:

determining the tangent lines of the tissue mass;

tracking the position of the tissue mass;

tracking the position of the instrument;

determining the disposition of the instrument relative to the tangent lines; and directing movement of the instrument so that a portion of the instrument is aligned with the tangent lines.

In another form of the invention, there is provided a system for directing the position of an instrument relative to a tissue mass carried by an anatomical structure, the system comprising:

a fiducial tracker for providing a fiducial signal representative of the position of the fiducial tracker, the fiducial tracker adapted to be secured in the anatomical structure in the vicinity of the tissue mass;

an instrument;

an instrument tracker for providing an instrument signal representative of the position of the instrument tracker, the instrument tracker being carried by the instrument; and a controller for determining the tangent lines of the tissue mass and for directing the position of the tracked instrument relative to the tangent lines.

In another form of the invention, there is provided a system for tracking the location of an anatomical structure, the system comprising:

a J-bar and electrical lead assembly comprising:

a J-bar comprising a tracker, a distal electrical connector formed on the tracker, and at least one mount for mounting the tracker to tissue, wherein the tracker is configured to provide a signal representative of the position of the tracker when the tracker is supplied with electrical power;

an expandable basket configured to assume (i) a radially-reduced profile when the expandable basket is radially constricted, and (ii) a radially-expanded profile when the expandable basket is not radially constricted, the expandable basket further comprising a distal electrical connector; and an electrical lead extending distally between the J-bar and the expandable basket, the electrical lead being electrically connected to (i) the distal electrical connector formed on the tracker, and (ii) the distal electrical connector of the expandable basket.

In another form of the invention, there is provided a method for tracking the location of an anatomical structure, wherein the anatomical structure is deformable, the method comprising:

providing a system comprising:

a deployment assembly comprising:

a scope comprising a proximal end, a distal end, and a lumen extending therebetween, the scope being sized to be disposed in a lumen of the anatomical structure and configured to remain in the lumen of the anatomical structure during deformation of the anatomical structure;

a needle cannula slidably disposed within the lumen of the scope, the needle cannula comprising a proximal end, a distal end, and a needle lumen extending therebetween;

an electrical lead assembly comprising:

a J-bar comprising a tracker and at least one mount for mounting the J-bar to tissue, wherein the tracker is configured to provide a signal representative of the position of the tracker when the tracker is supplied with electrical power;

an expandable basket configured to assume (i) a radially-reduced profile when the expandable basket is radially constricted, and (ii) a radially-expanded profile when the expandable basket is not radially constricted, the expandable basket further comprising a distal electrical connector; and an electrical lead extending distally between the J-bar and the expandable basket, the electrical lead being electrically connected to (i) a distal electrical connector formed on the tracker, and (ii) the distal electrical connector of the expandable basket;

a pusher slidably disposed in the needle lumen and configured to engage a proximal end of the J-bar, whereby to (i) apply a distally-directed force to the J-bar when the pusher is moved distally, such that the expandable basket may be selectively released from being radially constricted by the needle cannula, whereby to permit the expandable basket to assume its radially-expanded profile, and/or (ii) apply a distally-directed force to the J-bar when the needle cannula is moved proximally relative to the electrical lead assembly, such that by moving the needle cannula proximally while maintaining a distally-directed force against the J-bar using the pusher, the expandable basket may be selectively released from being radially constricted by the needle cannula, whereby to permit the expandable basket to assume its radially-expanded profile;

advancing the scope through an anatomical structure such that the distal end of the scope is disposed within the anatomical structure;

advancing the needle cannula through the lumen of the scope such that the distal end of the needle cannula pierces the anatomical structure and emerges outside the anatomical structure;

applying a distally-directed force against the J-bar using the pusher so that the expandable basket may be selectively released from being radially constrained, such that the expandable basket assumes a radially-expanded profile at a location exterior to the anatomical structure, and/or applying a distally-directed force against the J-bar using the pusher while moving the needle cannula proximally such that the position of the expandable basket is maintained while the needle cannula is withdrawn proximally, whereby to expose the expandable basket and release the expandable basket from the constraint of the needle cannula, such that the expandable basket assumes a radially-expanded profile at a location exterior to the anatomical structure;

moving the scope and the needle cannula proximally until the distal end of the needle cannula is disposed at the location within the anatomical structure at which the tracker is to be mounted, and such that the electrical lead extends between the distal connector on the tracker and the distal electrical connector of the expandable basket which is positioned exterior to the anatomical structure;

applying a distally-directed force against the J-bar using the pusher and/or moving the needle cannula and scope proximally so as to expose the at least one mount of the J-bar, whereby to permit the at least one mount of the J-bar to engage the surrounding tissue, whereby to anchor the J-bar and tracker in the anatomy; and withdrawing the needle cannula and the scope from the anatomy.

In another form of the invention, there is provided a system for tracking the location of an anatomical structure, the system comprising:

a J-bar and electrical lead assembly comprising:

a J-bar comprising a J-bar tracker, a distal electrical connector formed on the J-bar tracker, and at least one mount for mounting the J-bar tracker to tissue, wherein the J-bar tracker is configured to provide a signal representative of the position of the J-bar tracker when the J-bar tracker is supplied with electrical power;

an electrical lead extending distally from the J-bar, the electrical lead being electrically connected to the distal electrical connector formed on the J-bar tracker; and a deployment assembly for delivering the J-bar and electrical lead assembly to the anatomy, the deployment assembly comprising a lumen configured to receive the J-bar and electrical lead assembly therein, and a deployment assembly tracker mounted to the deployment assembly adjacent to where the J-bar and electrical lead assembly is received in the lumen, wherein the deployment assembly tracker is configured to provide a signal representative of the position of the deployment assembly tracker and hence the J-bar and electrical lead assembly when the deployment assembly tracker is supplied with electrical power.

In another form of the invention, there is provided a method for tracking the location of an anatomical structure, wherein the anatomical structure is deformable, the method comprising:

providing a system comprising:

a deployment assembly comprising:

a scope comprising a proximal end, a distal end, and a lumen extending therebetween, the scope being sized to be disposed in a lumen of the anatomical structure and configured to remain in the lumen of the anatomical structure during deformation of the anatomical structure;

a needle cannula slidably disposed within the lumen of the scope, the needle cannula comprising a proximal end, a distal end, and a needle lumen extending therebetween;

an electrical lead assembly comprising:

a J-bar comprising a J-bar tracker and at least one mount for mounting the J-bar to tissue, wherein the J-bar tracker is configured to provide a signal representative of the position of the J-bar tracker when the J-bar tracker is supplied with electrical power; and an electrical lead extending distally from the J-bar, the electrical lead being electrically connected to a distal electrical connector formed on the J-bar tracker;

a pusher slidably disposed in the needle lumen and configured to engage a proximal end of the J-bar, whereby to (i) apply a distally-directed force to the J-bar when the pusher is moved distally, such that the J-bar and/or the electrical lead extending distally from the J-bar may be selectively released from the needle cannula, and/or (ii) apply a distally-directed force to the J-bar when the needle cannula is moved proximally relative to the electrical lead assembly, such that by moving the needle cannula proximally while maintaining a distally-directed force against the J-bar using the pusher, the J-bar and/or the electrical lead extending distally from the J-bar may be selectively released from the needle cannula; and a deployment assembly tracker mounted to one of (i) the the needle cannula, and (ii) the pusher;

wherein the deployment assembly tracker is disposed proximate to the J-bar and electrical lead assembly when the J-bar and electrical lead assembly is disposed in the needle lumen, and further wherein the deployment assembly tracker is configured to provide a signal representative of the position of the deployment assembly tracker when the deployment assembly tracker is supplied with electrical power;

advancing the scope through an anatomical structure such that the distal end of the scope is disposed within the anatomical structure;

advancing the needle cannula through the lumen of the scope such that the distal end of the needle cannula pierces the anatomical structure and emerges outside the anatomical structure;

applying a distally-directed force against the J-bar using the pusher so that the electrical lead extending distally from the J-bar extends through the anatomical structure, and/or applying a distally-directed force against the J-bar using the pusher while moving the needle cannula proximally such that the position of the J-bar is maintained while the needle cannula is withdrawn proximally, whereby to expose the electrical lead extending distally from the J-bar such that the electrical lead extending distally from the J-bar extends through the anatomical structure;

moving the scope and the needle cannula proximally until the distal end of the needle cannula is disposed at the location within the anatomical structure at which the J-bar tracker is to be mounted, and such that the electrical lead extends between the distal connector on the J-bar tracker and through the anatomical structure to the exterior to the anatomical structure;

applying a distally-directed force against the J-bar using the pusher and/or moving the needle cannula and scope proximally so as to expose the at least one mount of the J-bar, whereby to permit the at least one mount of the J-bar to engage the surrounding tissue, whereby to anchor the J-bar and J-bar tracker in the anatomy; and withdrawing the needle cannula and the scope from the anatomy.

In another form of the invention, there is provided a system for tracking the location of first anatomical structure and a second anatomical structure disposed within a third anatomical structure, the system comprising:

a virtual model of the first anatomical structure, the second anatomical structure, and the third anatomical structure;

a scope, the scope being sized to be disposed in the first anatomical structure and configured to remain in the first anatomical structure during deformation of the third anatomical structure;

a tracker mounted to the scope, the tracker being configured to provide a signal representative of the position of the scope;

wherein the tracker may be used to place the scope into registration with the virtual model of the first anatomical structure, the second anatomical structure, and the third anatomical structure so as to show the position of the scope disposed within the first anatomical structure relative to the second anatomical structure and the third anatomical structure;

wherein the first anatomical structure and the second anatomical structure are in fixed disposition relative to one another, and further wherein the third anatomical structure is deformable, such that (i) when the third anatomical structure is in an first condition and the scope is disposed in the first anatomical structure, the second anatomical structure is identified on the virtual model, and (ii) when the third anatomical structure is in a second condition and the scope is disposed in the first anatomical structure, the second anatomical structure is identified on the virtual model.

In another form of the invention, there is provided a method for tracking the location of first anatomical structure and a second anatomical structure disposed within a third anatomical structure, the method comprising:

providing a system comprising:

a virtual model of the fist anatomical structure, the second anatomical structure, and the third anatomical structure;

a scope, the scope being sized to be disposed in the first anatomical structure and configured to remain in the first anatomical structure during deformation of the third anatomical structure;

a tracker mounted to the scope, the tracker being configured to provide a signal representative of the position of the scope;

wherein the tracker may be used to place the scope into registration with the virtual model of the first anatomical structure, the second anatomical structure, and the third anatomical structure so as to show the position of the scope disposed within the first anatomical structure relative to the second anatomical structure and the third anatomical structure;

wherein the first anatomical structure and the second anatomical structure are in fixed disposition relative to one another, and further wherein the third anatomical structure is deformable, such that (i) when the third anatomical structure is in an first condition and the scope is disposed in the first anatomical structure, the second anatomical structure is identified on the virtual model, and (ii) when the third anatomical structure is in a second condition and the scope is disposed in the first anatomical structure, the second anatomical structure is identified on the virtual model;

disposing the scope within the first anatomical structure;

using the tracker to track the position of the scope within the first anatomical structure;

using the tracker to place the scope into registration with the virtual model, such that the locations of the first anatomical structure and the second anatomical structure within the third anatomical structure are identified on the virtual model.

In another form of the invention, there is provided a system for identifying a predetermined location within an anatomical structure, the system comprising:

a scope comprising a tracker, the scope comprising a camera for displaying an image obtained by the scope, the scope being configured for insertion into the anatomical structure;

a virtual model of the anatomical structure, the virtual model of the anatomical structure comprising a predetermined location identified by a virtual object contained in the virtual model;

a surgical instrument for marking tissue;

wherein the scope is placed into registration with the virtual model by tracking the location of the tracker relative to the virtual model, such that the image obtained by the scope is modified to contain the virtual object contained in the virtual model as an overlay; and wherein the surgical instrument is configured to mark the tissue at a desired location relative to the virtual object.

In another form of the invention, there is provided a method for identifying a predetermined location within an anatomical structure, the method comprising: providing a system comprising:

a scope comprising a tracker, the scope comprising a camera for displaying an image obtained by the scope, the scope being configured for insertion into the anatomical structure; and a surgical instrument for marking tissue;

scanning the anatomical structure so as to obtain a virtual model of the anatomical structure;

identifying a predetermined location on the virtual model using a virtual object inserted into the virtual model;

using a scope to obtain a real-world image of the anatomical structure;

tracking the position of the scope using the tracker and placing the scope into registration with the virtual model;

projecting the virtual object onto the real-world image provided by the scope, whereby to identify the predetermined location on the real-world image provided by the scope;

using the surgical instrument to mark the tissue at a desired location relative to the virtual object.

In another form of the invention, there is provided a method for tracking the location of a tissue mass located within an anatomical structure in the body of a patient, the method comprising:

providing a system comprising:

a deployment system comprising:

an outer cannula comprising a distal end, a proximal end, and an outer cannula lumen extending therebetween;

a needle cannula comprising a distal end, a proximal end, and a needle cannula lumen extending therebetween, the needle cannula being sized to be slidably received within the outer cannula lumen;

a pusher comprising a distal end and a proximal end, the distal end of the pusher being slidably received within the needle cannula;

a J-bar and electrical lead assembly comprising:

a fiducial sensor comprising at least one mount for mounting the fiducial sensor to tissue, wherein the fiducial sensor is configured to assume (i) a radially-reduced profile when the fiducial sensor is radially constricted, and (ii) a radially-expanded profile when the fiducial sensor is not radially constricted;

an expandable basket configured to assume (i) a radially-reduced profile when the expandable basket is radially constricted, and (ii) a radially-expanded profile when the expandable basket is not radially constricted;

an electrical lead configured to extend between the fiducial sensor and the expandable basket so as to electrically connect the fiducial sensor to the expandable basket;

at least one connector mounted to the expandable basket in electrical communication with the electrical lead, such that electrical power supplied to the at least one connector powers the fiducial sensor;

disposing the J-bar and electrical lead assembly within the needle cannula lumen such that the fiducial sensor is disposed just proximal to the distal end of the needle cannula, the expandable basket is disposed proximal to the fiducial sensor, and the electrical lead is disposed intermediate the fiducial sensor and the expandable basket;

disposing the pusher within the needle cannula lumen such that the distal end of the pusher is disposed just proximal to the expandable basket;

disposing the needle cannula within the outer cannula lumen;

inserting the outer cannula into the anatomy of the patient until the distal end of the outer cannula is disposed against the anatomical structure;

moving the needle cannula distally relative to the outer cannula such that the needle cannula enters into the anatomical structure and moves distally to the location of the tissue mass;

applying a distally-directed force against the expandable basket using the pusher so that the J-bar and electrical lead assembly disposed within the needle cannula lumen moves distally, and/or applying a distally-directed force against the J-bar and electrical lead assembly using the pusher while moving the needle cannula proximally so that the position of the J-bar and electrical lead assembly is maintained while the needle cannula is withdrawn proximally, until the fiducial sensor is not constrained by the needle cannula, such that the fiducial sensor assumes the radially-expanded profile at a location proximate to the tissue mass, and such that the at least one mount anchors the fiducial sensor in the anatomical structure;

moving the outer cannula and needle cannula proximally in concert, whereby to move the expandable basket proximally, until the distal end of the outer cannula and the distal end of the needle cannula are disposed at the surface of the patient's skin;

applying a distally-directed force against the expandable basket using the pusher so that the expandable basket disposed within the needle cannula lumen moves distally, and/or applying a distally-directed force against the expandable basket using the pusher while moving the needle cannula and outer cannula proximally so that the position of the expandable basket is maintained while the needle cannula and outer cannula are withdrawn proximally, until the expandable basket is not constrained by the needle cannula or the outer cannula, such that the expandable basket assumes the radially-expanded profile at the surface of the patient's skin, and such that the electrical lead extends between the fiducial sensor and the expandable basket.

In another form of the invention, there is provided a system for tracking the location of a tissue mass located within an anatomical structure in the body of a patient, the system comprising:

a deployment system comprising:

an outer cannula comprising a distal end, a proximal end, and an outer cannula lumen extending therebetween;

a needle cannula comprising a distal end, a proximal end, and a needle cannula lumen extending therebetween, the needle cannula being sized to be slidably received within the outer cannula lumen;

a pusher comprising a distal end and a proximal end, the distal end of the pusher being slidably received within the needle cannula;

a J-bar and electrical lead assembly comprising:

a fiducial sensor comprising at least one mount for mounting the fiducial sensor to tissue, wherein the fiducial sensor is configured to assume (i) a radially-reduced profile when the fiducial sensor is radially constricted, and (ii) a radially-expanded profile when the fiducial sensor is not radially constricted;

an expandable basket configured to assume (i) a radially-reduced profile when the expandable basket is radially constricted, and (ii) a radially-expanded profile when the expandable basket is not radially constricted;

an electrical lead configured to extend between the fiducial sensor and the expandable basket so as to electrically connect the fiducial sensor to the expandable basket;

at least one connector mounted to the expandable basket in electrical communication with the electrical lead, such that electrical power supplied to the at least one connector powers the fiducial sensor;

wherein the J-bar and electrical lead assembly is disposed within the needle cannula lumen such that the fiducial sensor is disposed just proximal to the distal end of the needle cannula, the expandable basket is disposed proximal to the fiducial sensor, and the electrical lead is disposed intermediate the fiducial sensor and the expandable basket, wherein the pusher is disposed within the needle cannula lumen such that the distal end of the pusher is disposed just proximal to the expandable basket; and wherein the needle cannula is disposed within the outer cannula lumen so as to be selectively movable relative thereto.

In another form of the invention, there is provided a method for tracking the location of a tissue mass located within an anatomical structure in the body of a patient, the method comprising:

providing a system comprising:

a deployment system comprising:

an outer cannula comprising a distal end, a proximal end, and an outer cannula lumen extending therebetween;

a needle cannula comprising a distal end, a proximal end, and a needle cannula lumen extending therebetween, the needle cannula being sized to be slidably received within the outer cannula lumen;

a pusher comprising a distal end and a proximal end, the distal end of the pusher being slidably received within the needle cannula;

a J-bar and electrical lead assembly comprising:

a fiducial sensor comprising at least one mount for mounting the fiducial sensor to tissue, wherein the fiducial sensor is configured to assume (i) a radially-reduced profile when the fiducial sensor is radially constricted, and (ii) a radially-expanded profile when the fiducial sensor is not radially constricted;

an expandable basket configured to assume (i) a radially-reduced profile when the expandable basket is radially constricted, and (ii) a radially-expanded profile when the expandable basket is not radially constricted;

an electrical lead configured to extend between the fiducial sensor and the expandable basket so as to electrically connect the fiducial sensor to the expandable basket;

at least one connector mounted to the expandable basket in electrical communication with the electrical lead, such that electrical power supplied to the at least one connector powers the fiducial sensor;

disposing the J-bar and electrical lead assembly within the needle cannula lumen such that the fiducial sensor is disposed just proximal to the distal end of the needle cannula, the expandable basket is disposed proximal to the fiducial sensor, and the electrical lead is disposed intermediate the fiducial sensor and the expandable basket;

disposing the pusher within the needle cannula lumen such that the distal end of the pusher is disposed just proximal to the expandable basket;

disposing the needle cannula within the outer cannula lumen;

inserting the outer cannula into the anatomy of the patient until the distal end of the outer cannula is disposed against an outer surface of the anatomical structure;

moving the needle cannula distally relative to the outer cannula such that the needle cannula enters into the anatomical structure and moves distally to the location of the tissue mass, applying a distally-directed force against the expandable basket using the pusher so that the J-bar and electrical lead assembly disposed within the needle cannula lumen moves distally, and/or applying a distally-directed force against the J-bar and electrical lead assembly using the pusher while moving the needle cannula proximally so that the position of the J-bar and electrical lead assembly is maintained while the needle cannula is withdrawn proximally, until the fiducial sensor is not constrained by the needle cannula, such that the fiducial sensor assumes the radially-expanded profile at a location proximate to the tissue mass, and such that the at least one mount anchors the fiducial sensor in the anatomical structure;

moving the outer cannula and needle cannula proximally in concert, whereby to move the expandable basket proximally, until the distal end of the outer cannula and the distal end of the needle cannula are disposed at the outer surface of the anatomical structure;

applying a distally-directed force against the expandable basket using the pusher so that the expandable basket disposed within the needle cannula lumen moves distally, and/or applying a distally-directed force against the expandable basket using the pusher while moving the needle cannula and outer cannula proximally so that the position of the expandable basket is maintained while the needle cannula and outer cannula are withdrawn proximally, until the expandable basket is not constrained by the needle cannula or the outer cannula, such that the expandable basket assumes the radially-expanded profile at the outer surface of the anatomical structure, and such that the electrical lead extends between the fiducial sensor and the expandable basket.

These and other features, aspects, and advantages of the present invention will become better understood upon consideration of the following detailed description, drawings, and appended claims.

DETAILED DESCRIPTION

Figure 1:
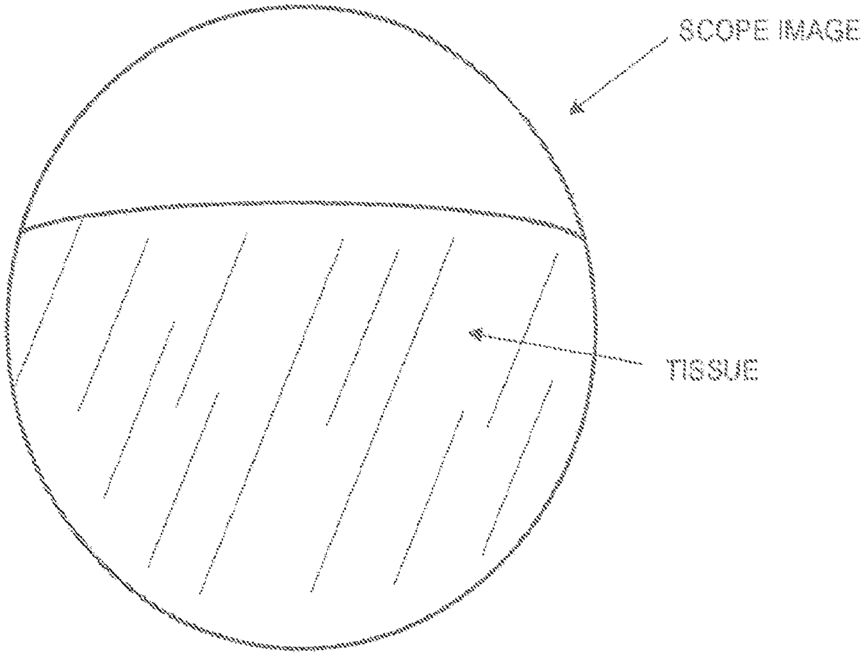
FIG. 1 is a schematic view showing an exemplary image of internal anatomy obtained via a scope.

Before any embodiments of the invention are explained in detail, it is to be understood that the invention is not limited in its application to the specific details of construction and the arrangement of components set forth in the following description or illustrated in the following drawings. The invention is capable of other embodiments and of being practiced or of being carried out in other ways. Also, it is to be understood that the phraseology and terminology used herein is for the purpose of description and should not be regarded as limiting. The use herein of "including," "comprising," or "having" and variations thereof is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from the scope of the present invention. Thus, embodiments of the invention are not intended to be limited to the specific embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present invention. Skilled artisans will recognize the examples provided herein have many useful alternatives and fall within the scope of embodiments of the invention.

It should be appreciated that, as used herein, the term "target tissue mass" is generally intended to denote a lesion or other tissue mass which is the target of an intended procedure, and the term "host tissue mass" is generally intended to denote a mass of tissue in which (or on which) the target tissue mass may be disposed. By way of example but not limitation, a lesion (i.e., "a target tissue mass") may be disposed in a lung (i.e., "a host tissue mass"), and the lesion may be the subject of a lung resection to remove the lesion from the lung.

Note that the host tissue mass may be deformable, e.g., such as in the case of a lung or breast.

Note also that where the host tissue mass is deformable, and where a fiducial sensor is to be used to identify the location of a target tissue mass disposed in or on the host tissue mass, the fiducial sensor is intended to be anchored (i) within the target tissue mass, or (ii) next to the target tissue mass in sufficiently close proximity to the target tissue mass that the fiducial sensor remains in known spatial relation to the target tissue mass.

It should also be appreciated that, as used herein, and as is well known in the art, the term "resection line" refers to a cutting line which is to be effected through tissue so as to separate one portion of the tissue (e.g., a portion of the tissue containing a target tissue mass such as a lesion) from another portion of the tissue (e.g., a portion of the tissue not containing the target tissue mass).

And it should be appreciated that, as used herein, and as is well known in the art, the term "resection margin" refers to a region of tissue surrounding a target tissue mass such as a lesion and which is to be removed along with the target tissue mass so as to ensure that there is complete removal of the lesion cells and there is no invasion of the target tissue mass into the host tissue mass.

It should also be appreciated that, as used herein, the term "model" (or "virtual model") is intended to denote, as is well known in the art, a mathematical representation of a three-dimensional structure (e.g., a "three-dimensional tissue mass model" is a mathematical representation of a real-world three-dimensional tissue mass, a "three-dimensional virtual margin model" is a mathematical representation of a virtual resection margin, etc.). It should also be appreciated that, as is well known in the art, a model (or virtual model) has a particular spatial coordinate system (e.g., an x-y-z spatial coordinate system) and a particular frame of reference for that spatial coordinate system (e.g., a "model frame of reference") which is established at the time that the model is created (e.g., by scanning a real-world structure with a CT or MRI machine, etc.). As is also well known in the art, when a model (or virtual model) is to be linked to a real-world sensor system (e.g., one comprising a fiducial sensor, an instrument sensor, a controller, etc. having a particular spatial coordinate system, e.g., an x-y-z spatial coordinate system, and its own particular frame of reference, e.g., a "real-world frame of reference"), the model frame of reference and the real-world frame of reference are placed into "registration" with one another so as to establish proper correspondence between their respective spatial coordinate systems, whereby to establish proper correspondence between virtual model structures and real-world structures. And it should be appreciated that, as is well known in the art, such correspondence between virtual model structures and real-world structures allows a real-world instrument (e.g., a surgical instrument such as a real-world surgical stapler) to be tracked (e.g., via optical or radio-frequency (RF) trackers of the sort well known in the art) relative to registered virtual model structures so as to provide "surgical navigation", whereby a real-world tracked instrument can be guided to a location identified in a virtual model so as to target a location in the model. Such surgical navigation is particularly useful in guiding a real-world instrument to a target real-world structure which is located within another real-world structure, where the target real-world structure is normally concealed from direct viewing but which is able to be visualized by scanning the real-world structure so that the target real-world structure is identified in the model.

By way of example but not limitation, an exemplary real-world structure may be the human lung, i.e., a hollow organ comprising a three-dimensional shape that varies as the organ is inflated/deflated during respiration. A virtual model of the lung, including the interior thereof, may be generated by a computer aggregating a plurality of slice scan images obtained through scanning (e.g., CT scanning), segmenting the scan data into specific tissue structures, and then creating a virtual model (e.g., a polygonal surface model) of the scanned anatomy. A target location inside the lung may be a lesion which can be identified in the virtual model so as to permit visualization of the lesion (e.g., on a display showing the virtual model) during the surgical procedure. A real-world instrument (e.g., a bronchoscope, a surgical stapler, etc.) may comprise a 3D object (i.e., a computer-generated object) inserted into the virtual model so as to permit visualization of the instrument vis-á-vis the other elements (e.g., a modeled lesion) of the model (e.g., on a display showing the virtual model) during the surgical procedure. It will be appreciated that, by establishing correspondence between the virtual model and a real-world instrument (i.e., placing the real-world instrument into registration with the virtual model), the surgeon can manipulate the real-world instrument during the surgical procedure while simultaneously watching (e.g., on a display) movement of the real-world instrument vis-á-vis the target location within the virtual model. It will also be appreciated that various types of models (or virtual models) are well known in the art, e.g., polygonal surface models, voxel models, etc.

More particularly, as is well known in the art, "models" (or "virtual models") of anatomical structures are typically created by (i) scanning the anatomical structures (e.g., via a CT machine, an MRI machine, etc.) so as to produce a three-dimensional ("3D") data set representative of the anatomical structures (e.g., in the case of a CT scan, a 3D data set of X-ray attenuation values associated with the anatomical structures), and then (ii) "segmenting" the 3D data set so as to identify the different tissue structures present in the scanned anatomical structures (e.g., in the case of a scan of the lung, identifying the outer surface of the lung, a lesion present in the lung, airways present in the lung, blood vessels present in the lung, etc.). And as is well known in the art, each of the different tissue structures identified through segmentation may be represented by a different "virtual object" within the model (e.g., the outer surface of the lung may be one virtual object, a lesion present in the lung may be another virtual object, an airway present in the lung might be a third virtual object, a blood vessel present in the lung might be a fourth virtual object, etc.). It will be appreciated that the positions of each of the virtual objects in the model corresponds to the positions of the different tissue structures in the scanned anatomical objects.

It should also be appreciated that, once the model has been created (e.g., by scanning the anatomical structures, segmenting the different tissue structures into various virtual objects, etc.), additional virtual objects may be inserted into the model, e.g., a virtual object in the form of a representation of a prosthesis may be inserted into the model so as to represent a planned location for the prosthesis in the anatomy, a virtual object in the form of a rod-like structure may be inserted into the model to represent an endoscope, etc. And it should be appreciated that virtual objects in the model may be "static" (in the sense that they maintain a fixed position within the model, such as in the case of a clamped bone) or "dynamic" (in the sense that they may move relative to other virtual objects in the model, such as in the case of a virtual object representing a tracked real-world endoscope which is moving relative to a virtual object representing a fixed real-world lesion).

As is well known in the art, real-world anatomy and real-world objects can be directly imaged by means of a scope. In this setting, a scope (e.g., an endoscope, a bronchoscope, a thorascope, etc.) is inserted into a hollow interior anatomical site, and then the scope is used to capture images of the hollow interior anatomy. The captured images may be video images or still images. The captured images may be displayed on a monitor and/or stored in a database. See, for example, FIG. 1 which shows an exemplary image of an anatomical structure (tissue) captured by an exemplary scope.

As is also well known in the art, the virtual model may be "imaged" by using an image rendering engine. In this setting, a "virtual camera" is used to generate images of the virtual model, e.g., by ray tracing techniques to determine which portions of the virtual model would be visible to the virtual camera, etc. In order for the image rendering engine to generate images of the virtual model, various parameters are specified, e.g., the virtual camera position relative to the remainder of the virtual model, the "optics" of the virtual camera (e.g., the "focal length" of the virtual camera, the "field of view" of the virtual camera, etc.), etc. If desired, virtual objects within the model may be rendered transparent or semi-transparent in order to visualize other virtual objects which may be located within those virtual objects, e.g., a virtual object representing the exterior surface of a lung may be rendered transparent or semi-transparent in order to visualize a virtual object representing a lesion located within the lung. The rendered images of the virtual model may be video images or still images. The rendered images of the virtual model may be displayed on a monitor and/or stored in a database.

And as is well known in the art, composite images may be produced which combine direct camera images (e.g., scope images) with rendered images (e.g., model images rendered by an image rendering engine). This allows the direct camera images to be supplemented with images of structures which are concealed from the real-world camera by using model images (generated by the image rendering engine) of the concealed structures. In order for these composite camera/model images to be produced, it is generally desirable for (i) the model frame of reference to be placed into registration with the real-world frame of reference, (ii) the virtual camera position to "match" the real-world camera position, and (iii) the "virtual camera" optics to match the real-world camera optics.

Figure 2:
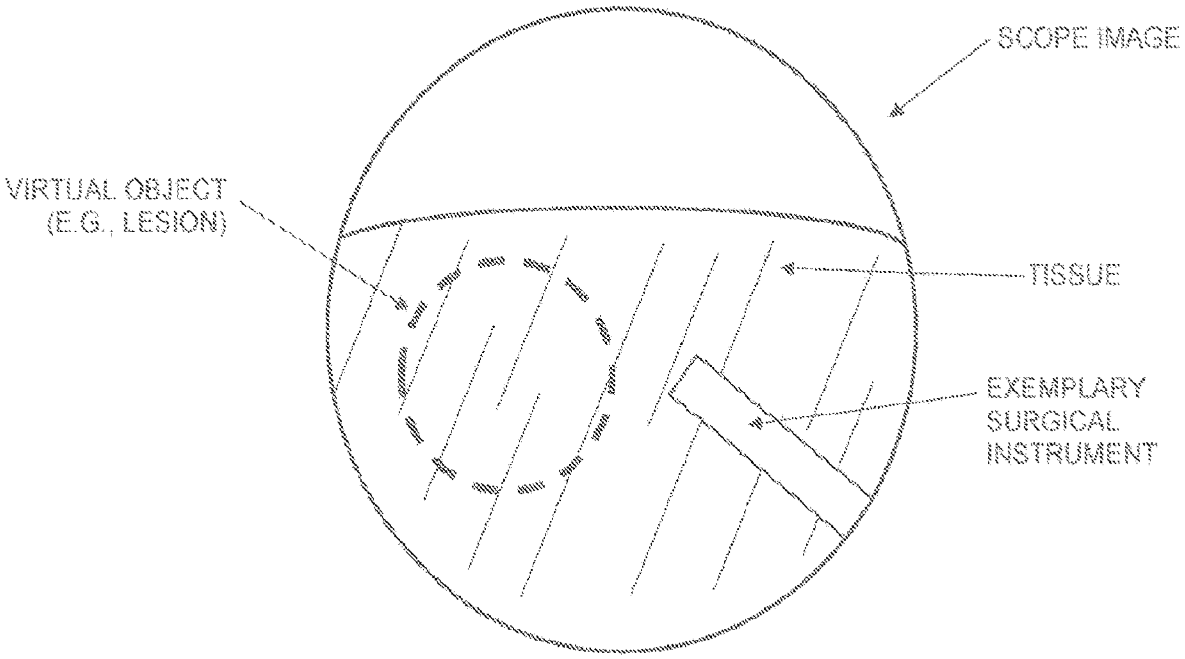
FIG. 2 is a schematic view showing an exemplary image of internal anatomy obtained via a scope, including a virtual object representative of a target lesion superimposed onto the scope image.

By way of example but not limitation, where a scope is used to visualize the exterior of an anatomical structure such as the human lung, and where a virtual object representing a lesion within the lung has been incorporated in a virtual model of the lung and the virtual model and real-world scope image have been placed into registration with one another, the virtual object may be projected onto the direct camera images received from the scope. See, for example, FIG. 2, which shows a virtual object representing a lesion superimposed onto a real-world scope image, as well as showing an exemplary surgical instrument in the field of view. It will be appreciated that as long as registration between the virtual model and the real-world scope image is maintained, the surgeon can continue to visualize the virtual object as the scope and/or surgical instrument are moved relative to the anatomy on the realworld images captured by the scope.

Figure 2A:
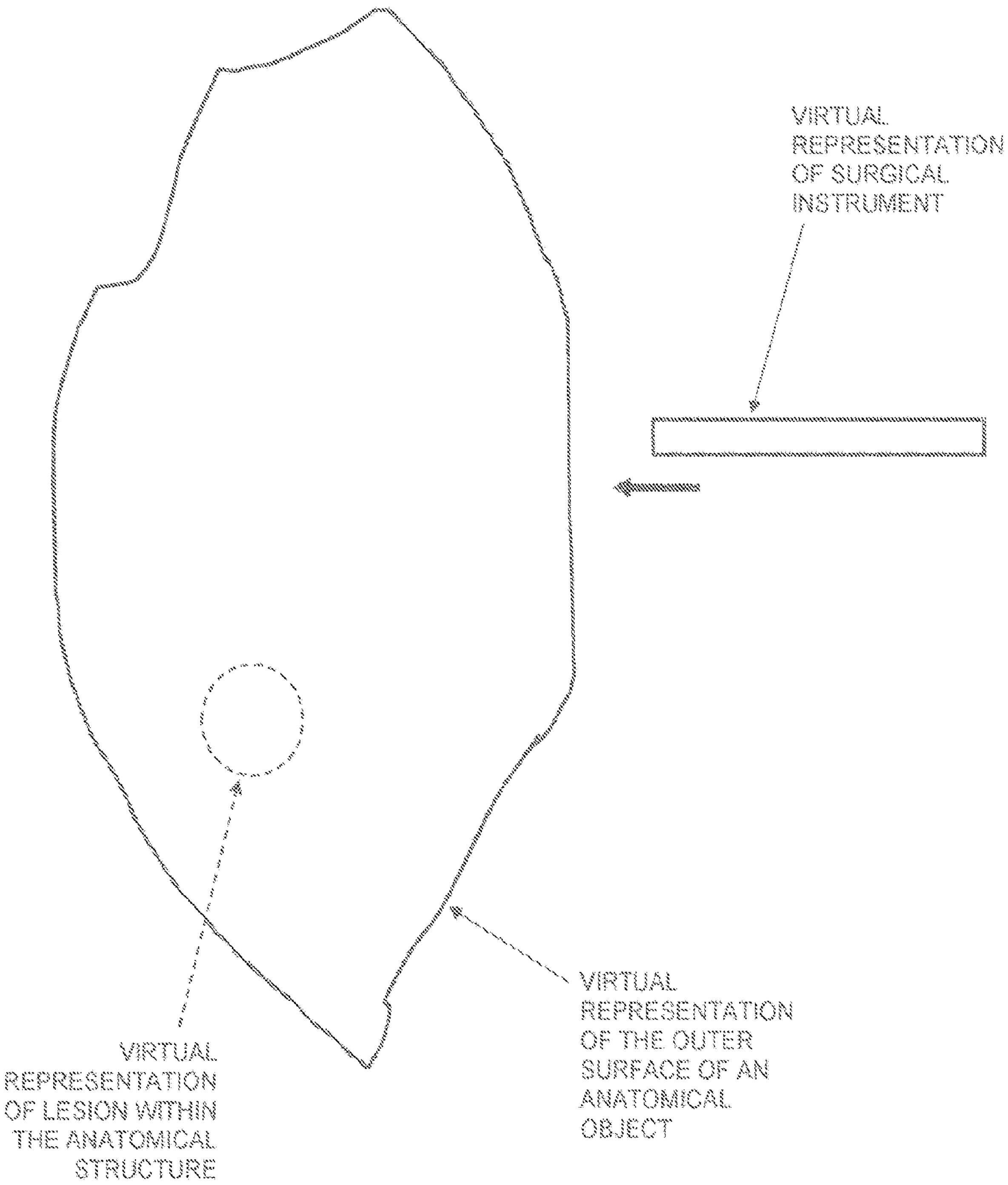
FIG. 2A is a schematic view showing an image rendered from a virtual model, wherein the virtual model comprises representations of an anatomical object, a lesion contained within the anatomical object and a surgical instrument.

It should also be appreciated that where a surgical instrument is being tracked, and where a virtual object representative of the surgical instrument has been inserted into the model, it is possible to generate an image of the objects in the model from substantially any "virtual" camera position. See, for example, FIG. 2A.

Tracking The Location Of A Tissue Mass Using Fiducial Sensors

Figure 3:
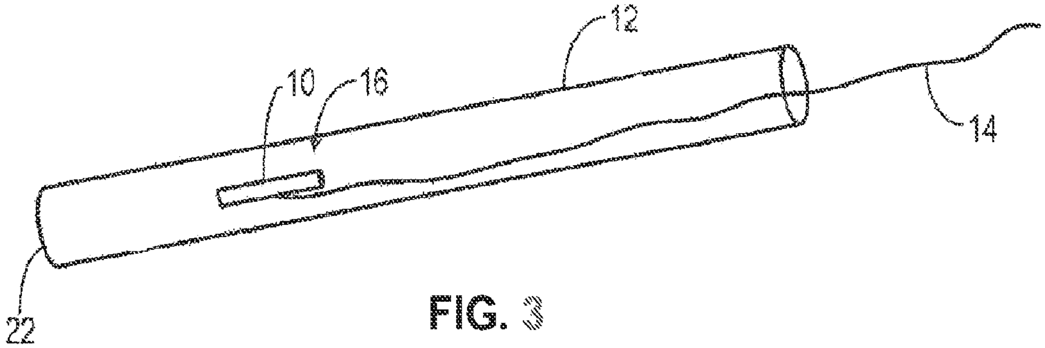
FIG. 3 is a perspective view of an exemplary fiducial sensor being deployed through a delivery needle according to one embodiment of the present invention.
Figure 4:
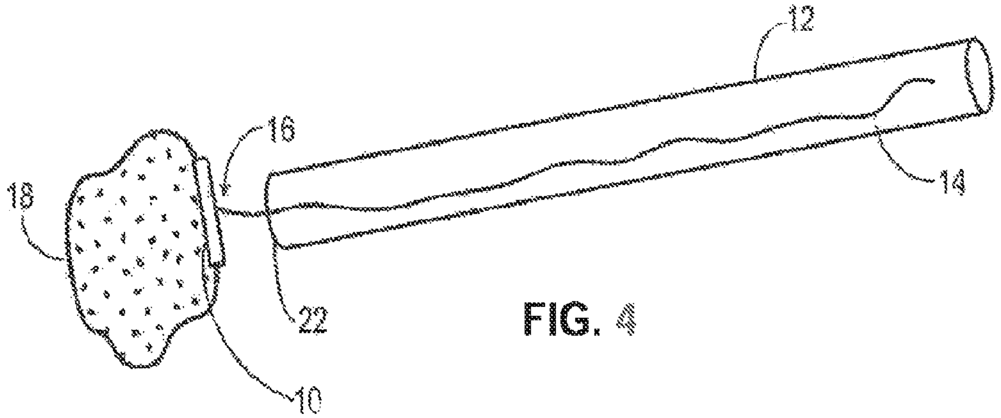
FIG. 4 is a perspective view of the exemplary fiducial sensor of FIG. 3 being deployed through the delivery needle next to a target tissue mass according to one embodiment of the present invention (note that the fiducial sensor may be placed adjacent to the target tissue mass so that the fiducial sensor is in contact with the target tissue mass or so that the fiducial sensor is slightly spaced from the target tissue mass).
Figure 5:
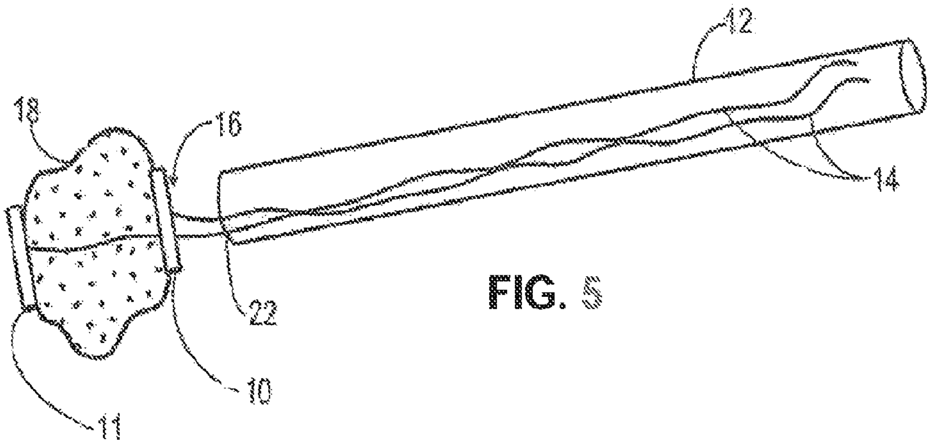
FIG. 5 is a perspective view of an additional fiducial sensor and the exemplary fiducial sensor of FIG. 3 being deployed through the delivery needle next to the target tissue mass according to one embodiment of the present invention.

FIGS. 3-5 illustrate an exemplary fiducial sensor 10 (also sometimes referred to as a fiducial marker or a fiducial tracker) being inserted through a delivery needle 12. The fiducial sensor 10 may be, for example, a marker that includes a transmitter that measures position and orientation of a target tissue mass 18 (e.g., a lesion) in real-time. The fiducial sensor 10 may be attached to a cable 14, as shown in FIGS. 3-5, or the fiducial sensor 10 may be wireless. The fiducial sensor 10 may be embedded within a hook structure 16, as shown in FIG. 3. The hook structure 16 of the fiducial sensor 10 can be made from a superelastic material, for example nitinol, or stainless steel, or any other suitable material. This will allow for the fiducial sensor 10 to be inserted through the delivery needle 12 and deployed through an opening 22 (i.e., the lumen) of the delivery needle 12 into the center of or at the periphery of the target tissue mass 18. The target tissue mass 18 may be, for example, a lesion (e.g., a tumor, a nodule, etc.).

Figure 6:
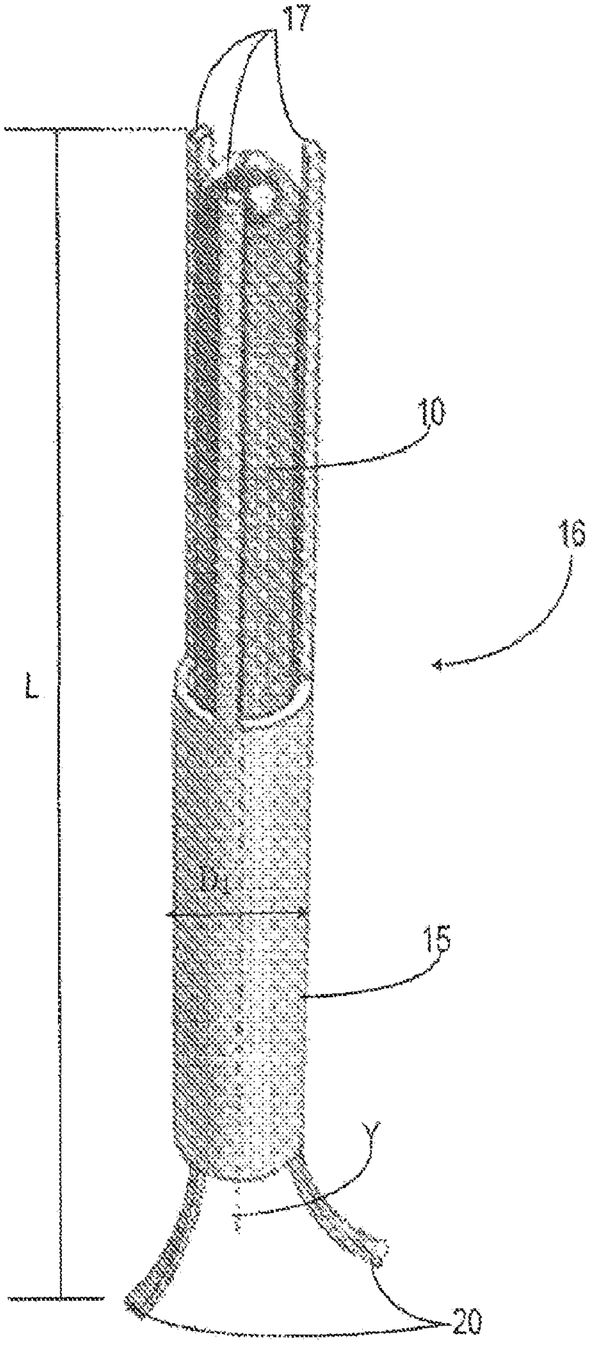
FIG. 6 is a perspective view of an exemplary fiducial sensor embedded within a hook structure according to another embodiment of the present invention.

As shown in FIG. 6, a more detailed view of the fiducial sensor 10 and hook structure 16 is shown. The hook structure 16 may include a tube portion 15 having a plurality of extensions 17 extending from one end of the tube portion 15 and a plurality of prongs 20 extending from an opposing end of the tube portion 15. The tube portion 15 may be, for example, a nitinol tube having an outer diameter $D_1$ between about 0.6 millimeters and about 0.8 millimeters, and the hook structure 16 may have an overall length L between about 8 millimeters and about 12 millimeters. The tube portion 15 may be laser micro-machined into a cylindrical shape having the plurality of extensions 17 extending therefrom to secure the fiducial sensor 10 in place. In some embodiments, the fiducial sensor 10 may be an electromagnetic sensor that is attached to the proximal end of the hook structure 16 using a medical grade epoxy adhesive, such as AA-Bond FDA22.

The plurality of prongs 20, as shown in FIG. 6, may be configured to anchor the hook structure 16, including the fiducial sensor 10, into a target tissue mass or at the periphery of a target tissue mass, such as the target tissue mass 18 of FIG. 4. The plurality of prongs 20 may be constructed from a superelastic shape memory alloy, such as nitinol. The plurality of prongs 20 may be bent, for example, and extend outwardly from a central axis Y of the hook structure 16. The plurality of prongs 20 may also be heat-treated to ensure that the prongs 20 retain the curved shape and the phase structure of the nitinol is in the Martensite phase, for example. In the embodiment shown in FIG. 6, the hook structure 16 includes three prongs 20, however, any suitable number of prongs may be provided in order to anchor the hook structure 16 to the target tissue mass or at the periphery of a target tissue mass, such as the target tissue mass 18.

The fiducial sensor 10 along with the hook structure 16 may be inserted through a distal end of the delivery needle 12, which may be an 18-gauge needle, for example. The plurality of prongs 20 of the hook structure 16 may be inserted into the lumen 22 of the delivery needle 12 first. Advantageously, due to the superelastic nature of nitinol, the hook structure 16 can be easily inserted into the lumen 22 of the delivery needle 12. The hook structure 16 may be deployed using a metal stylet (not shown) that is inserted through the lumen 22 of the delivery needle 12. Upon being completely deployed, the plurality of prongs 20 will regain their original curved shape and open up to firmly anchor the hook structure 16 into or at the periphery of the target tissue mass 18. The delivery needle 12 may then be removed after deployment of the hook structure 16.

Figure 7:
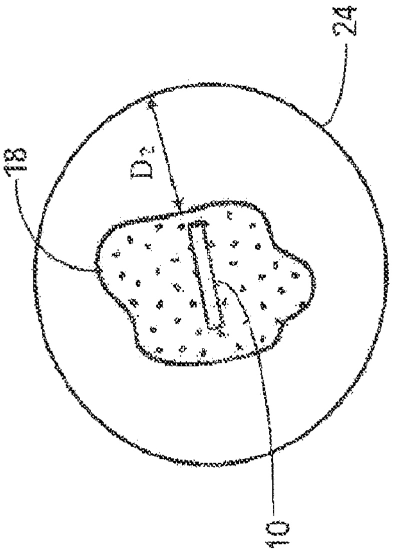
FIG. 7 is a perspective view of the fiducial sensor embedded in the target tissue mass of FIG. 4, with a resection margin surrounding the target tissue mass.
Figure 8:
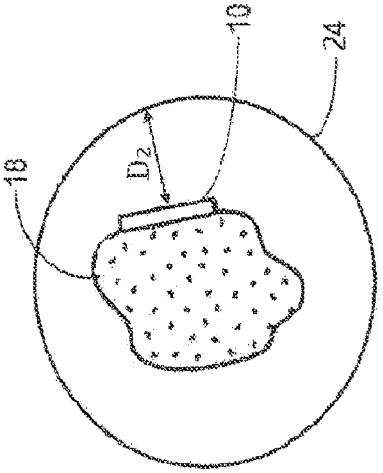
FIG. 8 is a perspective view of the fiducial sensor embedded next to the target tissue mass of FIG. 4, with the resection margin surrounding the target tissue mass (note that the fiducial sensor may be placed adjacent to the target tissue mass so that the fiducial sensor is in contact with the target tissue mass or so that the fiducial sensor is slightly spaced from the target tissue mass).

In some embodiments, the fiducial sensor 10 along with the hook structure 16 may be inserted through the delivery needle 12 under real-time image guidance (e.g., CT, C-arm CT, MRI, Ultrasound, etc.) and embedded within the target tissue mass 18, as shown in FIG. 7, or next to the target tissue mass 18 (e.g., in close proximity to), as shown in FIG. 8. The fiducial sensor 10 may be embedded within or next to the target tissue mass 18 before or during a surgical procedure. By using real-time image guidance, the spatial relationship (i.e., position and orientation) of the fiducial sensor 10 to the target tissue mass 18 in three dimensions is known at all times. The hook structure 16 may be in the form of a T-bar or J-bar, for example, to anchor the fiducial sensor 10 within, or next to, the target tissue mass 18 to inhibit migration. Advantageously, the force is at the center of the T-bar 16 due to the wire 14, thereby facilitating anchoring the fiducial sensor 10 within, or next to, the target tissue mass 18. The fiducial sensor 10 embedded within, or next to, the target tissue mass 18 will measure the position and orientation of the target tissue mass 18 in real-time in spite of any deformation introduced due to soft tissue deformation or physiological motion such as collapsing of the lung or respiration, for example, thereby easily identifying the location of the target tissue mass 18 that is often difficult to determine.

In an alternative embodiment, shown in FIG. 5, a second fiducial sensor 11 (in the form of a T-bar assembly, for example) may be put in a different location near the target tissue mass 18. The second fiducial sensor 11 may have a separate cable 14 from the first fiducial sensor 10, as shown in FIG. 5, or the first fiducial sensor 10 and the second fiducial sensor 11 may share the same cable 14. The second fiducial sensor 11, or any other such device, can be used to improve the localization of the target tissue mass 18, even when there may be deformation. For example, the second fiducial sensor 11 can be placed on the opposite side of the target tissue mass 18 from the first fiducial sensor 10 and be recognized by the first fiducial sensor 10 through distortions in the electromagnetic field. Therefore, by knowing that the target tissue mass 18 is disposed between these two sensors, the target tissue mass 18 can be localized despite changes in the soft tissue.

Referring now to FIGS. 7 and 8, once the position and orientation of the target tissue mass 18 is known, a resection margin 24 having a predetermined distance $D_2$ surrounding the target tissue mass 18 is determined by creating a three dimensional envelope around the target tissue mass 18. The resection margin 24 may be manually set to the desired predetermined distance $D_2$, for example, two centimeters, and is dependent on the surgeon's preference and the lesion type. The predetermined distance $D_2$ defines a threshold value so when a surgical device 26 (e.g., a surgical stapler), described in further detail below, is in a position less than the threshold value, auditory, visual and/or haptic cues may be provided to the surgeon or to the surgical device 26 to ensure precise and complete resection of the target tissue mass 18.

Tracking the Location of a Surgical Device Using an Instrument Sensor

Figure 9:
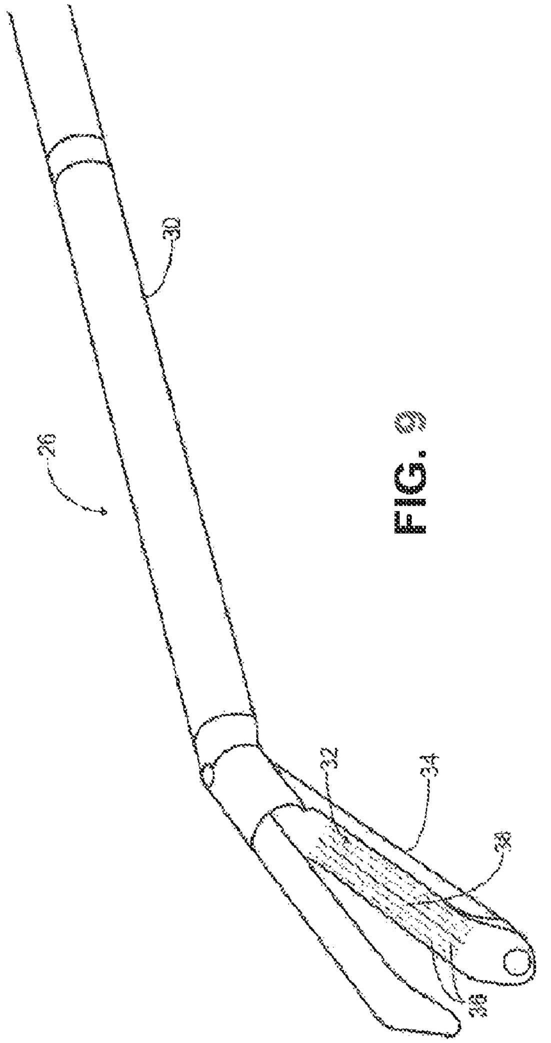
FIG. 9 is a partial perspective view of a conventional stapler device used for resecting a target tissue mass.

Referring now to FIG. 9, a conventional surgical device 26, such as a surgical stapler, Bovi pencil, kitner, laparoscope and/or any suitable cutting, resecting or ablating device, is shown. The surgical device 26 may include a handle 30 coupled to a fastening assembly 32 at an opposite end of the surgical device 26. The fastening assembly 32 may be a single-use component that is removably connected to the handle 30, i.e., the fastening assembly 32 may be a cartridge that connects to the handle 30 and is removed after use. The fastening assembly 32 includes a housing 34 that contains a plurality of fasteners 36 that are secured to tissue during resection of the target tissue mass 18. The fastening assembly 32 may also include a blade slot 38 that accommodates a blade (not shown) for cutting along (or preferably just outside of) the resection margin 24 of the target tissue mass 18.

Figure 10:
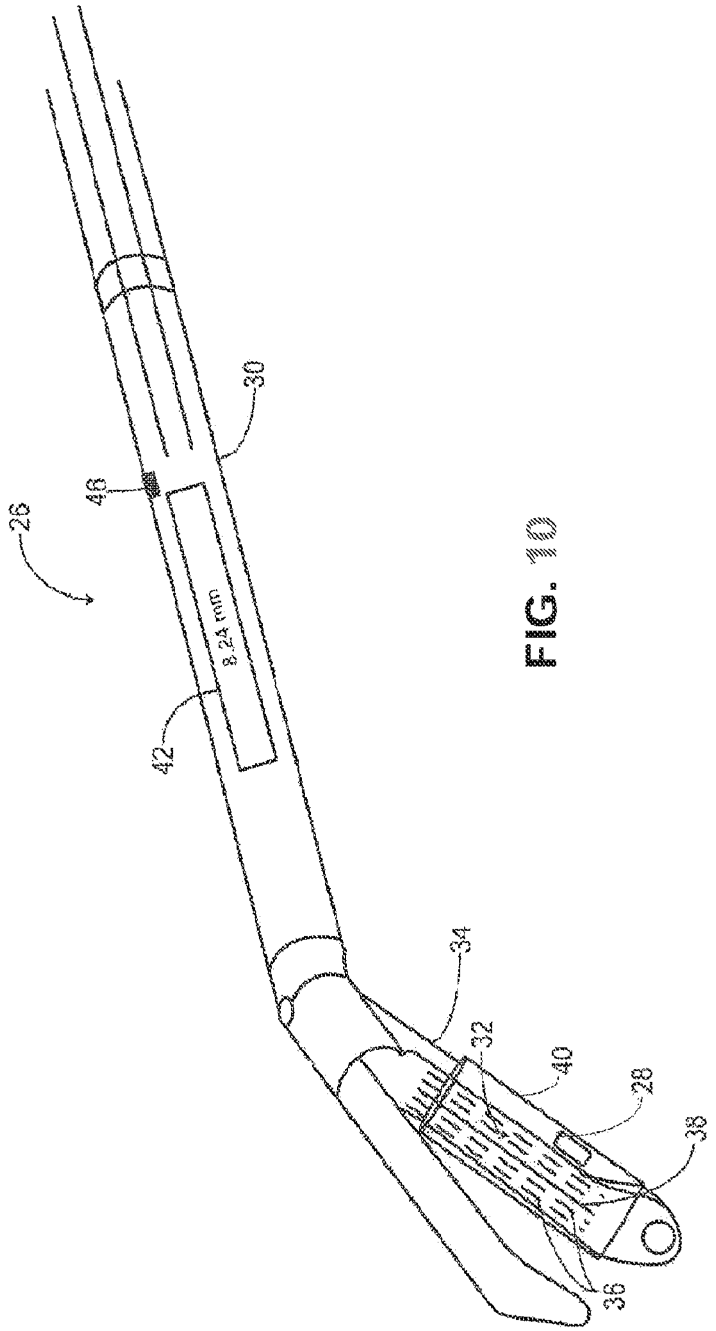
FIG. 10 is a partial perspective view of the stapler device of FIG. 9 with a sleeve including an instrument sensor over a housing of the stapler device according to one embodiment of the present invention.

In a embodiment, the surgical device 26 includes a sleeve 40 that is dimensioned to slide over the housing 34, for example, as shown in FIG. 10. The sleeve 40 may be any commercially available sleeve, for example, that is configured to go over the housing 34 of the surgical device 26. An instrument sensor 28 (sometimes referred to as an instrument tracker) may be attached, by stitching for example, to the sleeve 40. Alternatively, the instrument sensor 28 may be attached directly to the housing 34 of the surgical device 26 via any suitable adhesive or integrated within the housing 34 itself. Regardless of where the instrument sensor 28 is attached, either the sleeve 40 or the housing 34, the instrument sensor 28 can measure the position and orientation of the surgical device 26 in the same imaging reference frame as the fiducial sensor 10 embedded within or next to the target tissue mass 18. In other words, the position of the surgical device 26 may be precisely measured with respect to the fiducial sensor 10 which is within or next to the target tissue mass 18, as will be described in further detail below. Since both the fiducial sensor 10 and the instrument sensor 28 are measured in the same reference frame, errors introduced due to the registration and calibration steps, requiring a change of reference axis, can be minimized.

The sleeve 40 may also include a display 42 that shows the user a distance $D_3$, shown in FIG. 11, of the surgical device 26 from the resection margin 24, as will be described below. The display 42 may be attached to the handle 30 of the surgical device 26 and could be any commercially available organic light-emitting diode (OLED) display or liquid-crystal (LCD) display. In the case of an OLED display, a reformatted CT image of the target tissue mass 18 located at the tip of the surgical device 26, for example, may be displayed to the user.

Guiding the Surgical Device to the Tissue Mass

Figure 11:
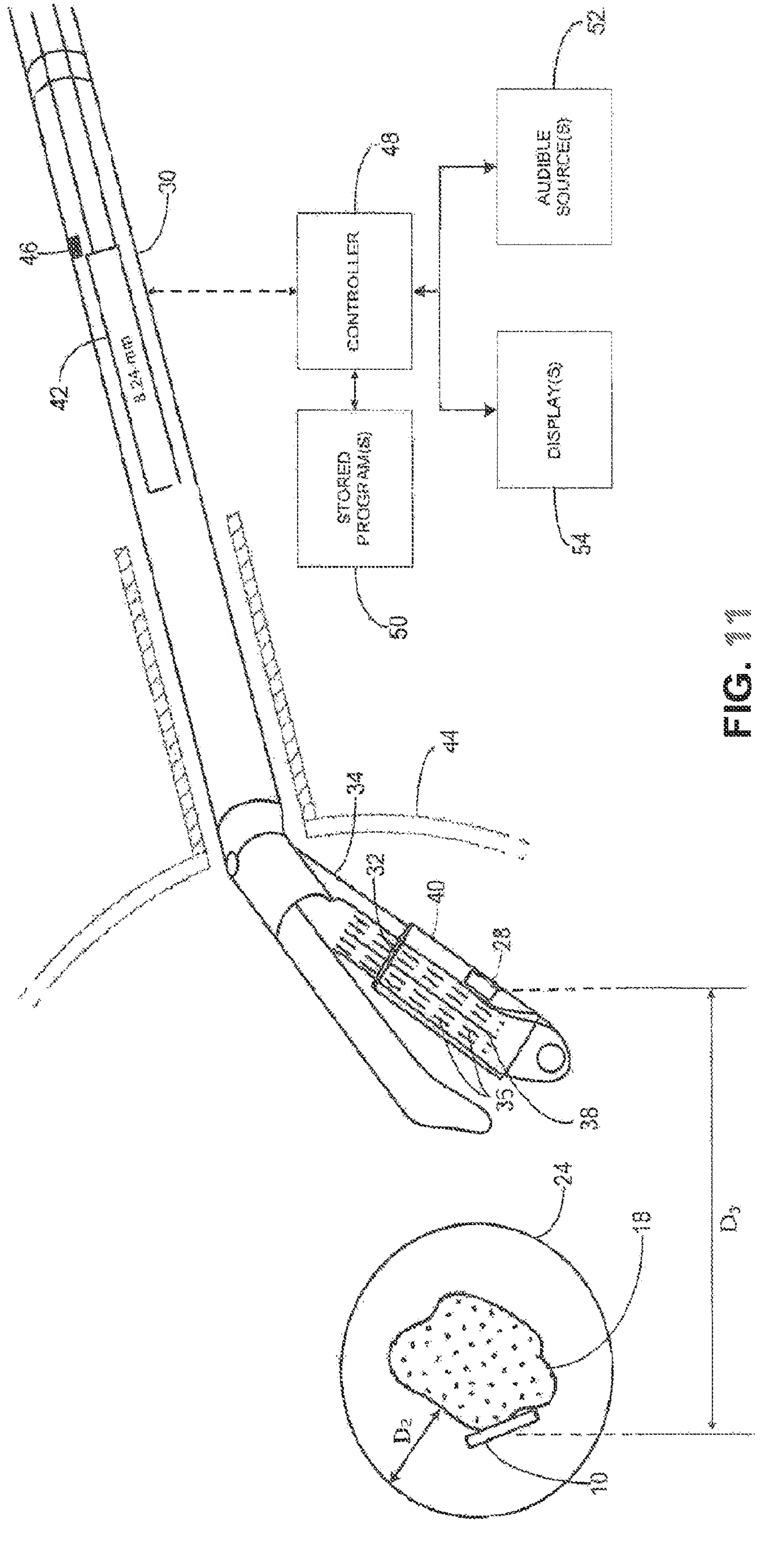
FIG. 11 is a perspective view of the stapler device of FIG. 10 inserted into a patient and shows a distance between the fiducial sensor and the instrument sensor.

Referring now to FIG. 11, during operation, the fiducial sensor 10 is positioned next to, or embedded within, the target tissue mass 18 using the plurality of prongs 20 of the hook structure 16, as previously described. A CT/MRI/fluoroscopic/C-arm CT examination, for example, is performed to acquire images of the fiducial sensor 10 positioned next to, or embedded within, the target tissue mass 18. The target tissue mass 18 is then segmented from the pre-operative diagnostic CT/MRI examination and a three dimensional virtual model (not shown) of the target tissue mass 18 is generated. The intra-operative images obtained during placement of the fiducial sensor 10 may be registered to the patient's diagnostic exam, and the location of the fiducial sensor 10 may be estimated. As previously discussed, the resection margin 24 having the predetermined distance $D_2$ surrounding the target tissue mass 18 is displayed to the user on a monitor (not shown) as a three dimensional virtual object (e.g., an envelope or proximity sphere) disposed around the target tissue mass 18. The predetermined distance $D_2$ of the resection margin 24 may be determined based on the surgeon's preferences and the type of target tissue mass 18.

The surgical device 26 is then inserted into a body 44 (i.e., the patient), as shown in FIG. 11, to cut the target tissue mass 18 along (or preferably just outside of) the resection margin 24. The fiducial sensor 10 embedded within, or close to, the target tissue mass 18 is in electrical or wireless communication with a controller 48. The controller 48 may be a programmable logic controller (PLC) and is configured to interpret a signal generated by the fiducial sensor 10. The fiducial sensor 10 may be an electromagnetic sensor, for example, that generates a signal indicative of the position and orientation (e.g., one or more spatial coordinates) of the fiducial sensor 10. The signal generated by the fiducial sensor 10 may be, for example, an electrical signal and the controller 48 may interpret this signal via a stored program 50. The stored program 50 may include, for example, a navigation system that is in communication with the fiducial sensor 10 and the instrument sensor 28.

Similarly, the instrument sensor 28 may be an electromagnetic sensor, for example, that generates a signal indicative of the position and orientation (e.g., one or more spatial coordinates) of the instrument sensor 28. The signal generated by the instrument sensor 28 may be, for example, an electrical signal and the controller 48 may interpret this signal via a stored program 50. The fiducial sensor 10 and the instrument sensor 28 communicate with the controller 48 and relay the position and orientation of the target tissue mass 18 and the surgical device 26 using the navigation system. In some embodiments, the stored program 50 may be configured to run calibration and/or registration algorithms to track the distal tip of the surgical device 26 and the normal vector to the surgical device 26. Thereafter, the stored program 50 of the controller 48 calculates the distance $D_3$, shown in FIG. 11, between the fiducial sensor 10 and the instrument sensor 28 such that when the surgical device 26 is below a threshold value of $D_3$, an auditory, visual or haptic cue is generated for the user.

As the surgical device 26 is navigated towards the resection margin 24 of the target tissue mass 18, the surgical device 26 may excise the target tissue mass 18 while minimizing damage to surrounding tissue due to both the fiducial sensor 10 and instrument sensor 28 being actively tracked. Minimal damage to the surrounding healthy tissue may also ensure normal physiological function, for example, lung function. Utilizing feedback from the fiducial sensor 10 and the instrument sensor 28 on the surgical device 26, the distance $D_3$ from the target tissue mass 18 and the surgical device 26 may be known to the user and visible on the display 42 at all times. As a result, the desired resection margin 24 may be maintained at all times, thereby ensuring complete resection of the target tissue mass 18. In one embodiment, the position and orientation data of the target tissue mass 18 and the surgical device 26 may be used to lock or unlock the surgical device 26 to inhibit erroneous resection of the target tissue mass 18.

Figure 11A:
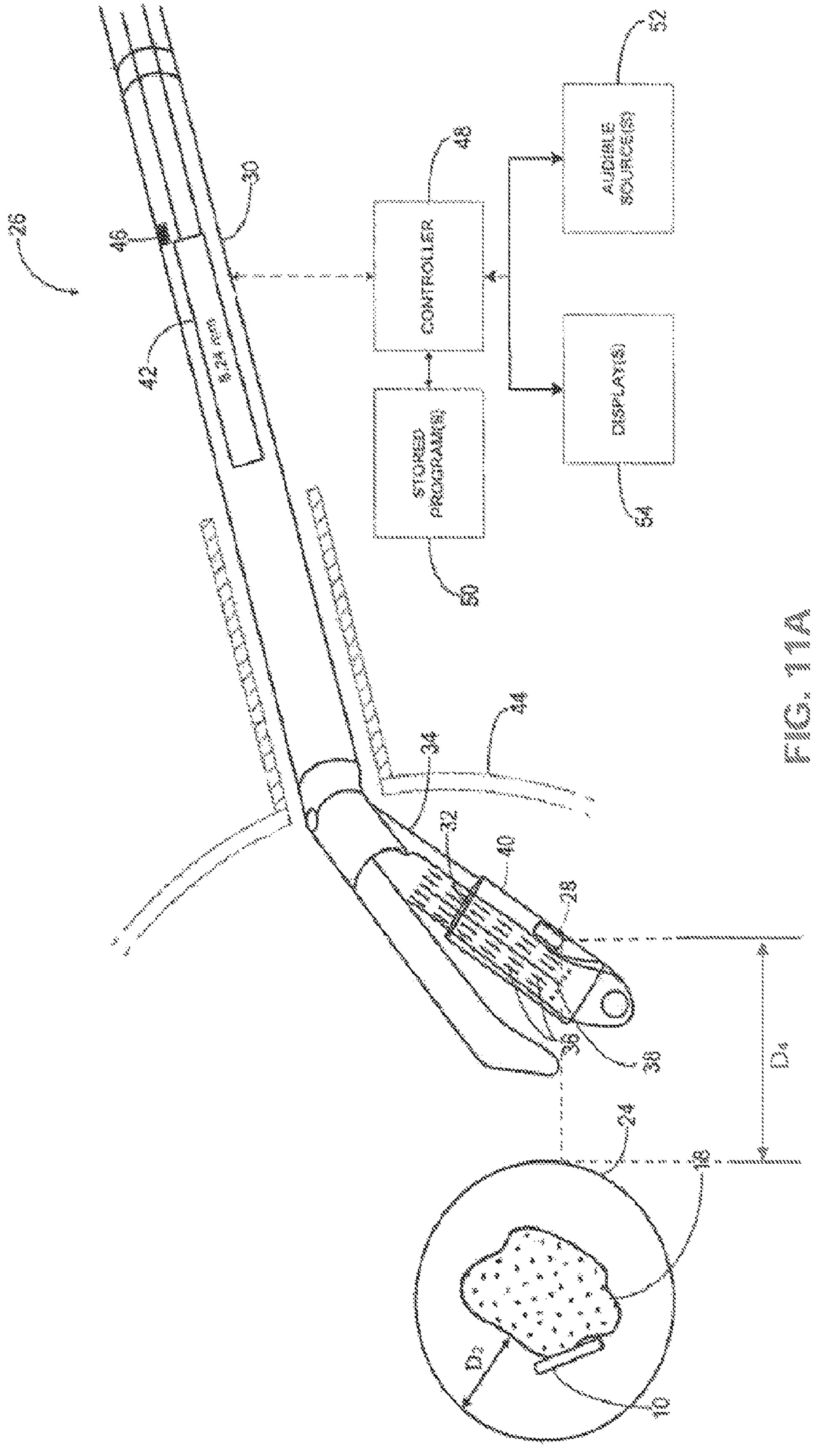
FIG. 11A is a perspective view of the stapler device of FIG. 10 inserted into a patient and shows a distance between the resection margin and the instrument sensor.

Alternatively, if desired, and looking now at FIG. 11A, it is possible to calculate a distance $D_4$ between instrument sensor 28 and the outer boundary of resection margin 24.

More particularly, with this form of the invention, during operation, fiducial sensor 10 is positioned next to, or embedded within, the target tissue mass 18 using the plurality of prongs 20 of the hook structure 16, as previously described. A CT/MRI/fluoroscopic/C-arm CT examination, for example, is performed to acquire images of the fiducial sensor 10 positioned next to, or embedded within, the target tissue mass 18. The target tissue mass 18 is then segmented from the pre-operative diagnostic CT/MRI examination and a three dimensional virtual model (not shown) of the target tissue mass 18 is generated. The intra-operative images obtained during placement of the fiducial sensor 10 may be registered to the patient's diagnostic exam, and the location of the fiducial sensor 10 may be estimated. As previously discussed, the resection margin 29 having the predetermined distance $D_2$ surrounding the target tissue mass 18 is displayed to the user on a monitor (not shown) as a three dimensional virtual object (e.g., an envelope or proximity sphere) disposed around the target tissue mass 18. The predetermined distance $D_2$ of the resection margin 24 may be determined based on the surgeon's preferences and the type of target tissue mass 18.

However, it should be appreciated that $D_2$ may vary in circumstances in which the target tissue mass comprises an irregularly-shaped outer border. Additionally, the surgeon may wish to define a resection margin 24 which is non-circular (e.g., to provide for a common distance between the outer border of an irregularly-shaped target tissue mass 18 and the outer border of the resection margin 24. Thus it is also desirable to be able to calculate a distance $D_4$ extending between instrument sensor 28 and the outer boundary of resection margin 24 (rather than the distance between instrument sensor 28 and fiducial sensor 10, as disclosed in the embodiment discussed above). Because resection margin 24 is a virtual object placed into the virtual model, once the real-world position of fiducial sensor 10 and instrument sensor 28 have been placed into registration with the virtual model, the distance between instrument sensor 28 and the outer border of the resection margin 24 at any given location can be calculated, as will hereinafter be discussed in further detail.

In use, the surgical device 26 is then inserted into a body 44 (i.e., the patient), as shown in FIG. 11A, to cut the target tissue mass 18 along a resection line which lies outside of the resection margin 24. The fiducial sensor 10 embedded within, or close to, the target tissue mass 18 is in electrical or wireless communication with the aforementioned controller 48 (which operates in substantially the same manner as discussed above).

Similarly, the aforementioned instrument sensor 28 operates in the manner discussed above to communicate with the controller 48 and relay the position and orientation of the target tissue mass 18 and the surgical device 26 using the navigation system.

Thereafter, the stored program 50 of the controller 48 calculates the distance $D_4$, shown in FIG. 11A, between the border of the resection margin 24 and the instrument sensor 28. Note that since the relative position of fiducial sensor 10 vis-á-vis the virtual object representative of resection margin 24 is known, and since the relative position of instrument sensor 28 vis-á-vis fiducial sensor 10 is known, stored program 50 can be used to calculate $D_4$ for any position of surgical device 26 vis-á-vis tissue mass 18.

As a result of this construction, when $D_4$ is calculated to be below a threshold value (i.e., indicating that surgical device 26 is approaching the outer border of the resection margin 24) an auditory, visual or haptic cue may be generated for the user. More particularly, as the surgical device 26 is navigated towards the resection margin 24 of the target tissue mass 18, the surgical device 26 may excise the target tissue mass 18 while minimizing damage to surrounding tissue. Minimal damage to the surrounding healthy tissue may also ensure normal physiological function, e.g., lung function. Utilizing feedback from continuous re-calculation of $D_4$ by stored program 50 as surgical device 26 is moved around tissue mass 18, the distance $D_4$ between surgical device 26 and the outer border of resection margin 24 may be known to the user and visible on the display 42 at all times. As a result, the desired resection margin 24 may be maintained at all times, thereby ensuring complete resection of the target tissue mass 18. If desired, the position and orientation data of the target tissue mass 18 and the surgical device 26 may be used to lock or unlock the surgical device 26 to inhibit erroneous resection of the target tissue mass 18.

Tissue Deformation Algorithms

In some embodiments, the stored program 50 of the controller 48 may be configured to include one or more deformation algorithms that estimate or model changes that can occur to the resection margin 24 during a procedure as a result of deformations of the target tissue mass 18 and/or the surrounding tissue. The deformation algorithms attempt to account for any such changes to the resection margin 24 to provide more accurate resection margins to a user during a procedure, which aids in complete resection of the target tissue mass 18 while limiting damage to, or removal of, healthy surrounding tissue.

In one non-limiting example, the stored program 50 includes a deformation algorithm that assumes that the target tissue mass 18 (e.g., a breast lesion) is rigid and that the surrounding tissue (e.g., the parenchyma) deforms. The algorithm assumes every point on the target tissue mass 18 moves along with the fiducial sensor 10, which is anchored to the target tissue mass 18 as described above. In another non-limiting example, the stored program 50 includes a deformation algorithm that assumes the target tissue mass 18 is a rigid object moving through a viscoelastic or fluid medium. In yet another non-limiting example, patient-specific properties of the target tissue mass 18 and the surrounding tissue can be measured, for example, via a CT/MRI/fluoroscopic examination, to predict deformations to target tissue mass 18 or resection margin 24 that occur during an operation for that specific patient. It should be appreciated that the deformation algorithms of the stored program 50 may operate on a real-time basis with the navigation system of the stored program 50.

More specifically, a target tissue mass 18 (e.g., a lesion) can be segmented from volumetric images obtained, for example, from the CT/MRI/fluoroscopic examination, to create a surface model. Based upon a default resection margin inputted into the navigation system by a user, a segmented lesion label map can be dilated to the desired resection margin to create a surface model corresponding to the resection margin. Due to deformation of the lesion and the surrounding tissue, the resection margin can change, for example, due to movement of the patient. A linear elastic volumetric finite element model ("FEM") mesh can therefore be created from the surface model of the lesion and the resection margin. Using the FEM model, an estimate of the displacement of the other nodes of target tissue mass 18 and resection margin 24 can be made, given the real-time position measurement of the fiducial sensor 10. Stiffness values may not be entirely accurate for the FEM model, and the FEM model may be constrained in one example to the target tissue mass 18 and the surrounding tissue. Uncertainty measurements of the target tissue mass 18 and the surrounding tissue deformation can therefore be provided to a user in real-time based upon the uncertainty in the estimated stiffness values of the FEM mesh.

Auditory, Visual, Quantitative and Haptic Cues

As described above, auditory, visual and haptic cues may be provided to the surgeon and/or the surgical device 26 to identify the resection margin 24 to ensure precise and complete resection of the target tissue mass 18. For example, an audible source 52 may be configured to emit an audible signal. The audible source 52 may be in communication with the controller 48 that is configured to execute the stored program 50 to alter the audible signal based on the distance $D_3$ between the instrument sensor 28 and the fiducial sensor 10. The instrument sensor 28 uses the signal generated by the fiducial sensor 10 to enable the controller 48 to execute the stored program 50 to calculate the distance $D_3$, shown in FIG. 11 and/or the distance $D_4$ shown in FIG. 11A such that when the surgical device 26 is below a threshold value of $D_3$ or $D_4$, the audible signal is generated. The audible signal may be, for example a tone, beep or alarm. The audible signal may also increase in frequency or duty cycle as the distance $D_3$ or $D_4$ decreases, such that as the surgical device 26 is navigated too close to the resection margin 24, the audible signal's frequency or duty cycle increases.

In addition to the auditory cues, visual cues may also be provided to the user on one or more displays 54 in communication with the controller 48. The one or more displays 54 may include, for example, visual cues provided on an endoscopic display or a separate monitor. For example, the endoscopic display or the separate monitor may be configured to emit a visual signal. The endoscopic display or the separate monitor may be in communication with the controller 48 that is configured to execute a stored program 50 to alter the visible signal based on the distance $D_3$ between the instrument sensor 28 and the fiducial sensor 10 and/or the distance $D_4$ between the instrument sensor 28 and the outer border of resection margin 24. The instrument sensor 28 uses the signal generated by the fiducial sensor 10 to enable the controller 48 to execute the stored program 50 to calculate the distance $D_3$, shown in FIG. 11, between the fiducial sensor 10 and the instrument sensor 28 (e.g., near the tip of the surgical device 26), and/or between the instrument sensor 28 (e.g., near the tip of the surgical device 26) and a vector normal to the hook structure 16, such that when the surgical device 26 is below a threshold value of $D_3$, the visual signal is generated. Alternatively and/or additionally, the stored program 50 may calculate the distance $D_4$, shown in FIG. 11A, between the instrument sensor 28 and the outer border of resection margin 24 (see above), such that when the distance $D_4$ is below a threshold value, the visual signal is generated. The visual signal may be, for example, a solid or flashing light shown on the one or more displays 54, such as the endoscopic display or the separate monitor. The visual signal may also increase in frequency or brightness, for example, as the distance $D_3$ (or $D_4$) decreases, such that as the surgical device 26 is navigated too close to the resection margin 24, the visual signal's frequency and/or brightness increases. Further, the distances from the tip, mid or base of the cutting surface of the instrument can also be determined based on a stored program and displayed to the user. Such a display of distance numerics may sometimes be referred to herein as a so-called quantitative cue.

In one non-limiting example, the visual cue may be shown as a color changing sphere, for example, on one of the displays 54. The color changing sphere may be representative of the tissue resection margin 24, for example, such that the color changes based on the distance $D_3$ between the instrument sensor 28 and the fiducial sensor 10 (or the distance $D_4$ between the instrument sensor 28 and the outer border of resection margin 24). Thus, as the instrument sensor 28 approaches the fiducial sensor 10, for example, the sphere may be shown in the display 54 in a first color. Likewise, as the instrument sensor 28 moves away from the fiducial sensor 10, the sphere may be shown on the display 54 in a second color, for example, thereby allowing the surgeon to appreciate, visually, the distance $D_3$ (or $D_4$) between the instrument sensor 28 and the fiducial sensor 10.

Figure 13:
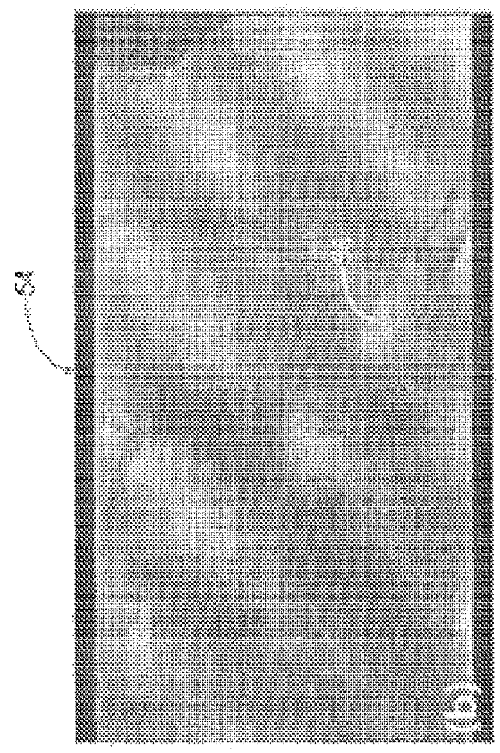
FIG. 13 is an example screenshot of a laparoscopy view of a target tissue mass.
Figure 12:
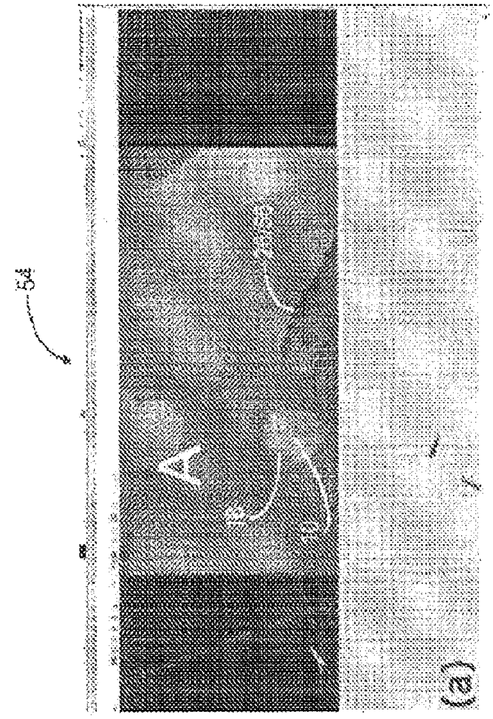
FIG. 12 is an example screenshot of a virtual endoscopy or "scope" view of a target tissue mass overlaid on a laparoscopy view.

Although quantitative, visual, and auditory cues may be provided to the clinician to identify the distance of the resection margin 24 from the surgical instrument 26, the visual cue may further include a video overlay provided to the user on one or more of the displays 54 in communication with the controller 48. For example, a video overlay may be implemented to fuse the laparoscopy images and virtual endoscopy images to confirm the position of the fiducial sensor 10 and the target tissue mass 18, as shown on the display 54 of FIG. 12. Based on the position of the laparoscope 56, as shown on the display 54 of FIG. 13, the virtual endoscopy video of the three dimensional anatomy can be generated. The focal length and field of view may be inputted to control the virtual endoscopy view generated using a visualization toolkit camera, for example, of the three dimensional view.

Haptic cues may also be provided to the user on the surgical device 26. For example, a piezoelectric actuator 46 may be attached to the handle 30 of the surgical device 26 that is configured to emit a haptic signal. The piezoelectric actuator 46 may be in electrical communication with the controller that is configured to execute a stored program to alter the haptic signal based on the distance $D_3$ between the instrument sensor 28 and the fiducial sensor 10 (or the distance $D_4$ between the instrument sensor 28 and the outer border of resection margin 24). The instrument sensor 28 uses the signal generated by the fiducial sensor 10 to enable the controller to execute the stored program to calculate the distance $D_3$, shown in FIG. 11, between the fiducial sensor 10 and the instrument sensor 28 (and/or to calculate the distance $D_4$ shown in FIG. 11A between the instrument sensor 28 and the outer border of resection margin 24) such that when the surgical device 26 is below a threshold value of $D_3$ (or $D_4$), the haptic signal is generated. The haptic signal may be, for example a vibration applied to the handle 30 of the surgical device 26. The haptic signal may also increase in amplitude and/or frequency, for example, as the distance $D_3$ (or $D_4$) decreases, such that as the surgical device 26 is navigated too close to the resection margin 24, the haptic signal's amplitude and/or frequency increases.

Tracking the Position of a Surgical Instrument Relative to a Resection Margin

In one form of the invention, and as discussed above with reference to the embodiment of FIG. 11A, the system is configured to show the position of a surgical instrument relative to the pre-determined resection margin extending around the tissue (e.g., a lesion) of interest, so that a surgeon using the system can ensure that the resection line effected by the surgical instrument is located beyond the outer border of the pre-determined resection margin, whereby to achieve the goal of excising the resection margin along with the lesion itself.

And in one form of the invention, the system is particularly well suited for resecting a target tissue mass from a host tissue mass, wherein the host tissue mass is deformable (e.g., the deformable tissue of a human lung).

To this end, the system is provided with a three-dimensional tissue mass model (sometimes also referred to as "a model", or "a virtual model", or a "virtual object", etc.) generated from previously-acquired scan data. Note that this three-dimensional tissue mass model is in the context of a model frame of reference. The system provides the surgeon with means for inserting a three-dimensional virtual margin model (sometimes also referred to as "a model", or "a virtual model", or a "virtual object", etc.) into the three-dimensional tissue mass model. Note that the three-dimensional virtual margin model is also in the context of the model frame of reference.

The system is also provided with a fiducial sensor and an instrument sensor which provide information on the location of those sensors in a real-world frame of reference. The fiducial sensor is configured to be disposed within, or next to, a target tissue mass, and the instrument sensor is configured to be disposed on a surgical instrument which is to be guided during surgery.

The system is also provided with a controller which (i) receives the three-dimensional tissue mass model and the three-dimensional virtual margin model, which are provided in the context of the model frame of reference, (ii) receives information from the fiducial sensor and the instrument sensor in a real-world frame of reference, (iii) places the model frame of reference and the real-world frame of reference in registration with one another, and (iv) outputs information showing the position of the instrument sensor relative to the three-dimensional virtual margin model. In this way, the surgeon will know the position of the surgical instrument relative to the three-dimensional virtual margin model, so that the surgeon can ensure that the resection line does not intrude into the resection margin.

Thus, in one form of the invention, there is provided a system for resecting a target tissue mass from a host tissue mass, wherein the host tissue mass is deformable, the system comprising:

- a surgical instrument;
- a first fiducial sensor dimensioned to fit at least one of inside of and next to the target tissue mass, the first fiducial sensor including a hook to anchor the first fiducial sensor at least one of inside of and next to the target tissue mass so that the first fiducial sensor remains in known spatial relation to the target tissue mass, the first fiducial sensor adapted to measure position (and preferably also orientation) of the first fiducial sensor within a first frame of reference;
- a second fiducial sensor coupled to the surgical instrument, the second fiducial sensor adapted to measure position (and preferably also orientation) of the second fiducial sensor within the first frame of reference; and
- a controller in communication with the first fiducial sensor and the second fiducial sensor, the controller being configured to:
  - receive a three-dimensional tissue mass model and a three-dimensional virtual margin model;
  - register the position (and preferably also orientation) of the first fiducial sensor, the second fiducial sensor, the three-dimensional tissue mass model, and the three-dimensional virtual margin model in a common frame of reference,
  - update, in real-time, the position (and preferably also orientation) of the implantable fiducial sensor, the tissue mass surface model, and the virtual margin surface model in the common frame of reference based on the measured position (and preferably also orientation) of the first implantable sensor within the first frame of reference; and
  - update, in real-time, the position (and preferably also orientation) of the second fiducial sensor in the common frame of reference based on the measured position (and preferably also orientation) of the second fiducial sensor within the first frame of reference;

such that the positions (and preferably also orientations) of the three-dimensional tissue mass model, the three-dimensional virtual margin model, and the instrument fiducial sensor are determined relative to one another regardless of deformation of the host tissue mass.

And in one form of the invention, there is provided a method for resection of a target tissue mass from a host tissue mass inside a patient, wherein the host tissue mass is deformable, the method comprising:

(a) anchoring a first fiducial sensor at least one of inside and next to the target tissue mass so that the first fiducial sensor remains in known spatial relation to the target tissue mass, the first fiducial sensor adapted to measure position (and preferably also orientation) of the first fiducial sensor within a first frame of reference;

(b) inserting a surgical instrument into the patient, the surgical instrument coupled to a second fiducial sensor, the second fiducial sensor adapted to measure position (and preferably also orientation) of the second fiducial sensor within the first frame of reference;

(c) receive a three-dimensional tissue mass model and a three-dimensional virtual margin model;

(d) register the position (and preferably also orientation) of the first fiducial sensor, the second fiducial sensor, the three-dimensional tissue mass model, and the three-dimensional virtual margin model in a common frame of reference;

(e) update, in real-time, the position (and preferably also orientation) of the implantable fiducial sensor, the tissue mass surface model, and the virtual margin surface model in the common frame of reference based on the measured position (and preferably also orientation) of the first implantable sensor within the first frame of reference; and (f) update, in real-time, the position (and preferably also orientation) of the second fiducial sensor in the common frame of reference based on the measured position (and preferably also orientation) of the second fiducial sensor within the first frame of reference;

such that the positions (and preferably also orientations) of the three-dimensional tissue mass model, the three-dimensional virtual margin model, and the instrument fiducial sensor are determined relative to one another regardless of deformation of the host tissue mass.

Figure 14:
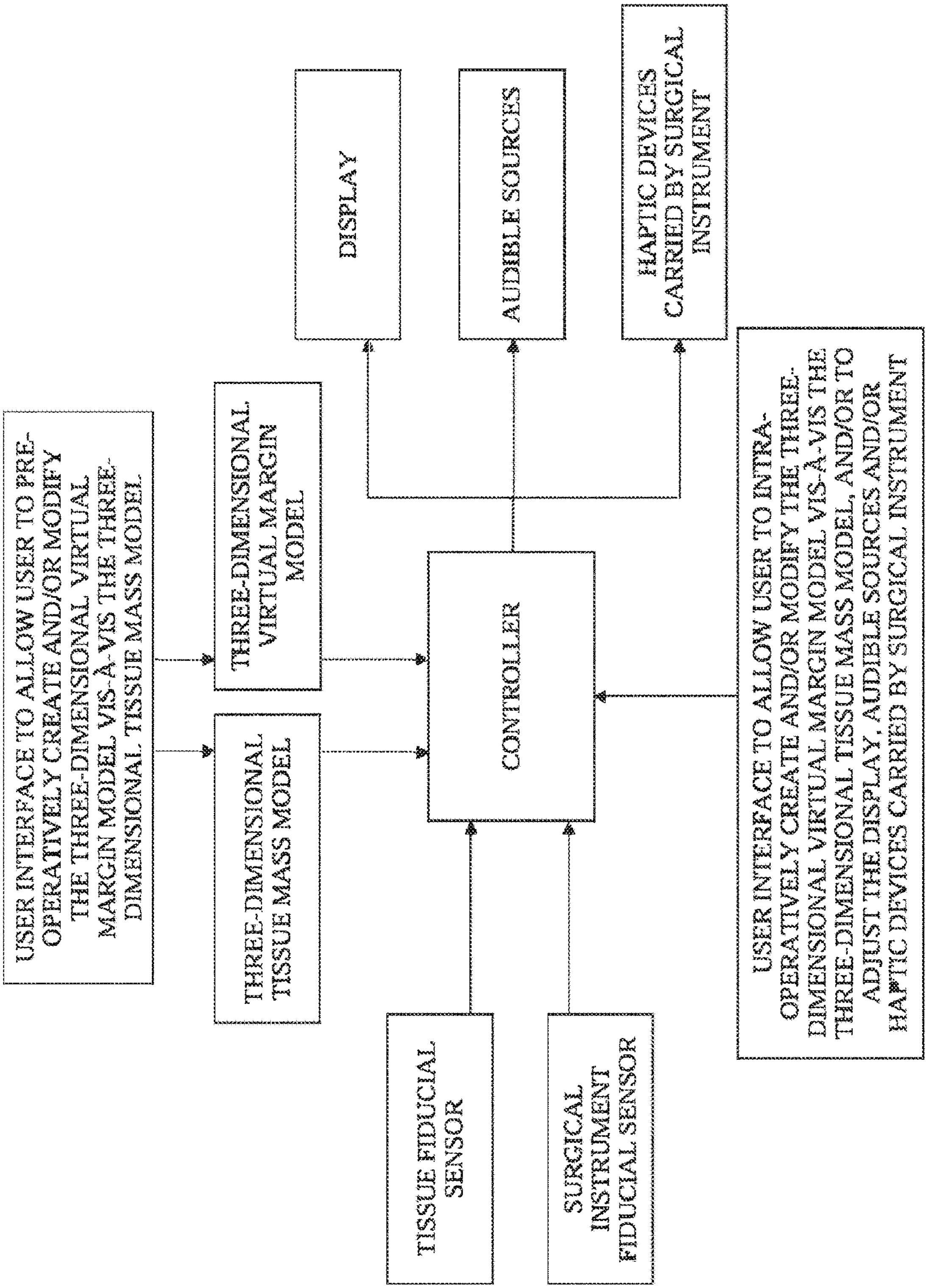
FIG. 14 is a schematic view showing one system for tracking the position of a surgical instrument relative to a resection margin.

FIG. 14 is a schematic view showing one system for tracking the position of a surgical instrument relative to a resection margin. Note that FIG. 14 includes a user interface to allow the user to create (i.e., overlay) and/or modify the three-dimensional virtual margin model vis-á-vis the three-dimensional tissue mass model, and a user interface to allow user to intra-operatively create and/or modify the three-dimensional virtual margin model vis-á-vis the three-dimensional tissue mass model, and/or to adjust the display, audible sources and/or haptic devices carried by surgical instrument.

Application To Lung Cancer Surgery

Nearly 230,000 new cases of lung cancer are diagnosed each year in the United States, at an estimated cost of $12.1 billion to the healthcare system. Patients with lung cancer have 1-year and 5-year survival rates of 44% and 17%, respectively. For treatment of early stage small lesions, a parenchymal-sparing, minimally invasive Wedge Resection Surgery (WRS) or segmentectomy is becoming the method of surgical resection over lobectomy. The preservation of healthy lung function becomes even more important when the lung physiology is compromised due to excessive smoking, old age, multiple lesions, previous lung surgery, cardiac comorbidity or Chronic Obstructive Pulmonary Disease (COPD). Although these approaches (i.e., WRS and segmentectomy) result in better lung function, the lesion recurrence rate is almost double that of a lobectomy, with significantly poorer 5-year survival rates. In addition, segmentectomy is associated with significant complications. The loco-regional recurrence and complications associated with segmentectomy may be attributed to the difficulty in accurately localizing and resecting the lesions in a deflated lung, and the difficulty in identifying the intersegmental plane. To avoid peri- and post-operative complications, precise anatomic landmarks (e.g., vascular and bronchial anatomic variations) need to be carefully identified and followed.

In the preceding sections, it is taught that a fiducial sensor 10 (e.g., a T-bar or J-bar assembly) is placed close to the lesion 18 in order to track the lesion in real-time. The surgical stapler (or other surgical device) 26 is also tracked in real-time using an instrument sensor 28 to precisely guide the resection of the lung lesion 18. More particularly, navigation software computes the distance of the surgical stapler 26 to the fiducial sensor 10 (e.g., the T-bar or J-bar assembly) and hence the distance of the surgical stapler 26 to the lesion 18, and displays the distance measurement to the surgeon in real-time so as to ensure complete lesion resection. Further, the distances of the fiducial sensor 10 or the tumor surface to the tip, middle and base of the stapler cutting line (also sometimes referred to herein as a resection line) can also be computed and displayed in real-time.

Using the System to Identify a Specific Airway in the Lung so as to Assist a Surgeon in Identifying That Airway During Surgery From the Chest Side of the Operation The system can also be used to identify a specific airway in the lung so as to assist a surgeon in identifying that airway during surgery from the chest side of the operation.

Figure 15:
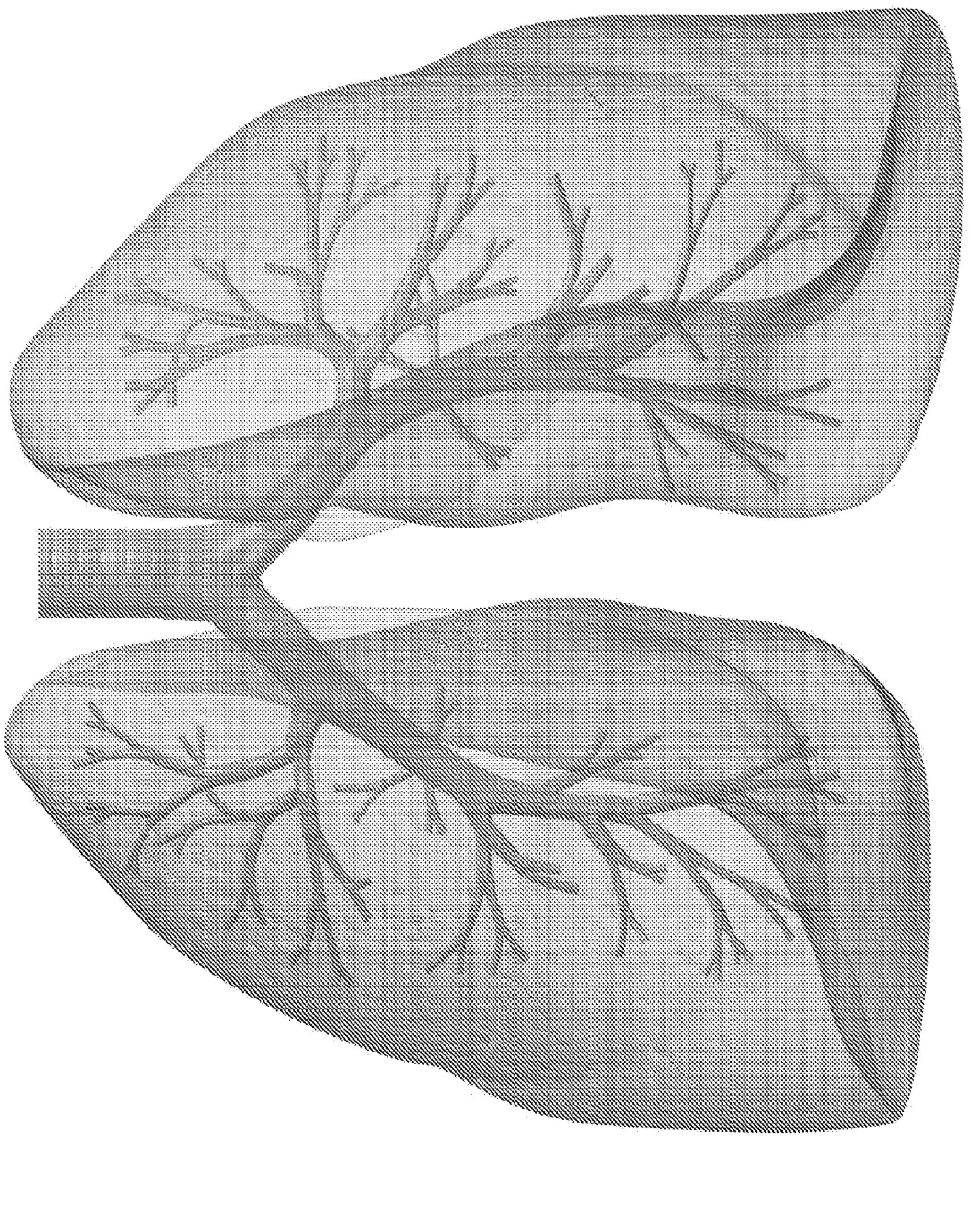
FIG. 15 is a schematic view showing the tree-like structure of the airways of the lung.

More particularly, the airways of the lung have a complex tree-like structure. See FIG. 15.

When treating a lesion in the lung, and particularly where the treatment may involve a resection of the lung in order to remove the lesion, it can be important to plan the resection relative to specific airways, i.e., to remove a specific airway, to avoid a specific airway, etc. Therefore, it can be important to know the location of relevant airways when conducting the resection surgery.

During bronchoscopy, it is possible to identify the location of the bronchoscope relative to specific airways, since the bronchoscope follows a descending path characterized by specific branching as the bronchoscope proceeds down the tree-like structure of the airways. However, the bronchoscope can typically traverse only a limited distance down the airways of the lung given its size and the progressively decreasing size of the airways. Furthermore, during surgery from the chest side of the operation, the visualization provided to the surgeon from the chest side is limited to a direct field of view and it can be highly problematic to identify, from the chest side, a specific airway due to the limited view provided to the surgeon from the chest side.

The present invention can be used to identify a specific airway in the lung so as to assist a surgeon in identifying that airway during surgery from the chest side of the operation.

Figure 16:
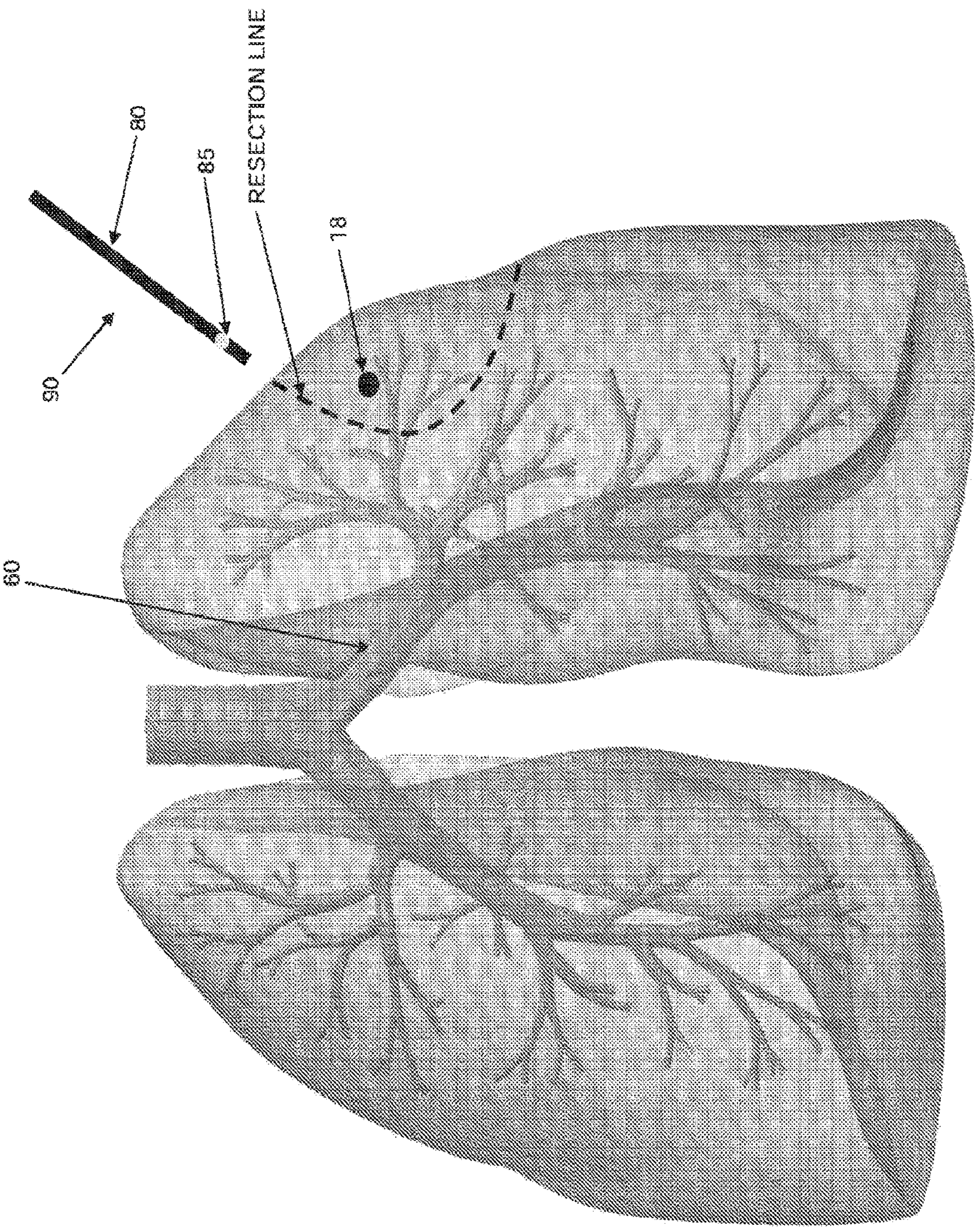
FIGS. 16-18 are schematic views showing how a bronchoscope can be used to position a tracked catheter (i.e., a catheter carrying a sensor) in a specific airway of the lung, whereby to identify that specific airway of the lung, and how a surgical instrument carrying another sensor can be guided relative to that airway (e.g., to target that airway, to avoid that airway, etc.).
Figure 17:
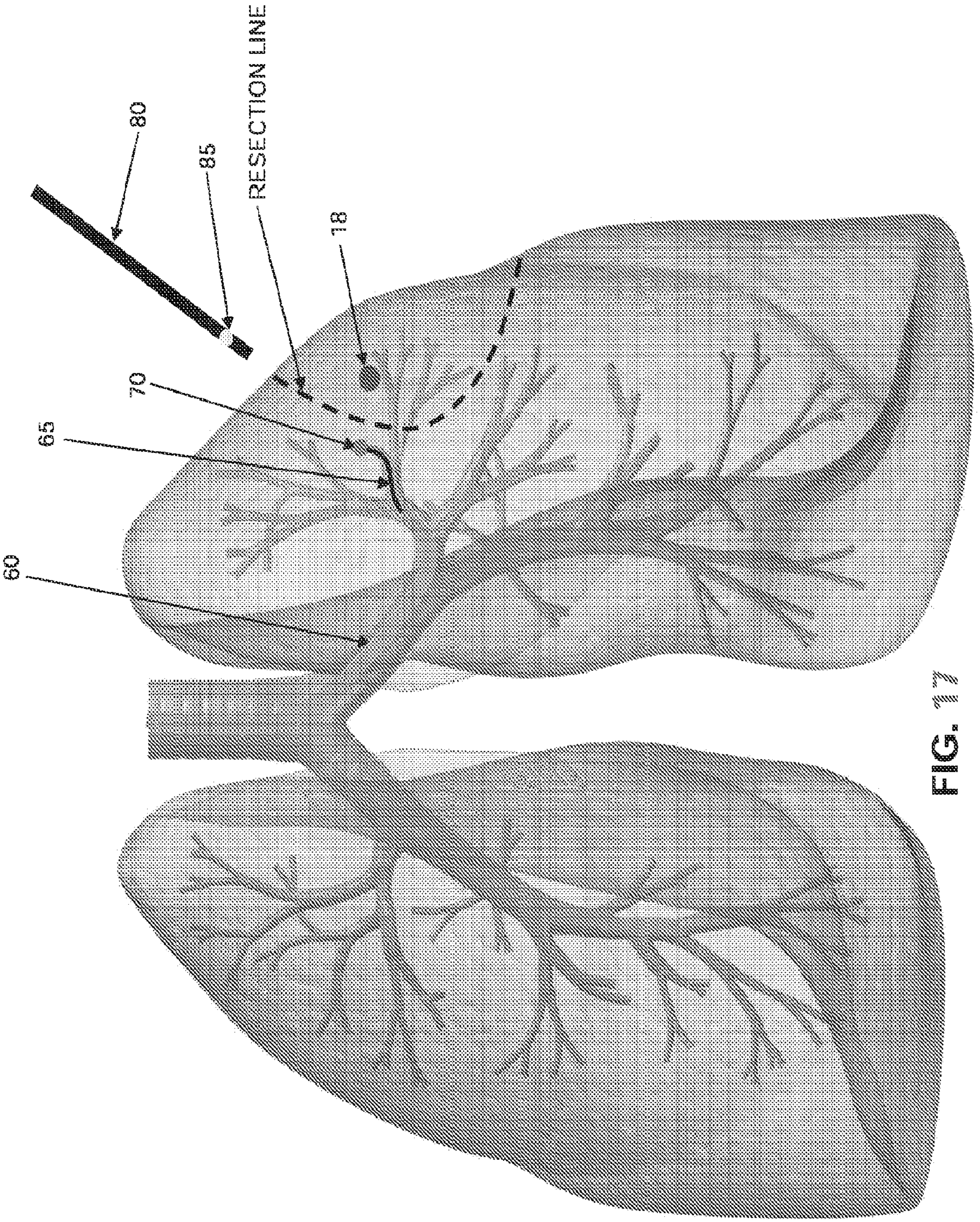
Figure 18:
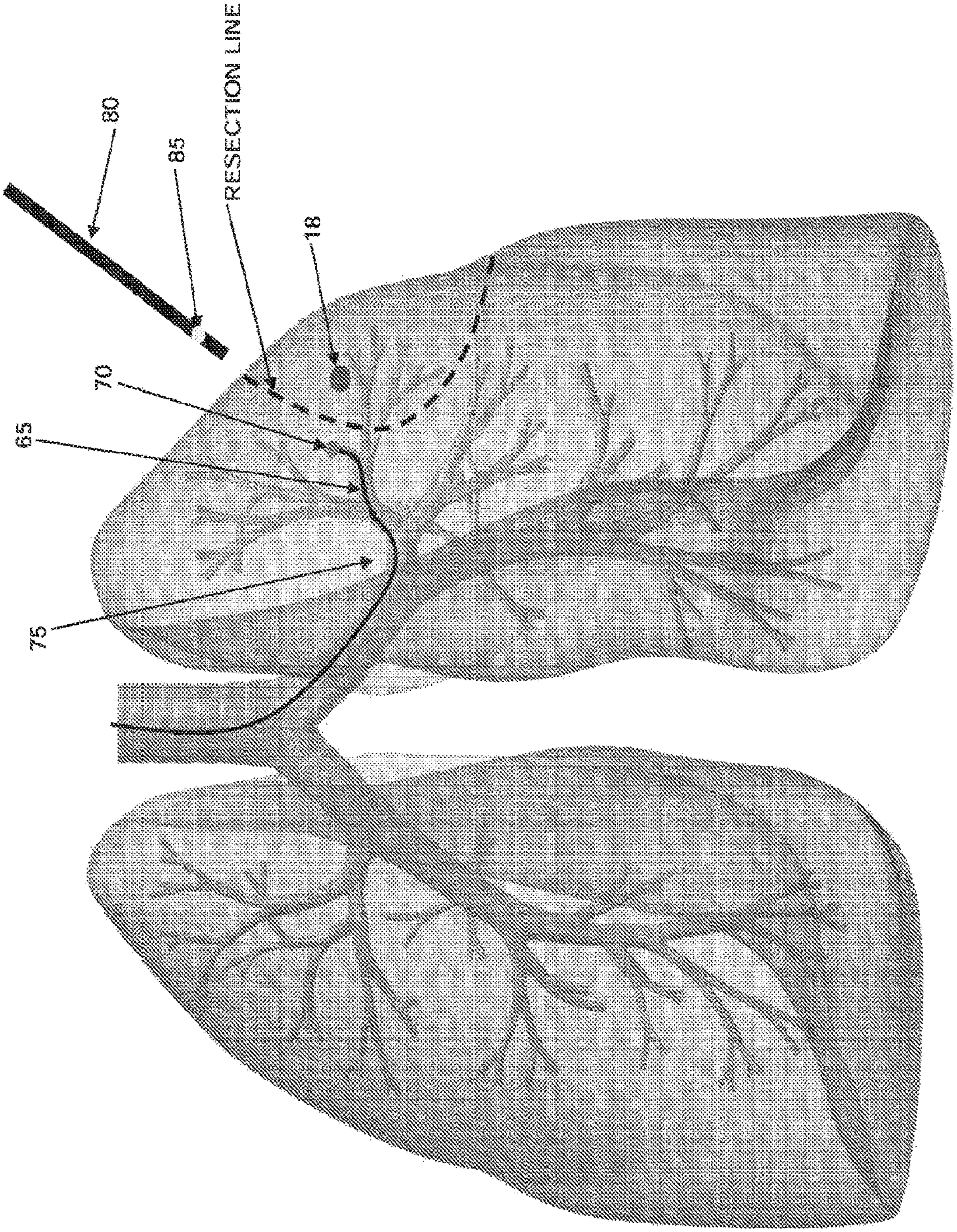
Figure 20:
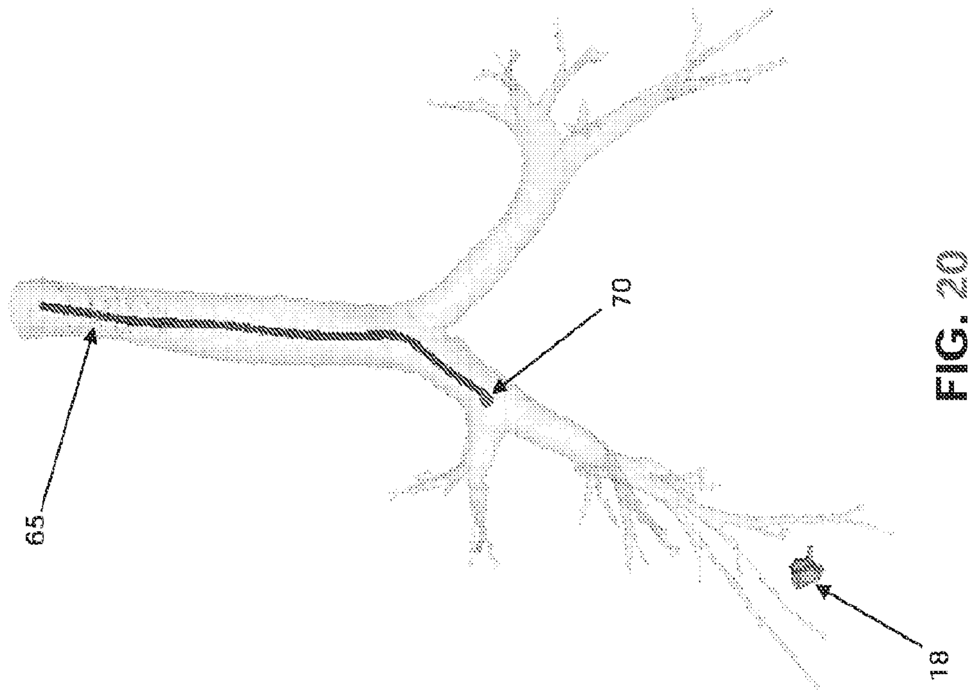
FIGS. 19-23 are schematic views showing how a tracked catheter can be used to identify the location of an airway.
Figure 19:
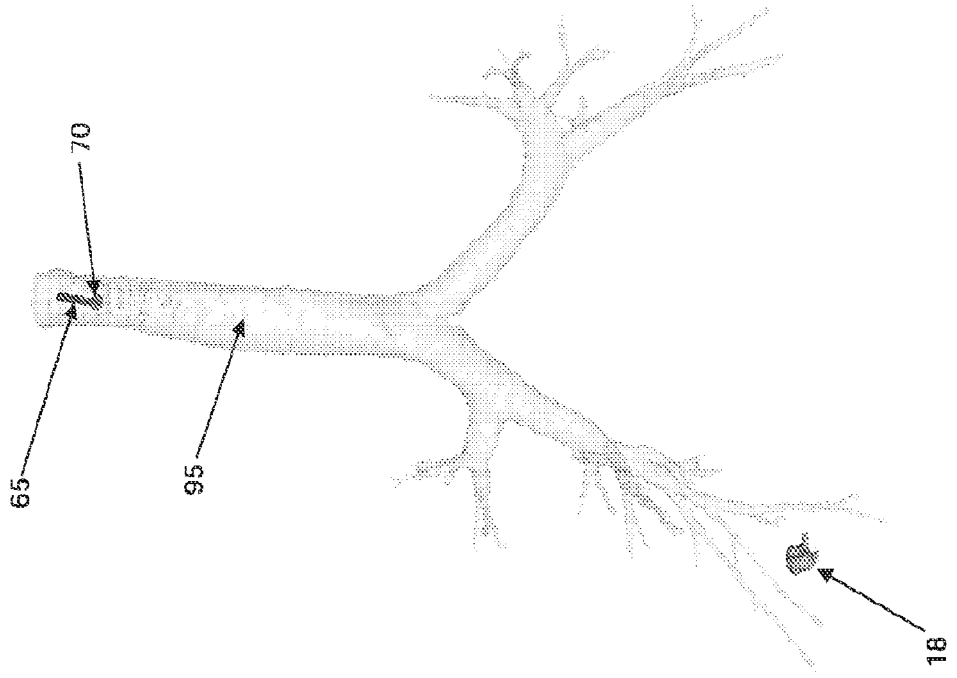
Figure 22:
Figure 21:
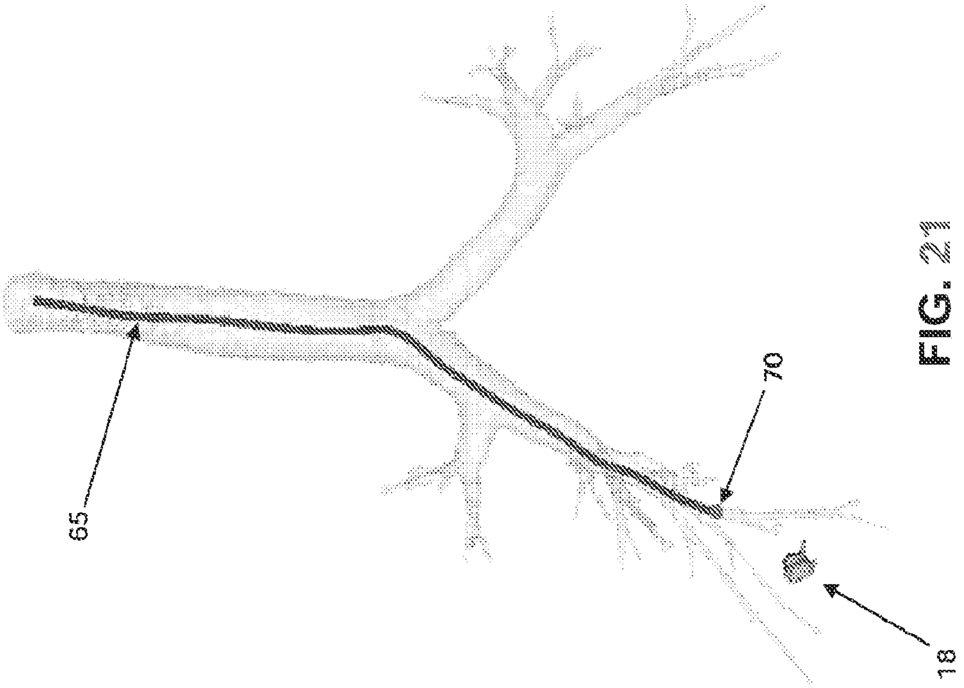

More particularly, and looking now at FIGS. 16-18, in this form of the invention, a bronchoscope 60 is used to position a catheter 65 carrying a sensor 70 (i.e., a "tracked catheter" 75) into a relevant airway of the lung. More particularly, in one form of the invention, the bronchoscope 60 can be advanced through the airways under bronchoscopic guidance or by some other form of guidance, e.g., CT imaging, C-arm imaging, etc. until the bronchoscope 60 is advanced as far as possible toward the relevant airway. See FIG. 16. Then a tracked catheter 75 (i.e., a catheter 65 carrying a sensor 70) is advanced down the bronchoscope 60 and then out the end of the bronchoscope 60 into the relevant airway of the lung. See FIG. 17. Note that, preferably, the tracked catheter 75 is not advanced through the bronchoscope 60 until after the bronchoscope 60 has been positioned in the lung in order to maintain maximum flexibility for the bronchoscope 60. Once the tracked catheter 75 has been advanced out the bronchoscope 60 and into position in the relevant airway, the bronchoscope 60 can be withdrawn. See FIG. 18. Withdrawal of the bronchoscope 60 is generally desirable at this point since it can impede ventilation.

The bronchoscopic positioning of a sensor in a relevant airway of the lung (i.e., by bronchoscopically positioning a tracked catheter in a relevant airway of the lung) can then be used to define the lobar, segmental or subsegmental bronchus for surgery such as segmentectomy, lobectomy or wedge resection during the actual operation. More particularly, the position of the sensor identifying the bronchus (i.e., the sensor 70 on the tracked catheter 75) can be correlated with the position of another device (e.g., a surgical instrument) 80 carrying another sensor 85 (i.e., a tracked instrument 90) so that the surgeon can use the system to identify the correct bronchus for surgery from the chest side of the operation (when direct visualization is limited and frequently ambiguous with respect to specific airways). Thus, in this form of the invention, one sensor 70 is positioned on a catheter 65 which is inserted into a specific airway so as to identify the location of that specific airway, and another sensor 85 is positioned on a surgical instrument 80 which is advanced for surgery from the chest side of the operation, and the system then tracks the position of the surgical instrument 80 vis-á-vis the tracked catheter 75 (and hence vis-á-vis the position of the airway in which the tracked catheter 75 is positioned). In this way, the surgeon can identify the location of the surgical instrument 80 relative to the airway of interest (which is identified by the sensor 70 on the tracked catheter 75), even though direct visualization from the chest side of the operation may be limited and ambiguous with respect to specific airways. As a result, the surgeon can use the system to target the airway identified by the sensor 70 on the tracked catheter 75, or to avoid the airway identified by the sensor 70 on the tracked catheter 75, etc.

Significantly, the tracked catheter 75 may be inserted into a relevant airway of the lung while the lung is in a first configuration (e.g., an inflated configuration) and maintained in position within that airway while the lung transforms to a second configuration (e.g., a deflated configuration). This can be particularly advantageous when trying to identify a relevant airway of the lung during a limited access surgical procedure (e.g., where visualization is provided by a scope advanced into the chest) and the lung transforms between a first configuration and a second configuration.

Note that, if desired, the tracked catheter 75 may be inserted into the bronchoscope 60 before the bronchoscope 60 is advanced down the airways of the lung. However, as noted above, it is generally desirable to insert the tracked catheter 75 into the bronchoscope 60 after the bronchoscope 60 has been positioned in the lung since this provides maximum flexibility to the bronchoscope 60.

Note also that, if desired, the bronchoscope 60 may be left in position in the lung after the tracked catheter 75 has been advanced into the relevant airway. However, as noted above, in many cases it is desirable to remove the bronchoscope 60 after the tracked catheter 75 has been advanced into the relevant airway since this provides better ventilation of the lung.

In addition to the foregoing, it should also be appreciated that, if desired, the bronchoscope 60 itself can carry a sensor (not shown), such that the bronchoscope 60 itself can be tracked in the airways of the lung. This approach can be useful where the bronchoscope 60 is able to advance into the airway of interest, e.g., where the airway of interest is a relatively large airway which can be directly accessed by the bronchoscope 60.

Note that, if desired, the tracked catheter 75 (and/or a tracked bronchoscope) may also be used to map a plurality of airways in the lung while the lung is in a given configuration (e.g., a first, inflated configuration).

In one form of the invention, a fiducial sensor 10 (e.g., a T-bar or J-bar assembly) is placed within the lung while the lung is in a first (e.g., inflated) configuration; a tracked catheter 75 is placed in a selected airway of the lung while the lung is in its first (e.g., inflated) configuration, the relative dispositions of the fiducial sensor 10 and the tracked catheter 75 are determined while the lung is in its first (e.g., inflated) configuration; the lung is transformed to a second (e.g., deflated) configuration; the relative dispositions of the fiducial sensor 10 and the tracked catheter 75 are determined while the lung is in its second (e.g., deflated) configuration; and the change in the relative dispositions of the fiducial sensor 10 and the tracked catheter 75 is determined after the lung transforms from its first (e.g., inflated) configuration to its second (e.g., deflated) configuration and used to estimate the extent of lung deformation and the location of lung structures when the lung is in its second (e.g., deflated) configuration.

Mapping and Tracking of the Surrounding Airways

The foregoing system can be enhanced by mapping and tracking the surrounding airways (along with the lesion) so as to ensure that the correct segment of the lung is excised. This is because during deflation of the lung, the anatomy will shift and the tissue section to be excised may not be obvious to the surgeon.

The procedure for mapping and tracking the airways of the lung may be done as follows.

Figure 23:
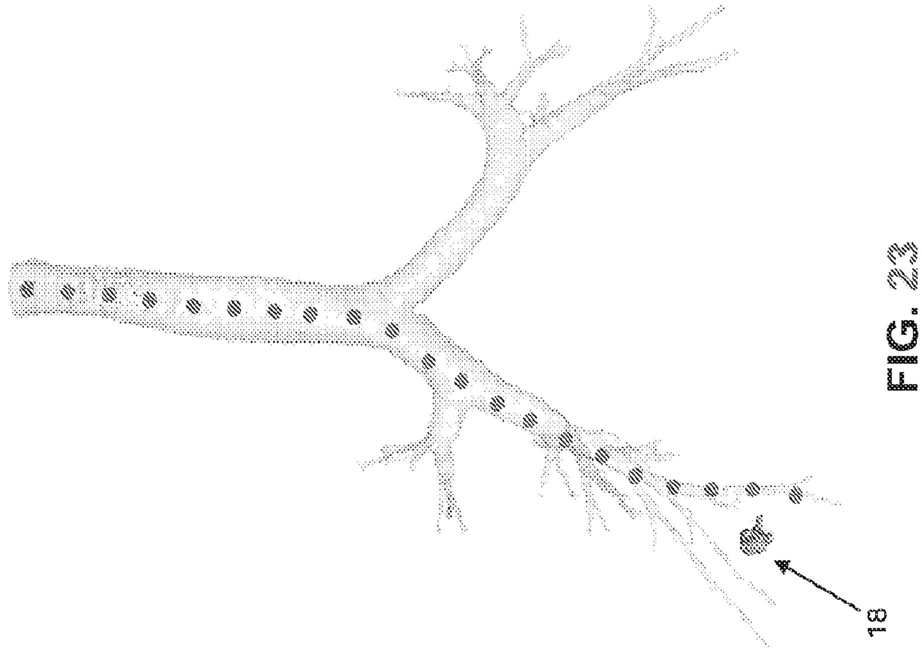

First, the patient is placed in the supine position. Then, bronchoscopically, a flexible catheter 65 having an on-board catheter sensor 70 is placed in the nearest/target bronchus of the lung segment containing the lesion 18. This is done either by identifying the correct bronchus visually or by some form of guidance (e.g., CT imaging, C-arm imaging, etc.). The tracked catheter 75 is inserted into the targeted bronchus near to the mass of the lesion 18, and as the catheter 65 is inserted, the trajectory of the catheter 65 is logged using the on-board catheter sensor 70 and an electromagnetic tracker system configured to identify the position and orientation of the catheter sensor 70 (and hence the position and orientation of the catheter 65). This trajectory marks the position of the airway 95 in the coordinate space of the electromagnetic tracker system. See FIGS. 19-22. The successive detected locations of the catheter sensor 70 as the catheter 65 advances down the airway 95 can be concatenated so as to provide the centerline of the targeted airway. See FIG. 23.

Figure 24:
FIGS. 24 and 25 are schematic views showing another way that a tracked catheter can be used to identify the location of an airway.
Figure 25:
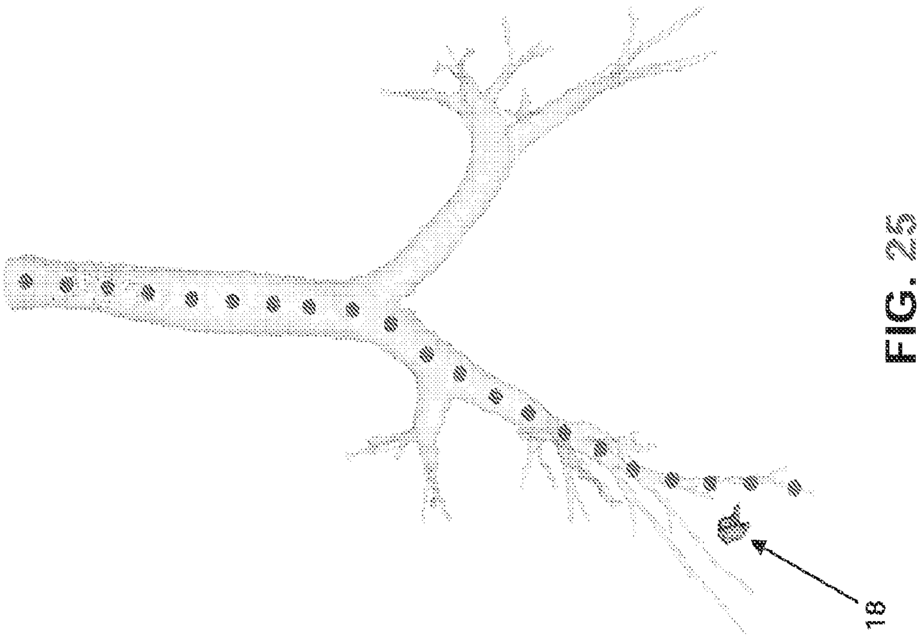

Alternatively, the catheter 65 can comprise a plurality of catheter trackers 70 located along its length so that airway mapping can be conducted by simply logging the locations of the various catheter sensors 70 after the catheter 65 has been fully inserted in an airway. See FIGS. 24 and 25. Note that the catheter 65 can be advanced through the airways under bronchoscopic guidance or by some other form of guidance, e.g., CT imaging, C-arm imaging, etc.

The process can then be repeated with adjacent airways so as to map out the airways surrounding the lesion.

Once the mapping of the relevant airways has been completed, the position of the fiducial sensor 10 (e.g., the T-bar or J-bar assembly or similar tracker) and mapped airways are recorded in the inflated lung (and, ultimately, in the deflated lung).

Figure 26:
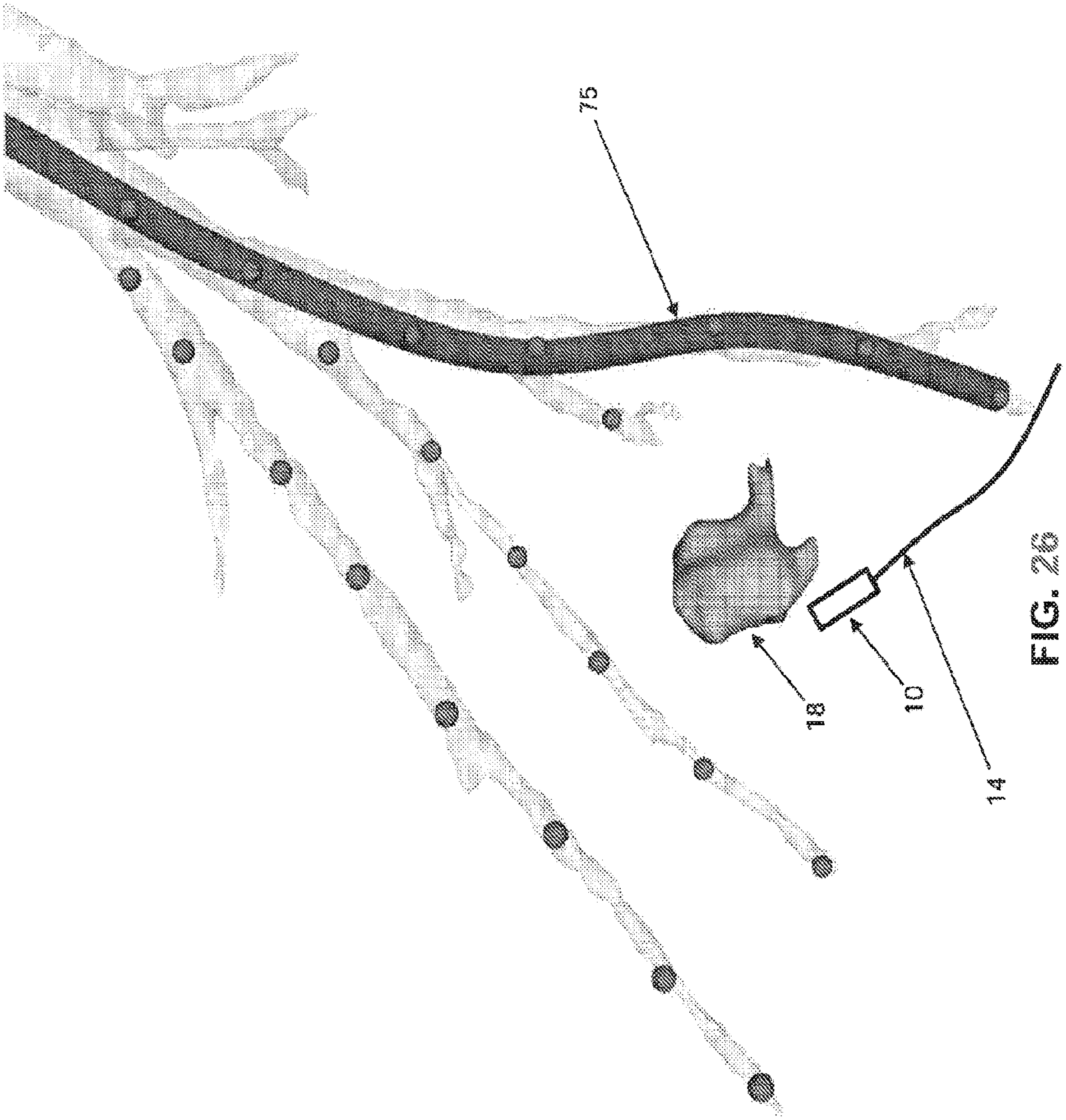
FIG. 26 is a schematic view showing an anatomical site containing a target tissue mass (e.g., a lesion), a fiducial sensor and a tracked catheter.

Thereafter, with a fiducial sensor 10 next to the lesion 18 and the tracked catheter 75 disposed in a critical airway near the lesion, the lung is collapsed prior to the start of the surgery. The fiducial sensor 10 (e.g., the T-bar or J-bar assembly) and the tracked catheter 75 are tracked in real-time as the lung is collapsed. See FIG. 26. The position of the fiducial sensor 10 (e.g., the T-bar or J-bar assembly) and the critical airway (e.g., the airway containing the tracked catheter 75) is recorded in the deflated lung. Using a finite element-based particle filter or FEM deformation algorithm, the spatial translation of the fiducial sensor 10 (e.g., the T-bar or J-bar assembly) and the critical airway from the inflated condition to the deflated condition is estimated. A smooth deformation field around the critical airway is estimated. The deformation field is then applied to the other airways mapped in the inflated lung so as to estimate the position of those other airways in the deflated lung. The "deformed" airways (i.e., the airways in the deflated lung) are displayed to the surgeon in the navigation system, along with the lesion, to precisely guide the surgical stapler 26 to the optimal resection margin while ensuring that critical anatomy is spared. This approach also, even without stapler navigation, helps define the correct segment for resection (as well as the correct bronchial segment to resect or not resect as part of the planned operation). Once the appropriate bronchial segment is identified in the thoracoscopic, or thoracic point of view, the catheter 65 may be removed prior to any surgical resection, by simply pulling it out of the airway from the mouth, nose or endotracheal tube.

In one aspect of the invention, a plurality of lumens in a deformable anatomical structure may be mapped and tracked by:

- providing a virtual model of the anatomical structure while the anatomical structure is in a first configuration;
- while the anatomical structure is in the first configuration, positioning a tracked catheter in one of the lumens in the anatomical structure which is to be mapped and tracked, and determining the position of the tracked catheter in that lumen so as to map the position of that lumen;

- repeating the foregoing step for each of the lumens in the anatomical structure which is to be mapped and tracked so that those lumens are mapped;
- supplementing the virtual model with the mapped lumens, whereby to provide a supplemented virtual model of the anatomical structure and the mapped lumens while the anatomical structure is in its first configuration;
- maintaining the tracked catheter in one of the mapped lumens of the anatomical structure as the anatomical structure is deformed from its first configuration to a second configuration;
- determining the position of the tracked catheter in the anatomical structure while the anatomical structure is in the second configuration; and
- modifying the supplemented virtual model so as to represent the anatomical structure and the mapped lumens while the anatomical structure is in its second configuration, whereby to provide a modified supplemented virtual model, wherein modification is effected by:
  - determining the spatial transformation of the tracked catheter as the anatomical structure deforms from its first configuration to its second configuration; and
  - applying the spatial transformation of the tracked catheter to the mapped lumens of the supplemented virtual model so as to provide the modified supplemented virtual model of the anatomical structure and the mapped lumens while the anatomical structure is in its second configuration.

In another aspect of the invention, a selected lumen in a deformable anatomical structure may be mapped and tracked by:

- positioning a tracked catheter in the selected lumen of the anatomical structure while the anatomical structure is in a first configuration;
- determining the position of the tracked catheter while the anatomical structure is in the first configuration;
- scanning the anatomical structure and the tracked catheter positioned in the selected lumen of the anatomical structure while the anatomical structure is in the first configuration;
- creating a virtual model of the scanned anatomical structure and the tracked catheter positioned in the selected lumen of the anatomical structure while the anatomical structure is in its first configuration,
- maintaining the tracked catheter in position within the selected lumen of the anatomical structure while the anatomical structure deforms to a second configuration;
- determining the position and orientation of the tracked catheter while the anatomical structures is in its second configuration, whereby to determine the position of the selected lumen of the anatomical structure while the anatomical structure is in the second configuration; and
- adjusting the virtual model so as to represent the anatomical structure and the selected lumen while the anatomical structure is in its second configuration, whereby to provide an adjusted virtual model, wherein modification is effected by:
  - determining the spatial transformation of the tracked catheter as the anatomical structure deforms from its first configuration to its second configuration; and
  - applying the spatial transformation of the tracked catheter to the selected lumen of the virtual model so as to provide the adjusted virtual model of the anatomical structure and the selected lumen while the anatomical structure is in its second configuration.

Bronchoscopic Deployment Of The Fiducial Sensor

Figure 27:
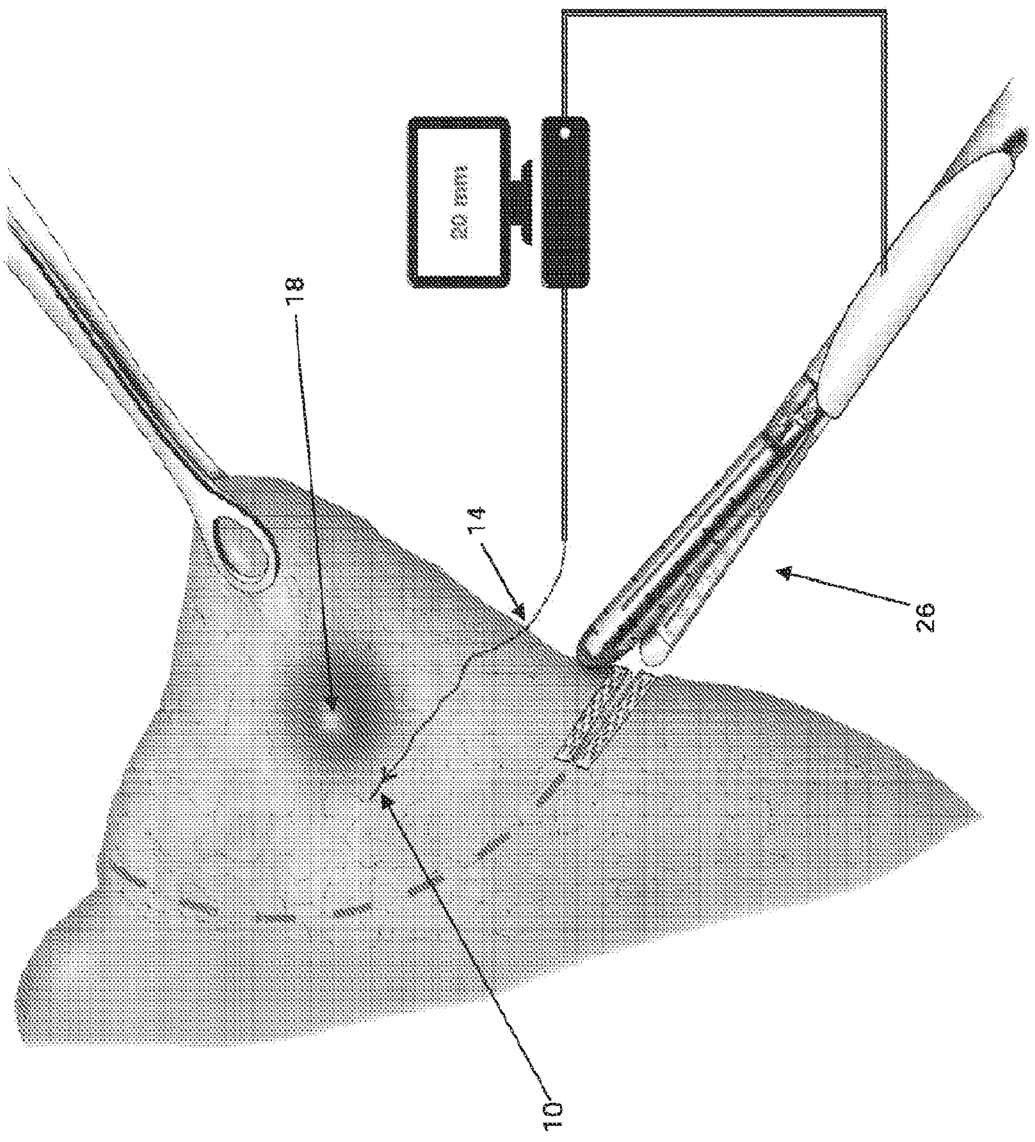
FIG. 27 is a schematic view showing a fiducial sensor deployed using a percutaneous access.

In the system described above, the fiducial sensor 10 (e.g., the T-bar or J-bar assembly) is described as being deployed percutaneously. See FIG. 27. However, if desired, the fiducial sensor 10 (e.g., the T-bar or J-bar assembly) can be deployed via a bronchoscopic approach, or open chest approach or VATS approach.

Figure 28:
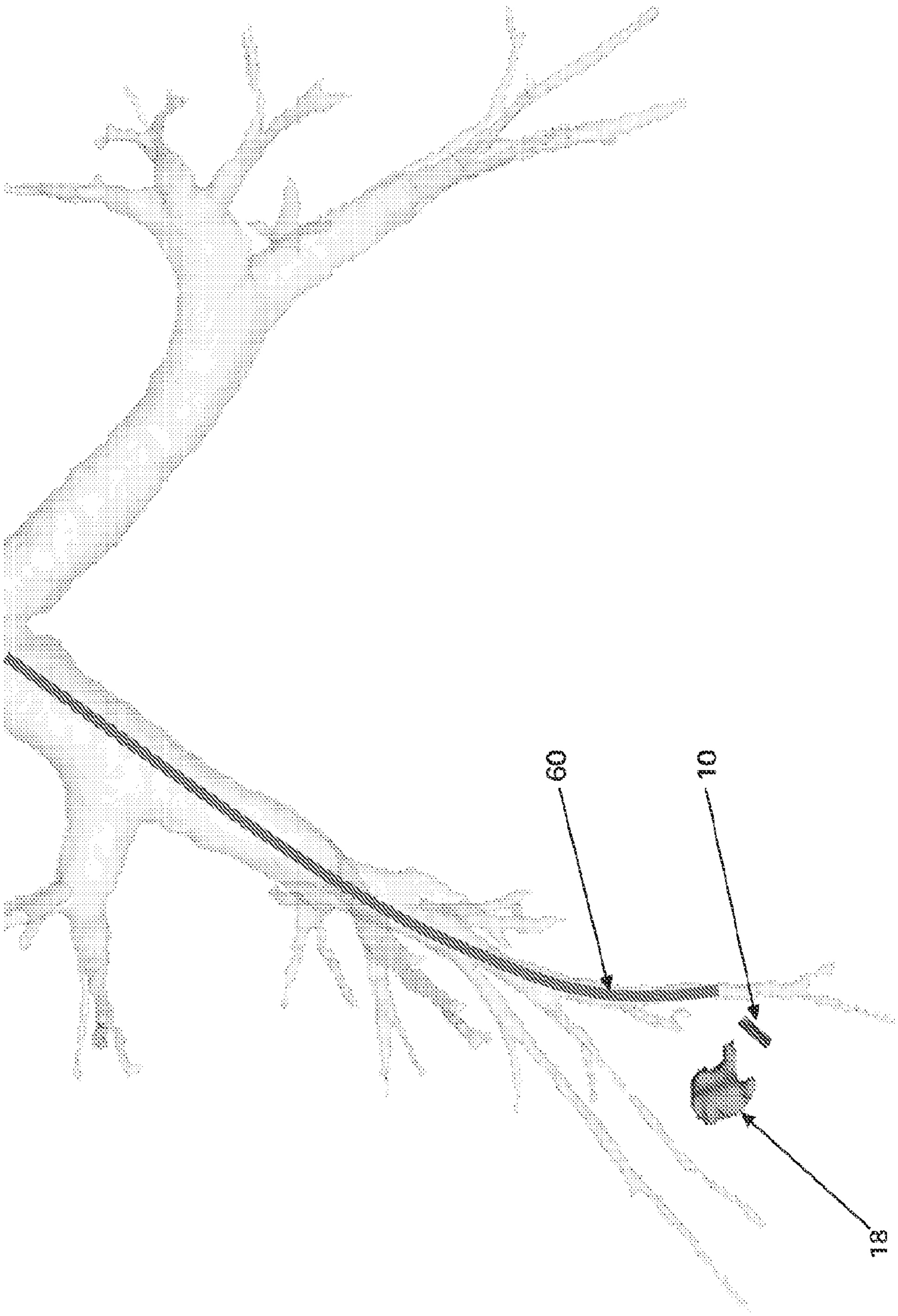
FIGS. 28 and 29 are schematic views showing a wireless fiducial sensor deployed through a bronchoscope.
Figure 29:
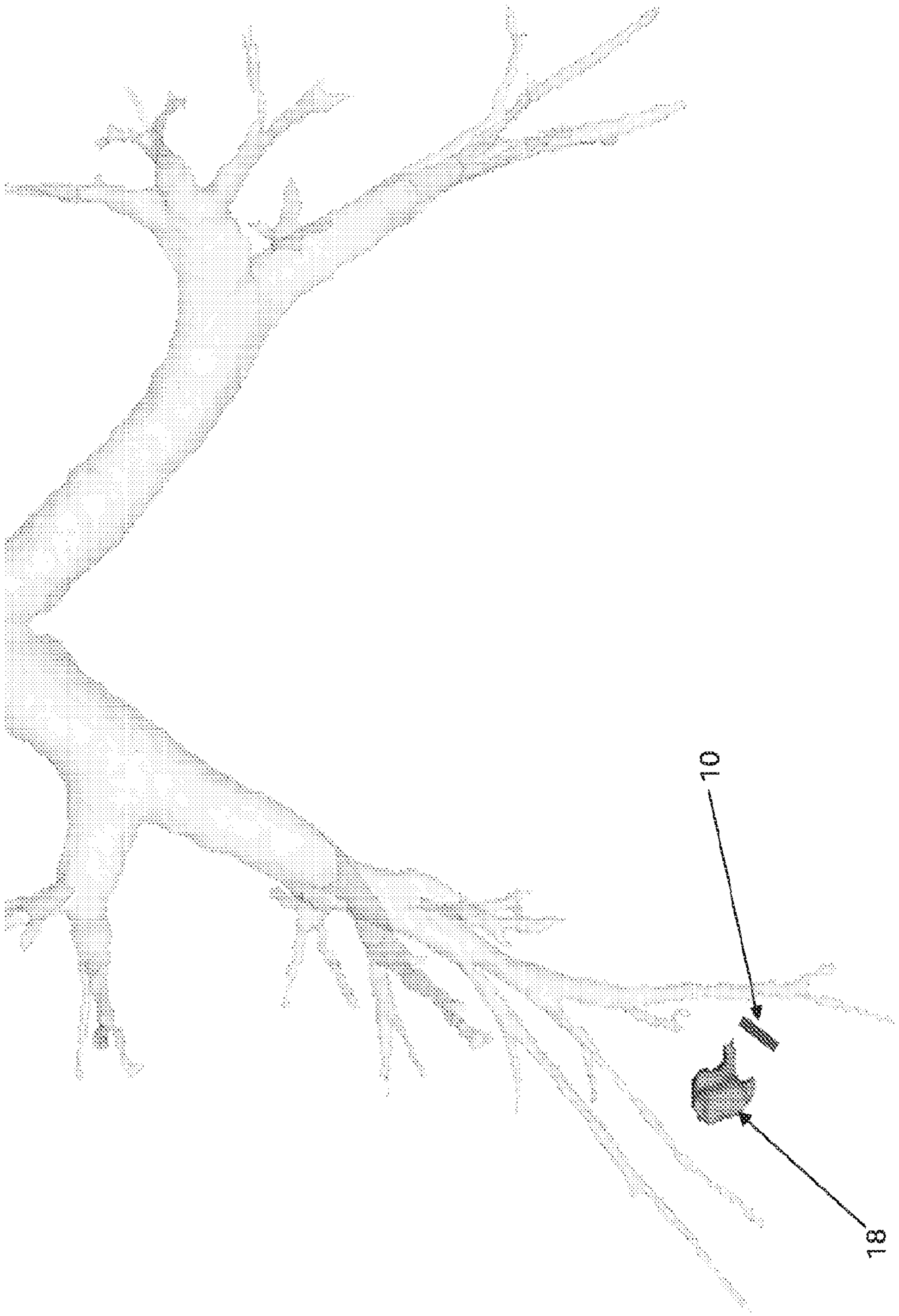

More particularly, the fiducial sensor 10 (e.g., the T-bar or J-bar assembly) is a metal anchor with a wireless electromagnetic sensor embedded within a hook-like structure. The metal anchor could be made from superelastic material, for example nitinol, or it could be made from stainless steel. The fiducial sensor 10 (e.g., the T-bar or J-bar assembly) is placed within a long flexible hollow tube with a bevel tip at the end. This hollow tube is inserted through the working channel of the bronchoscope 60. Under real-time image guidance using the navigation system, the wireless fiducial sensor 10 (e.g., the T-bar or J-bar assembly) is navigated through the airways using the bronchoscope 60 and placed close to the lesion. See FIG. 28. Once the fiducial sensor 10 (e.g., the T-bar or J-bar assembly) has been deployed close to the lesion 18, the bronchoscope 60 (and the hollow tube extending through the working channel of the bronchoscope) is removed. See FIG. 29. Thereafter, the lung is collapsed and the lesion 18 is tracked in real-time using the fiducial sensor 10 (e.g., the T-bar or J-bar assembly). The surgical stapler (not shown) is also tracked in real-time using the instrument sensor attached to the surgical stapler. Note that the surgical stapler is tracked in the same reference frame as the fiducial sensor 10 (e.g., the T-bar or J-bar assembly). The surgical stapler can then be navigated to the optimal resection margin using the navigation system.

Figure 30:
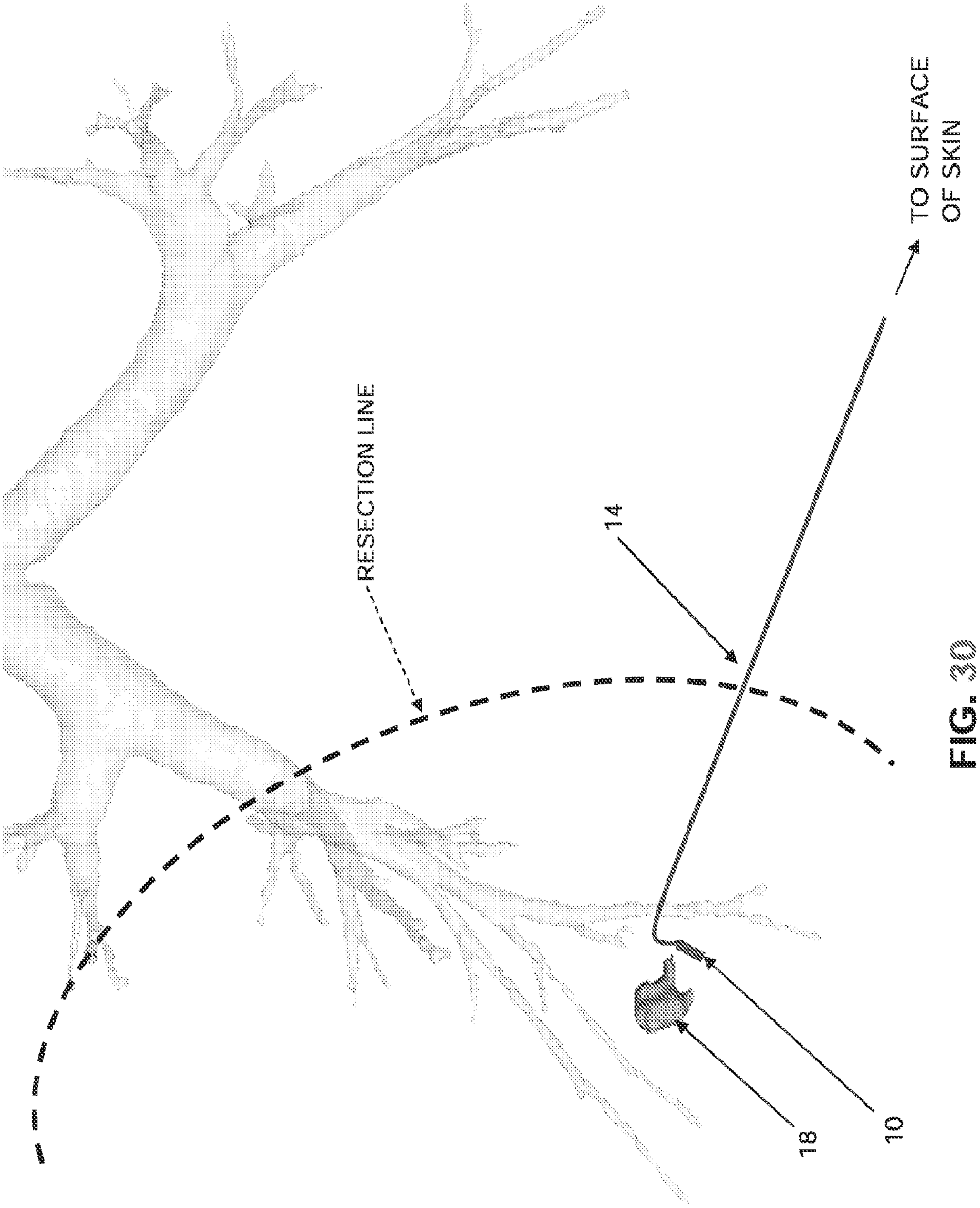
FIG. 30 is a schematic view showing a wire-based fiducial sensor deployed through a bronchoscope and having its wire then pushed bronchoscopically, under image guidance, through the lung parenchyma to the surface of the skin.

Alternatively, if desired, the fiducial sensor 10 (e.g., the T-bar or J-bar assembly) could carry a wire-based electromagnetic sensor. In this case, after the fiducial sensor 10 (e.g., the T-bar or J-bar assembly) has been deployed, the wire 14 of the fiducial sensor is then pushed bronchoscopically, under image guidance, through the lung parenchyma to the surface of the skin at the nearest spot to the lesion 18 so as to mark the lesion 18. See FIG. 30.

Figure 31:
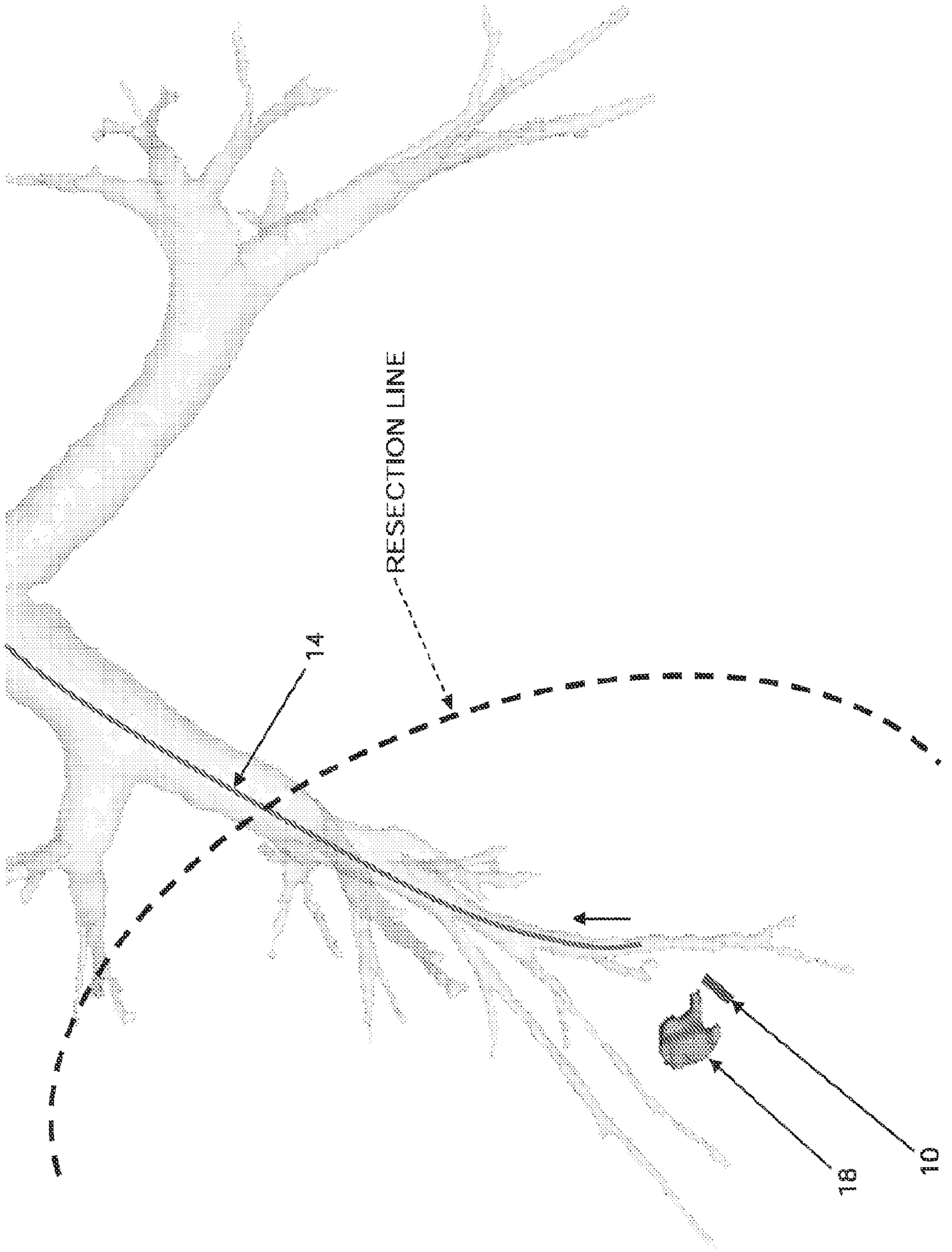
FIG. 31 is a schematic view showing a wire-based fiducial sensor deployed through a bronchoscope and having its wire thereafter detached from the fiducial sensor and withdrawn up the airway.

In still another form of the invention, where the fiducial sensor 10 (e.g., the T-bar or J-bar assembly) carries a wire-based electromagnetic sensor, the wire 14 has a detachable connection to the electromagnetic sensor. Then, after the stapler has been used to establish the resection line, the wire 14 is detached from the electromagnetic sensor and pulled back up the airway. See FIG. 31.

In yet another form of the invention, and looking now at FIGS. 32-42, a bronchoscopic sensor unit 100 is provided for bronchoscopic deployment of fiducial sensor 10 into target tissue mass 18 or adjacent to target tissue mass 18.

Figure 32:
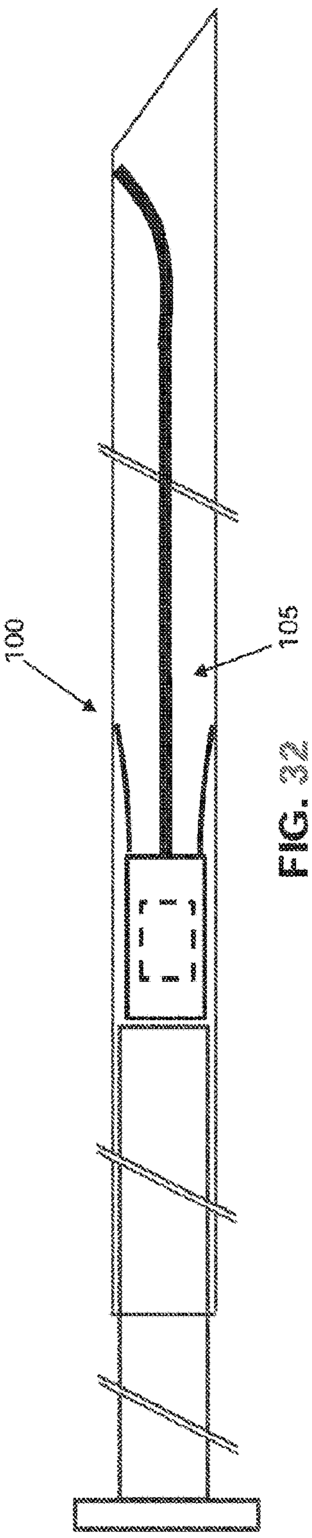
FIGS. 32-34 are schematic views showing apparatus for another approach for bronchoscopic deployment of the fiducial sensor into tissue (e.g., bronchoscopic deployment of the fiducial sensor into the target tissue mass or adjacent to the target tissue mass).
Figure 33:
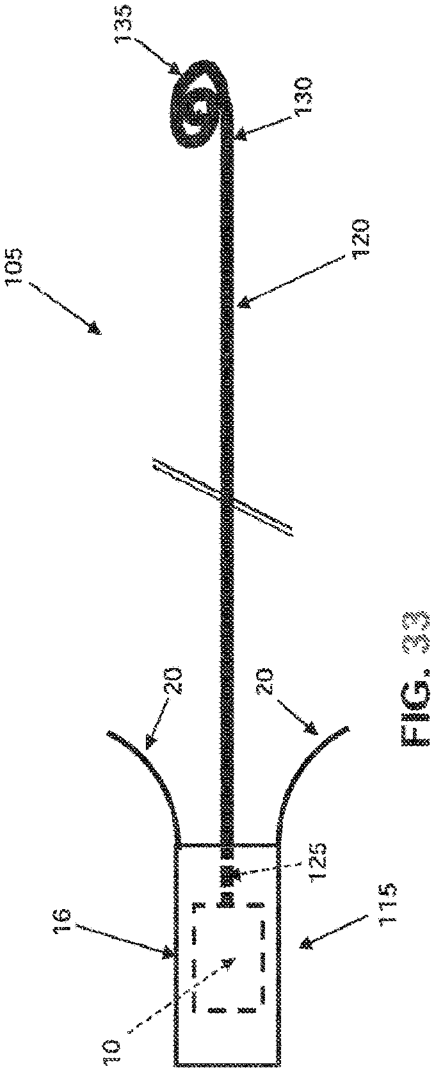
Figure 34:
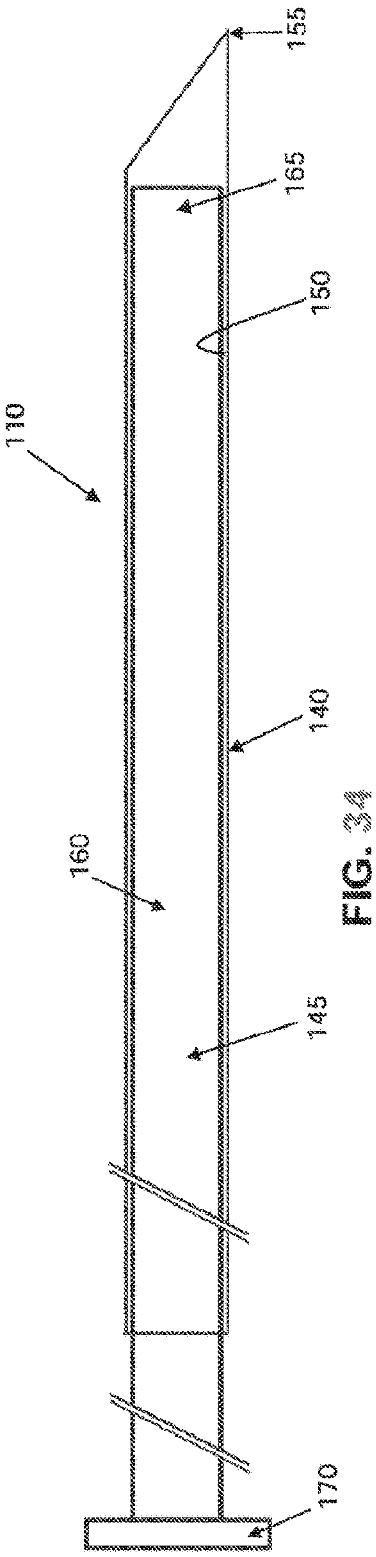
Figure 35:
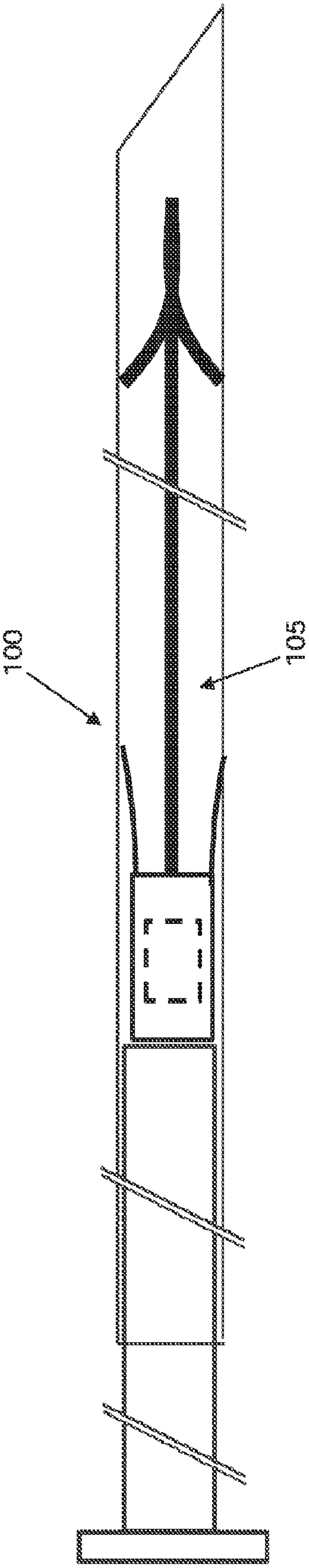
FIGS. 35 and 36 are schematic views showing another apparatus for bronchoscopic deployment of the fiducial sensor into tissue (e.g., bronchoscopic deployment of the fiducial sensor into the target tissue mass or adjacent to the target tissue mass).
Figure 36:
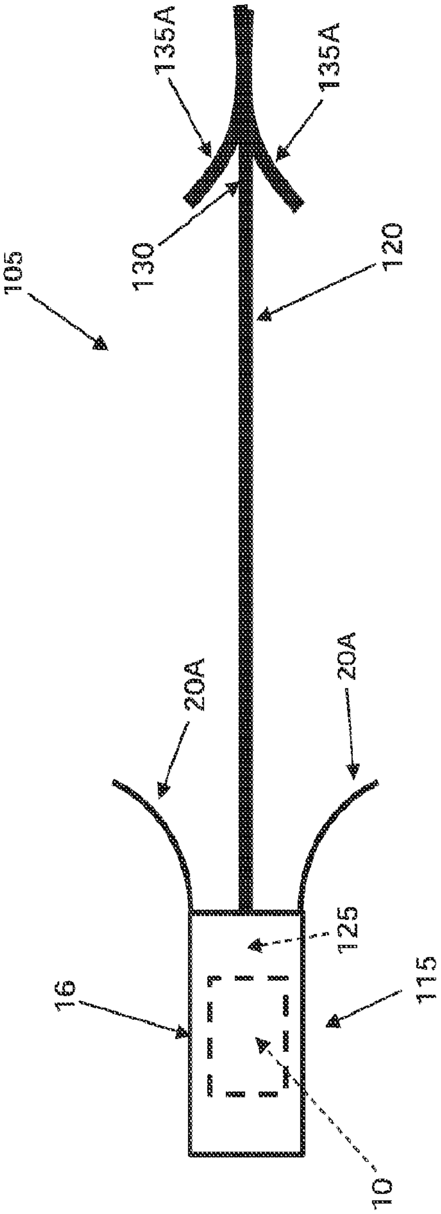
Figure 37:
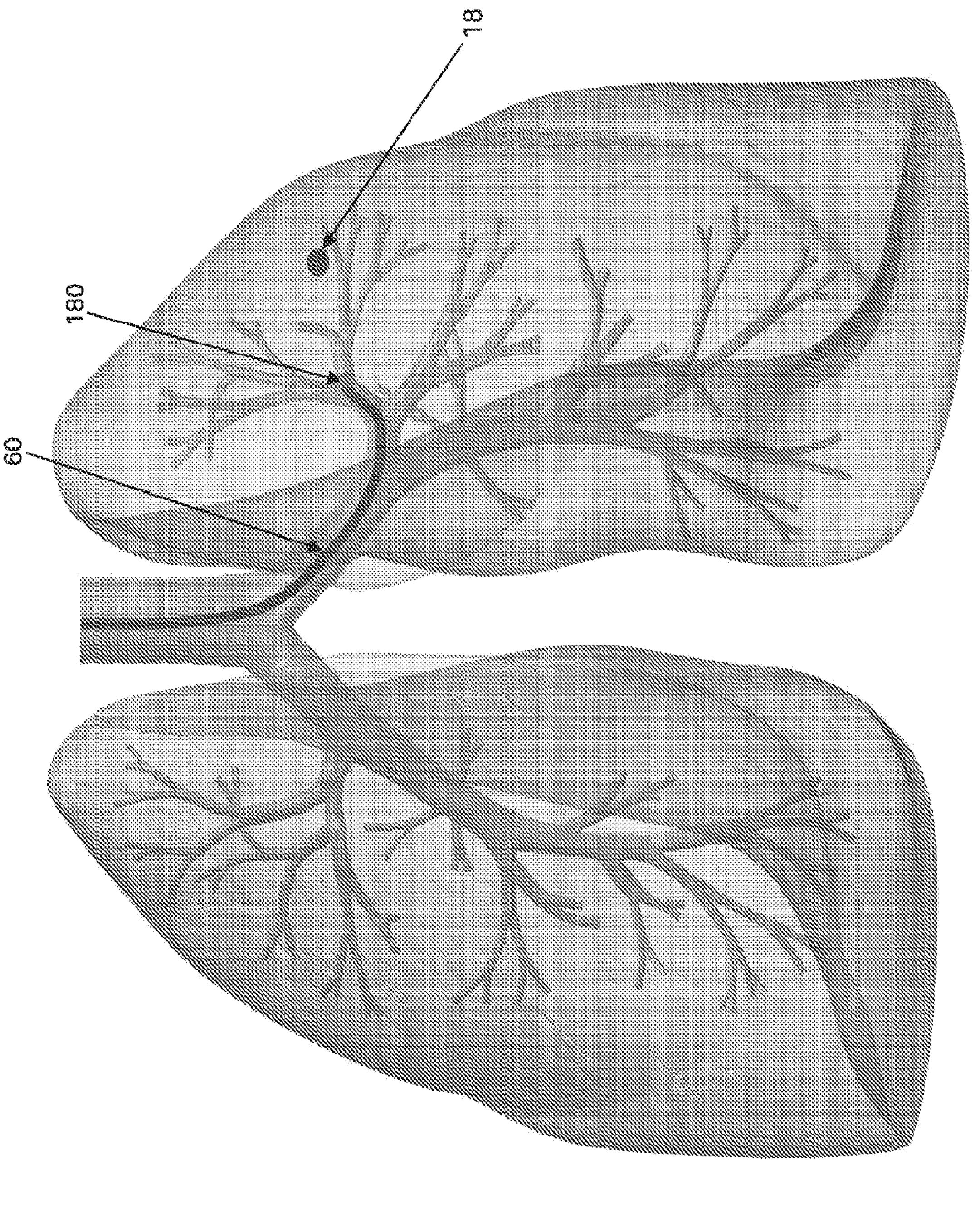
FIGS. 37-42 are schematic views showing how the apparatus of FIGS. 32-34 may be used for bronchoscopic deployment of the fiducial sensor into tissue (e.g., bronchoscopic deployment of the fiducial sensor into the target tissue mass or adjacent to the target tissue mass).
Figure 38:
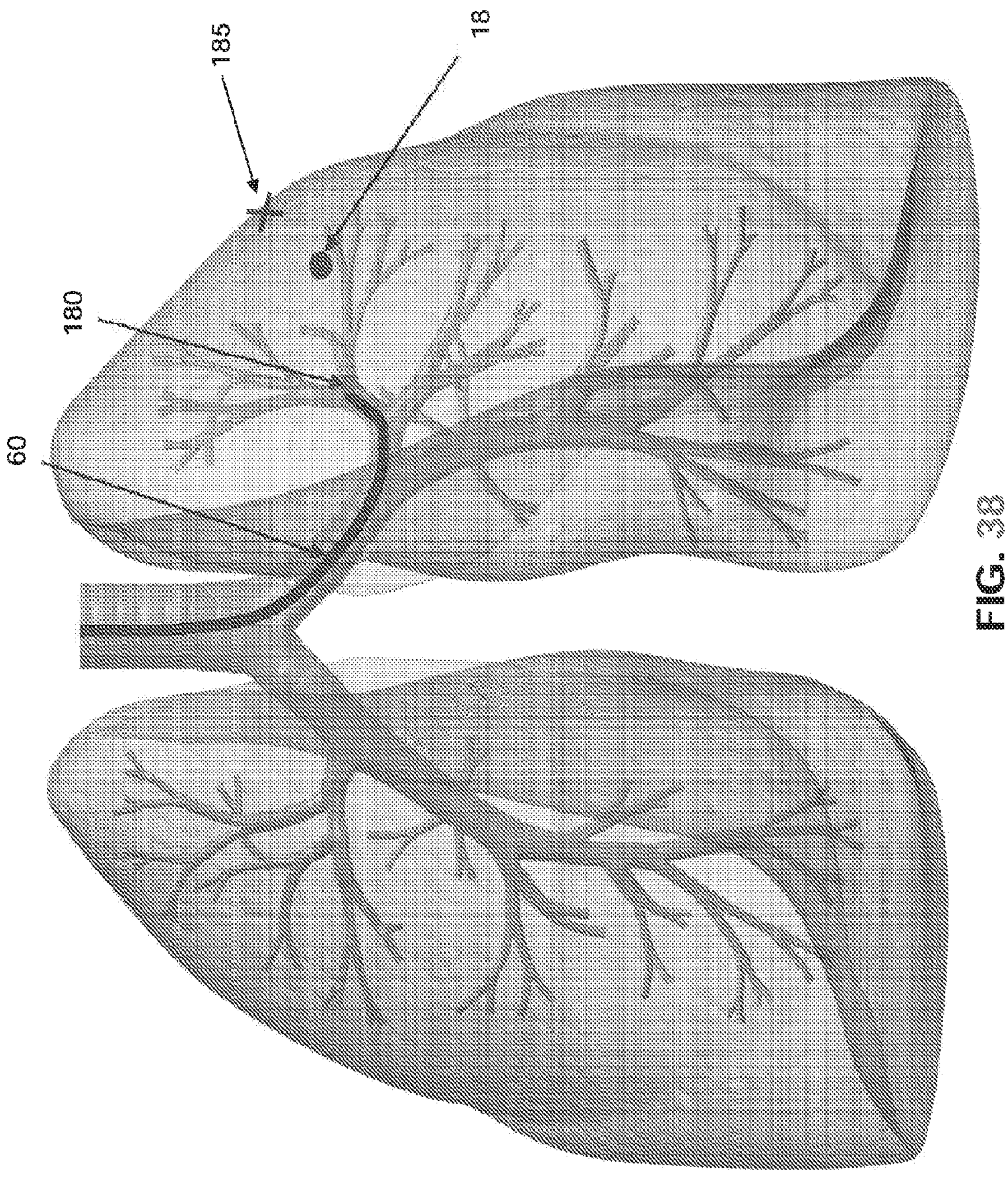
Figure 39:
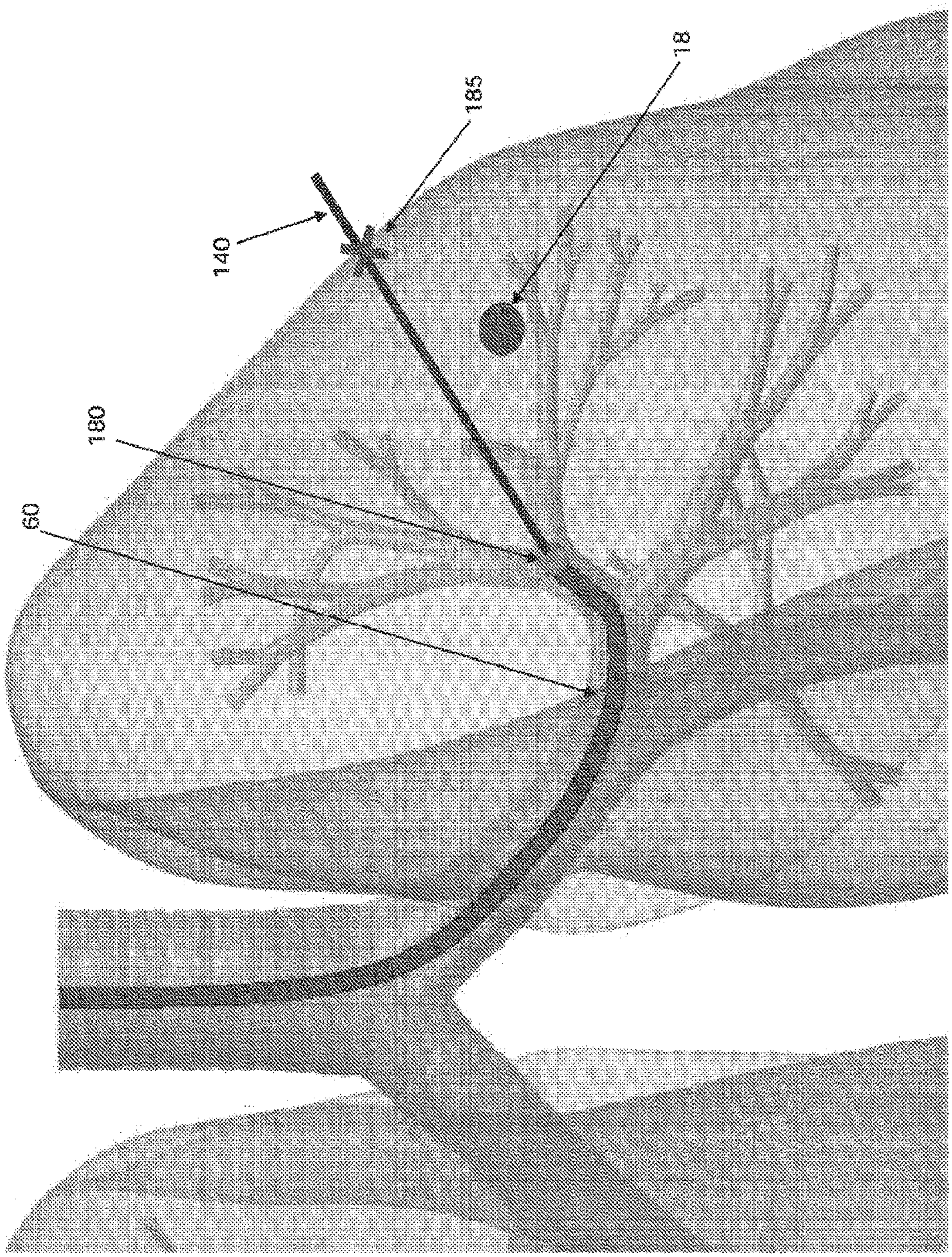
Figure 40:
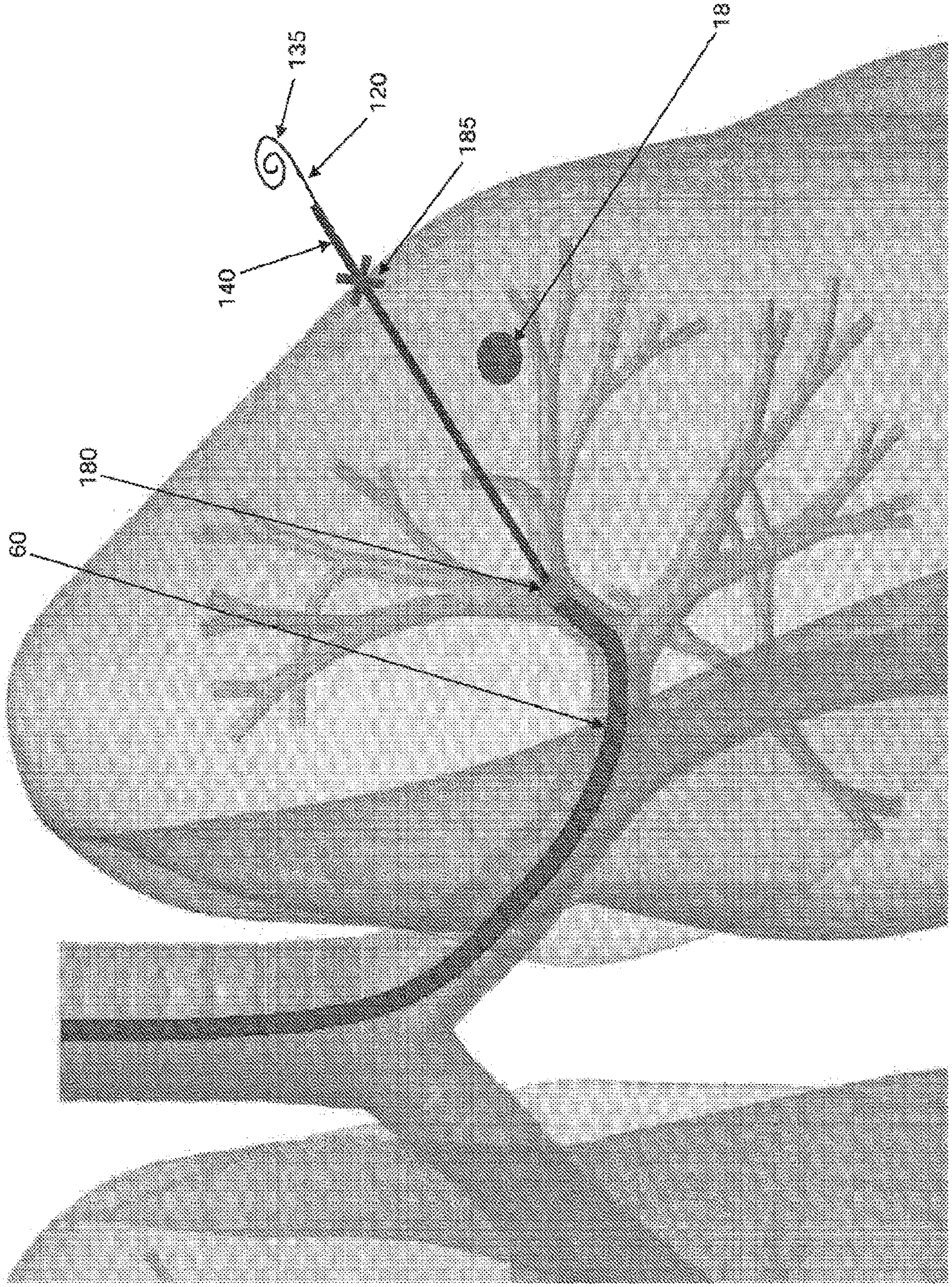
Figure 41:
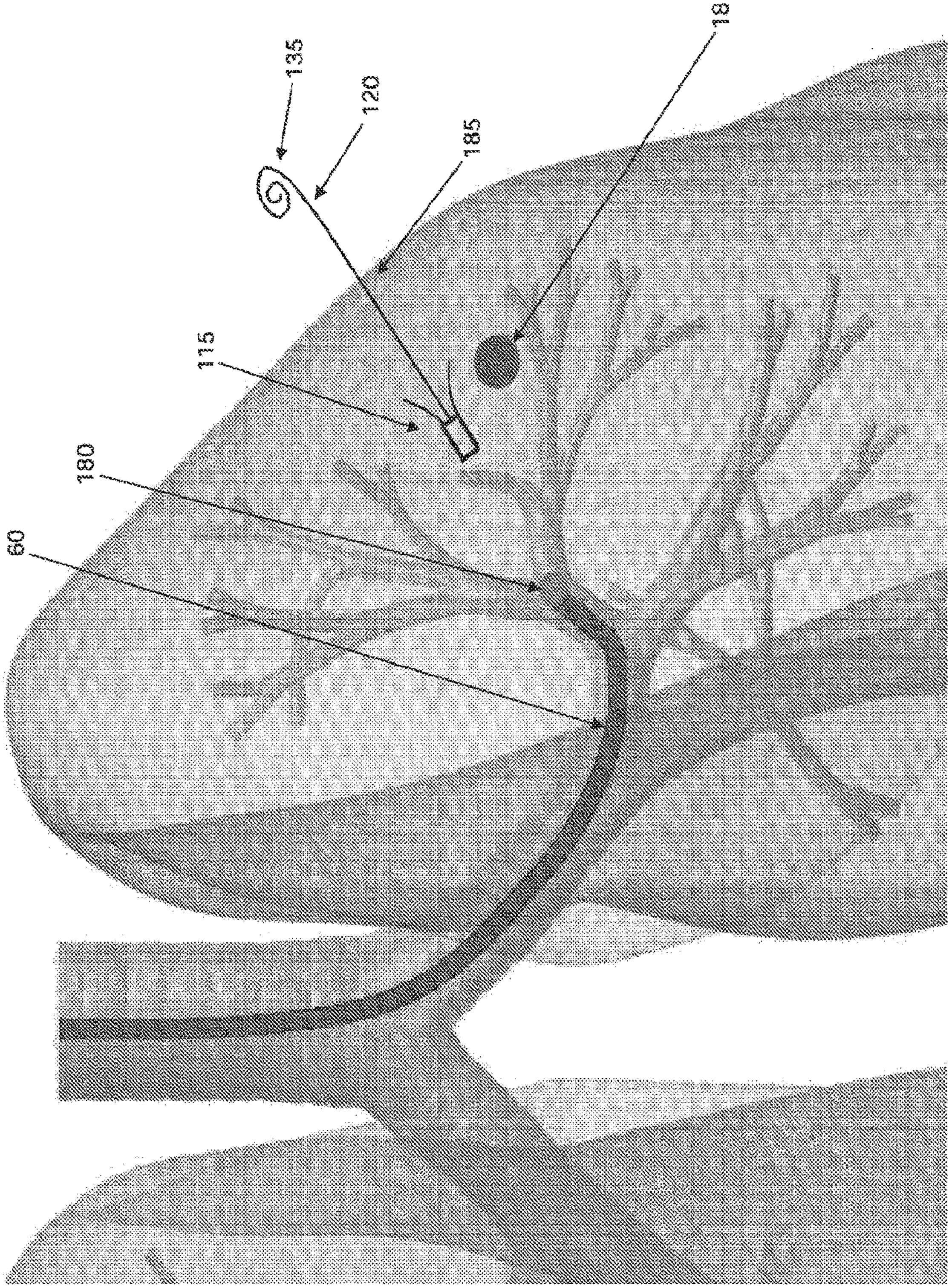
Figure 42:
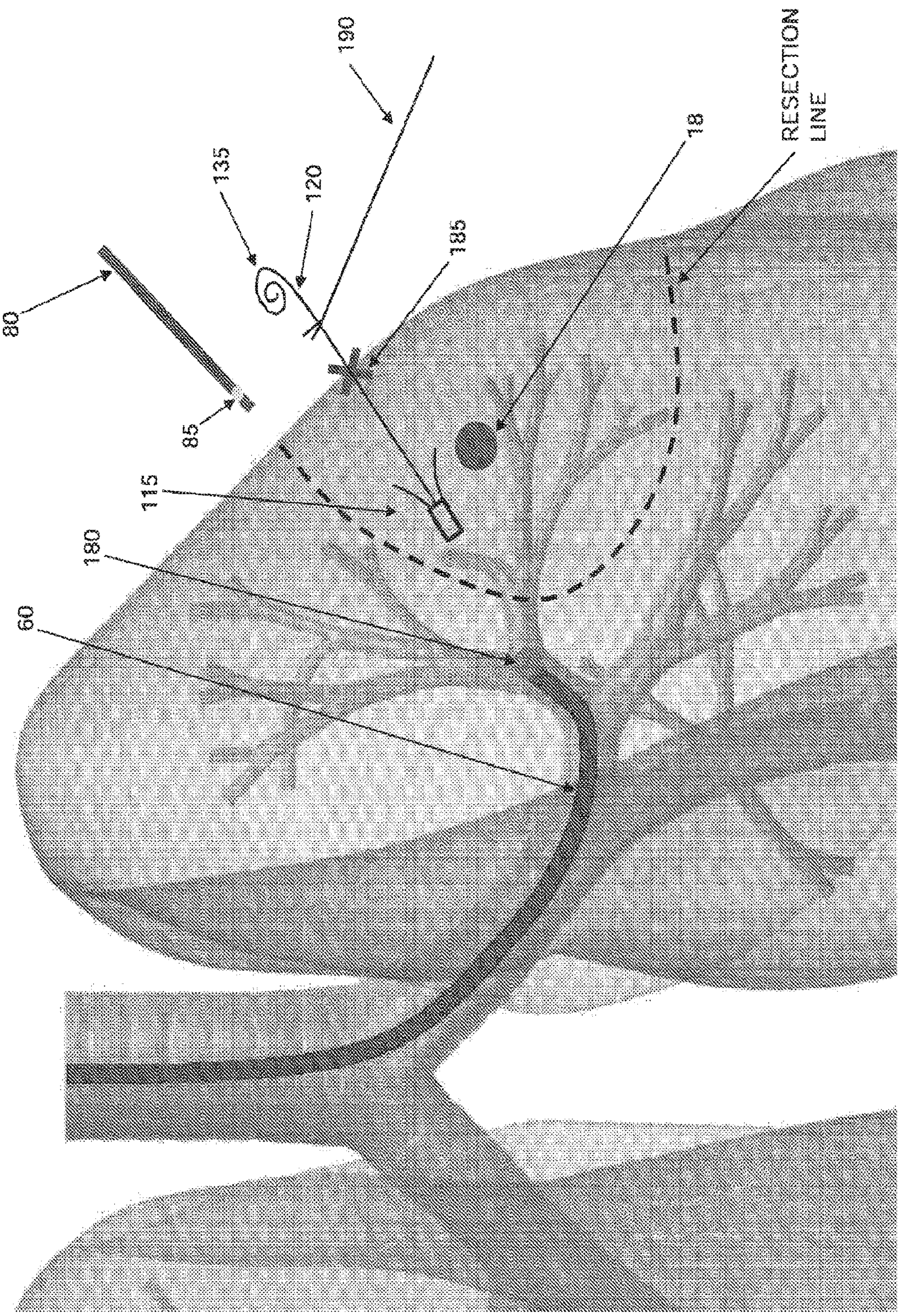

More particularly, and looking now at FIGS. 32-34, bronchoscopic sensor unit 100 (FIG. 32) generally comprises a J-bar and electrical lead assembly 105 (FIG. 33) and a deployment assembly 110 (FIG. 34).

J-bar and electrical lead assembly 105 generally comprises a J-bar assembly 115 and an electrical lead 120. J-bar assembly 115 comprises the aforementioned hook structure 16 which carries the aforementioned fiducial sensor 10 and the aforementioned prongs 20. One end 125 of electrical lead 120 is connected to fiducial sensor 10 such that electrical power delivered to electrical lead 120 can power fiducial sensor 10. The other end 130 of electrical lead 120 comprises an atraumatic tip 135. Electrical lead 120 may be covered with a hydrophobic braided wire to allow for easy insertion and retraction of J-bar and electrical lead assembly 105 through lumen 150 (see below) of deployment assembly 110.

Alternatively, if desired, instead of an atraumatic tip 135, the distal end of J-bar and electrical lead assembly 105 may comprise a second anchor that could prevent electrical lead 120 from re-entering the lung once the distal end of electrical lead 120 has emerged from the lung. In other words, this second anchor would prevent retrograde movement of the distal end of electrical lead 120 after deployment. Furthermore, in such a form of the invention, prongs 120 of J-bar assembly 115 could have a configuration which prevents antegrade movement of J-bar assembly 115 once it is released from deployment assembly 110. See, for example, FIGS. 35 and 36, which show prongs 135A at the distal end of electrical lead 120, and prongs 20A at the distal end of J-bar assembly 115, with prongs 135A preventing post-deployment proximal movement of the distal end of electrical lead 120 and prongs 20A preventing post-deployment distal movement of J-bar assembly 115.

Deployment assembly 110 comprises a needle cannula 140 and a pusher 145. Needle cannula 140 comprises a hollow lumen 150 and terminates in a sharp tip 155. Pusher 145 comprises a shaft 160. One end of shaft 160 ends in a blunt distal end 165. The other end of shaft 160 terminates in a handle 170. Shaft 160 of pusher 145 is sized to be slidably received in lumen 150 of needle cannula 140. Note that needle cannula 140 of deployment assembly 110 is sized so that it can be inserted through the working channel of a bronchoscope.

As seen in FIG. 32, J-bar and electrical lead assembly 105 and shaft 160 of pusher 145 are initially disposed within lumen 150 of needle cannula 140, with prongs 20 of J-bar assembly 115 being elastically deformed into a straighter configuration so as to be received within lumen 150 of needle cannula 140, and with the proximal ends of the elastically deformed prongs 20 residing just distal to blunt end 165 of pusher 145. Note also that when J-bar and electrical lead assembly 105 is disposed within lumen 150 of needle cannula 140, atraumatic tip 135 of electrical lead 120 is elastically deformed so that it sits substantially straight within needle cannula 140 (note that FIG. 32 is intended to be schematic in nature, and in practice electrical lead 120 has a diameter which more closely fills lumen 150 of needle cannula 140, such that atraumatic tip 135 of electrical lead 120 sits substantially straight when it is confined within needle cannula 140, and returns to the coiled configuration shown in FIG. 33 when atraumatic tip 135 is not confined within needle cannula 140). In this way, needle cannula 140 can carry J-bar and electrical lead assembly 105, with needle cannula 140 shielding J-bar and electrical lead assembly 105 from contact with surrounding structures (e.g., a bronchoscope, tissue, etc.). However, distal movement of pusher 145 can eject J-bar and electrical lead assembly 105 from lumen 150 of needle cannula 140.

In a method of use, the intended position of J-bar and electrical lead assembly 105 vis-á-vis the anatomy of the patient is planned prior to deployment in the lung using diagnostic or intraprocedural CT, C-arm CT, MRI or other imaging modalities, i.e., the intended position of J-bar assembly 115, and the exit point of electrical lead 120 as it emerges from the lung surface, are planned in advance on diagnostic or intraprocedural CT, C-arm CT, MRI or other imaging modalities. The electromagnetic (EM) tracking coordinates are mapped to the diagnostic/intraprocedural imaging coordinates using image registration algorithms well known in the art to track the bronchoscope and J-bar and electrical lead assembly 105 in the imaging coordinates. The position of J-bar assembly 115 is chosen to be in the proximity of the target tissue mass (i.e., tumor), preferably along the line joining the bronchoscope target position and the exit position of the electrical lead, while the exit point of electrical lead 120 from the lung is chosen to be (i) the shortest path from the J-bar location to the lung surface (or the fissure surface), or (ii) according to surgeon preference.

By way of example but not limitation, in a method of use, and looking now at FIGS. 37-42, a bronchoscope 60 is advanced through the airways of the patient until the distal tip of bronchoscope 60 is disposed near the lesion (i.e., the target tissue mass) 18. See FIG. 37. Note that bronchoscope 60 may be advanced under direct visualization and its position may be tracked using one or more sensors 180 carried by bronchoscope 60. Alternatively, the position of bronchoscope 60 may be tracked using J-bar assembly 115, provided that a temporary electrical connection is provided for J-bar assembly 115 (i.e., via an electrical connection extending through the interior of needle cannula 140, such as by electrifying a portion of pusher 145). The position of the tracked bronchoscope 60 can be mapped to the imaging coordinates (see above) using image registration algorithms of the sort well known in the art in order to guide the bronchoscope 60 to the lesion 18.

Next, if it has not already been done, a target point 185 is identified on the outer surface of the lung as the point where it is desired that needle cannula 140 will emerge from the lung and enter the pleural space. See FIG. 38.

Then bronchoscopic sensor unit 100 (comprising deployment assembly 110 and its passenger J-bar and electrical lead assembly 105) has its distal end advanced through bronchoscope 60, through the lung, through target point 185 and into the pleural space. See FIG. 39. Note that the distal end of bronchoscopie sensor unit 100 can be guided visually via bronchoscope 60, and/or via scanner visualization (e.g., CT imaging, C-arm imaging, ultrasound imaging, etc.), or by using the temporarily-electrically-connected J-bar assembly 115, if a temporary electrical connection has been established through the interior of needle cannula 140.

Next, pusher 145 of deployment assembly 110 may be used to push J-bar and electrical lead assembly 105 distally so that (i) atraumatic tip 135 and a portion of electrical lead 120 pass out of needle cannula 140 and into the pleural space, and (ii) J-bar assembly 115 is disposed adjacent to lesion 18 (note, however, that at this point J-bar assembly 115 and a portion of electrical lead 120 remain within needle cannula 140). See FIG. 40.

Next, needle cannula 140 is retracted proximally while maintaining pusher 145 in position, thereby exposing (i) the portion of electrical lead 120 extending from target point 185 to J-bar assembly 115, and (ii) J-bar assembly 115. As needle cannula 140 retracts past prongs 20 of J-bar assembly 115, prongs 20 are no longer constrained within lumen 150 of needle cannula 140 and are free to spring outboard and set into the tissue, whereby to anchor J-bar assembly 115 (and hence fiducial sensor 10) adjacent to lesion 18. See FIG. 41. At this point, if J-bar assembly 115 was temporarily connected to electrical power through the interior of needle cannula 140, the wires of the J-bar are disconnected and retracted to within needle cannula 140. Note that this disconnection and retraction of the electrical leads passing through needle cannula 140 is desirable, since it removes them from the intended resection line.

Then a power supply clamping tool 190 is advanced into the pleural space and clamped onto the portion of electrical lead 120 extending out of the lung, whereby to provide electrical power to electrical lead 120 and hence fiducial sensor 10 of J-bar assembly 115. See FIG. 42. Note that by supplying electrical power to J-bar assembly 115 via a power supply clamping tool 190 advanced into the pleural space from a point outside the body (rather than through needle cannula 140 and bronchoscope 60 advanced through the bronchi), the electrical leads do not cross the intended resection line.

Power supply clamping tool 190 can take various forms. In essence, it is an elongated tool which is configured to extend from outside the body into the pleural space, and to make an electrical connection to the portion of electrical lead 120 extending out of the lung and into the pleural space, whereby to deliver power to J-bar assembly 115. By way of example but not limitation, power supply clamping tool 190 may comprise a pair of electrically-connected jaws which can be closed about the portion of electrical lead 120 extending out of the lung and into the pleural space. Note that power supply clamping tool 190 can be deployed either through a needle extending through the skin or through a port created on the skin surface. The power supplied by power supply clamping tool 190 to electrical lead 120 enables J-bar assembly 115 to connect to the EM tracking system.

Once powered, fiducial sensor 10 communicates with the electromagnetic (EM) tracking system and the location of fiducial sensor 10 (and hence the location of lesion 18) can be determined by controller 48.

At this point, a surgical instrument 80 (carrying an instrument sensor 85) can be used to effect the desired resection line in the lung, whereby to excise lesion 18 from the remainder of the lung. Note that J-bar and electrical lead assembly 105 extends from lesion 18 to the pleural space, and hence is contained within the tissue which is being excised, and does not cross the resection line. In other words, J-bar and electrical lead assembly 105 is always outboard of lesion 18. As a result, fiducial sensor 10 of J-bar assembly 115 can remain powered throughout the resection procedure, does not interfere with the resection procedure, and J-bar and electrical lead assembly 105 is carried away with the resected tissue after resection has been completed.

As noted above, in one form of the invention, a bronchoscope 60 is advanced through the airways of the patient until the distal tip of bronchoscope 60 is disposed near the lesion (i.e., target tissue mass) 18. As also noted above, the bronchoscope 60 may be advanced under direct visualization and its position may be tracked using one or more sensors 180 carried by bronchoscope 60. Alternatively, the position of bronchoscope 60 may be tracked using J-bar assembly 115, provided that a temporary electrical connection is provided for J-bar assembly 115 (i.e., via an electrical connection extending through the interior of needle cannula 140, such as by electrifying a portion of pusher 145). Thus, it can be desirable to provide a temporary electrical connection for J-bar assembly 115 (i.e., via an electrical connection extending through the interior of needle cannula 140, such as by electrifying a portion of pusher 145) so that J-bar assembly 115 can be powered while the J-bar assembly is in needle cannula 140.

It can also be desirable to provide a temporary electrical connection for J-bar assembly 115 (i.e., via an electrical connection extending through the interior of needle cannula 140, such as by electrifying a portion of pusher 145) so that J-bar assembly 115 can be powered prior to connecting power supply clamping tool 190 to the portion of the electrical lead 120 extending out of the lung.

Figure 43:
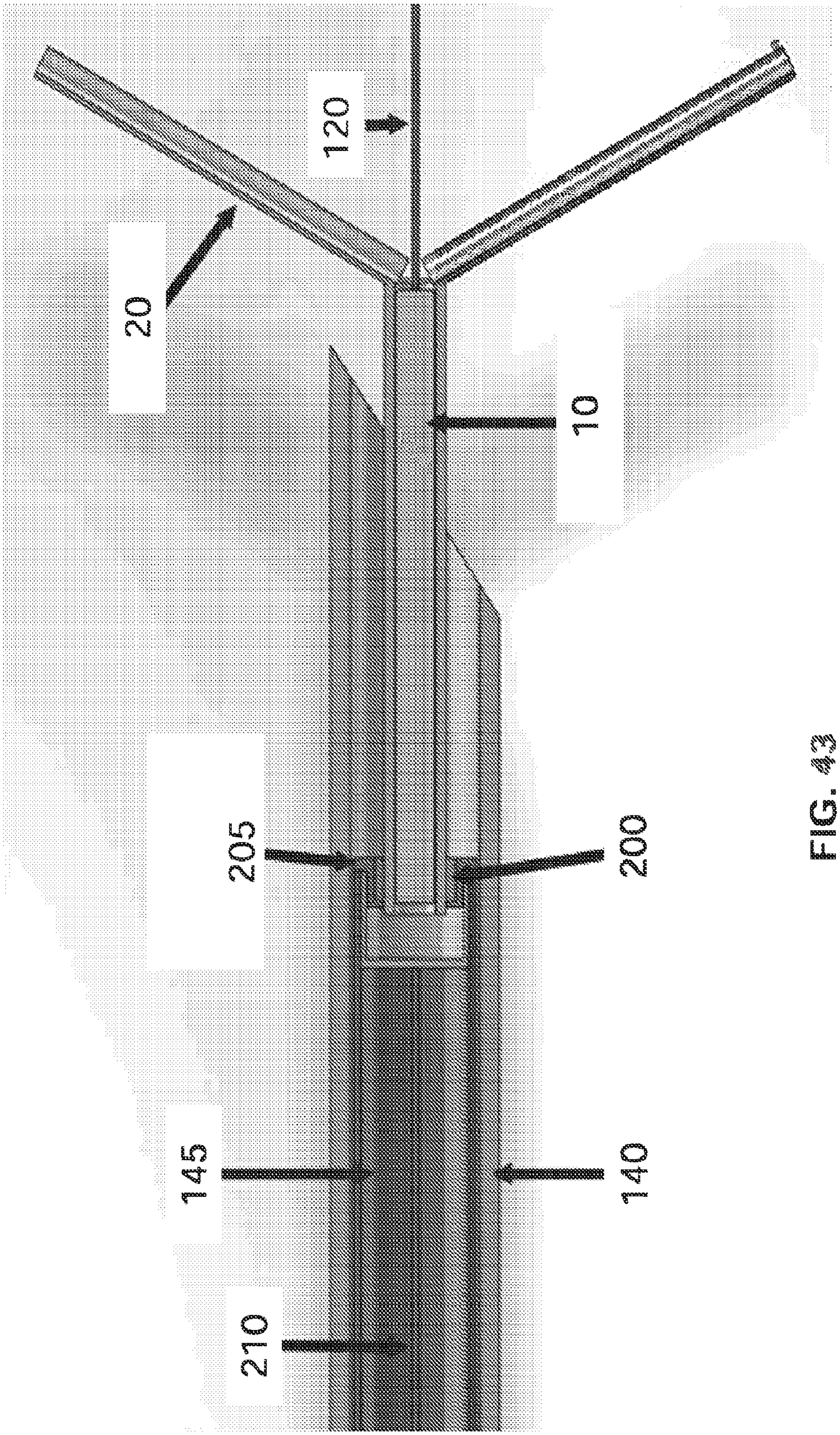
FIG. 43 is a schematic view showing how a temporary proximal electrical connection may be provided for the fiducial sensor, e.g., such as when the fiducial sensor is deployed through a bronchoscope.

In one form of the invention, and looking now at FIG. 43, a temporary electrical connection for J-bar assembly 115 can be provided as follows. Fiducial sensor 10 of J-bar assembly 115 comprises a proximal electrical connector 200 (as well as the electrical lead 120, which extends distally from fiducial sensor 10). Pusher 145 is cannulated and comprises a distal electrical connector 205. Electrical power is provided to distal electrical connector 205 of pusher 145 by a wire 210 which extends through pusher 145 (and which connects to a power source, not shown). While J-bar assembly 115 is seated in needle cannula 140, proximal electrical connector 200 of J-bar assembly 115 is connected to distal electrical connector 205 of pusher 145, whereby to power fiducial sensor 10. After J-bar assembly 115 has been deployed in the anatomy of a patient (and after prongs 20 have set in the tissue), pusher 145 is retracted, separating distal electrical connector 205 of pusher 145 from proximal electrical connector 200 of J-bar assembly 115, thereby disconnecting J-bar assembly 115 from the power supplied by wire 210 extending through pusher 145. However, it will be appreciated that power may still be delivered to J-bar assembly 115 via electrical lead 120 and power supply clamping tool 190 (connected to electrical lead 120).

In yet another form of the invention, and looking now at FIGS. 44-58, a bronchoscopic sensor unit 100A is provided for bronchoscopic deployment of fiducial sensor 10 into target tissue mass 18 or adjacent to target tissue mass 18. Bronchoscopic sensor unit 100A is substantially similar to bronchoscopic sensor unit 100 described above, except that (i) electrical lead 120 comprises a spring coil, and (ii) atraumatic tip 135 comprises an expandable basket.

Figure 44:
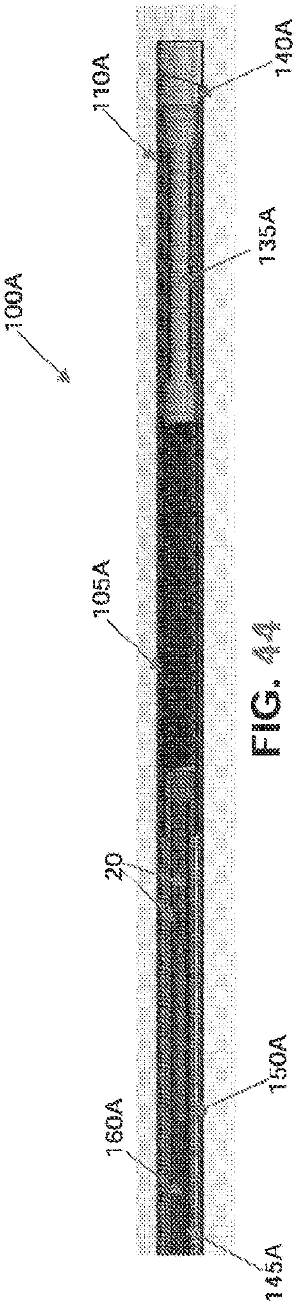
FIGS. 44-46 are schematic views showing another apparatus for bronchoscopic deployment of the fiducial sensor into tissue (e.g., bronchoscopic deployment of the fiducial sensor into the target tissue mass or adjacent to the target tissue mass).
Figure 45:
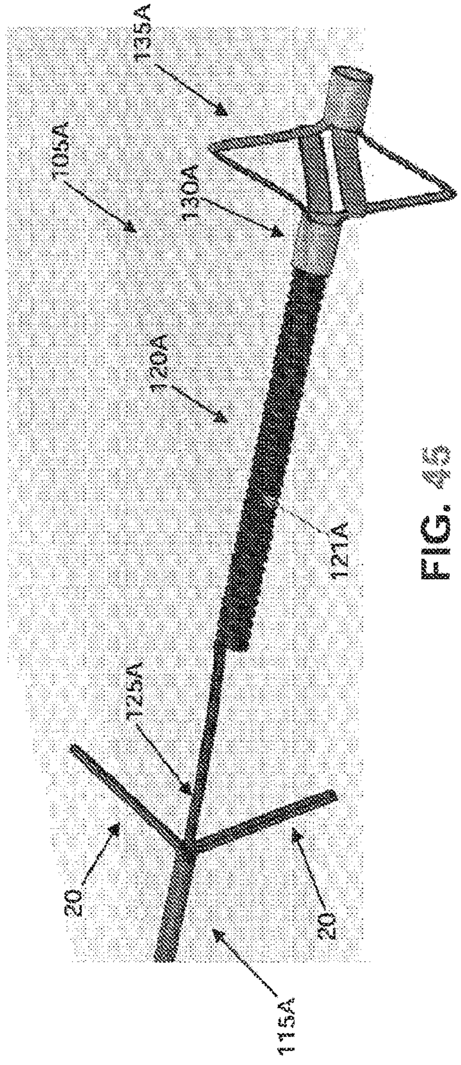
Figure 46:
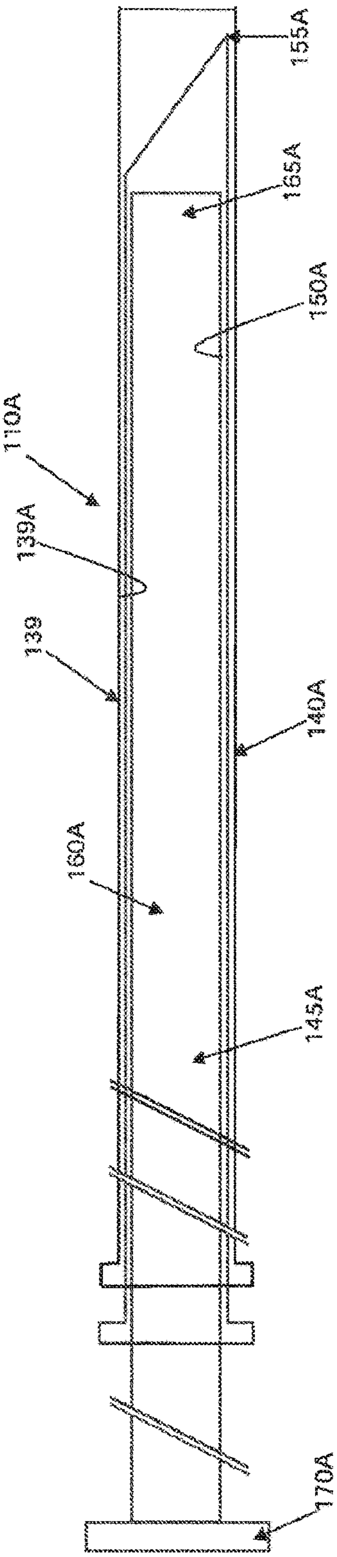

More particularly, and looking now at FIGS. 44-46, bronchoscopic sensor unit 100A (FIG. 44) generally comprises a J-bar and electrical lead assembly 105A (FIG. 45) and a deployment assembly 110A (FIG. 46).

Figure 46A:
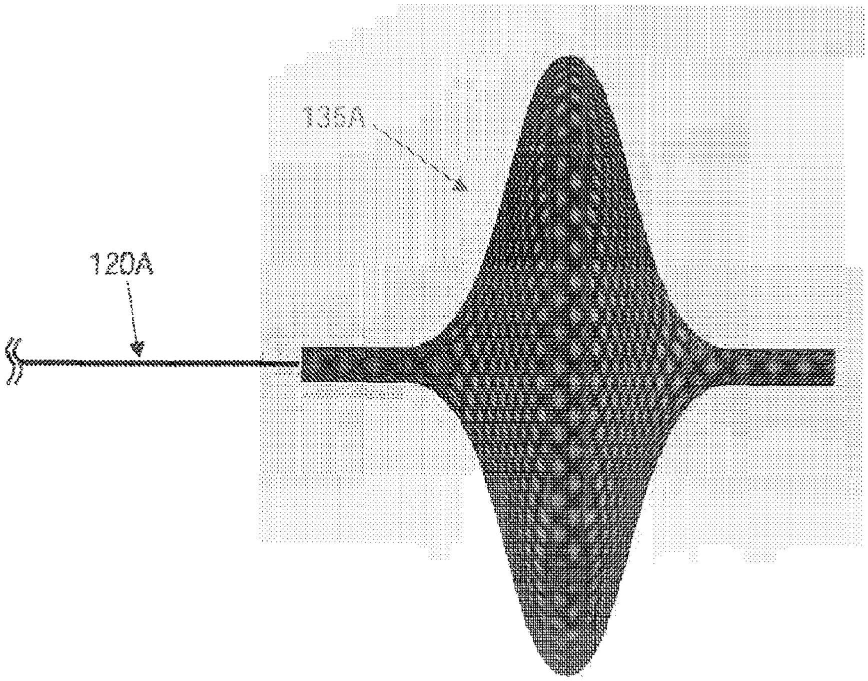
FIGS. 46A and 46B are schematic views showing alternative baskets for use with the apparatus of FIGS. 44-46.
Figure 46B:
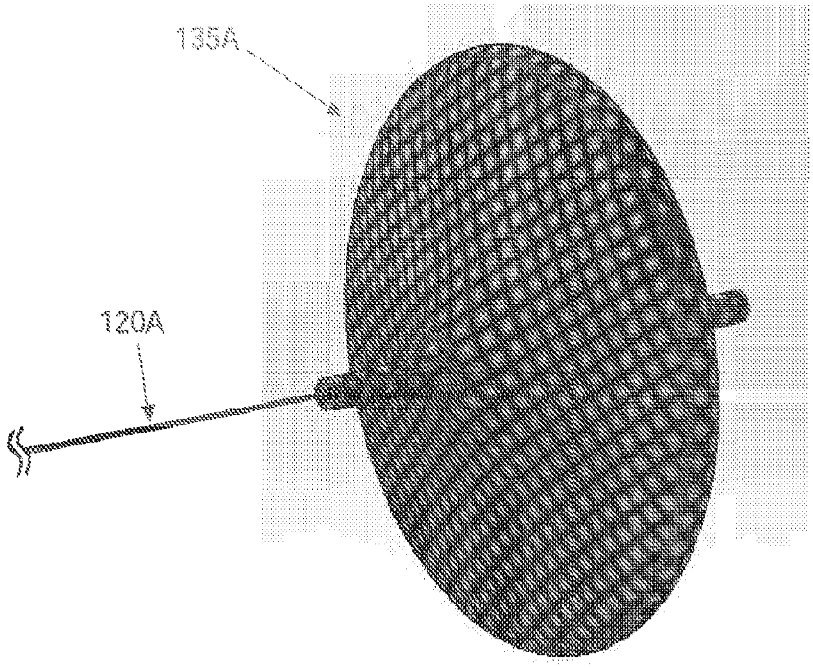
Figure 47:
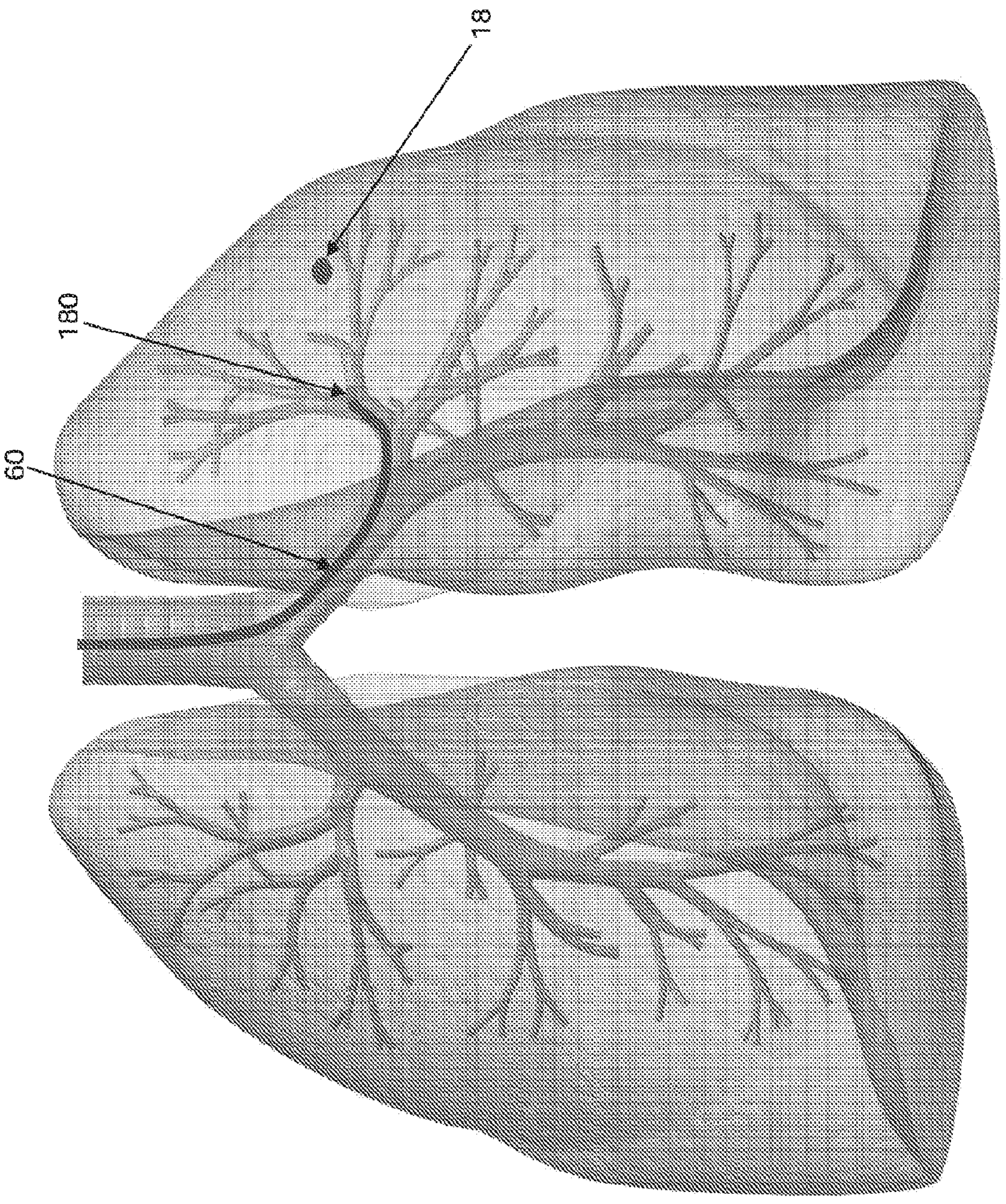
FIGS. 47-62 are schematic views showing how the apparatus of FIGS. 44-46 may be used for bronchoscopic deployment of the fiducial sensor into tissue (e.g., bronchoscopic deployment of the fiducial sensor into the target tissue mass or adjacent to the target tissue mass).
Figure 48:
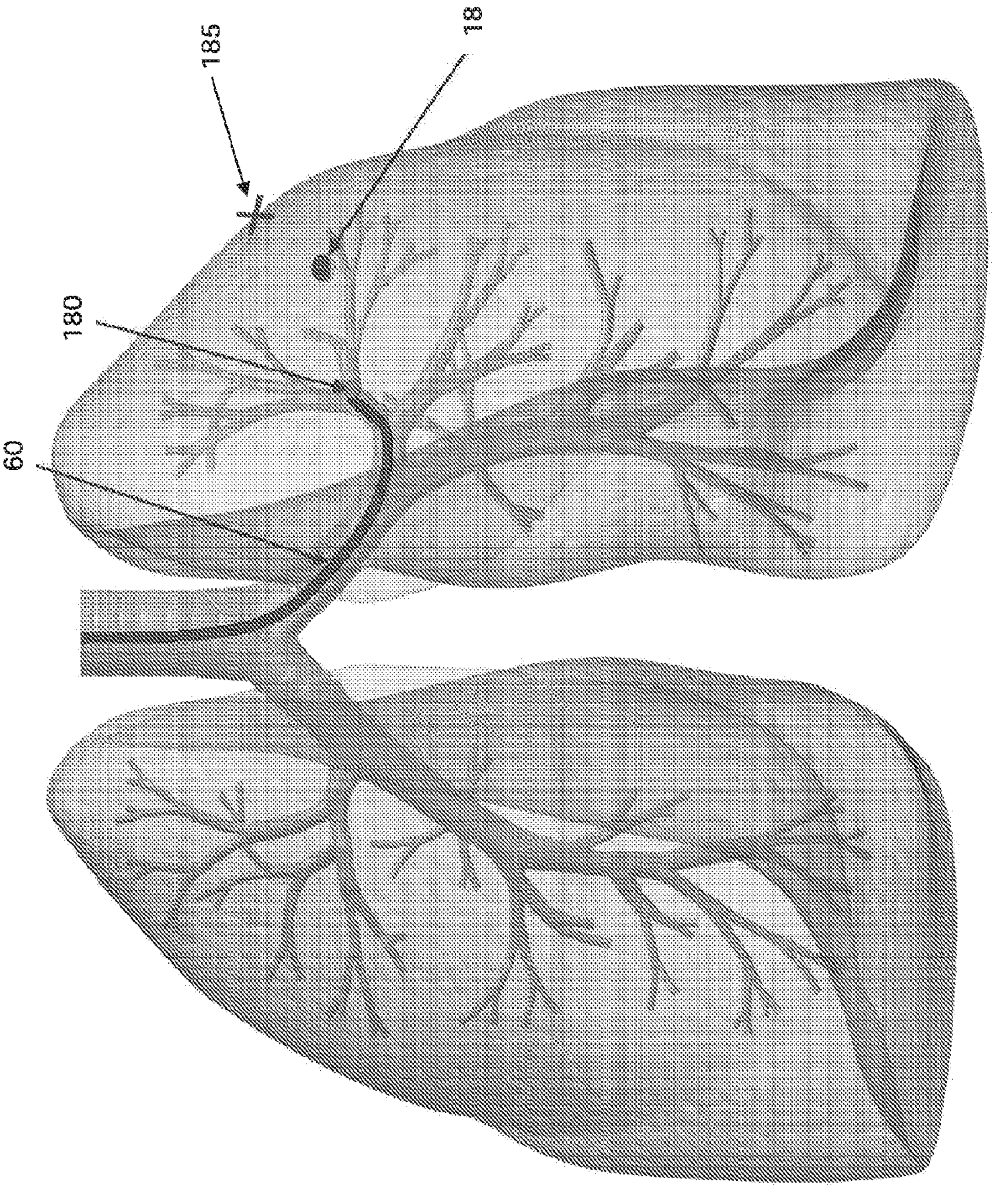

J-bar and electrical lead assembly 105A generally comprises a J-bar assembly 115A and an electrical lead 120A. J-bar assembly 115A comprises the aforementioned hook structure 16 which carries the aforementioned fiducial sensor 10 and the aforementioned prongs 20. One end 125A of electrical lead 120A is connected to fiducial sensor 10 such that electrical power delivered to electrical lead 120A can power fiducial sensor 10. The other end 130A of electrical lead 120A comprises an expandable basket 135A. Electrical lead 120A comprises a spring coil 121A intermediate end 125A of electrical lead 120A and expandable basket 135A, so that the distance between end 125A of electrical lead 120A and expandable basket 135A may be varied, whereby to accommodate differences in patient anatomy and lesion location. Electrical lead 120A may be covered with a hydrophobic braided wire to allow for easy insertion and retraction of J-bar and electrical lead assembly 105A through lumen 150A (see below) of deployment assembly 110A. Expandable basket 135A may comprise substantially any geometry that is suitable for expansion against the side wall of tissue in order to maintain J-bar and electrical lead assembly 105A in position. In one form of the present invention, expandable basket 135A comprises a plurality of spring-biased legs configured to expand radially outboard once released from the confinement of deployment assembly 110A. Alternatively, and looking now at FIGS. 46A and 46B, if desired, expandable basket 135A may be formed out of a braided material (e.g., Nitinol) so as to form a radially expanding structure once released from the confinement of deployment assembly 110A, whereby to secure J-bar and electrical lead assembly 105A in position.

Note that, when expanded, expandable basket 135A prevents retrograde movement of the distal end of electrical lead 120A after deployment. Furthermore, in such a form of the invention, prongs 20 of J-bar assembly 115A could have a configuration which prevents antegrade movement of J-bar assembly 115A once it is released from deployment assembly 110A.

Deployment assembly 110A comprises an outer cannula 139, a needle cannula 140A and a pusher 145A. Outer cannula 139 comprises a hollow lumen 139A which can terminate in a blunt distal tip. Needle cannula 140A comprises a hollow lumen 150A and terminates in a sharp tip 155A. Needle cannula 140A is sized to be slidably received in hollow lumen 139A of outer cannula 139. Pusher 145A comprises a shaft 160A. One end of shaft 160A ends in a blunt distal end 165A. The other end of shaft 160A terminates in a handle 170A. Shaft 160A of pusher 145A is sized to be slidably received in lumen 150A of needle cannula 140A. Note that outer cannula 139 of deployment assembly 110A is sized so that it can be inserted through the working channel of a bronchoscope.

As seen in FIG. 44, needle cannula 140A is initially disposed within lumen 139A of outer cannula 139, J-bar and electrical lead assembly 105A and shaft 160A of pusher 145A are initially disposed within lumen 150A of needle cannula 140A, with prongs 20 of J-bar assembly 115A being elastically deformed into a straighter configuration so as to be received within lumen 150A of needle cannula 140A, and with the proximal ends of the elastically deformed prongs 20 residing just distal to blunt end 165A of pusher 145A. Note also that when J-bar and electrical lead assembly 105A is disposed within lumen 150A of needle cannula 140A, expandable basket 135A of electrical lead 120A is elastically deformed so that it sits substantially straight within needle cannula 140A. In this way, needle cannula 140A can carry J-bar and electrical lead assembly 105A, with needle cannula 140A shielding J-bar and electrical lead assembly 105A from contact with surrounding structures (e.g., a bronchoscope, tissue, etc.). However, distal movement of pusher 145A can eject J-bar and electrical lead assembly 105A from lumen 150A of needle cannula 140A.

In a method of use, the intended position of J-bar and electrical lead assembly 105A vis-á-vis the anatomy of the patient is planned prior to deployment in the lung using diagnostic or intraprocedural CT, C-arm CT, MRI or other imaging modalities, i.e., the intended position of J-bar assembly 115A, and the exit point of electrical lead 120A as it emerges from the lung surface, are planned in advance on diagnostic or intraprocedural CT, C-arm CT, MRI or other imaging modalities. The electromagnetic (EM) tracking coordinates are mapped to the diagnostic/intraprocedural imaging coordinates using image registration algorithms well known in the art to track the bronchoscope and J-bar and electrical lead assembly 105A in the imaging coordinates. The position of J-bar assembly 115A is chosen to be in the proximity of the target tissue mass (i.e., tumor), preferably along the line joining the bronchoscope target position and the exit position of the electrical lead, while the exit point of electrical lead 120A from the lung is typically chosen to be (i) the shortest path from the J-bar location to the lung surface (or the fissure surface), or (ii) according to surgeon preference.

By way of example but not limitation, in a method of use, and looking now at FIGS. 47-58, a bronchoscope 60 is advanced through the airways of the patient until the distal tip of bronchoscope 60 is disposed near the lesion (i.e., tissue mass) 18. See FIG. 47. Note that bronchoscope 60 may be advanced under direct visualization and its position may be tracked using one or more sensors 180 carried by bronchoscope 60. Alternatively, the position of bronchoscope 60 may be tracked using J-bar assembly 115A, provided that a temporary electrical connection is provided for J-bar assembly 115A (e.g., via an electrical connection extending through the interior of needle cannula 140A, such as by electrifying a portion of pusher 145A). The position of the tracked bronchoscope 60 can be mapped to the imaging coordinates (see above) using image registration algorithms of the sort well known in the art in order to guide the bronchoscope 60 to the lesion 18.

Next, if it has not already been done, a target point 185 is identified on the outer surface of the lung as the point where it is desired deployment assembly 110A will emerge from the lung and enter the pleural space. See FIG. 48.

Figure 49:
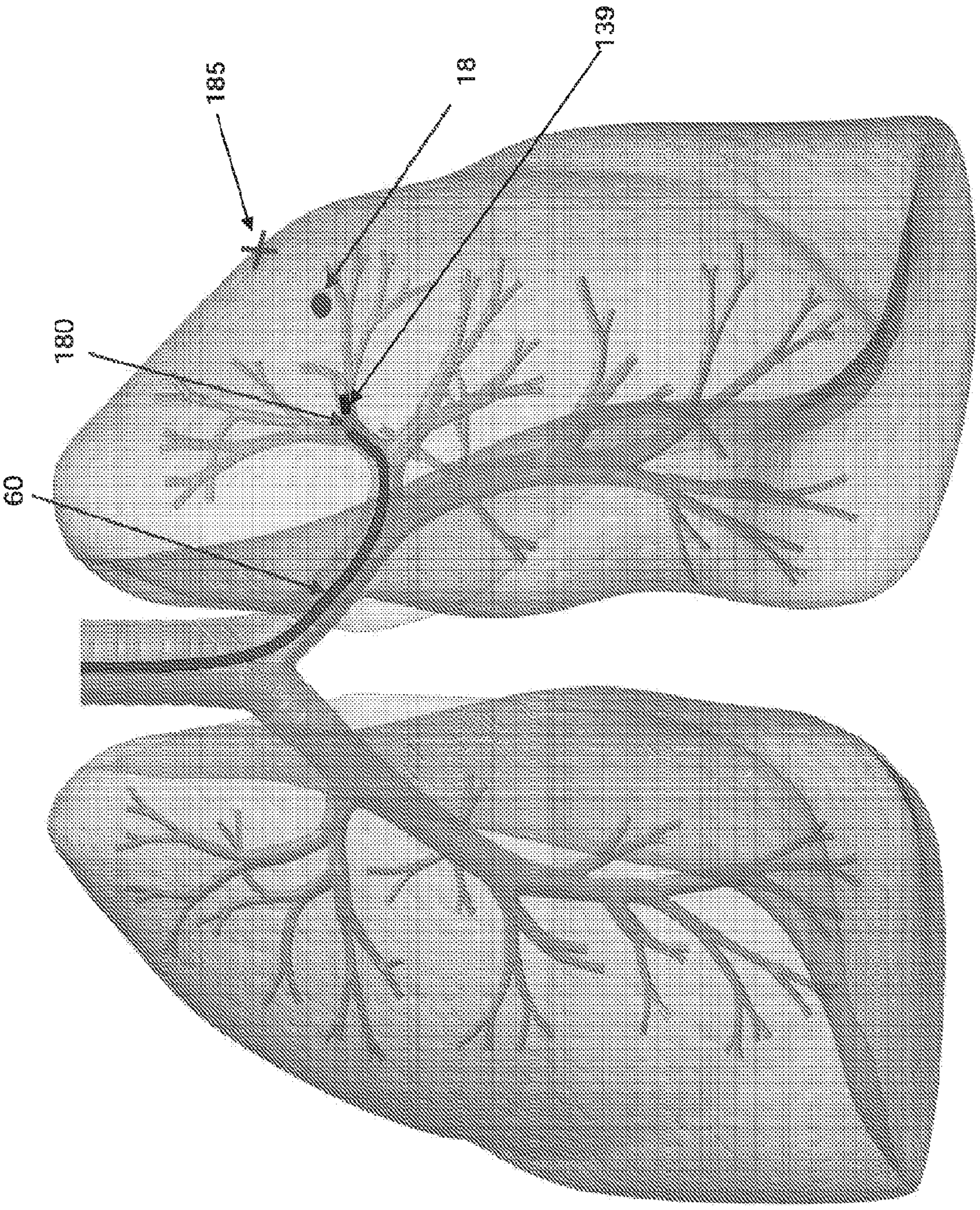
Figure 50:
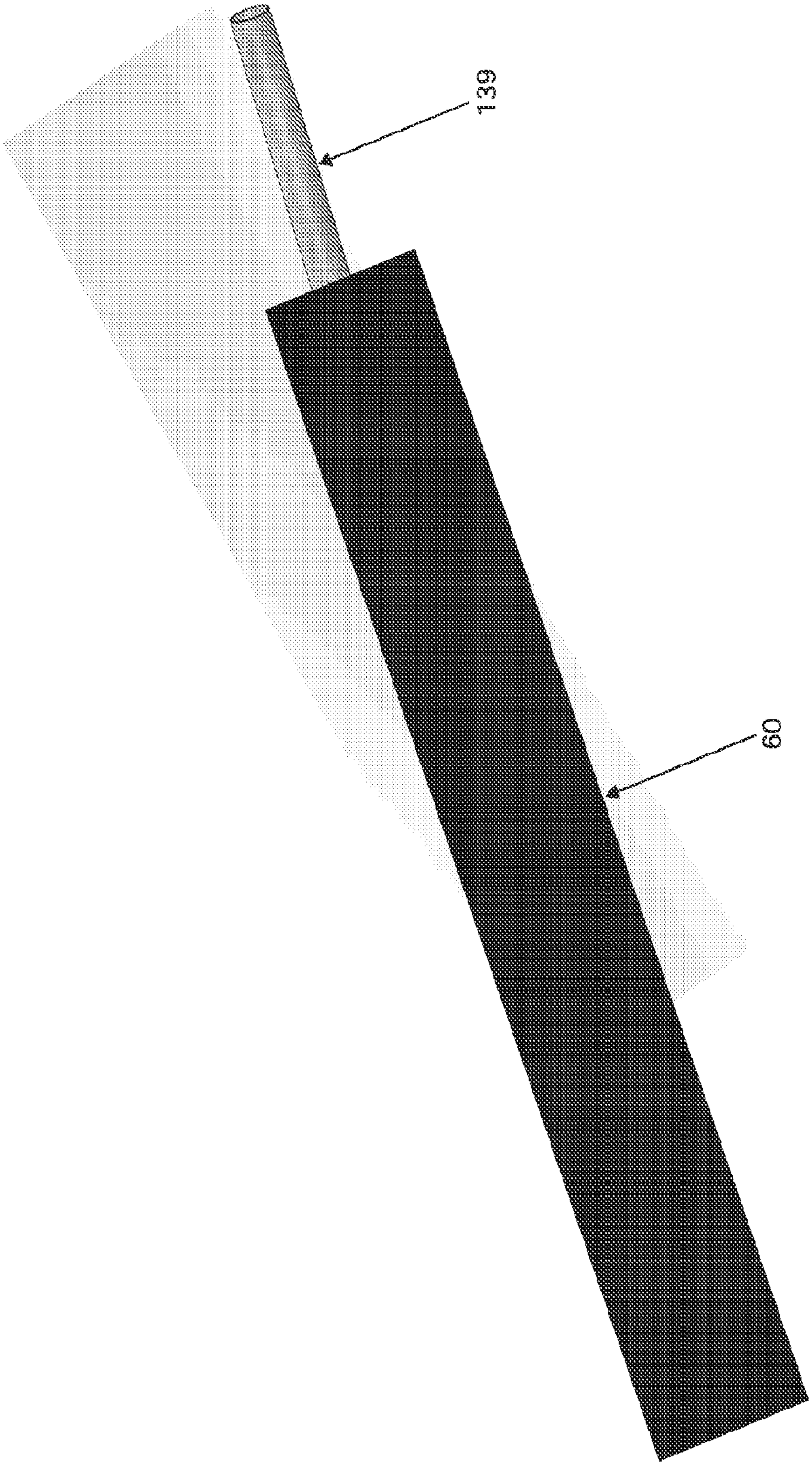
Figure 51:
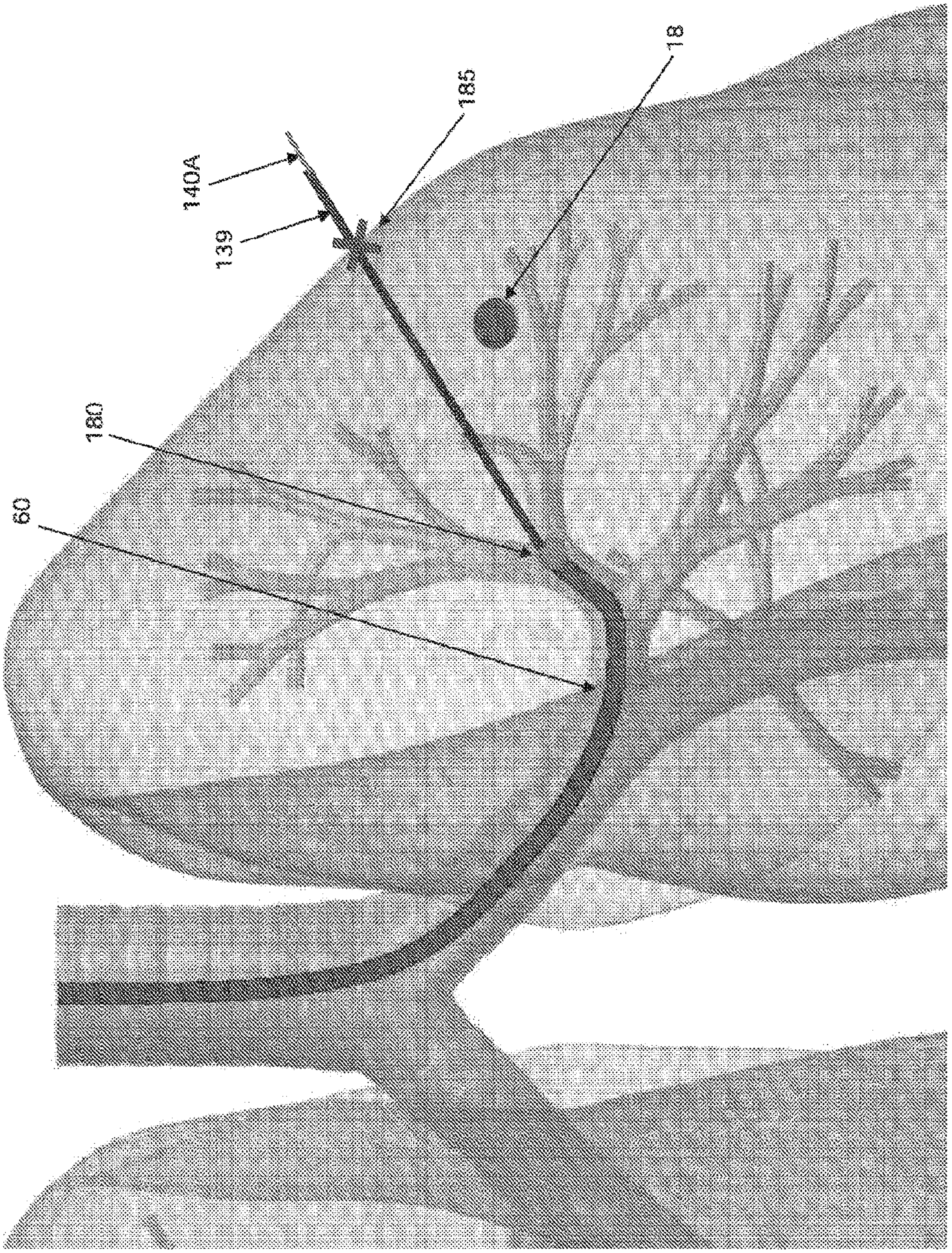
Figure 52:
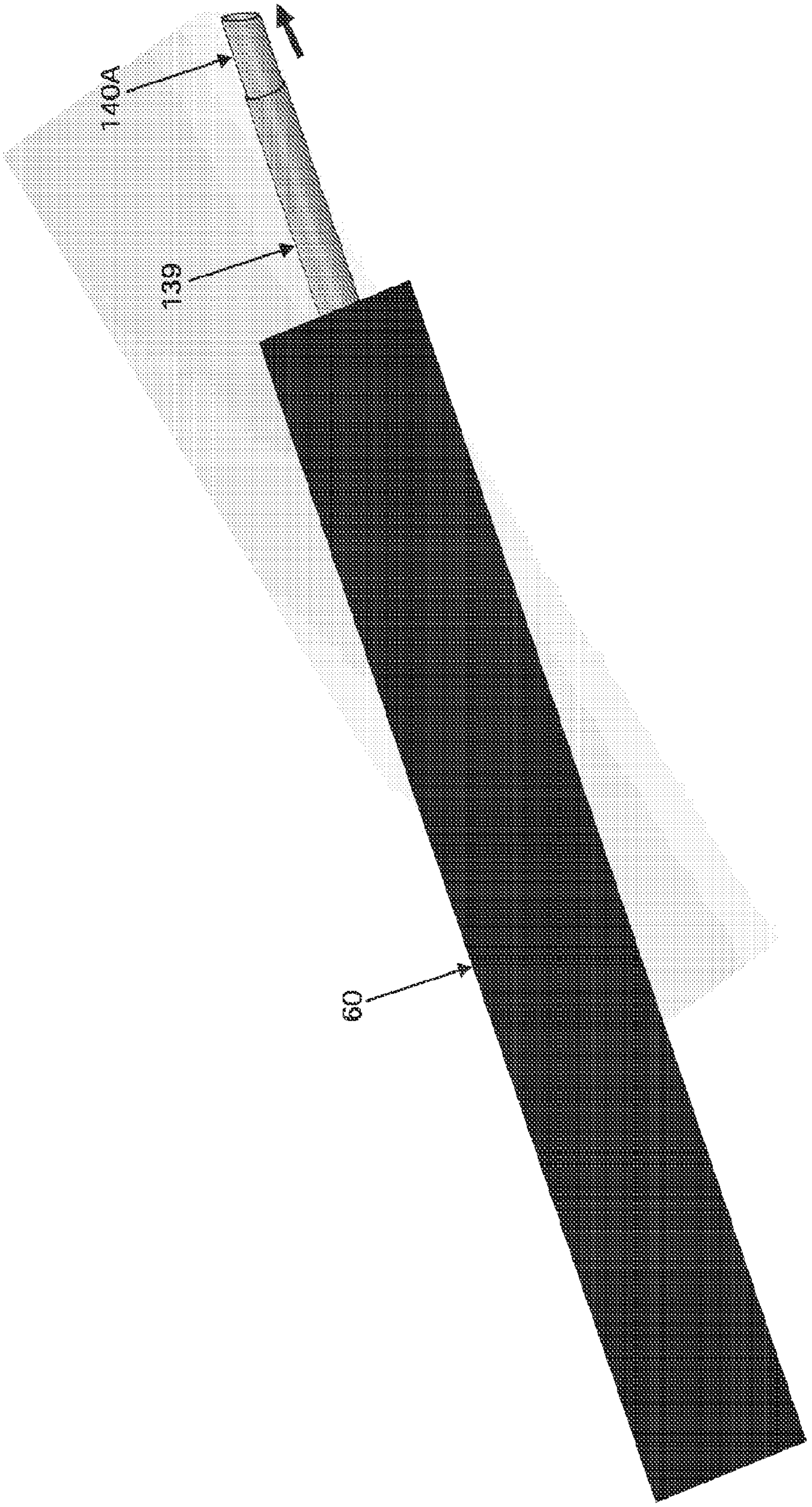

Then bronchoscopic sensor unit 100A (comprising deployment assembly 110A and its passenger J-bar and electrical lead assembly 105A) has its distal end advanced out of the bronchoscope, e.g., so that the blunt distal tip of outer cannula 139 sits slightly distal to the distal end of the bronchoscope (FIGS. 49 and 50). Then needle cannula 140A (carrying J-bar and electrical lead assembly 105A and pusher 145A) is advanced out of outer cannula 139 so that needle cannula 140A is leading outer cannula 139, and then bronchoscopic sensor unit 100A is advanced through the lung, through target point 185 and into the pleural space. See FIGS. 51 and 52. Note that the distal end of bronchoscopic sensor unit 100A can be guided visually via bronchoscope 60, and/or via scanner visualization (e.g., CT imaging, C-arm imaging, ultrasound imaging, etc.), or by using the temporarily-electrically-connected J-bar assembly 115A (if a temporary electrical connection has been established through the interior of needle cannula 140A).

Figure 53:
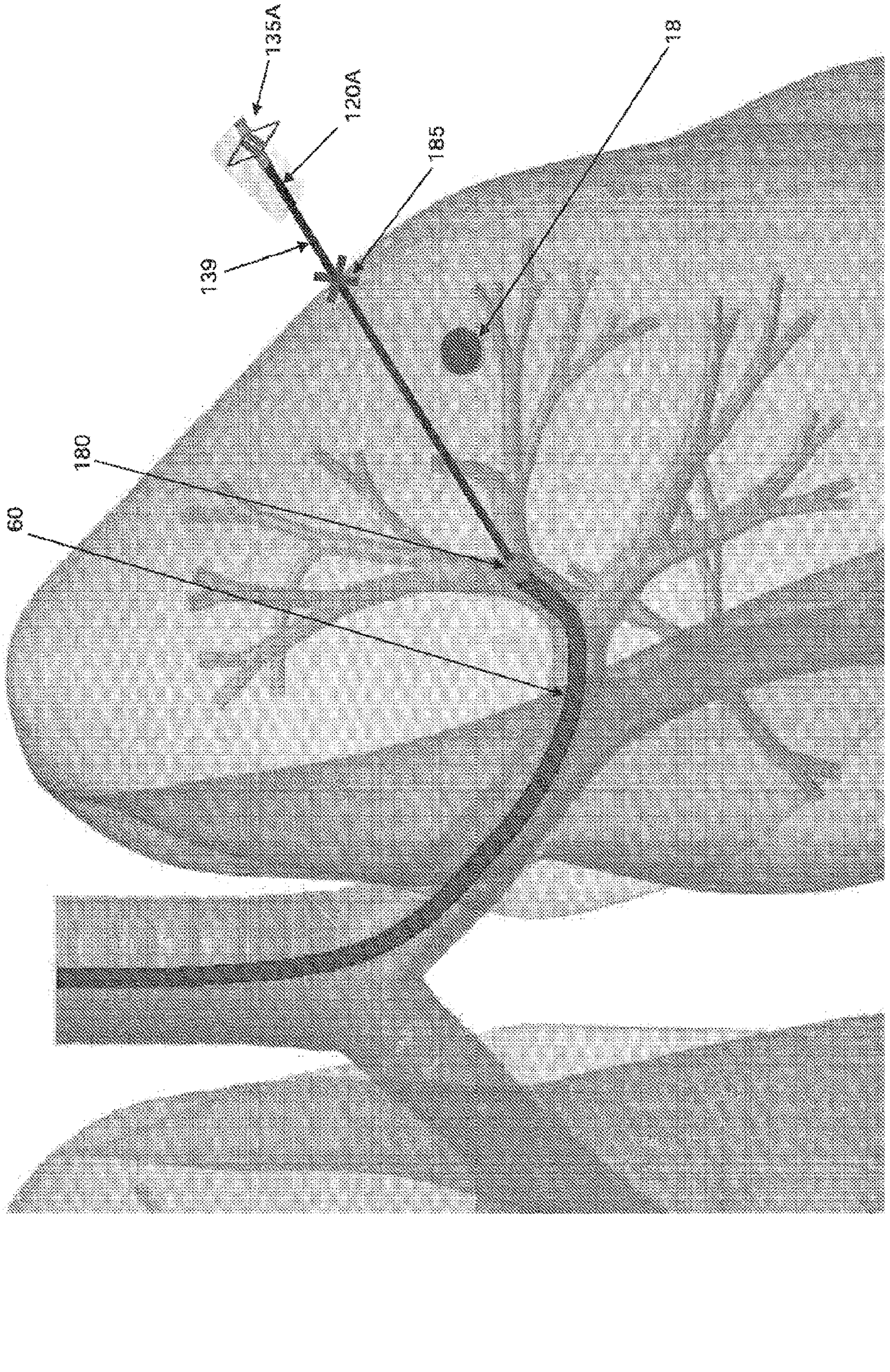
Figure 54:
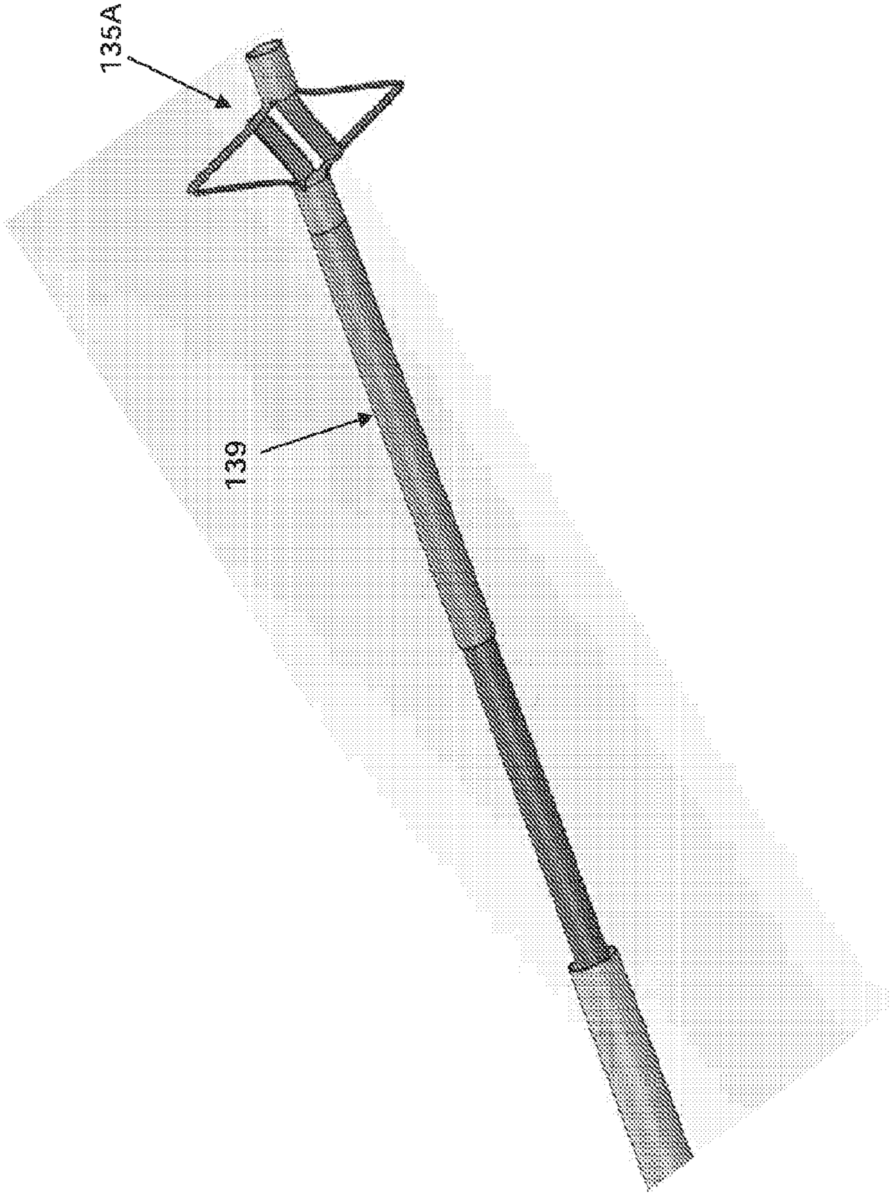
Figure 55:
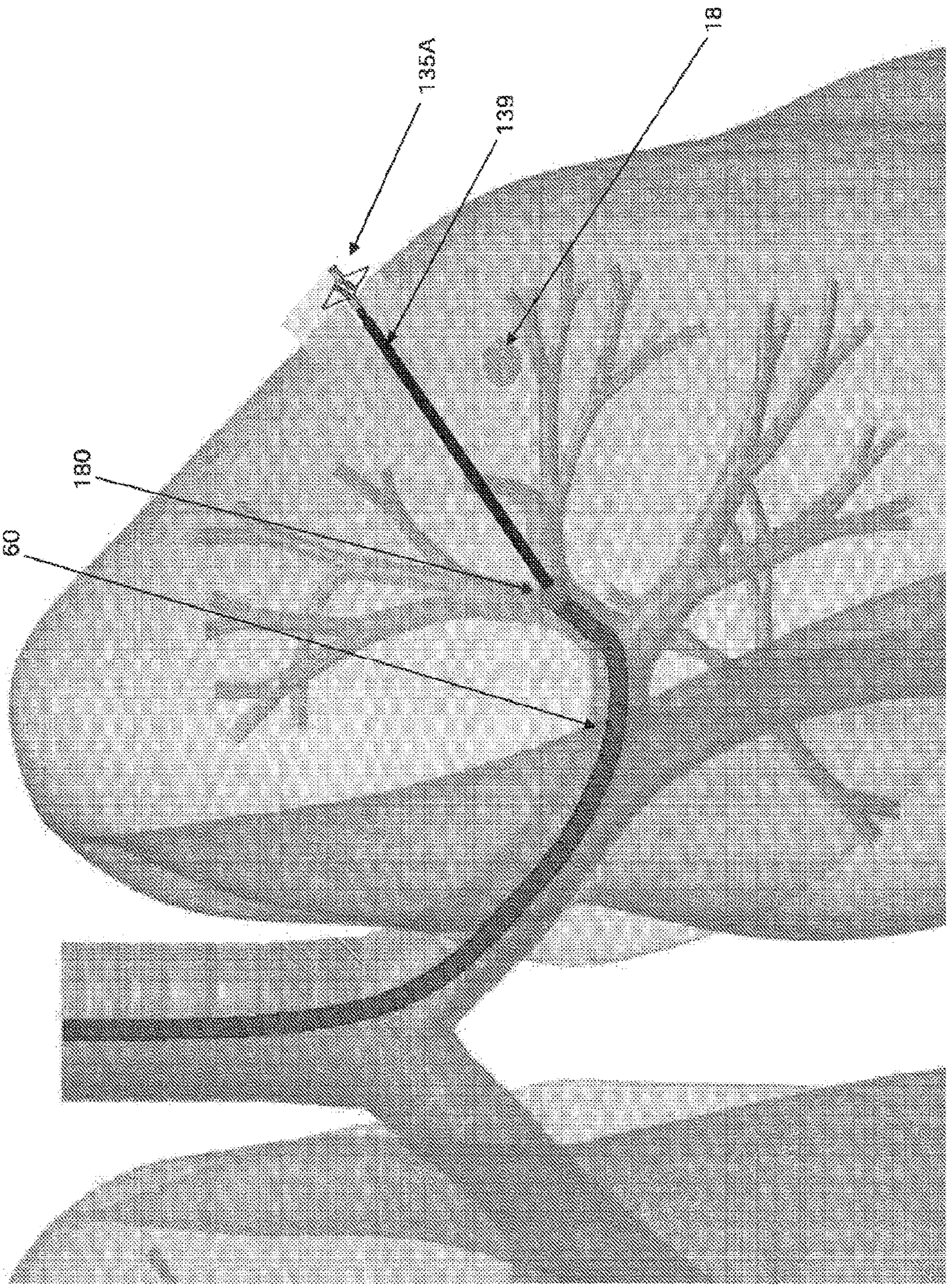
Figure 56:
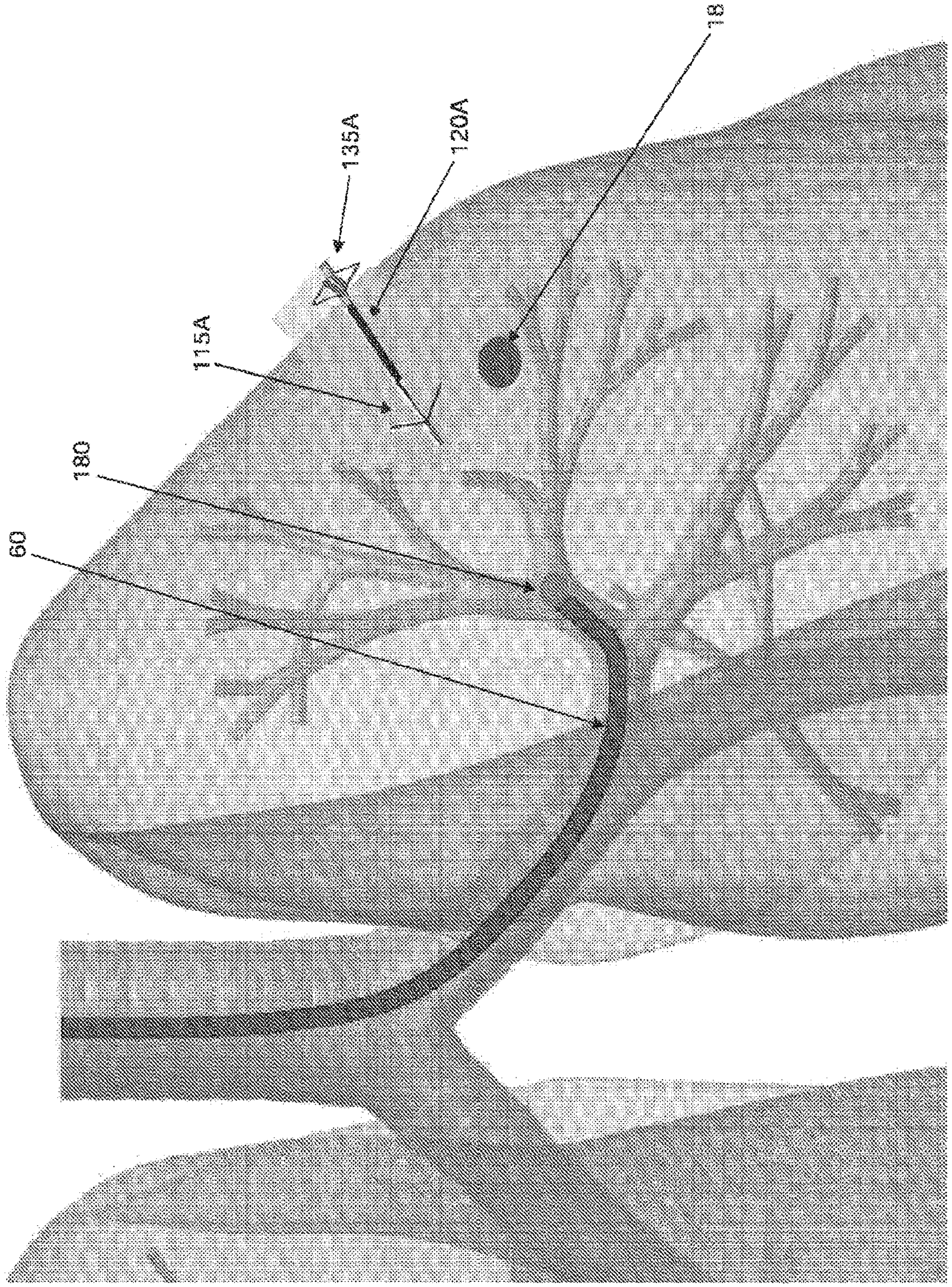
Figure 57:
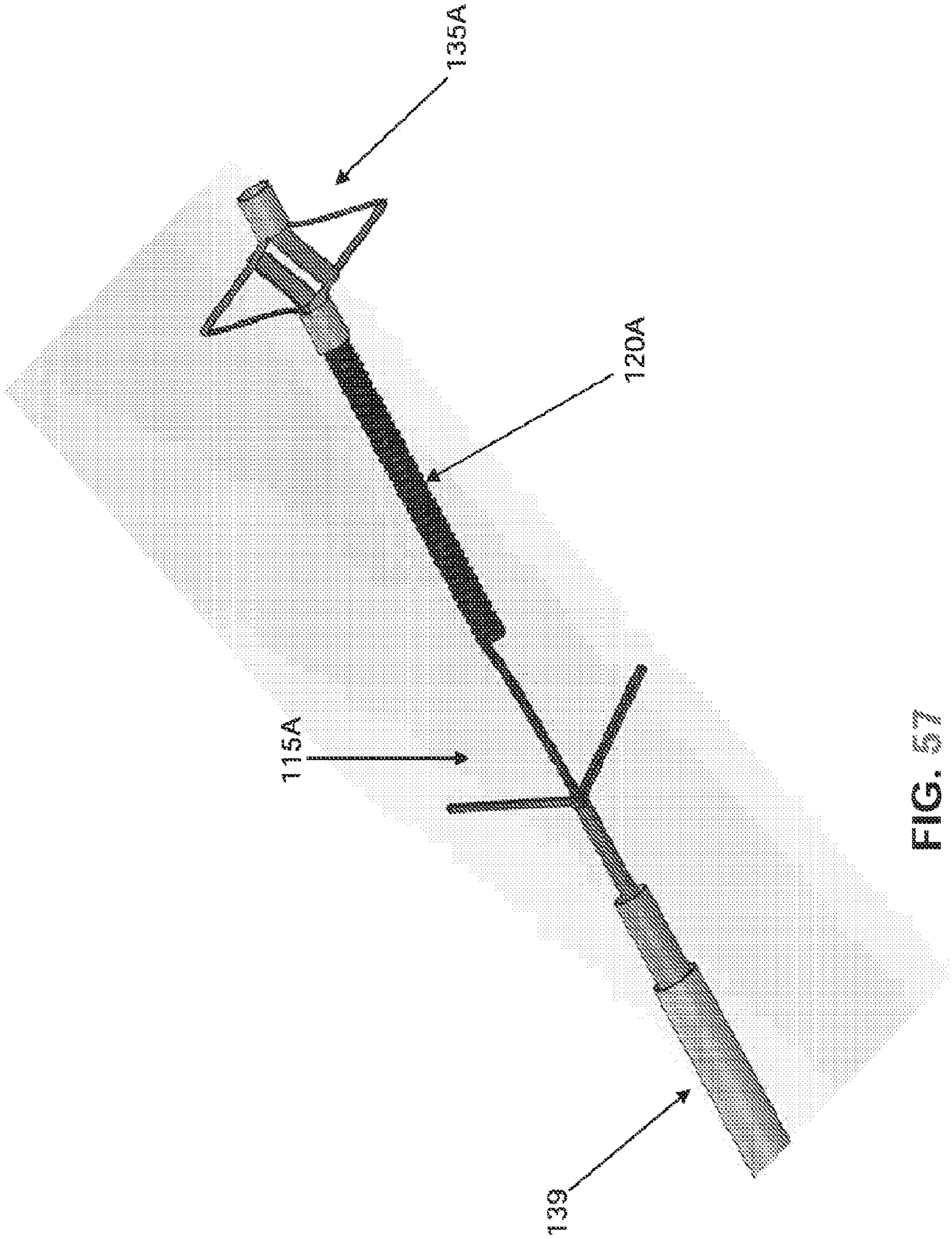
Figure 58:
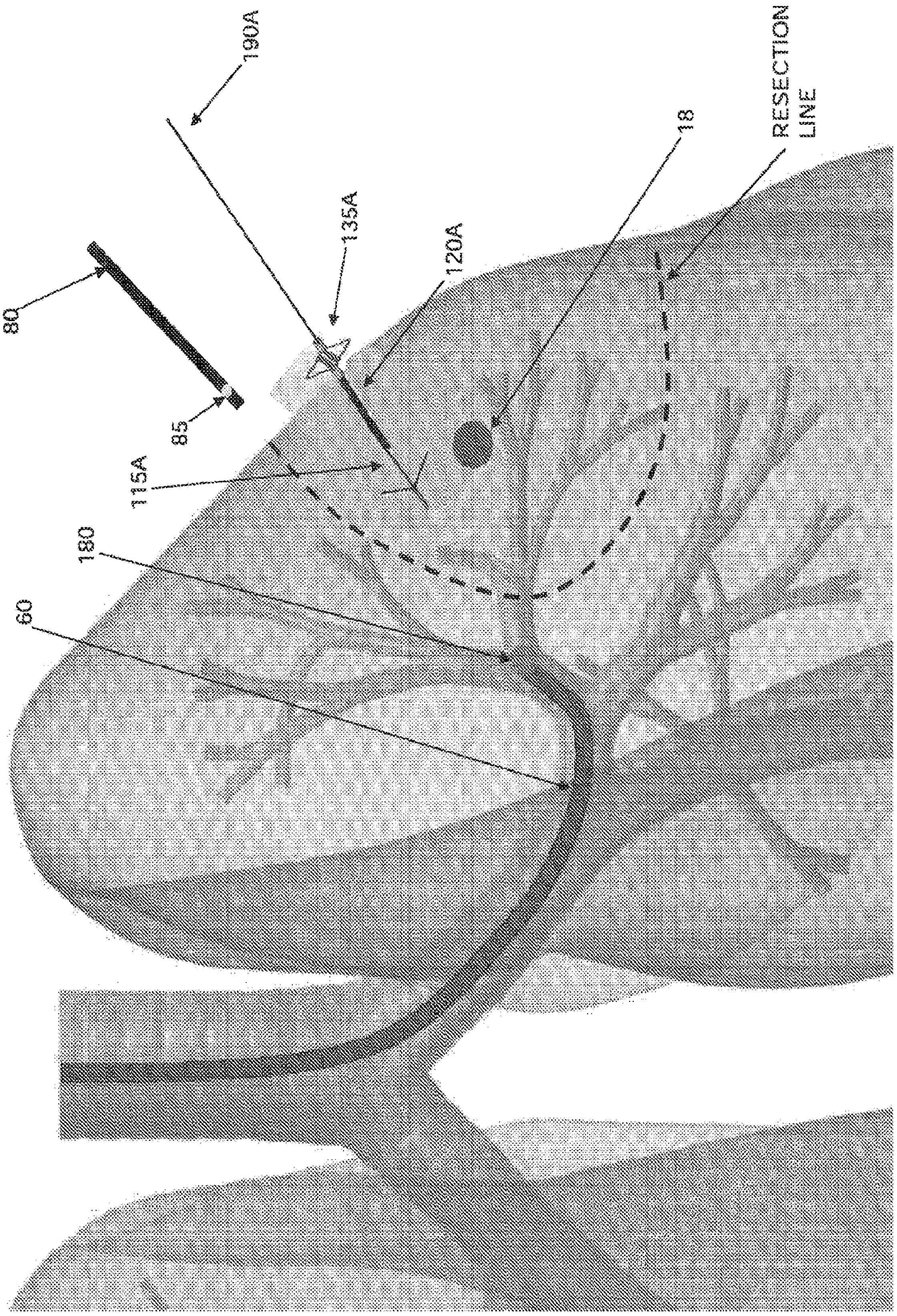

Next, needle cannula 140A is retracted proximally so that expandable basket 135A and a portion of electrical lead 120A are freed from needle cannula 140A in the pleural space, with expandable basket 135A opening up into its expanded position (see FIGS. 53 and 54). Note that, however, that at this point the remainder of J-bar assembly 115A and a portion of electrical lead 120A remain within outer cannula 139.

Next, the outer cannula 139 and its passenger J-bar and electrical lead assembly 105A are withdrawn proximally so that (i) expandable basket 135A is drawn flush against the outer surface of the lung (FIG. 55), and (ii) J-bar assembly 115A is carried to a position adjacent to the lesion 18, with electrical lead 120A uncoiling to the extent required to span the distance between expandable basket 135A and the retreating J-bar assembly 115A. Finally, outer cannula 139 is retracted proximally, exposing J-bar assembly 115A. As the outer cannula 139 retracts past prongs 20 of J-bar assembly 115A, prongs 20 are no longer constrained within lumen 139A of outer cannula 139 and are free to spring outboard and set into the tissue, whereby to anchor J-bar assembly 115A (and hence fiducial sensor 10) adjacent to lesion 18. See FIGS. 56 and 57. At this point, if J-bar assembly 115A was temporarily connected to electrical power through the interior of deployment assembly 110A, the wires of the J-bar are disconnected and retracted. Note that this disconnection and retraction of the electrical leads passing through deployment assembly 110A is desirable, since it removes them from the intended resection line.

Then a power supply connector 190A is advanced into the pleural space and connected to the portion of electrical lead 120A extending out of the lung (e.g., expandable basket 135A), whereby to provide electrical power to electrical lead 120A and hence fiducial sensor 10 of J-bar assembly 115A. See FIG. 58. Note that by supplying electrical power to J-bar assembly 115A via a power supply connector 190A advanced into the pleural space from a point outside the body (rather than through deployment assembly 110A and bronchoscope 60 advanced through the bronchi), the electrical leads do not cross the intended resection line.

Figure 59:
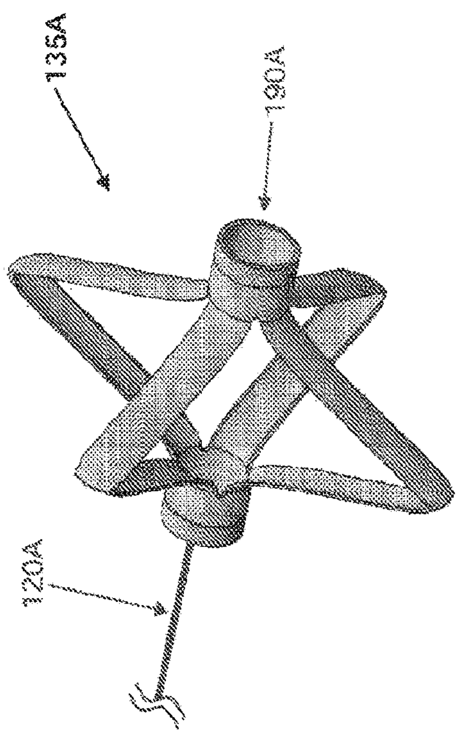
Figure 60:
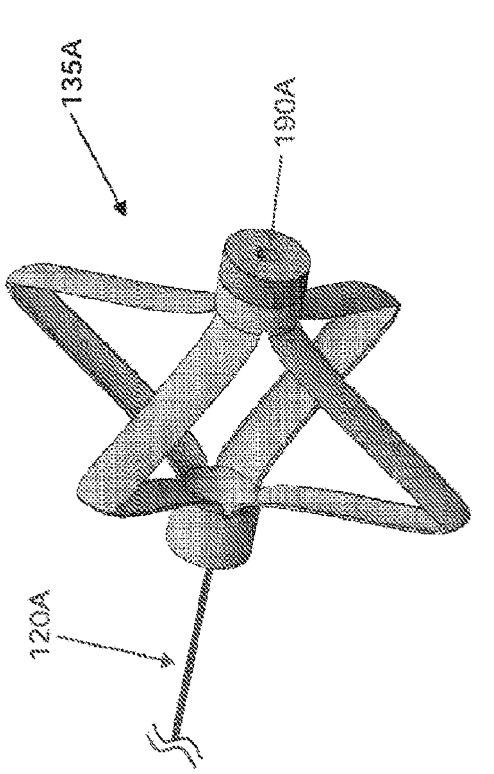
Figure 61:
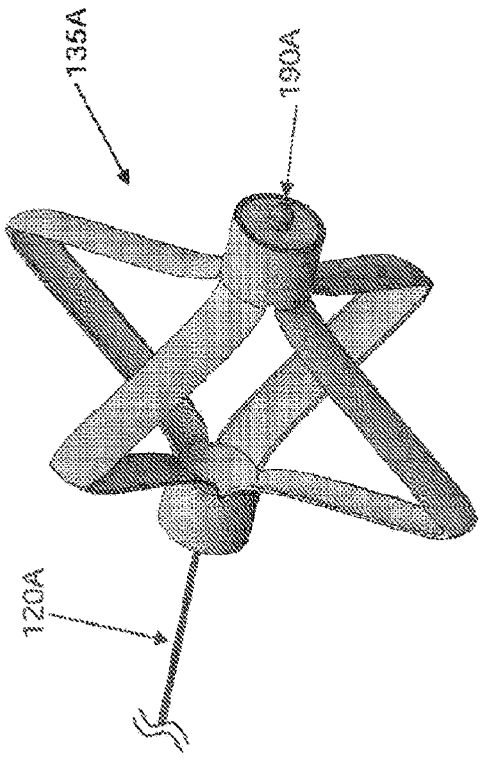
Figure 62:
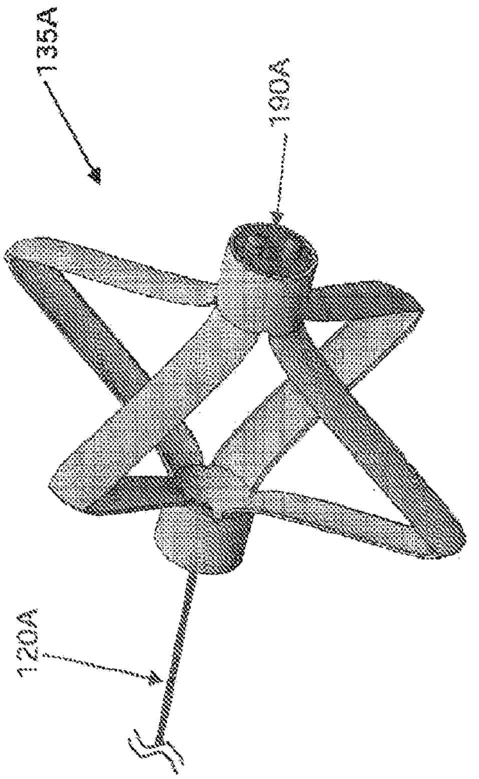

Power supply connector 190A can take various forms, depending on the counterpart electrical connector provided on the end of electrical lead 120A (e.g., expandable basket 135A). In essence, power supply connector 190A is an elongated tool which is configured to (i) extend from outside the body into the pleural space, and (ii) make an electrical connection to the portion of electrical lead 120A extending out of the lung and into the pleural space, whereby to deliver power to J-bar assembly 115A. By way of example but not limitation, power supply connector 190A can comprise a coaxial cable (e.g., one which can connect to the expandable baskets 135A shown in FIGS. 59-61), or a two prong cable (e.g., one which can connect to the expandable basket 135A shown in FIG. 62). Note that power supply connector 190A can be deployed, for example, either through a needle extending through the skin or through a port created on the skin surface. The power supplied by power supply connector 190A to electrical lead 120A enables J-bar assembly 115A to connect to the EM tracking system.

Figure 62A:
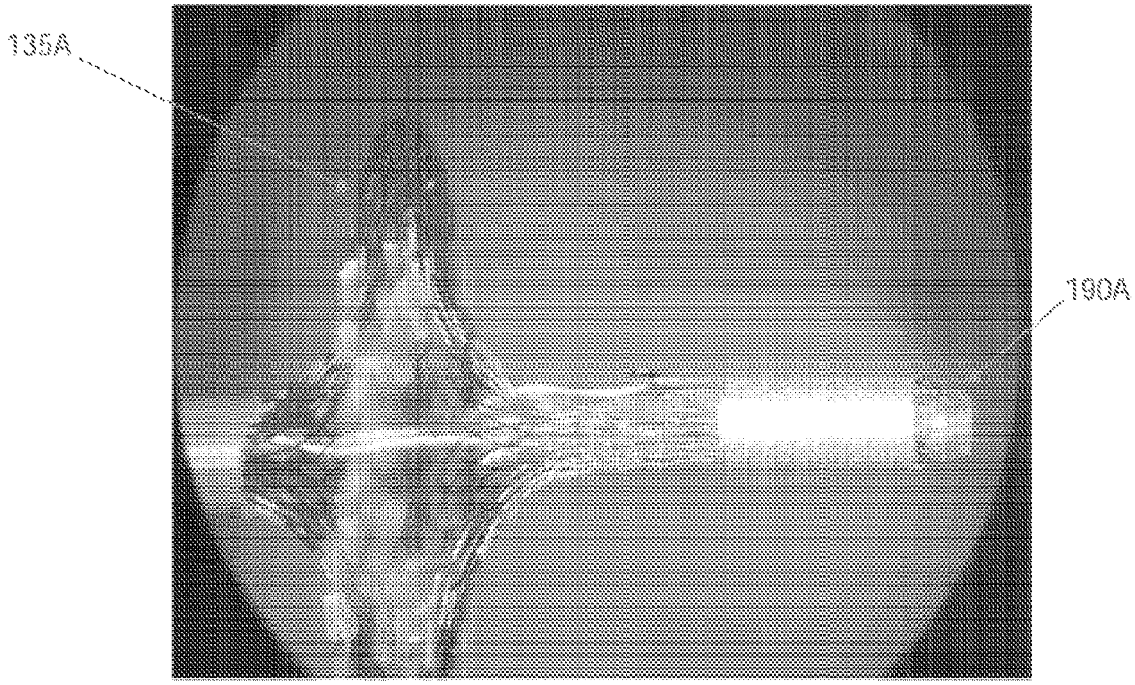
FIGS. 62A, 62B and 62C are schematic views showing further aspects of the apparatus shown in FIGS. 47-62.
Figure 62B:
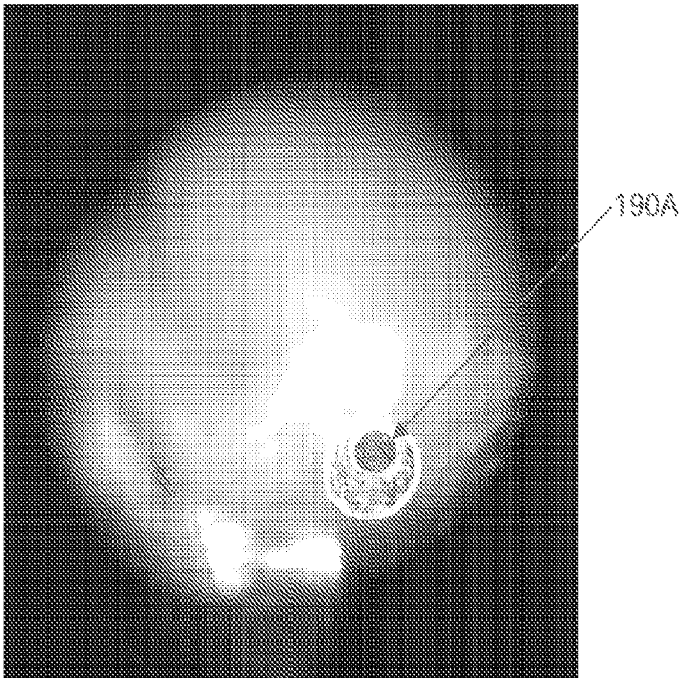
Figure 62C:
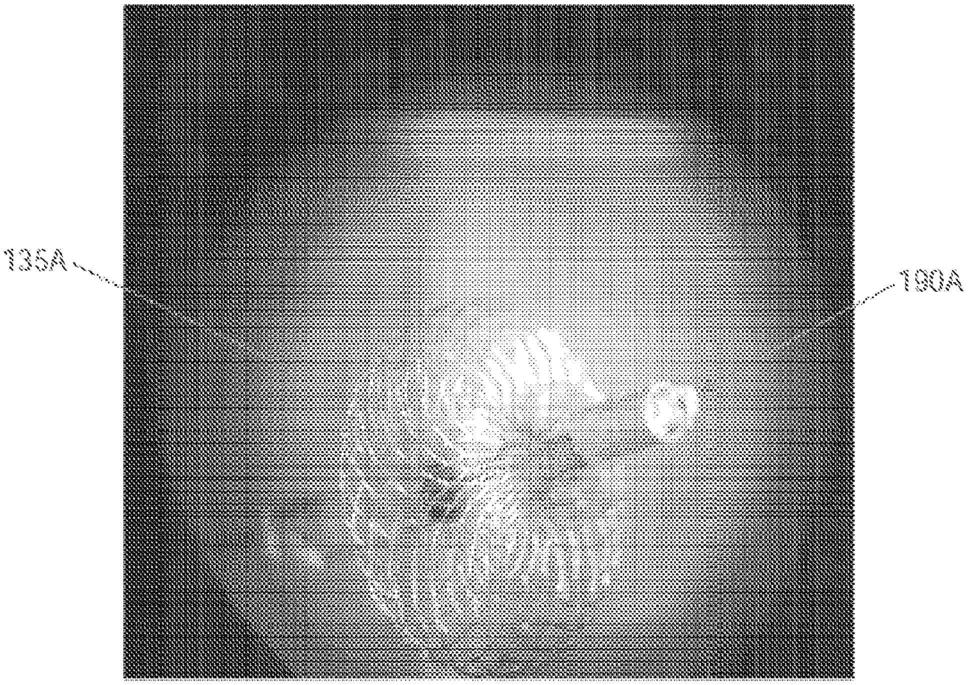

It should be appreciated that power supply connector 190A may be provided in various forms, depending upon the configuration of expandable basket 135A, which forms will be apparent to one of skill in the art in view of the present disclosure. By way of example but not limitation, and looking now at FIGS. 62A-62C, expandable basket 135A may comprise a "plug style" power supply connector 190A disposed at its distal end so as to be accessible from the pleural space. With this form of connector 190A, a pair of insulated wires (i.e., one wire electrically connected to an external conductor of connector 190A and the other wire electrically connected to an internal conductor of connector 190A) extend proximally through the center of expandable basket 135A so as to electrically connect J-bar assembly 115A with connector 190A, as will be apparent to one of skill in the art in view of the present disclosure. To this end it should also be appreciated that the "plug" of connector 190A may be disposed parallel to the longitudinal axis of J-bar assembly 115A (FIGS. 62A and 62B) or perpendicular to the longitudinal axis of J-bar assembly 115A (FIG. 62C).

Once powered, fiducial sensor 10 communicates with the electromagnetic (EM) tracking system and the location of fiducial sensor 10 (and hence the location of lesion 18) can be determined by controller 48.

At this point, a surgical instrument 80 (carrying an instrument sensor 85) can be used to effect the desired resection line in the lung, whereby to excise lesion 18 from the remainder of the lung. Note that J-bar and electrical lead assembly 105A extends from lesion 18 to the pleural space, and hence is contained within the tissue which is being excised, and does not cross the resection line. In other words, J-bar and electrical lead assembly 105A is always outboard of lesion 18. As a result, fiducial sensor 10 of J-bar assembly 115A can remain powered throughout the resection procedure, does not interfere with the resection procedure, and J-bar and electrical lead assembly 105A is carried away with the resected tissue after resection has been completed.

As noted above, in one form of the invention, a bronchoscope 60 is advanced through the airways of the patient until the distal tip of bronchoscope 60 is disposed near the lesion (i.e., tissue mass) 18. As also noted above, the bronchoscope 60 may be advanced under direct visualization and its position may be tracked using one or more sensors 180 carried by bronchoscope 60. Alternatively, the position of bronchoscope 60 may be tracked using J-bar assembly 115A, provided that a temporary electrical connection is provided for J-bar assembly 115A (i.e., via an electrical connection extending through the interior of needle cannula 140A, such as by electrifying a portion of pusher 145A). Thus, it can be desirable to provide a temporary electrical connection for J-bar assembly 115A (i.e., via an electrical connection extending through the interior of needle cannula 140A, such as by electrifying a portion of pusher 145A) so that J-bar assembly 115A can be powered while the J-bar assembly is in deployment assembly 110A.

It can also be desirable to provide a temporary electrical connection for J-bar assembly 115A (i.e., via an electrical connection extending through the interior of deployment assembly 110A, such as by electrifying a portion of pusher 145A) so that J-bar assembly 115A can be powered prior to connecting power supply connector 190A to the portion of the electrical lead 120A extending out of the lung.

Figure 63:
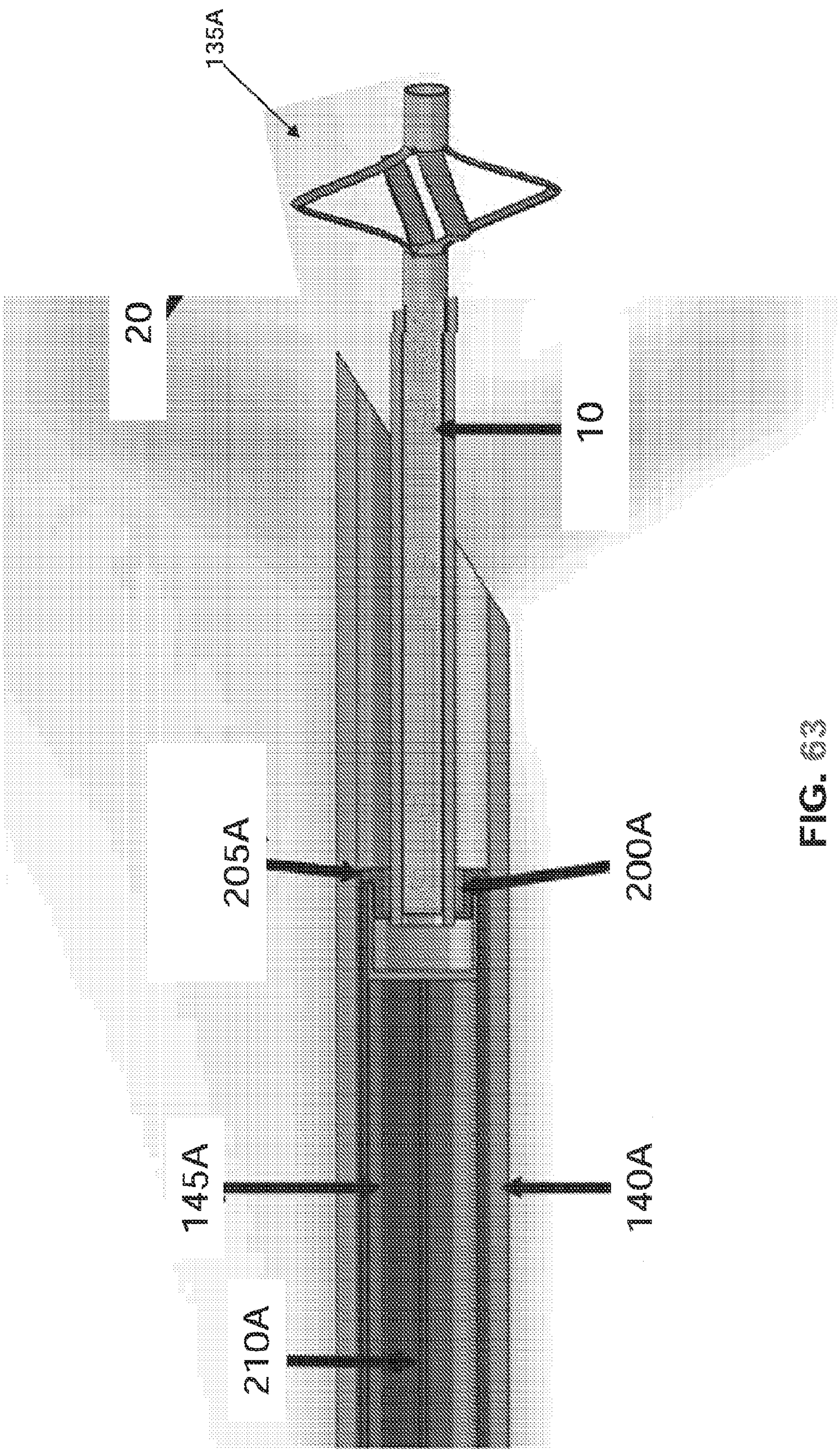
FIG. 63 is a schematic view showing how a temporary proximal electrical connection may be provided for the tissue fiducial sensor, e.g., such as when the fiducial sensor is deployed through a bronchoscope.

In one form of the invention, and looking now at FIG. 63, a temporary electrical connection for J-bar assembly 115A can be provided as follows. Fiducial sensor 10 of J-bar assembly 115A comprises a proximal electrical connector 200A (as well as the electrical lead 120A, which extends distally from fiducial sensor 10). Pusher 145A is cannulated and comprises a distal electrical connector 205A. Electrical power is provided to distal electrical connector 205A of pusher 145A by a wire 210A which extends through pusher 145A (and which connects to a power source, not shown). While J-bar assembly 115A is seated in needle cannula 140A, proximal electrical connector 200A of J-bar assembly 115A is connected to distal electrical connector 205A of pusher 145A, whereby to power fiducial sensor 10. After J-bar assembly 115A has been deployed in the anatomy of a patient (and after prongs 20 have set in the tissue), pusher 145A is retracted, separating distal electrical connector 205A of pusher 145A from proximal electrical connector 200A of J-bar assembly 115A, thereby disconnecting J-bar assembly 115A from the power supplied by wire 210A extending through pusher 145A. However, it will be appreciated that power may still be delivered to J-bar assembly 115A via electrical lead 120A and power supply connector 190A (connected to electrical lead 120A).

As noted above, it is generally desirable to know the position of J-bar assembly 115A relative to lesion 18, so that fiducial sensor 10 (carried by hook structure 16) can be secured in or adjacent to lesion 18. As also noted above, the position of fiducial sensor 10 can be known at all times if fiducial sensor 10 is being powered, e.g., by a power line temporarily provided through bronchoscope 60 and by a percutaneously-delivered power line which is secured to expandable basket 135A. Alternatively, the location of fiducial sensor 10 can be provided through the provision and use of an additional sensor located within deployment assembly 110A adjacent to hook structure 16 or by an additional sensor located on deployment assembly 110A itself.

Figure 64:
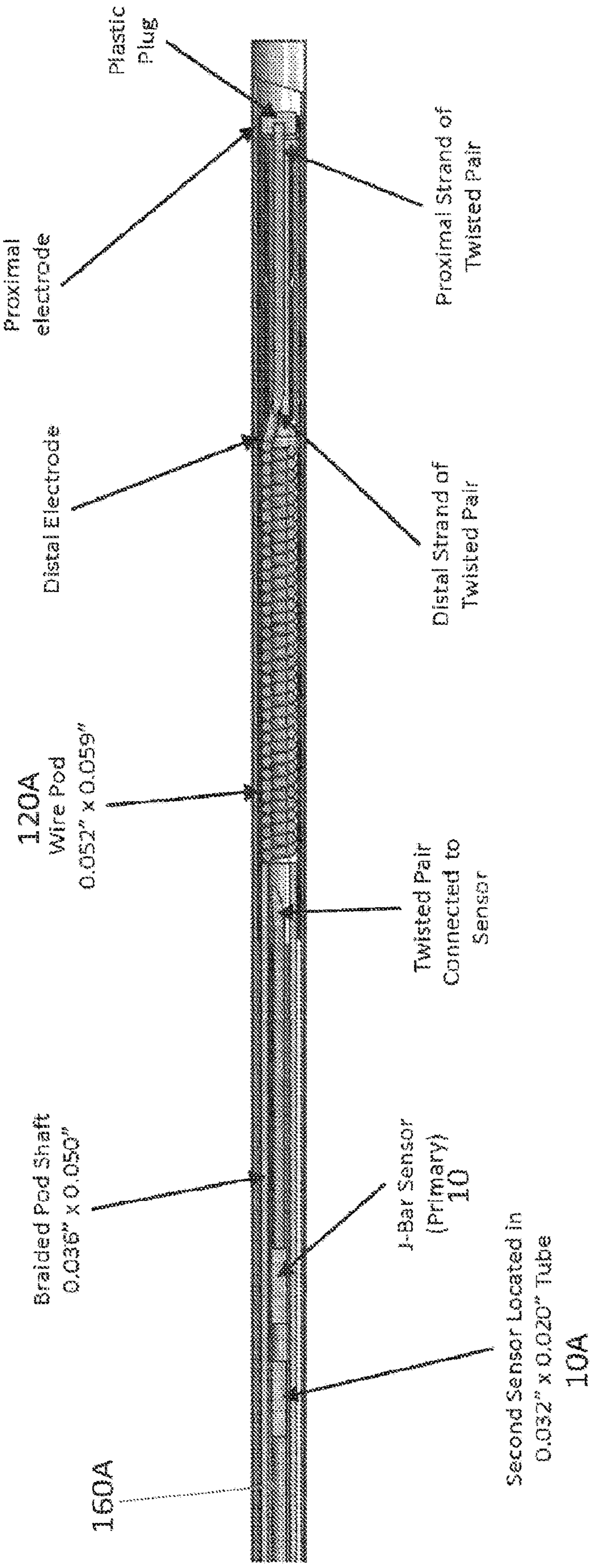
FIG. 64 is a schematic view showing how an additional sensor may be provided on the deployment assembly to identify the location of the tissue fiducial sensor during deployment.

More particularly, and looking now at FIG. 64, there is provided an additional fiducial sensor 10A which is mounted to the distal end of pusher 145A, adjacent to hook structure 16. The additional fiducial sensor 10A is powered via a power line carried pusher 145A (e.g., a portion of pusher 145A may comprise the power line). As a result of this construction, the location of additional fiducial sensor 10A can be determined by the system, and hence the position of fiducial sensor 10 can be determined by the system, without powering fiducial sensor 10 itself, as long as the additional fiducial sensor 10A is positioned adjacent to fiducial sensor 10. It will be appreciated that, after J-bar assembly 115A has been deployed in the tissue, fiducial sensor 10 may thereafter by suppled with power via a percutaneously-delivered power line connected to expandable basket 135A.

Figure 65:
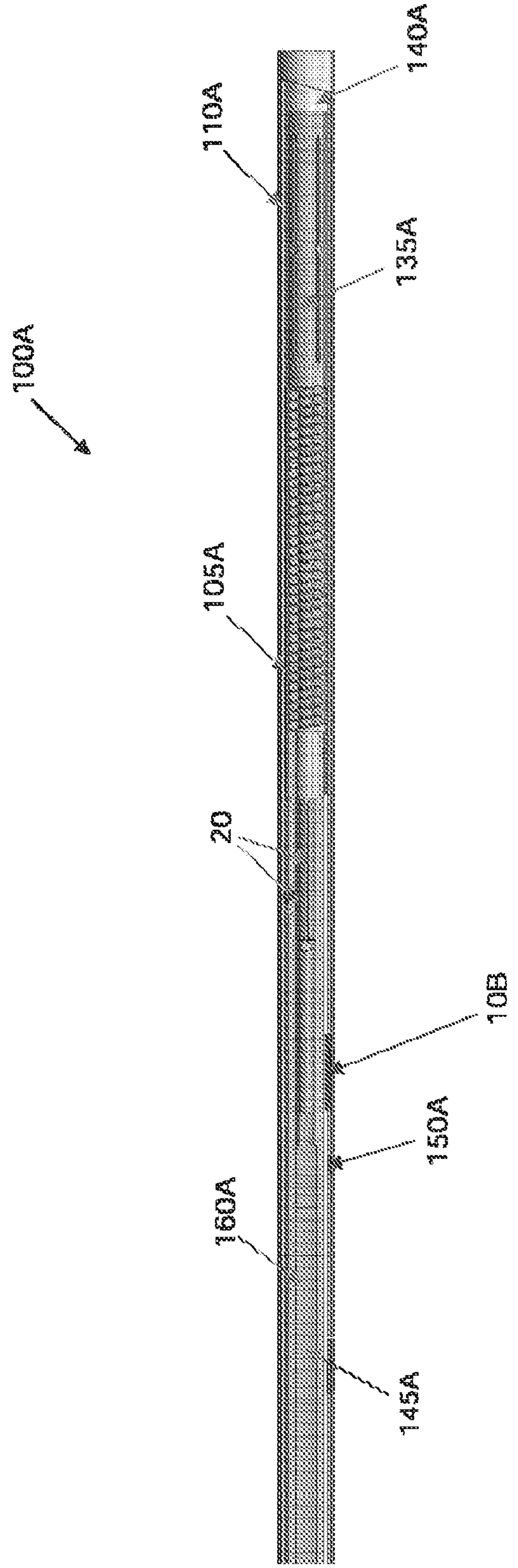
FIG. 65 is a schematic view showing another way that an additional sensor may be provided on the deployment assembly to identify the location of the tissue fiducial sensor during deployment.

Alternatively, and looking now at FIG. 65, an additional fiducial sensor 10B may be provided on deployment assembly 110A itself, with power being supplied to additional fiducial sensor 10B through a power line provided on deployment assembly 110A (not shown), adjacent to the starting position of hook structure 16. As a result of this construction, the location of additional fiducial sensor 10B, and hence the position of fiducial sensor 10, can be determined by the system, without powering fiducial sensor 10 itself, as long as the additional fiducial sensor 10B is positioned adjacent to fiducial sensor 10. Again, it will be appreciated that, after J-bar assembly 115A has been deployed in the tissue, fiducial sensor 10 may thereafter by suppled with power via a percutaneously-delivered power line connected to expandable basket 135A.

Means to Locate Pulmonary Artery During Surgery

During surgery it is generally important for the surgeon to know the location of the pulmonary artery so that the surgeon does not inadvertently damage the pulmonary artery, e.g., by stapling across the pulmonary artery during a resection procedure. This is clinically challenging, however, since surgery is generally conducted with the lung deflated and it can be difficult for the surgeon to identify the location of the pulmonary artery in the deflated lung during surgery, particularly given the limited visualization available with endoscopes/thorascopes (i.e., the surgeon is looking at the exterior of the lung through a thorascope, and the location of the pulmonary artery within the lung is concealed by the opaque outer surface of the lung).

Significantly, a new way to identify the location of the pulmonary artery during surgery has now been developed.

More particularly, the surgeon typically has a CT scan of the inflated lung prior to surgery. This CT scan can be segmented in ways well known in the art to identify the locations of the pulmonary artery and the trachea and bronchi relative to one another in the CT model.

Applicants have determined that there is very little deformation of the pulmonary artery, the trachea, and bronchi relative to one another as the lung is deflated, i.e., the locations of the pulmonary artery, the trachea and bronchi tend to remain substantially constant relative to one another as the lung is deflated.

In the preceding sections there is disclosed the idea of using a tracked bronchoscope and/or a bronchoscope-placed tracked catheter to map the trachea and bronchi of the lung.

In accordance with the present invention, the lung is scanned in the inflated condition prior to surgery, the tissue is segmented and the locations of the pulmonary artery and the trachea and bronchi are located in the CT model. Then the tracked bronchoscope (or bronchoscope-placed tracked catheter) is inserted into the inflated lung. As this is done, the bronchoscope (or catheter) is tracked in the sensor (i.e., real-world) frame of reference so that the locations of the trachea and bronchi carrying the bronchoscope are known in the sensor (i.e., real-world) frame of reference. Then the lung is deflated while the tracked bronchoscope (or tracked catheter) remains in the trachea and/or bronchi. As this occurs, the position of the bronchoscope is tracked in the sensor (i.e., real-world) frame of reference. Then this information is used to place the CT model (i.e., virtual world) into registration with the sensor (i.e., real-world) frame of reference by correlating the position(s) of the trachea and/or bronchi in the CT model (i.e., virtual world) with the position(s) of the bronchoscope-tracked (or catheter-tracked) trachea and/or bronchi in the sensor frame of reference. Once this is done, the position of the pulmonary artery (in the CT model) can be displayed on a monitor in the sensor frame of reference (e.g., in combination with a tracked stapler, tracked lesion, etc.) so that the surgeon will know the location of the pulmonary artery during surgery.

Note that registration may be done before or after the lung is collapsed (i.e., deflated). In general, it may be preferable to effect registration before the lung is collapsed since scanning typically occurs with the lung inflated.

In another form of the invention, the tracked bronchoscope (or tracked catheter) is inserted into the lung after the lung has been deflated, the tracked bronchoscope (or tracked catheter) is used to identify the locations of the trachea and the bronchi in the deflated lung, and then this information is used to place the CT model (i.e., virtual world) in proper registration with the sensor (i.e., real-world) frame of reference. This then allows the position of the pulmonary artery to be displayed on the monitor in the sensor (i.e., real-world) frame of reference.

Notably, the pulmonary artery and the trachea and bronchi have a fixed relationship to one another regardless of whether the lung is inflated or deflated, so a CT scan (i.e., virtual world image or model) of the inflated lung can be used to establish the relationship between the pulmonary artery, and the trachea and bronchi, and the tracked bronchoscope (or tracked catheter) can be used to locate the positions of the trachea and bronchi in the sensor (i.e., real-world) frame of reference, so the pulmonary artery can then be located in the sensor (i.e., real-world) frame of reference to display the location of the pulmonary artery during surgery.

Note that the same technique can be used to locate blood vessels other than the pulmonary artery during surgery, so long as those blood vessels remain in a substantially fixed position relative to the trachea and bronchi (e.g., it can be used to locate the pulmonary vein during surgery).

Marking Lesion so Can Easily Find Lesion For J-Bar Placement

Disclosed below are methods for marking a tissue mass (e.g., a lesion) within the human body, whereby to facilitate placement of a tracker (e.g., fiducial sensor 10) within, or next to, the target tissue mass. For the sake of clarity, the methods discussed below will be discussed in the context of facilitating deployment of the aforementioned J-bar assembly 115A (carrying the aforementioned fiducial sensor 10). However, it should be appreciated that the methods discussed below may be utilized in concert with substantially any apparatus used to place a tracker within, or next to, a target tissue mass.

(i) Drug Uptake Into Lesion

A variety of compounds have become available which uptake into a lesion and which can subsequently be located within the body (e.g., by fluorescence) so as to identify the location of the lesion.

One example of such a compound is Indocyanine Green (ICG), which is identified by fluorescence.

So with this form of the invention, the compound is administered to the patient, the compound concentrates in the body at the lesion, then the location of the lesion is identified by locating the concentrated compound (e.g., by using an appropriate scanner and visualizing the fluorescing drug on the scan image), and finally the J-bar is placed at the located lesion. Once the J-bar is deployed at the lesion, the system is then used in the manner discussed above.

(ii) Non-Drug Marking

In many situations the lesion may be located at a first location and/or first point in time, and the J-bar may be placed into the patient at a second, different location and/or a second, different point in time.

By way of example but not limitation, the lesion may be located while the patient is in interventional radiology for a biopsy, and the J-bar may be placed into the patient several days later in the operating room just prior to surgery.

In this situation, it would be desirable to mark the lesion during its initial location at interventional radiology in order to avoid having to re-locate the lesion just prior to J-bar emplacement in the operating room.

With this form of the invention, the lesion is marked when it is first located using a marking modality consistent with the locating modality, and then the marking is used to easily re-locate the lesion in the operating room (i.e., so that the J-bar can be deployed adjacent to the lesion).

By way of example but not limitation, if the lesion is initially located under image guidance during a biopsy, the location of the lesion may be marked by injecting a dye or ink (i) at the actual site of the lesion, and/or (ii) along the route to the lesion, and/or (iii) at the pleural surface. The J-bar is then subsequently advanced to the site of the lesion in the operating room by simply following the route indicated by the dye or ink path. Alternatively and/or additionally, if desired, the location of the lesion may be marked in another manner (e.g., applying a mark via electrocautery directly to tissue that is affected by the heat of the electrocautery device) that will be apparent to one of skill in the art in view of the present disclosure.

By way of further example but not limitation, if the lesion is initially located using interventional radiology during a biopsy, the location of the lesion might be marked by injecting radiopaque beads at the site of the lesion during the biopsy, and then the J-bar is subsequently advanced to the site of the lesion in the operating room by detecting the location of the radiopaque beads (e.g., by using C-arm imaging in the operating room).

If desired, a virtual model may be used in conjunction with interventional radiology during a biopsy in order to locate and mark the location of the lesion. With this form of the invention, a virtual model is obtained using a scanning modality such as CT scanning (see above). During the interventional radiology procedure, the radiologist locates the lesion (e.g., in the inflated lung) and inserts the J-bar into the anatomy in the area of the lesion. An intra-operative imaging modality (e.g., CT scanning) may be used to place the implanted J-bar into registration with the virtual model, such that the location of the lesion may be identified on the virtual model by a virtual object representative of the lesion (and/or a virtual object representative of the lesion and an appropriate resection margin extending about the lesion, see above) which is inserted into the virtual model.

During a later surgical procedure to mark the location of the lesion, the surgeon inserts a scope comprising a tracker into the anatomy (e.g., into the deflated lung), using the J-bar and the tracker on the scope to place the image obtained by the scope into registration with the virtual model. Once the surgeon has located the lesion using the tracked scope/modified scope image showing the lesion, the surgeon uses another surgical instrument (e.g., an electrocautery tool) to mark the tissue at the location of the lesion.

Subsequently, when the surgeon performs the resecting procedure, the markings added to the tissue may be used as visual cues to show the surgeon (e.g., on a scope image) the location of the lesion, without requiring tracking of the surgical instruments used in the subsequent procedure and without requiring that those instruments be placed into registration with the virtual model.

And it should also be appreciated that other locations may be marked using the methods and apparatus discussed above. By way of example but not limitation, the surgeon may mark a line to follow for a resecting procedure by injecting a dye or ink (or radiopaque beads) along the route to be followed for the resecting procedure (e.g., a "dotted" line), and/or the surgeon may mark the line to follow for a resecting procedure in another manner (e.g., applying a mark via electrocautery directly to tissue that is affected by the heat of the electrocautery device) that will be apparent to one of skill in the art in view of the present disclosure.

Using Tracked Bronchoscope to Target Percutaneously-advanced J-bar

In the preceding sections there was disclosed the concept of using a bronchoscope to deliver the J-bar to the site of the lesion by advancing the J-bar through the working channel of the bronchoscope. However, this approach has the disadvantage that, where the J-bar must be powered via a wire, there is a need to deal with the wire that powers the J-bar, so that the clinician must either:

(i) staple carefully around the power lead so that the lesion portion of the lung can be isolated from the remainder of the lung without stapling through the power lead, or (ii) use two different power leads to power the J-bar, i.e., one power lead extending through the bronchoscope which is used to power the J-bar as the J-bar is positioned adjacent to the lesion, and a second power lead extending through the wall of the lung which is used to power the J-bar after the J-bar is in place and during stapling, or (iii) the J-bar must be a wireless J-bar.

In a form of the invention, the bronchoscope is inserted into the inflated lung, a tracked needle is advanced through the bronchoscope until the tracked needle is adjacent to the lesion, the bronchoscope is withdrawn while leaving the tracked needle in place, the J-bar is advanced percutaneously to the lesion using the tracked needle to guide J-bar placement either in the inflated or deflated lung, and then the tracked needle is withdrawn before resecting the lesion. This approach is advantageous in that it solves the problem of stapling while the electrical lead extends out through the bronchi, or the problem of having to use two different power leads (i.e., one through the bronchoscope to power the J-bar during J-bar deployment and one through the lung wall to power the J-bar during stapling) and having to switch off between the two power leads, or the problem of having to use a wireless J-bar.

Magnetic Electrical Connectors

Where two different power leads are used to power the J-bar (i.e., one power lead extending through the bronchoscope which is used to power the J-bar as the J-bar is positioned adjacent to the lesion, and a second power lead extending through the wall of the lung which is used to power the J-bar after the J-bar is in place and during stapling), electrical connections between the second power lead and the J-bar can be difficult in a surgical setting.

To that end, super magnets may be used to align and connect the two counterpart connectors, i.e., a connector on the second power lead and a connector on the J-bar. Other elements, which are adjacent to magnets, are used to actually carry the electrical current.

Stapler Articulation Measurement

Figure 66:
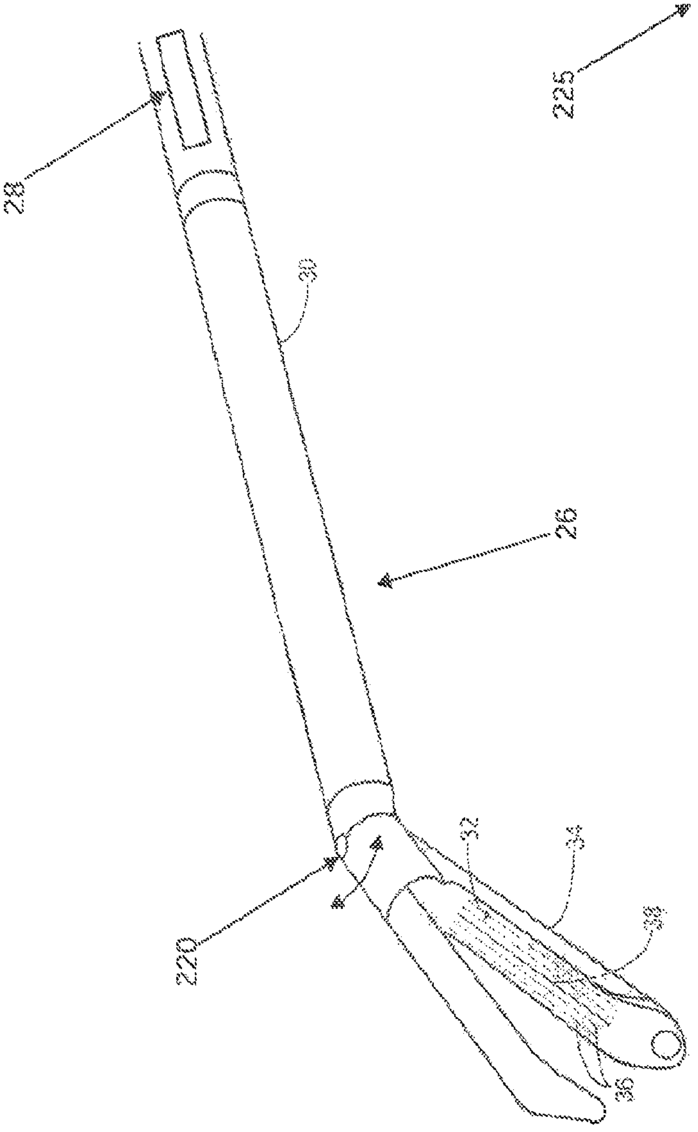

Surgical stapler heads can be articulated about a pivot point 220 to provide the desired orientation while resecting the lesion. While the instrument sensor 28 may be placed on the articulating head of the surgical stapler 26 (e.g., such as is shown in FIGS. 10 and 11), this can cause interference from ferromagnetic material on the stapler head. Therefore, in practice, the instrument sensor 28 is typically positioned on the shaft of the surgical stapler 26, just proximal to the articulation point, e.g., about 10 cm from the stapler tip, in order to avoid interference from ferromagnetic material on the stapler head. In this position, the instrument sensor 28 is proximal to the pivot point 220 on the surgical stapler 26, so that the instrument sensor 28 sits on the non-articulating portion of the stapler 26. See FIG. 66. As a result, the instrument sensor 28 placed on the non-articulating portion of the surgical stapler 26 does not capture the articulation motion of the surgical stapler 26.

Figure 67:
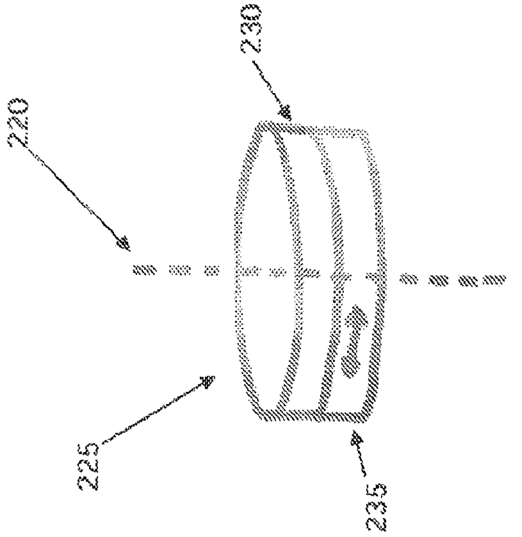
FIGS. 66 and 67 are schematic views showing a surgical stapler with an articulation sensor for detecting the articulation of the head of the surgical stapler.

Therefore, in another form of the invention, the surgical stapler 26 is configured to measure the articulation angle of the stapler head. More particularly, an articulation sensor 225 is provided which preferably comprises two parts. The first part 230 of the articulation sensor 225 is placed on the stapler shaft. The second part 235 of the articulation sensor 225 is placed on the articulating stapler head. The connection between the first and second parts 230, 235 of the articulation sensor 225 is through a flexible encoder circuit that measures the angulation of the articulating end of the stapler head. The encoder circuit is preferably a modified circular potentiometer to measure the angulation of the stapler head. See FIG. 67. A Wheatstone bridge circuit measures the variable resistance produced on the encoder circuit so as to estimate the stapler articulation angle. In addition, the surgical stapler 26 may also include an LED indicator (not shown) on the stapler shaft to confirm the placement of the articulation sensor 225 on the surgical stapler 26. Once the articulation sensor 225 is placed on the surgical stapler 26, the circuit is completed to light up the LED indicator.

If desired, the articulation sensor 225 may use schemes other than electrical resistance to measure stapler head articulation, e.g., an optical encoder may be used to measure stapler head articulation, or a magnetic encoder may be used to measure stapler head articulation, etc. The articulation sensor 225 can also be internalized to the specific working internal of the stapler device 26. Alternatively, a second sensor (not shown) can be placed on an elastic extension from the sleeve towards the tip and past the articulation to allow direct measurement of the stapler articulation angle. This extension may be secured with tape or other adhesive.

Marking the Boundary of a Resection Margin and Stapler Positioning

Figure 69:
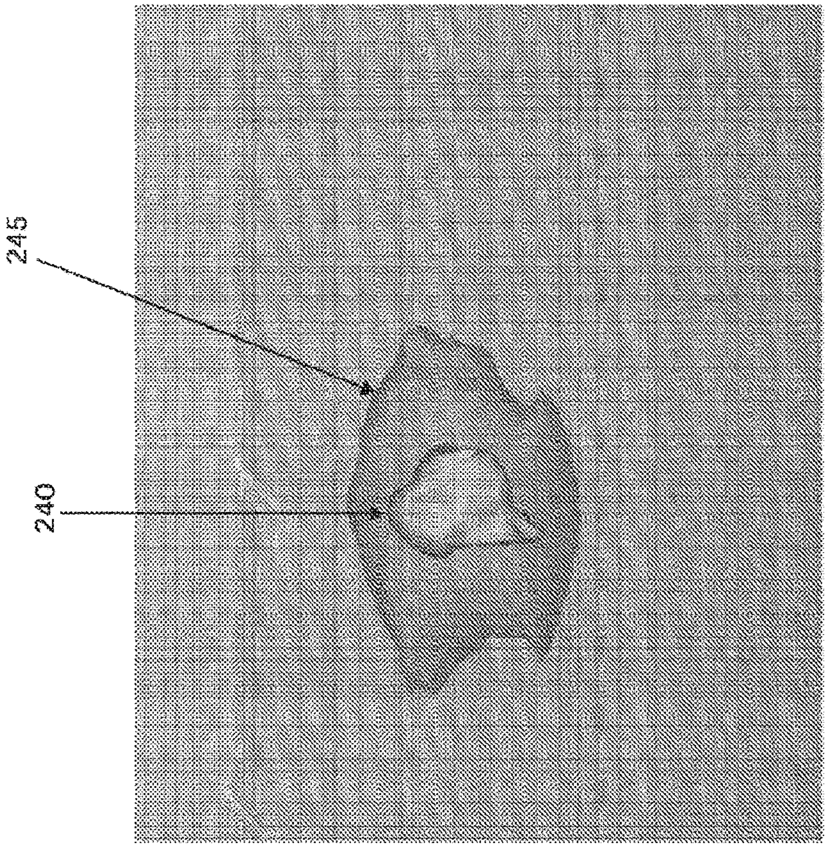
FIGS. 68 and 69 are schematic views showing (i) a model of a lesion, and (ii) a model of a resection margin in combination with a model of a lesion.
Figure 68:
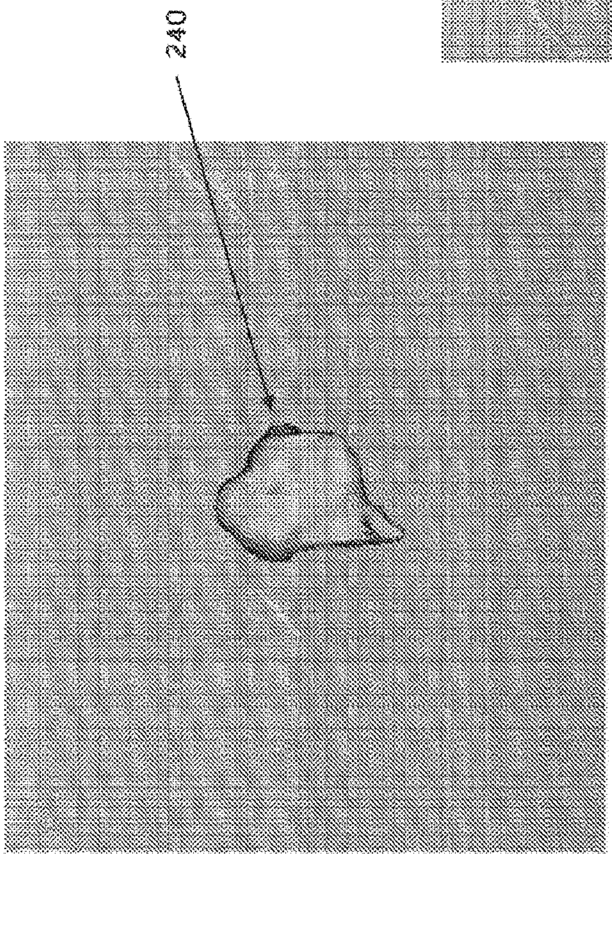

In one form of the invention, the lesion (i.e., the target tissue mass) will be segmented from the diagnostic CT imaging so as to create a 3D model of the lesion 240 that will be inputted to the navigation system. In another form of the invention, the lesion may be segmented based on a direct visualization of the lesion by the surgeon, with or without input from radiologic findings. Based on input from the surgeon or a machine learning algorithm, the resection margin will be determined. A segmented model for the resection margin 245 is generated by expanding the lesion label map by the desired resection margin. See FIGS. 68 and 69. With knowledge of the position of the fiducial sensor (e.g., the T-bar or J-bar assembly) and the lesion model 240, the position of the tracked surgical stapler can be precisely estimated with respect to the lesion model 240 and the estimated resection margin model 245.

Figure 70:
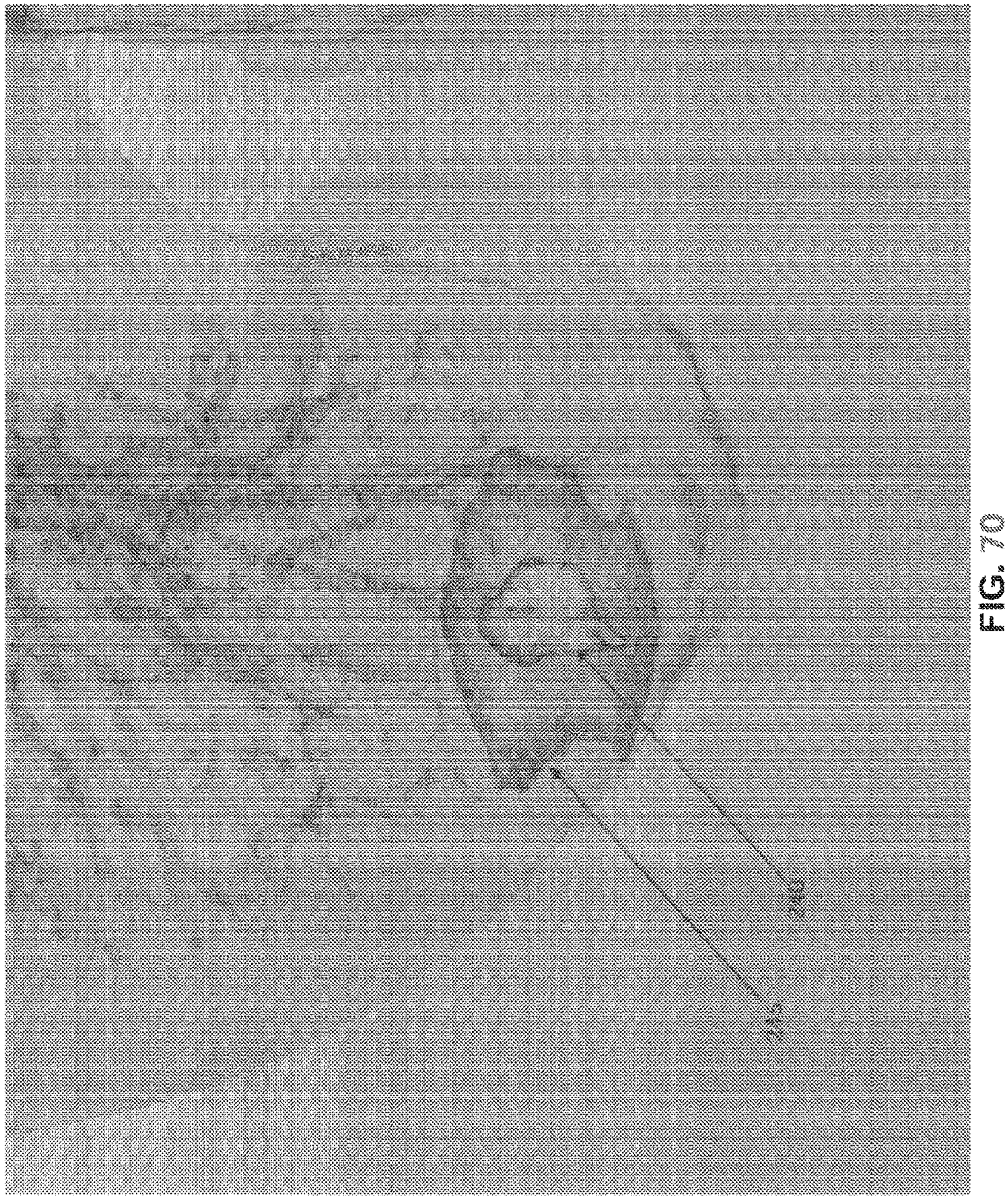
FIGS. 70-73 are schematic views showing how staples may be deployed adjacent to the resection margin of a lesion.
Figure 71:
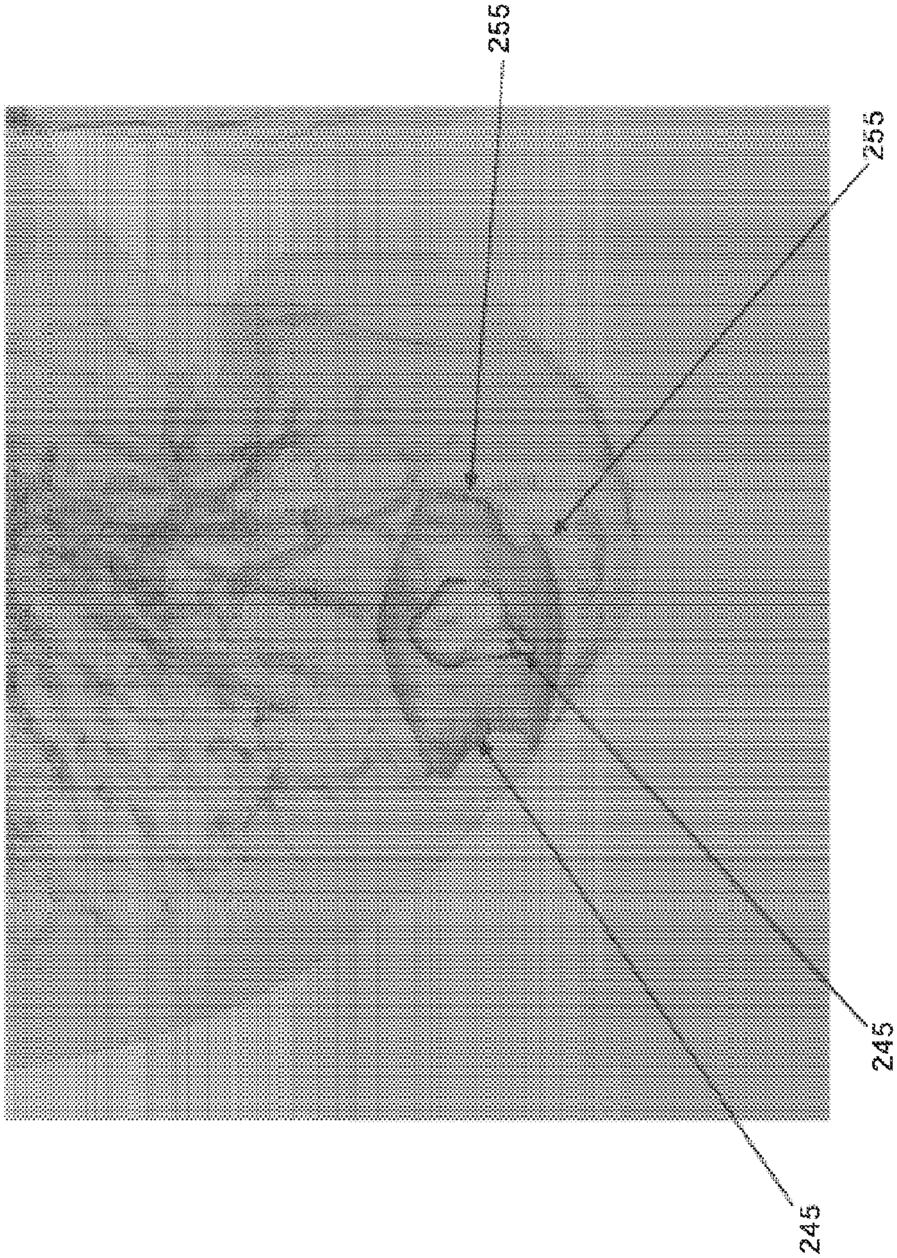
Figure 72:
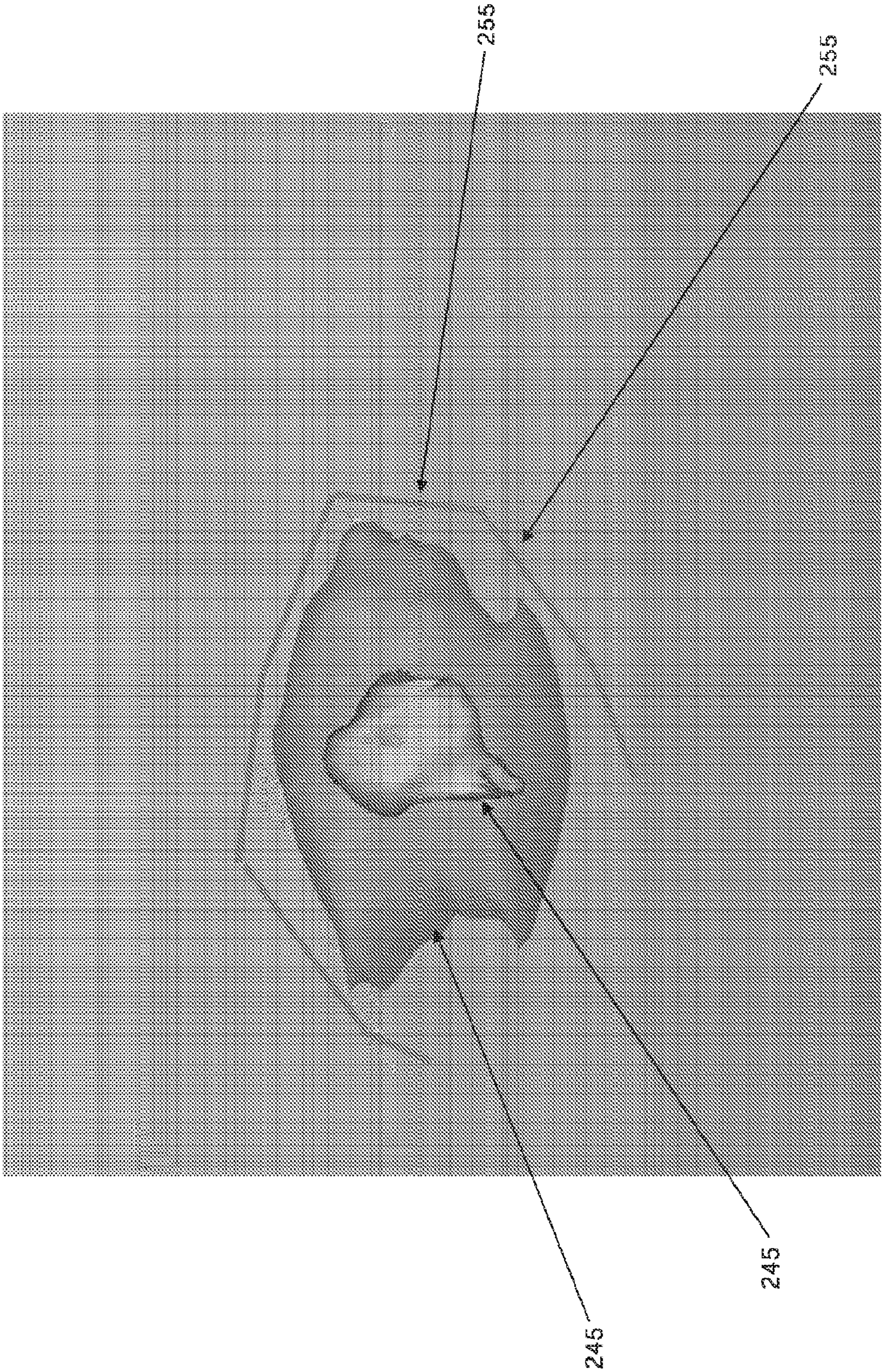
Figure 73:
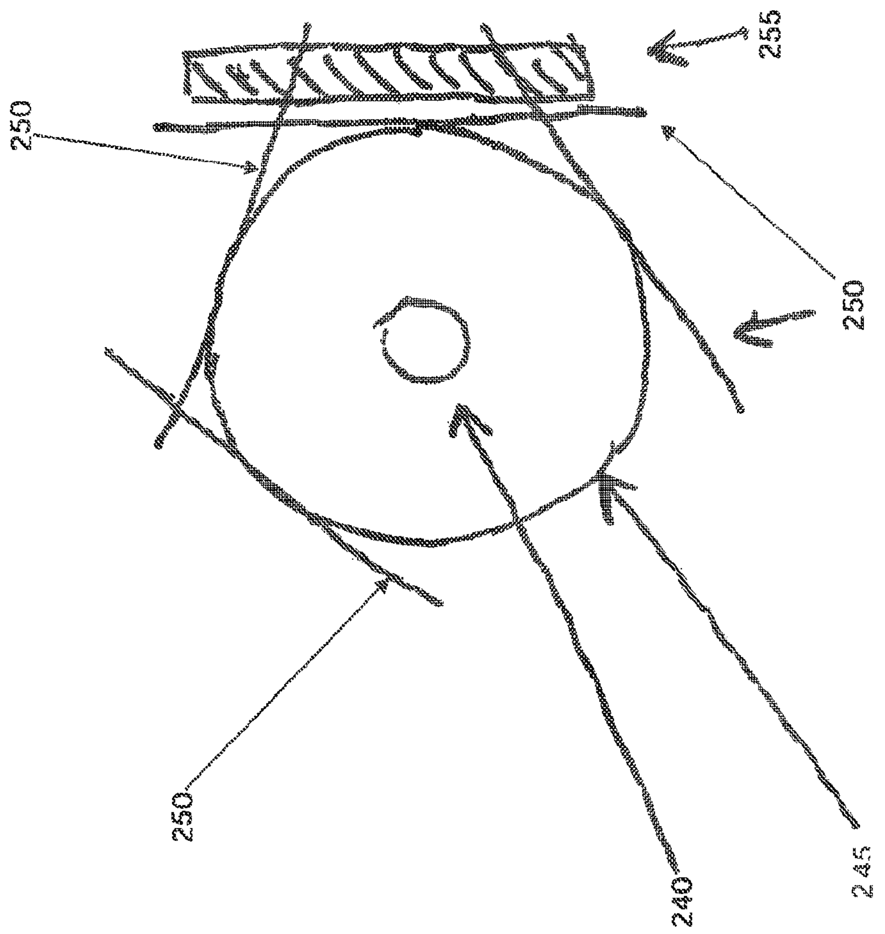

In addition to the foregoing, in one form of the invention, the navigation software can guide the surgeon to precisely resect around the lesion, based on a distance to secure a sufficient margin defined by the surgeon based on the mass size and presumed diagnosis. See FIGS. 70-72. More particularly, in one form of the invention, and looking now at FIG. 73, the navigation software computes the tangent lines 250 at the perimeter of the modeled resection margin 245, and then guides the surgeon to place the staples 255 just outside those tangent lines 250, so that the staples 255 follow a tangential path around the estimated resection margin model 245.

Figure 74:
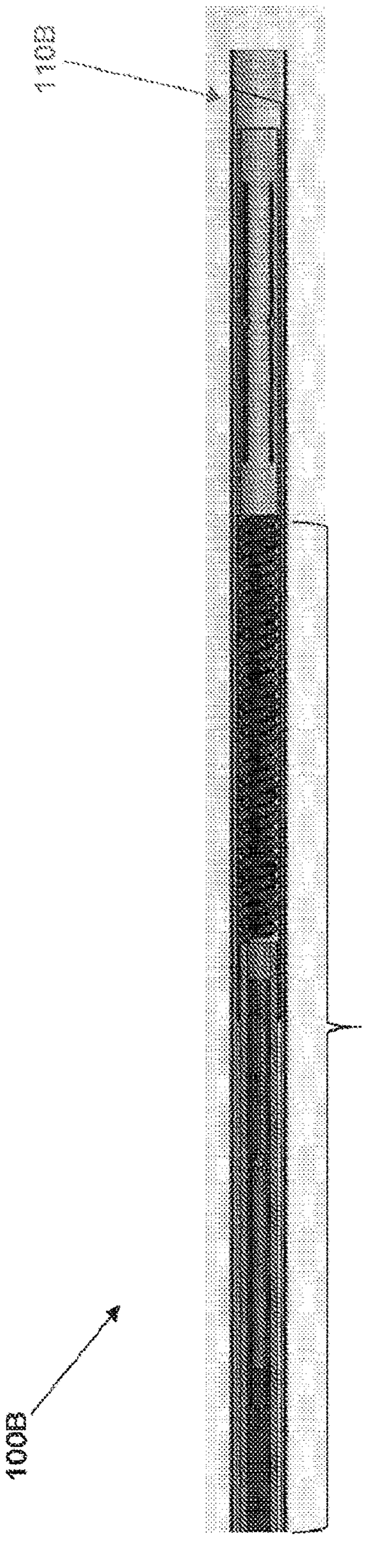
FIGS. 74-76 are schematic views showing another apparatus configured for "outside in" deployment of the fiducial sensor into tissue of an anatomical structure.

Alternative Method and Apparatus for Percutaneous "outside-in" Deployment of a Fiducial Sensor In still another embodiment of the invention, and looking now at FIG. 74, there is shown a sensor unit 100B configured for percutaneous deployment of fiducial sensor 10 into (or adjacent to) target tissue mass 18. Sensor unit 100B is substantially similar to bronchoscopic sensor unit 100A described above, except that (i) the electrical lead of sensor unit 100B is configured to span a longer distance than electrical lead 120 of bronchoscopic sensor unit 100A, and (ii) the orientation of the J-bar and electrical lead assembly of sensor unit 100B within the deployment assembly is reversed relative to the orientation of J-bar and electrical lead assembly 105A of sensor unit 100A within its respective deployment assembly, as will hereinafter be discussed in further detail.

More particularly, and still looking at FIG. 74, sensor unit 100B generally comprises a J-bar and electrical lead assembly 105B disposed within a deployment assembly 110B.

Figure 75:
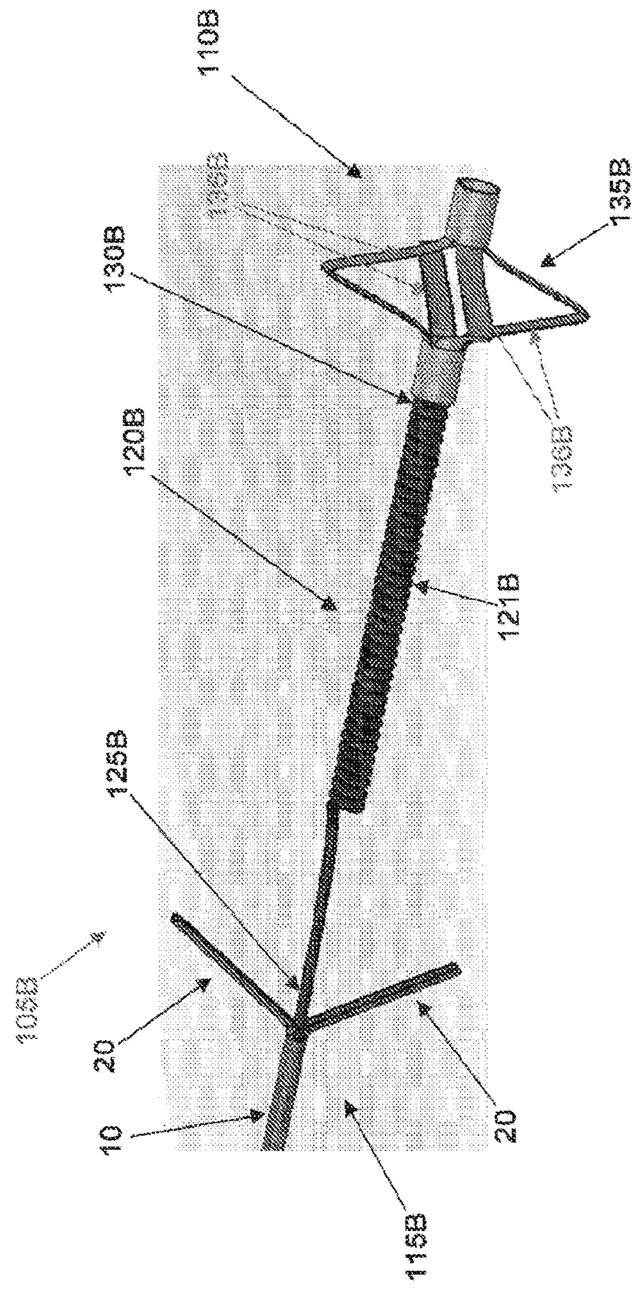

Looking now at FIG. 75, J-bar and electrical lead assembly 105B generally comprises a J-bar assembly 115B, an expandable backet 135B, and an electrical lead 120B extending between J-bar assembly 115B and expandable basket 135B. J-bar assembly 115B comprises the aforementioned hook structure 16 carrying the aforementioned fiducial sensor 10 and the aforementioned prongs 20 for mounting fiducial sensor 10 to tissue (see above). A first end 125B of electrical lead 120B is electrically connected to fiducial sensor 10 such that electrical power delivered to electrical lead 120B can power fiducial sensor 10. A second end 130B of electrical lead 120B is electrically connected to expandable basket 135B. It should be appreciated that expandable basket 135B can be identical to, or substantially identical to, the aforementioned expandable basket 135A. Hence, expandable basket 135B may be exchanged with the aforementioned expandable basket 135A without departing from the scope of the present invention.

Electrical lead 120B comprises a spring coil 121B intermediate (i) first end 125B of electrical lead 120B and (ii) expandable basket 135B mounted to second end 130B of electrical lead 120B. Spring coil 121B is configured to unspool as second end 130B of electrical lead 120B is moved away from first end 125B of electrical lead 120B, such that the distance between first end 125B of electrical lead 120B and expandable basket 135B may be selectively varied, whereby to accommodate differences in patient anatomy and lesion location within the anatomy. Inasmuch as sensor unit 100B is configured for percutaneous deployment through an insertion path that may differ depending on the target anatomy for emplacement of fiducial sensor 10 (e.g., the path to a deployment site located within the lung may be longer than the path to a deployment site located near the skin surface of the breast), and inasmuch as the length of the insertion path may differ between patients having different sized anatomy (e.g., the path to a deployment site located within the lung of an obese patient may be longer than the path to a deployment site located within the lung of a non-obese patient), it should be appreciated that, if desired, electrical lead 120B may be provided in various lengths in the form of a kit, such that insertion paths of varying lengths may be accommodated.

If desired, electrical lead 120B may be covered with a hydrophobic braided wire to facilitate easy insertion and retraction of J-bar and electrical lead assembly 105B through lumen 150B (see below) of deployment assembly 110B.

Expandable basket 135B may comprise substantially any geometry that is suitable for expansion against the side wall of tissue (e.g., the side wall of an internal organ such as a lung, the outer surface of the skin, etc.) in order to maintain J-bar and electrical lead assembly 105B in position. In one form of the invention, expandable basket 135B comprises a plurality of spring-biased legs 136B configured to expand radially outboard once released from the confinement of deployment assembly 110B, as will hereinafter be discussed in further detail. To this end, if desired, spring-biased legs 136B of expandable basket 135B may be formed out of a shape memory metal (e.g., Nitinol).

It will be appreciated that, when legs 136B of expandable basket 135B are expanded radially outboard (i.e., under the spring bias of their own resiliency), expandable basket 135B prevents retrograde movement of the electrical lead 120B after deployment. Furthermore, as noted above, prongs 20 of J-bar assembly 115B are configured to prevent antegrade movement of J-bar assembly 115B once J-bar assembly 115B is released from deployment assembly 110B.

Figure 76:
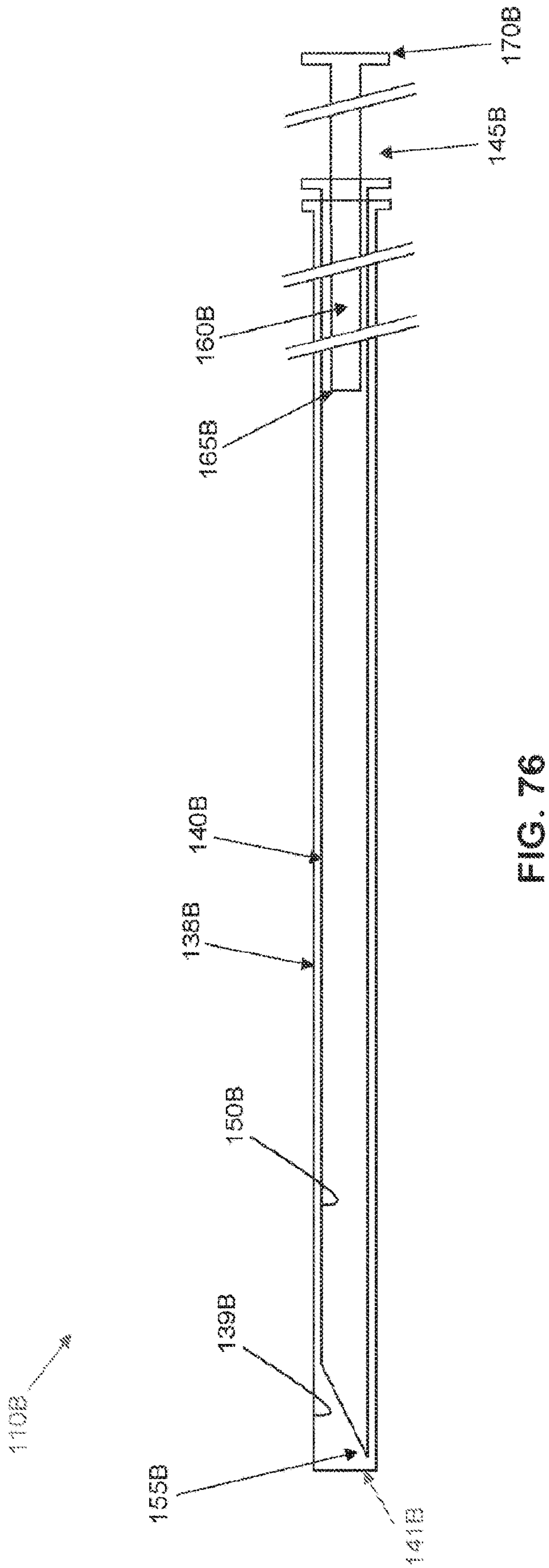

Deployment assembly 110B is generally similar to the aforementioned deployment assembly 110A discussed above. More particularly, and looking now at FIG. 76, deployment assembly 110B comprises an outer cannula 138B, a needle cannula 140B and a pusher 145B. Outer cannula 138B comprises a hollow lumen 139B which preferably terminates in in a blunt distal surface 141B extending about the perimeter of the distal end of outer cannula 138B and open onto lumen 139B. Needle cannula 140B is sized to be slidably received in hollow lumen 139B of outer cannula 138B. Pusher 145B comprises a shaft 160B. One end of shaft 160B terminates in a blunt distal end 165B. The other end of shaft 160B terminates in a handle 170B. Shaft 160B of pusher 145B is sized to be slidably received in lumen 150B of needle cannula 140B.

Figure 77:
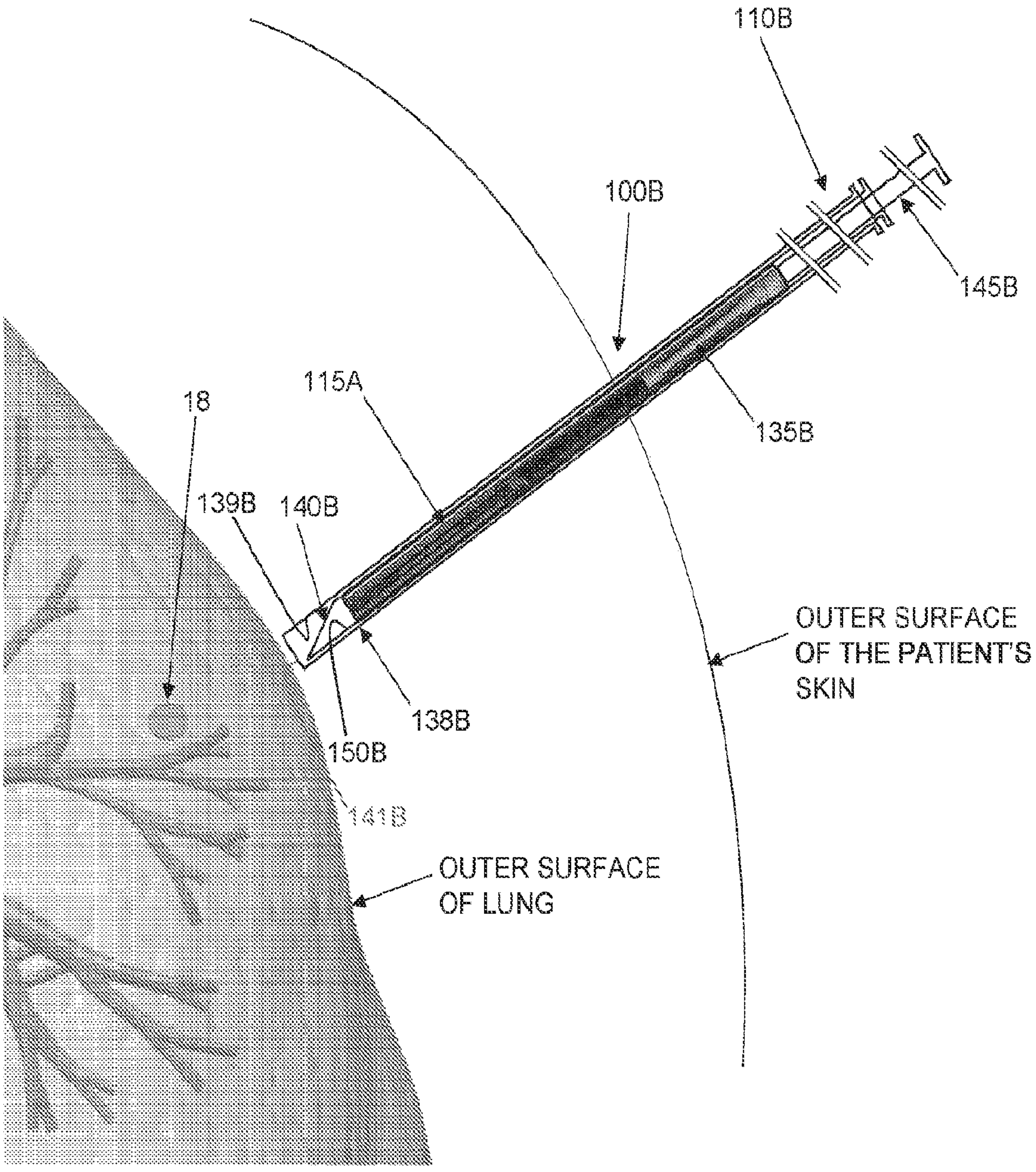
FIGS. 77-80 are schematic views showing a method for deploying the apparatus of FIGS. 74-76 in the anatomy.

Looking now at FIG. 77, needle cannula 140B is initially disposed within lumen 139B of outer cannula 138B, J-bar and electrical lead assembly 105B and shaft 160B of pusher 145B are initially disposed within (or partially within) lumen 150B of needle cannula 140B, with prongs 20 of J-bar assembly 115A being elastically deformed into a straightened configuration such that the sidewall defining lumen 150B constrains prongs 20 of J-bar assembly 115A in a radially-reduced, longitudinally-elongated configuration. Expandable basket 135B is elastically deformed so that it is constrained in a radially-reduced, longitudinally-elongated configuration within lumen 150B of needle cannula 140B. In this way, needle cannula 140B is configured to carry J-bar and electrical lead assembly 105B, with needle cannula 140B shielding J-bar and electrical lead assembly 105B from contact with surrounding structures (e.g., surrounding tissue, when needle cannula 140B is deployed percutaneously out of outer cannula 138B into a patient as will hereinafter be discussed in further detail). Pusher 145B is received within needle cannula 140B such that blunt distal end 165B of shaft 160B of pusher 145B is disposed just proximal to the proximalmost portion of expandable basket 135B disposed in needle cannula 140B (see FIG. 77), and such that distal movement of shaft 160B of pusher 145B causes blunt distal end 165B of shaft 160B to engage the proximalmost portion of expandable basket 135B, whereby to permit selective movement of J-bar and electrical lead assembly 105B distally relative to needle cannula 140B by moving shaft 160B of pusher 145B distally, and hence to permit J-bar and electrical lead assembly 105B to be selectively ejected from lumen 150B of needle cannula 140B, as will hereinafter be discussed in further detail.

In use, and still looking now at FIG. 77, the intended position of J-bar and electrical lead assembly 105B vis-á-vis the anatomy of the patient is preferably planned prior to deployment in the desired anatomical structure (e.g., the lung) using diagnostic or intraprocedural CT, C-arm CT, MRI or other imaging modalities which will be apparent to one of skill in the art in view of the present disclosure. Stated another way, the intended position of J-bar assembly 115B within the anatomy, and the exit point of electrical lead assembly 120B where it extends out of the surface of the patient's skin (or other tissue), are preferably planned in advance using diagnostic or intraprocedural CT, C-arm CT, MRI or other imaging modalities. The electromagnetic (EM) tracking coordinates are mapped to the diagnostic/intraprocedural imaging coordinates using image registration algorithms known in the art to track the J-bar and electrical lead assembly 105B in the imaging coordinates. The position of J-bar assembly 115B is chosen to be in the proximity of the target tissue mass (e.g., a tissue mass located on or within the anatomical structure), preferably along the line joining the target position and the exit location of the electrical lead, which exit location of electrical lead 120B from the anatomy (e.g., from the surface of the patient's skin) is typically chosen to be (i) the shortest path from the J-bar location to the outer surface of the patient's skin, or (ii) according to surgeon preference.

By way of example but not limitation, in one embodiment of the invention, and still looking at FIG. 77, an incision is made in the patient's skin so as to form an opening therein sufficiently sized to receive outer cannula 138B. Outer cannula 138B is inserted through the opening and into the anatomy until the blunt distal surface 141B of outer cannula 138B is disposed against the outer surface of the anatomical structure (e.g., the outer surface of the lung) into which fiducial sensor 10 is to be implanted. To this end, outer cannula 138B may comprise a temporary element such as a trochar (not shown) disposed within hollow lumen 139B of outer cannula 138B to maintain lumen 139B free of tissue/debris/fluid as the outer cannula is moved distally into the anatomy, as will be apparent to one of skill in the art in view of the present disclosure. Alternatively, if desired, needle cannula 140B (comprising J-bar and electrical lead assembly 105B disposed in needle lumen 150B of needle cannula 140B) may be disposed within outer cannula 138B when outer cannula 138B is advanced distally, with sharp distal tip 155B of needle cannula 145B providing a distal leading edge for facilitating movement through tissue.

It will be appreciated that the position of J-bar assembly 115B may be tracked in real-time provided that electrical power is provided to fiducial sensor 10 of J-bar assembly 115B. To this end, electrical power may be supplied to electrical lead 120B (and hence, to fiducial sensor 10 electrically connected to first end 125B of electrical lead 120B) by connecting a power source to a connector (not shown) disposed on the proximal end of expandable basket 135B which is in electrical connection with second end 130B of electrical lead 120B. As a result, the position of fiducial sensor 10 (and hence, the position of J-bar assembly 115B) may be mapped to the imaging coordinates (see above) using image registration algorithms of the sort known in the art in order to guide outer cannula 138B to the appropriate location at the outer surface of the lung, in line with the tissue mass 18.

Figure 78:
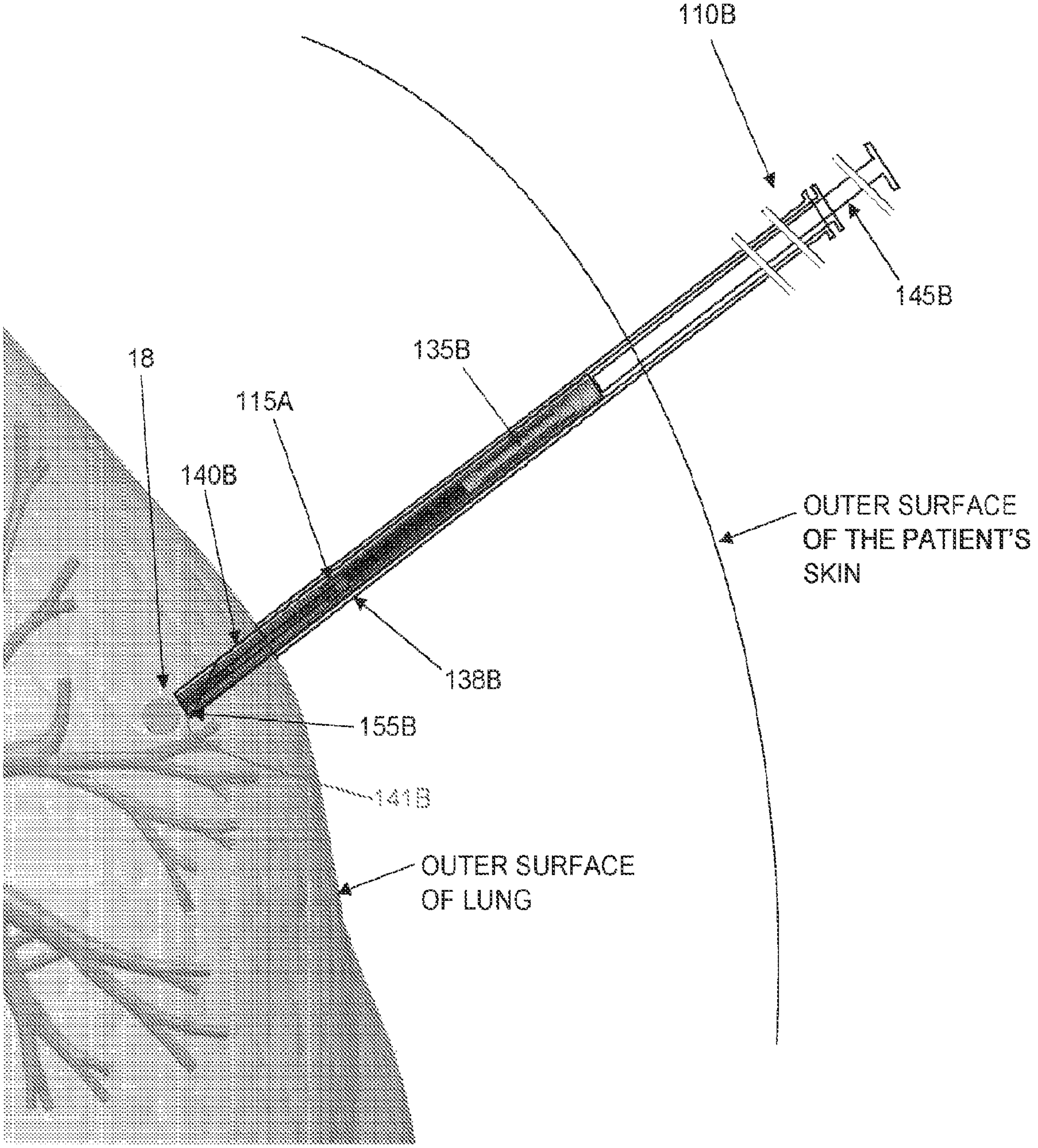

Once the distal end of outer cannula 138B is disposed against the outer surface of the organ/tissue (e.g., the lung) in alignment with tissue mass 18, and looking now at FIG. 78, needle cannula 140B (carrying J-bar and electrical lead assembly 105B and pusher 145B) is moved distally relative to outer cannula 138B such that sharp distal tip 155B of needle cannula 140B engages the tissue of the anatomical structure (e.g., the outer surface of a lung), whereby to permit distal movement of needle cannula 140B through the outer surface of the anatomical structure and into the tissue of the anatomical structure towards tissue mass 18. Note that the distal end of needle cannula 140B can be guided visually via a scope (e.g., a bronchoscope disposed in the lung, such as the aforementioned bronchoscope 60), and/or via scanner visualization (e.g., CT imaging, C-arm imaging, ultrasound imaging, etc.), or by using the temporarily-electrically-connected J-bar assembly 115B to track fiducial sensor 10 directly (see above).

After needle cannula 140B has been advanced through the tissue of the anatomical structure such that the distal end of needle cannula 140B (i.e., sharp distal tip 155B) is disposed at (or directly next to) tissue mass 18, needle cannula 140B is retracted proximally while blunt distal end 165B of shaft 160B of pusher 145B is maintained in position (or advanced distally) so as to engage the proximal end J-bar assembly 115B, whereby to apply a distally-directed force thereto which holds J-bar assembly 115B in position while needle cannula 140B is retracted proximally. As needle cannula 140B is retracted proximally relative to J-bar assembly 115B, needle cannula 140B retracts past prongs 20 of J-bar assembly 115A with the result that prongs 20 are no longer radially constrained within lumen 150B of needle cannula 140B (or within lumen 139B of outer cannula 138B), with the result that prongs 20 are free to spring radially outboard and set into tissue, whereby to anchor J-bar assembly 115B (and hence fiducial sensor 10) adjacent to tissue mass 18. See FIG. 79.

Figure 79:
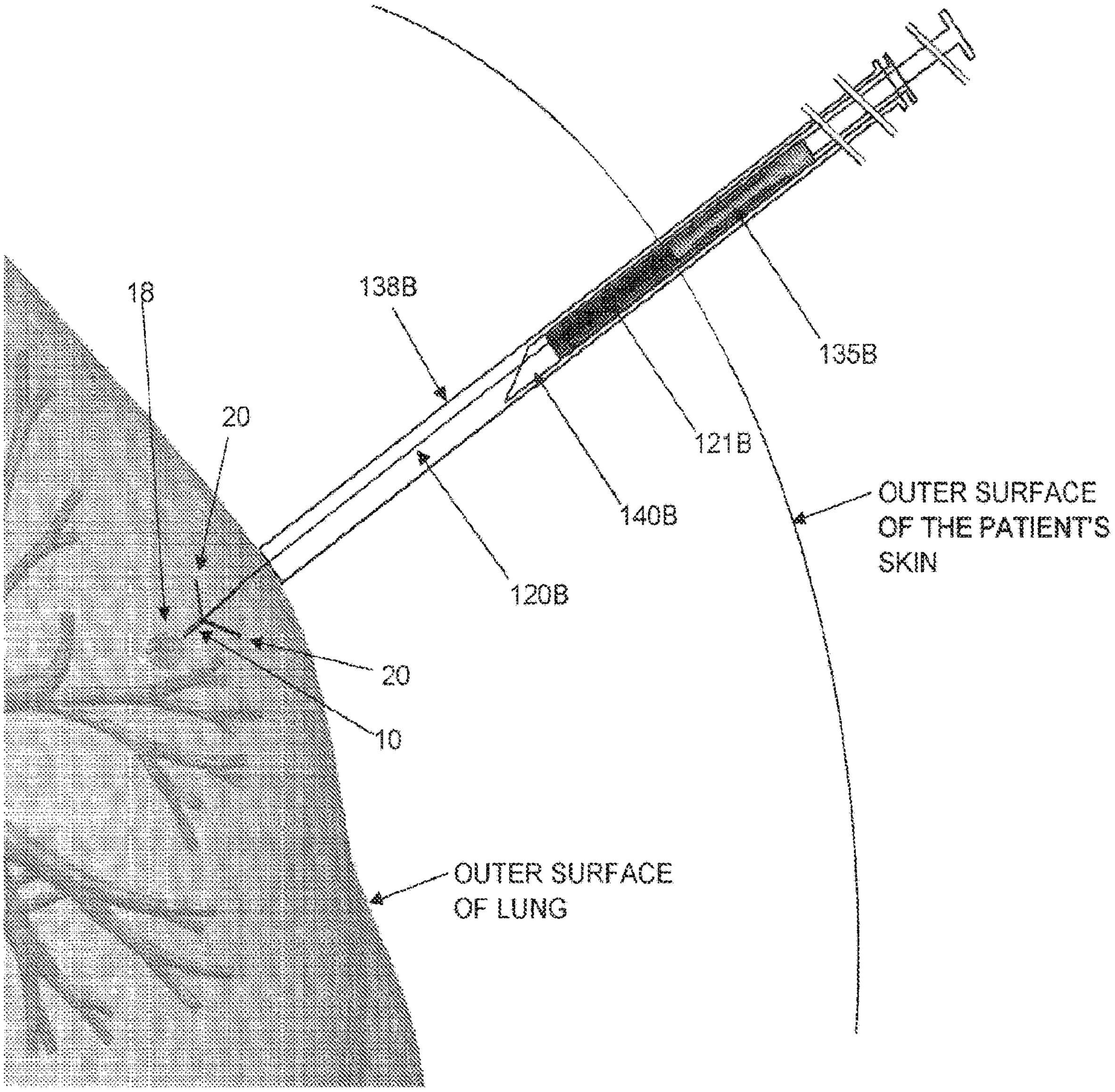

After J-bar assembly 115B has been deployed into the tissue such that fiducial sensor 10 is anchored adjacent to tissue mass 18, and looking now at FIG. 79, needle cannula 140B and outer cannula 138B are retracted proximally in concert as a unit. As this occurs, the interference fit between expandable basket 135B and the inner wall of needle cannula 140B while basket 135B is in a constrained, radially-reduced, longitudinally-elongated configuration acts to maintain expandable basket 135B in position within needle cannula 140B as the needle cannula is retracted proximally. As a result, spring coil 121B of electrical lead 120B unspools/elongates, permitting electrical lead 120B to span the indeterminate distance between (i) the location at which fiducial sensor 10 is implanted into the tissue, and (ii) expandable basket 135B deployed on the outer surface of the patient's skin, as will hereinafter be discussed in further detail.

Once outer cannula 138B and needle cannula 140B have been fully retracted proximally such that the distal end of outer cannula 138B is at (or very near) the outer surface of the patient's skin, pusher 145B is moved distally so as to engage the proximal end of expandable basket 135B within needle cannula 140B. Once blunt distal end 165B of shaft 160B of pusher 145B has engaged the proximal end of expandable basket 135B, pusher 145B may be moved distally in order to push expandable basket 135B distally, whereby to eject expandable basket 135B out of the distal end of needle cannula 140B. As this occurs, legs 136B of expandable basket 135B are released from the radial restraint of needle cannula 140B and assume their radially-expanded configuration against the outer surface of the patient's skin. Alternatively and/or additionally, if desired, pusher 145B may be used to apply a distally-directed force to expandable basket 135B at the same time that outer cannula 138B and needle cannula 140B are withdrawn proximally, with the result that outer cannula 138B and needle cannula 140B move proximally relative to expandable basket 135B, whereby to eject expandable basket 135B out of the distal end of needle cannula 140B (with the same effect).

Figure 80:
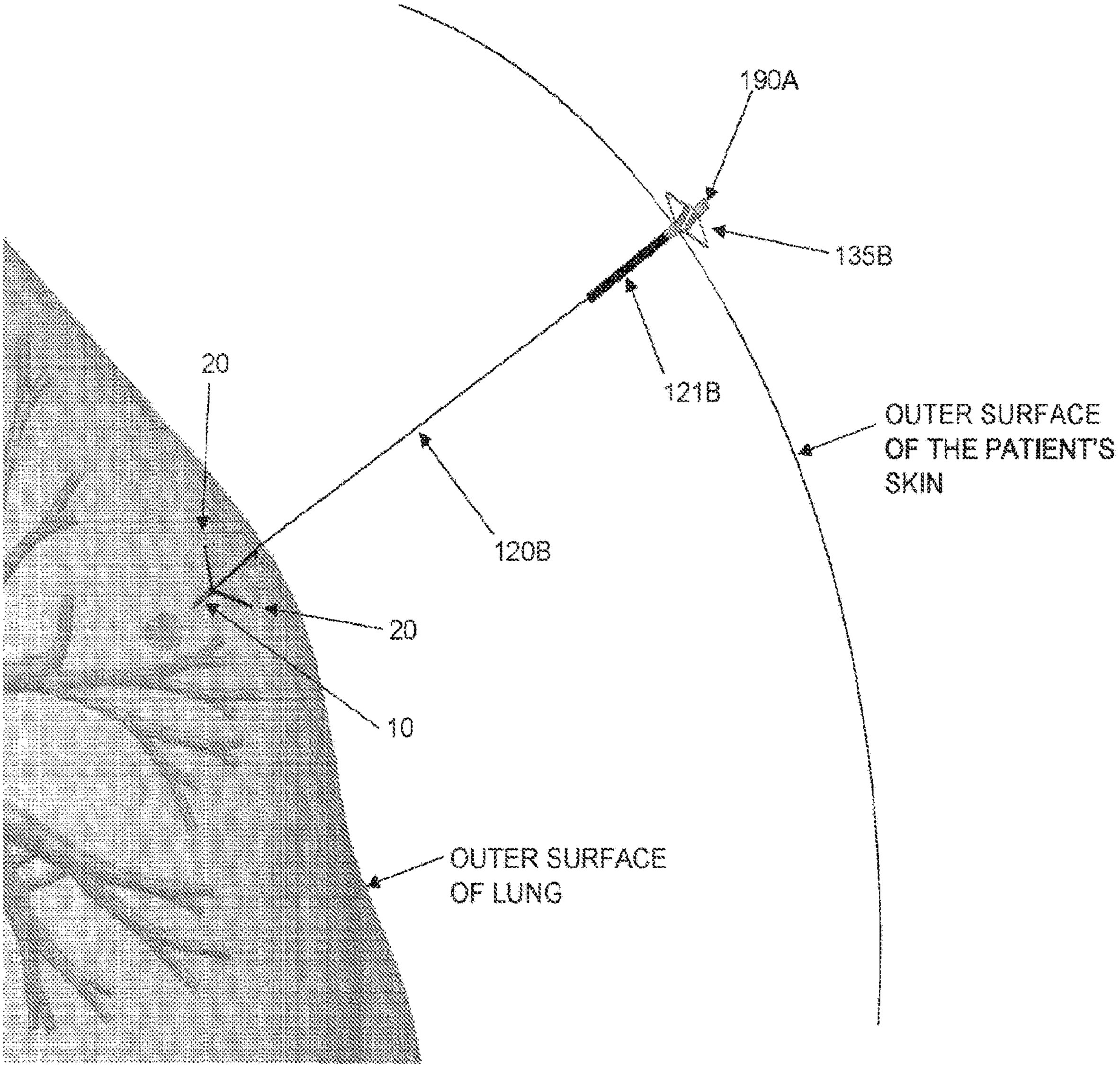
Figure 81:
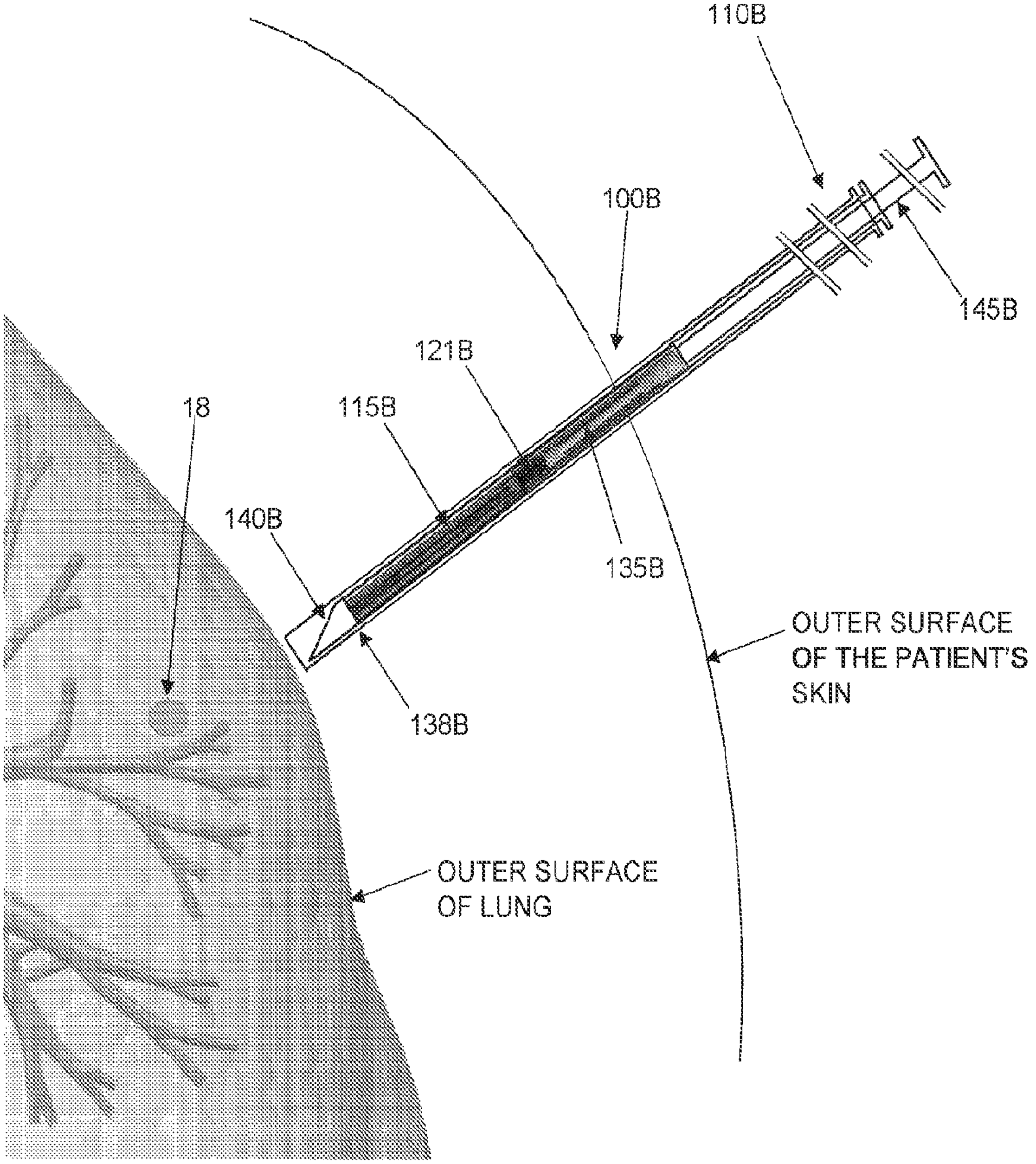
FIGS. 81-84 are schematic views showing another method for deploying the apparatus of FIGS. 74-76 in the anatomy.

Looking now at FIG. 80, as expandable basket 135B is ejected out of the distal end of needle cannula 140B (and outer cannula 138B is moved proximally so as to expose the distal end of needle cannula 140B), expandable basket 135B is no longer radially constrained by needle cannula 140B or outer cannula 138B. As a result, legs 136B of expandable basket 135B assume their radially-expanded, longitudinally-shortened configuration, whereby to bear against the outer surface of the patient's skin while maintaining electrical lead 120B in position.

It will be appreciated that expandable basket 135B comprises an electrical connector electrically connected to second end 130B of electrical lead 120B. By way of example but not limitation, expandable basket 135B may comprise the aforementioned power supply connector 190A (FIG. 80), whereby to permit an external power source (not shown) to be electrically connected to electrical lead 120B, and hence electrically connected to fiducial sensor 10 (whereby to power fiducial sensor 10). As discussed above, once powered, fiducial sensor 10 communicates with the electromagnetic (EM) tracking system and the location of fiducial sensor 10 (and hence the location of tissue mass 18) can be determined by controller 48.

Once the location of tissue mass 18 is established, a surgical instrument (e.g., the aforementioned surgical instrument 80 carrying an instrument sensor 85) may be used to effect the desired surgical procedure (e.g., excision of tissue mass 18).

It will be appreciated that the novel method and apparatus discussed above is particularly well-suited for percutaneous implantation of fiducial sensor 10 during a pre-operative planning procedure. By way of example but not limitation, a radiologist may implant sensor unit 100B under substantially any image guidance (e.g., CT, C-arm CT, fluoroscopy, ultrasound, etc.) immediately after locating the tissue mass, regardless of whether the anatomical structure that the tissue mass is located within is a deformable anatomical structure (e.g., the lungs, the stomach, the bladder, etc.). Specifically, fiducial sensor 10 may be mounted in the anatomy in the manner discussed above when the anatomical structure is in an inflated condition (e.g., during a radiological procedure), and thereafter located during an interventional surgical procedure when the anatomical structure is in a deflated condition (e.g., during a surgical procedure to excise the tissue mass and/or a portion of the tissue comprising the tissue mass, such as a resecting procedure). Additionally, the ability to mount fiducial sensor 10 in the anatomy under radiological guidance finds particular utility where the tissue mass is located in a highly-vascularized organ such as the liver. And once fiducial sensor 10 is successfully installed adjacent tissue mass 18, the location of fiducial sensor 10 may provide the surgeon with information that can be useful in planning the subsequent surgical procedure such as, for example, identifying which quadrant of the anatomical structure the tissue mass 18 is located in.

Additionally, it will be appreciated that by disposing expandable basket 135B at the external surface of the patient's skin, it is relatively simple for the surgeon to temporarily disconnect the power supplied to the aforementioned power supply connector 190A (e.g., by unplugging the external power source from power supply connector 190A) so that the patient may be moved from one area to another. By way of example but not limitation, power may be disconnected after fiducial sensor 10 has been successfully implanted, the patient may be moved from the radiological suite to an appropriate operating room for the subsequent surgical procedure, and power supply connector 190A may be easily located and re-connected to a power source in the operating room.

Once the surgical procedure (e.g., a resecting procedure performed on the lung) is completed, fiducial sensor 10 may be removed (e.g., together with excised tissue), electrical lead 120B may be cut intermediate its length, and expandable basket (and the portion of electrical lead 120B extending distally therefrom) may be removed from the anatomy.

By way of further example but not limitation, in another embodiment of the invention, and looking now at FIGS. 81-84, it is possible to employ the percutaneous "outside in" approach described above in order to dispose expandable basket 135B at a location within the anatomy located between the outer surface of the patient's skin and fiducial sensor 10 implanted within the interior of an anatomical structure. By way of example but not limitation, it is possible to employ the percutaneous "outside in" approach described above in order to dispose expandable basket 135B at the outer surface of the lung.

Figure 82:
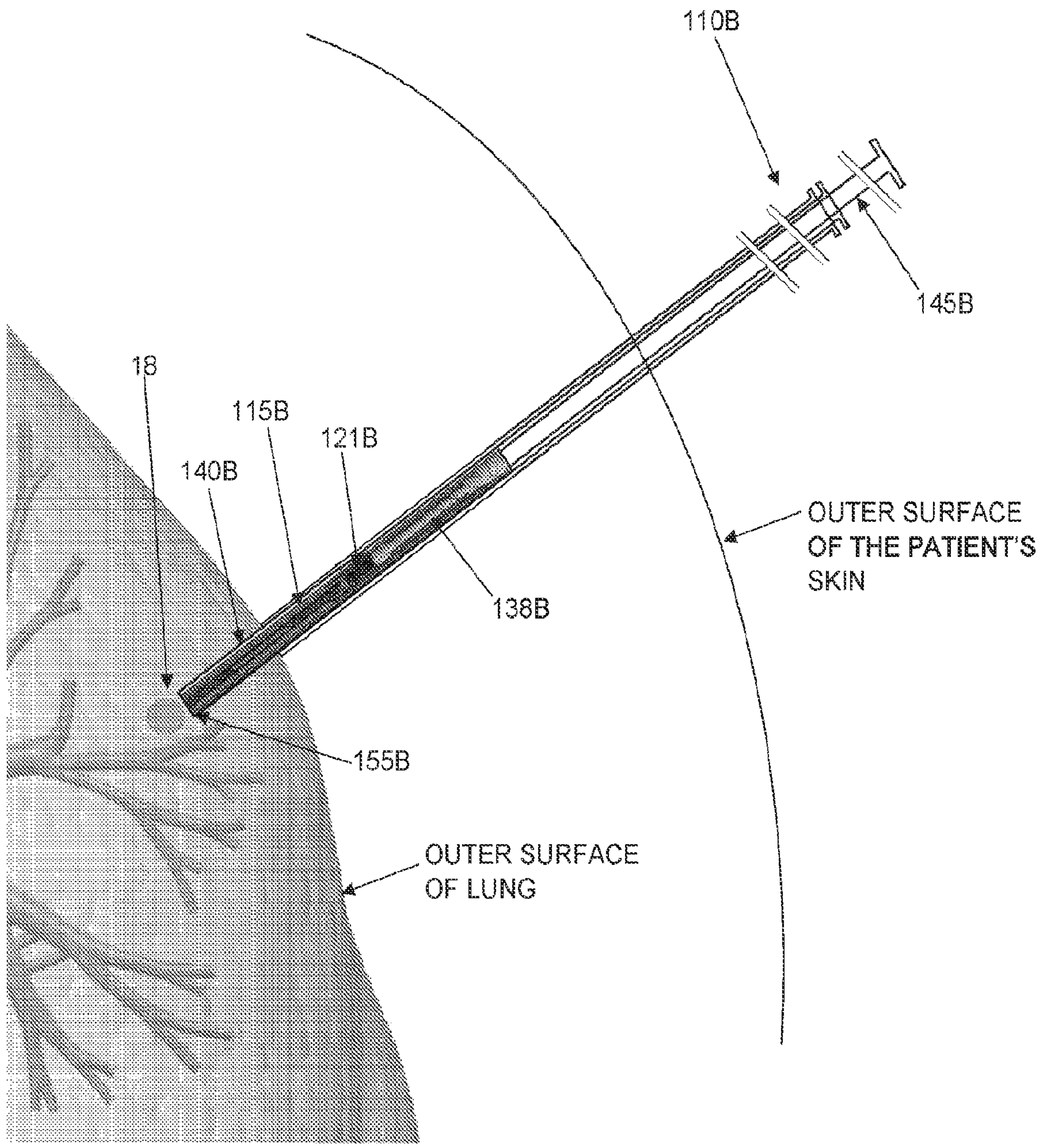

With this embodiment of the invention, and looking now at FIG. 82, an incision is made in the patient's skin and outer cannula 138B is inserted into the anatomy in the manner discussed above until the blunt distal edge 141B of outer cannula 138B is disposed against the outer surface of the anatomical structure (e.g., the outer surface of the lung) into which fiducial sensor 10 is to be implanted. Needle cannula 140B (comprising J-bar and electrical lead assembly 105B disposed in needle lumen 150B of needle cannula 140B) may be disposed within outer cannula 138B (see above) and advanced distally relative to outer cannula 138B, such that sharp distal tip 155B of needle cannula 140B penetrates into the tissue of the anatomical structure into which fiducial sensor 10 is to be mounted. As discussed above, the location of fiducial sensor 10 relative to the anatomy (and the lesion) may be tracked in real time by providing electrical power to fiducial sensor 10 in the manner discussed above.

Once the distal end of needle cannula 140B is disposed at (or directly next to) tissue mass 18, needle cannula 140B is retracted proximally while pusher 145B is utilized to apply a distally-directed force to J-bar assembly 115B in the manner discussed above. As a result, as needle cannula 140B is retracted proximally relative to J-bar assembly 115B, needle cannula 140B retracts past prongs 20 of J-bar assembly 115A and prongs 20 expand radially outboard in the manner discussed above, whereby to anchor fiducial sensor 10 in the tissue adjacent to lesion 18. See FIG. 83.

Figure 83:
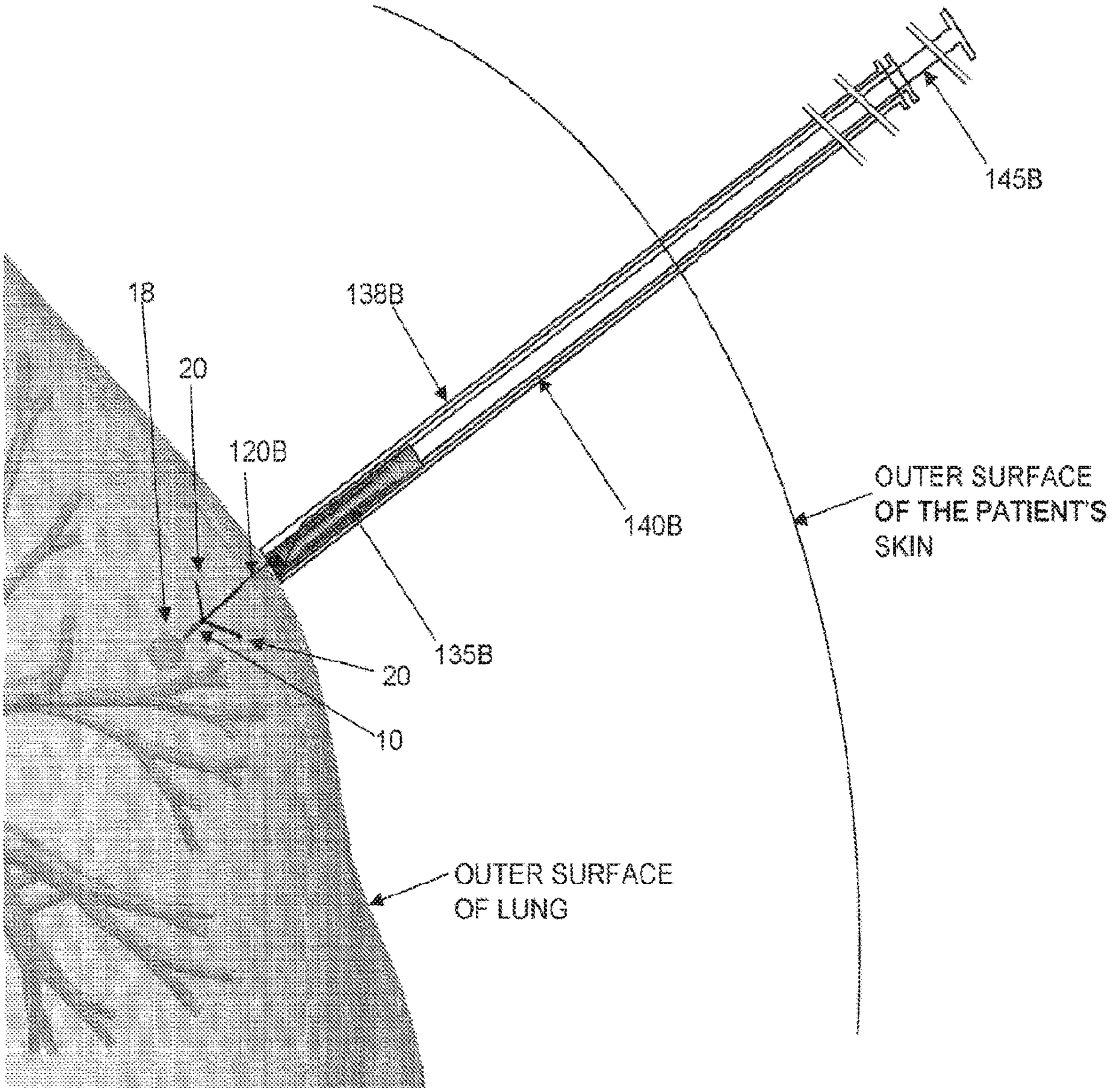

After J-bar assembly 115B has been deployed into the tissue such that fiducial sensor 10 is anchored adjacent to tissue mass 18, and looking now at FIG. 83, needle cannula 140B is retracted proximally so as to dispose expandable basket 135B just proximal to blunt distal edge 141B of outer cannula 138B. As this occurs, the interference fit between expandable basket 135B and the inner wall of needle cannula 140B while basket 135B is in a constrained, radially-reduced longitudinally-elongated configuration acts to maintain expandable basket 135B in position within needle cannula 140B as the needle cannula is retracted proximally. As a result, spring coil 121B of electrical lead 120B unspools/elongateds, permitting electrical lead 120B to span the indeterminate distance between (i) the location at which fiducial sensor 10 is implanted into the tissue of the anatomical structure, and (ii) expandable basket 135B. To this end, it should be appreciated that spring coil 121B may be formed with fewer turns (e.g., such that the unspooled electrical lead 120B has a shorter length than the unspooled electrical lead 120B discussed above). The shortened spring coil 121B permits the mounting of fiducial sensor 10 within the anatomy in the manner discussed above when only a small distance is to be spanned by electrical lead 120B (e.g., the distance from a tissue mass internal to the lung and the surface of the lung itself, a distance which may be considerably shorter than the distance from a tissue mass internal to the lung and the outer surface of the patient's skin).

Still looking at FIG. 83, once needle cannula 140B has been fully retracted proximally such that the blunt distal end surface 141B of outer cannula 135B is disposed at (or very near) the outer surface of the organ (e.g., the lung), pusher 145B is moved distally so as to engage the proximal end of expandable basket 135B, whereby to either eject expandable basket 135 out of the distal end of the outer cannula 138B or to permit outer cannula 138B to be retracted proximally while maintaining the positioning of expandable basket 135B relative to the organ (see discussion above).

Figure 84:
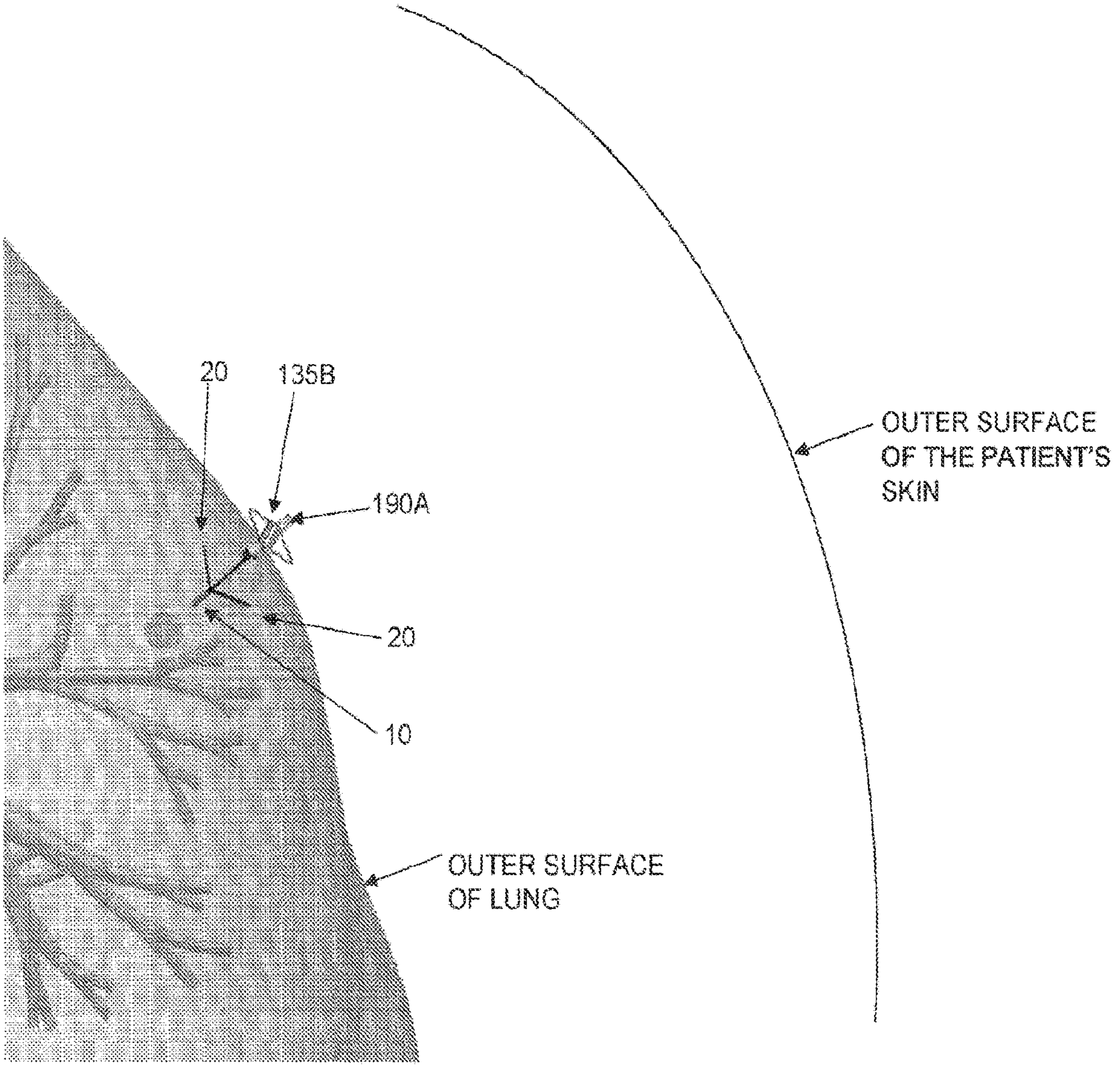

Looking now at FIG. 84, as expandable basket 135B is ejected out of the distal end of outer cannula 138B, expandable basket 135B is no longer radially constrained by needle lumen 150B or lumen 139B of outer cannula 138B. As a result, legs 136B of expandable basket 135B assume their radially-expanded, longitudinally shortened configuration, whereby to bear against the outer surface of the organ (e.g., the lung), while maintaining electrical lead 120B in position.

As discussed above in the context of the embodiment of FIGS. 77-80, with this embodiment of the invention, an external power source may thereafter be electrically connected to the aforementioned power supply connector 190A of expandable basket 135B so as to power fiducial sensor 10 such that the location of lesion 18 can be determined by controller 48 in the manner discussed above. By disposing expandable basket 135B internal to the anatomy, it is possible for the surgeon to close up the incision, leaving expandable basket 135B in place, and to thereafter (e.g., at a later date when a resection procedure is to be performed) locate expandable basket 135B and access power supply connector 190A so as to connect an external power supply so that the location of fiducial sensor 10 (and hence, lesion 18) can be identified.

Modifications

It should be understood that many additional changes in the details, materials, steps and arrangements of parts, which have been herein described and illustrated in order to explain the nature of the present invention, may be made by those skilled in the art while still remaining within the principles and scope of the invention.

Among other things, although the above described system and method for resecting a tissue mass was described for surgery involving the lung, it is also applicable to resection of lesions in any other organ or structure of the body, for example, resection for breast conserving surgery, liver resection, sarcoma resection, partial nephrectomy or lung wedge resection surgery. In addition, the above described system and method for resecting a tissue mass is not limited to VATS or minimally invasive surgery.

And it should also be appreciated that although the present invention is sometimes discussed above in the context of resection procedures relating to lesions in the lung, the methods and apparatus of the present invention are applicable to substantially any deformable anatomical structure including, but not limited to the lungs, the stomach, the bladder, the intestine, the heart, the liver, etc.

What is claimed is:

1. A method for tracking the location of a tissue mass located within an anatomical structure in the body of a patient, the method comprising:

tracking the location of the tissue mass based on diagnostic images and a virtual model;

providing a system comprising: a deployment system comprising: an outer cannula comprising a distal end, a proximal end, and an outer cannula lumen extending therebetween; a needle cannula comprising a distal end, a proximal end, and a needle cannula lumen extending therebetween, a needle cannula comprising a distal end, a proximal end, and a needle cannula lumen extending therebetween, the needle cannula being sized to be slidably received within the outer cannula lumen;

a pusher comprising a distal end and a proximal end, the distal end of the pusher being slidably received within the needle cannula;

a J-bar and electrical lead assembly comprising:

a fiducial sensor comprising at least one mount for mounting the fiducial sensor to tissue, wherein the fiducial sensor is configured to assume (i) a radially-reduced profile when the fiducial sensor is radially constricted, and (ii) a radially-expanded profile when the fiducial sensor is not radially constricted;

an expandable basket configured to assume (i) a radially-reduced profile when the expandable basket is radially constricted, and (ii) a radially-expanded profile when the expandable basket is not radially constricted;

an electrical lead configured to extend between the fiducial sensor and the expandable basket to electrically connect the fiducial sensor to the expandable basket;

at least one connector mounted to the expandable basket in electrical communication with the electrical lead, such that electrical power supplied to the at least one connector powers the fiducial sensor;

disposing the J-bar and electrical lead assembly within the needle cannula lumen such that the fiducial sensor is disposed adjacent to the distal end of the needle cannula, the expandable basket is disposed proximal to the fiducial sensor, and the electrical lead is disposed intermediate the fiducial sensor and the expandable basket;

disposing the pusher within the needle cannula lumen such that the distal end of the pusher is disposed proximal to the expandable basket;

disposing the needle cannula within the outer cannula lumen;

inserting the outer cannula into the anatomy of the patient until the distal end of the outer cannula is disposed against the anatomical structure;

moving the needle cannula distally relative to the outer cannula such that the needle cannula enters into the anatomical structure and moves distally to the location of the tissue mass, applying a distally-directed force against the expandable basket using the pusher so that the J-bar and electrical lead assembly disposed within the needle cannula lumen moves distally, and/or applying a distally-directed force against the J-bar and electrical lead assembly using the pusher while moving the needle cannula proximally so that the position of the J-bar and electrical lead assembly is maintained while the needle cannula is withdrawn proximally, until the fiducial sensor is not constrained by the needle cannula, such that the fiducial sensor assumes the radially-expanded profile at a location proximate to the tissue mass, and such that the at least one mount anchors the fiducial sensor in the anatomical structure;

moving the outer cannula and needle cannula proximally in concert, whereby to move the expandable basket proximally, until the distal end of the outer cannula and the distal end of the needle cannula are disposed at the surface of the patient's skin;

applying a distally-directed force against the expandable basket using the pusher so that the expandable basket disposed within the needle cannula lumen moves distally, and/or applying a distally-directed force against the expandable basket using the pusher while moving the needle cannula and outer cannula proximally so that the position of the expandable basket is maintained while the needle cannula and outer cannula are withdrawn proximally, until the expandable basket is not constrained by the needle cannula or the outer cannula, such that the expandable basket assumes the radially-expanded profile at the surface of the patient's skin, and such that the electrical lead extends between the fiducial sensor and the expandable basket.

2. The method according to claim 1 wherein the at least one mount of the fiducial sensor comprises a prong configured to engage tissue.

3. The method according to claim 1 wherein the expandable basket comprises a radially-expandable structure formed of a shape memory material, wherein the radially-expandable structure is spring biased to assume the radially-expanded profile when the radially-expanded structure is not radially constrained; and wherein the radially-expandable structure comprises a proximal end mounted to the electrical lead, a distal end comprising the at least one connector, and an internal volume between the distal end and the proximal end of the radially-expandable structure.

4. The method according to claim 3 wherein the expandable structure comprises an open structure defined by a plurality of legs when the radially-expandable structure assumes the radially-expanded profile.

5. The method according to claim 1 wherein the at least one connector of the expandable basket forms a socket configured to receive a plug.

6. The method according to claim 1 wherein the electrical lead extending between the fiducial sensor and the expandable basket forms a deformable spring comprising a plurality of turns, such that as the expandable basket is moved away from the fiducial sensor, the electrical lead unspools to extend the variable distance between the fiducial sensor and the expandable basket.

7. The method according to claim 1 wherein, prior to inserting the outer cannula into the anatomy of the patient, the intended position of the J-bar and electrical lead assembly is selected by locating the tissue mass and the anatomical structure using an imaging modality, and further wherein the imaging modality comprises one of: diagnostic or intraprocedural computed tomography (CT), C-arm computed tomography (CT), and magnetic resonance imaging (MRI).

8. The method according to claim 7 wherein, the fiducial sensor assumes the radially-expanded profile at a location proximate to the tissue mass, power is supplied to the fiducial sensor to determine the position of the fiducial sensor in the frame of reference of the imaging modality, and further wherein an image produced by the imaging modality is modified to show the position of the fiducial sensor in the image.

9. The method according to claim 1 wherein, after the expandable basket is deployed in the radially-expanded configuration in contact with the patient's skin, the position of the fiducial sensor relative to the tissue mass within the anatomical structure is confirmed using an imaging modality, and further wherein the imaging modality comprises one of: diagnostic or intraprocedural computed tomography (CT), C-arm computed tomography (CT), and magnetic resonance imaging (MRI).

10. The method according to claim 1 wherein the distal end of the needle cannula forms a sharp distal tip configured to pierce tissue.

11. A system for tracking the location of a tissue mass located within an anatomical structure in the body of a patient, the system comprising:

diagnostic images to track the location of the tissue mass and a virtual model;

a deployment system comprising: an outer cannula comprising a distal end, a proximal end, and an outer cannula lumen extending therebetween;

a needle cannula comprising a distal end, a proximal end, and a needle cannula lumen extending therebetween, the needle cannula being sized to be slidably received within the outer cannula lumen;

a pusher comprising a distal end and a proximal end, the distal end of the pusher being slidably received within the needle cannula;

a J-bar and electrical lead assembly comprising:

a fiducial sensor comprising at least one mount for mounting the fiducial sensor to tissue, wherein the fiducial sensor is configured to assume (i) a radially-reduced profile when the fiducial sensor is radially constricted, and (ii) a radially-expanded profile when the fiducial sensor is not radially constricted;

an expandable basket configured to assume (i) a radially-reduced profile when the expandable basket is radially constricted, and (ii) a radially-expanded profile when the expandable basket is not radially constricted;

an electrical lead configured to extend between the fiducial sensor and the expandable basket to electrically connect the fiducial sensor to the expandable basket;

at least one connector mounted to the expandable basket in electrical communication with the electrical lead, such that electrical power supplied to the at least one connector powers the fiducial sensor;

wherein the J-bar and electrical lead assembly is disposed within the needle cannula lumen such that the fiducial sensor is disposed proximal to the distal end of the needle cannula, the expandable basket is disposed proximal to the fiducial sensor, and the electrical lead is disposed intermediate the fiducial sensor and the expandable basket;

wherein the pusher is disposed within the needle cannula lumen such that the distal end of the pusher is disposed proximal to the expandable basket; and wherein the needle cannula is disposed within the outer cannula lumen to be selectively movable relative thereto.

12. The system according to claim 11 wherein the at least one mount of the fiducial sensor comprises a prong configured to engage tissue.

13. The system according to claim 11 wherein the expandable basket comprises a radially-expandable structure formed of a shape memory material, wherein the radially-expandable structure is spring biased to assume the radially-expanded profile when the radially-expanded structure is not radially constrained; and wherein the radially-expandable structure comprises a proximal end mounted to the electrical lead, a distal end comprising the at least one connector, and an internal volume between the distal end and the proximal end of the radially-expandable structure.

14. The system according to claim 13 wherein the expandable structure comprises an open structure defined by a plurality of legs when the radially-expandable structure assumes the radially-expanded profile.

15. The system according to claim 11 wherein the at least one connector of the expandable basket forms a socket configured to receive a plug.

16. The system according to claim 11 wherein the electrical lead extending between the fiducial sensor and the expandable basket forms a deformable spring comprising a plurality of turns, wherein the deformable spring is configured such that as the expandable basket is moved away from the fiducial sensor, the electrical lead unspools to extend the variable distance between the fiducial sensor and the expandable basket.

17. The system according to claim 11 wherein the distal end of the needle cannula forms a sharp distal tip configured to pierce tissue.

18. A method for tracking the location of a tissue mass located within an anatomical structure in the body of a patient, the method comprising:

tracking the location of the tissue mass based on diagnostic images and a virtual model;

providing a system comprising:

a deployment system comprising: an outer cannula comprising a distal end, a proximal end, and an outer cannula lumen extending therebetween;

a needle cannula comprising a distal end, a proximal end, and a needle cannula lumen extending therebetween, the needle cannula being sized to be slidably received within the outer cannula lumen;

a pusher comprising a distal end and a proximal end, the distal end of the pusher being slidably received within the needle cannula;

a J-bar and electrical lead assembly comprising:

a fiducial sensor comprising at least one mount for mounting the fiducial sensor to tissue, wherein the fiducial sensor is configured to assume (i) a radially-reduced profile when the fiducial sensor is radially constricted, and (ii) a radially-expanded profile when the fiducial sensor is not radially constricted;

an expandable basket configured to assume (i) a radially-reduced profile when the expandable basket is radially constricted, and (ii) a radially-expanded profile when the expandable basket is not radially constricted;

an electrical lead configured to extend between the fiducial sensor and the expandable basket to electrically connect the fiducial sensor to the expandable basket;

at least one connector mounted to the expandable basket in electrical communication with the electrical lead, such that electrical power supplied to the at least one connector powers the fiducial sensor;

disposing the J-bar and electrical lead assembly within the needle cannula lumen such that the fiducial sensor is disposed proximal to the distal end of the needle cannula, the expandable basket is disposed proximal to the fiducial sensor, and the electrical lead is disposed intermediate the fiducial sensor and the expandable basket;

disposing the pusher within the needle cannula lumen such that the distal end of the pusher is disposed proximal to the expandable basket;

disposing the needle cannula within the outer cannula lumen;

inserting the outer cannula into the anatomy of the patient until the distal end of the outer cannula is disposed against an outer surface of the anatomical structure;

moving the needle cannula distally relative to the outer cannula such that the needle cannula enters into the anatomical structure and moves distally to the location of the tissue mass, applying a distally-directed force against the expandable basket using the pusher so that the J-bar and electrical lead assembly disposed within the needle cannula lumen moves distally, and/or applying a distally-directed force against the J-bar and electrical lead assembly using the pusher while moving the needle cannula proximally so that the position of the J-bar and electrical lead assembly is maintained while the needle cannula is withdrawn proximally, until the fiducial sensor is not constrained by the needle cannula, such that the fiducial sensor assumes the radially-expanded profile at a location proximate to the tissue mass, and such that the at least one mount anchors the fiducial sensor in the anatomical structure;

moving the outer cannula and needle cannula proximally in concert, whereby to move the expandable basket proximally, until the distal end of the outer cannula and the distal end of the needle cannula are disposed at the outer surface of the anatomical structure;

applying a distally-directed force against the expandable basket using the pusher so that the expandable basket disposed within the needle cannula lumen moves distally, and/or applying a distally-directed force against the expandable basket using the pusher while moving the needle cannula and outer cannula proximally so that the position of the expandable basket is maintained while the needle cannula and outer cannula are withdrawn proximally, until the expandable basket is not constrained by the needle cannula or the outer cannula, such that the expandable basket assumes the radially-expanded profile at the outer surface of the anatomical structure, and such that the electrical lead extends between the fiducial sensor and the expandable basket.

19. The method according to claim 18 wherein the electrical lead extending between the fiducial sensor and the expandable basket forms a deformable spring comprising a plurality of turns, such that as the expandable basket is moved away from the fiducial sensor, the electrical lead unspools to extend the variable distance between the fiducial sensor and the expandable basket.

20. The method according to claim 1 wherein, prior to inserting the outer cannula into the anatomy of the patient, the intended position of the J-bar and electrical lead assembly is planned by locating the tissue mass and the anatomical structure using an imaging modality, and further wherein the imaging modality comprises one selected from the group consisting of:

diagnostic or intraprocedural computed tomography (CT), C-arm computed tomography (CT), and magnetic resonance imaging (MRI).

* * * * *